US012275791B2

(12) United States Patent
Chang et al.

(10) Patent No.: US 12,275,791 B2
(45) Date of Patent: Apr. 15, 2025

(54) MULTI-SPECIFIC BINDING PROTEINS THAT BIND HER2, NKG2D, AND CD16, AND METHODS OF USE

(71) Applicant: Dragonfly Therapeutics, Inc., Waltham, MA (US)

(72) Inventors: Gregory P. Chang, Medford, MA (US); Ann F. Cheung, Lincoln, MA (US); Daniel Fallon, Winchester, MA (US); Asya Grinberg, Lexington, MA (US); William Haney, Wayland, MA (US); Steven O'Neil, Wayland, MA (US); Nicolai Wagtmann, Concord, MA (US); Ronnie Wei, Weston, MA (US); Bradley M. Lunde, Lebanon, NH (US); Bianka Prinz, Lebanon, NH (US)

(73) Assignee: Dragonfly Therapeutics, Inc., Waltham, MA (US)

( * ) Notice: Subject to any disclaimer, the term of this patent is extended or adjusted under 35 U.S.C. 154(b) by 1075 days.

(21) Appl. No.: 17/265,876

(22) PCT Filed: Aug. 7, 2019

(86) PCT No.: PCT/US2019/045561
§ 371 (c)(1),
(2) Date: Feb. 4, 2021

(87) PCT Pub. No.: WO2020/033587
PCT Pub. Date: Feb. 13, 2020

(65) Prior Publication Data
US 2021/0198369 A1 Jul. 1, 2021

Related U.S. Application Data

(60) Provisional application No. 62/716,259, filed on Aug. 8, 2018.

(51) Int. Cl.
*C07K 16/28* (2006.01)
*C07K 16/32* (2006.01)

(52) U.S. Cl.
CPC ........ *C07K 16/2851* (2013.01); *C07K 16/283* (2013.01); *C07K 16/32* (2013.01); *C07K 2317/21* (2013.01); *C07K 2317/31* (2013.01); *C07K 2317/55* (2013.01); *C07K 2317/622* (2013.01); *C07K 2317/73* (2013.01); *C07K 2317/92* (2013.01)

(58) Field of Classification Search
CPC .............. C07K 16/2851; C07K 16/283; C07K 16/32; C07K 2317/21; C07K 2317/31; C07K 2317/55; C07K 2317/622; C07K 2317/73; C07K 2317/92
See application file for complete search history.

(56) References Cited

U.S. PATENT DOCUMENTS

| | | |
|---|---|---|
| 5,776,427 A | 7/1998 | Thorpe et al. |
| 5,807,706 A | 9/1998 | Carter et al. |
| 5,863,538 A | 1/1999 | Thorpe et al. |
| 5,959,084 A | 9/1999 | Ring et al. |
| 6,036,955 A | 3/2000 | Thorpe et al. |
| 6,054,297 A | 4/2000 | Carter et al. |
| 6,129,914 A | 10/2000 | Weiner et al. |
| 6,165,464 A | 12/2000 | Hudziak et al. |
| 6,210,670 B1 | 4/2001 | Berg |
| 6,294,167 B1 | 9/2001 | Lindhofer et al. |
| 6,387,371 B1 | 5/2002 | Hudziak et al. |
| 6,399,063 B1 | 6/2002 | Hudziak et al. |
| 6,407,213 B1 | 6/2002 | Carter et al. |
| 6,572,856 B1 | 6/2003 | Taylor et al. |
| 6,737,056 B1 | 5/2004 | Presta |
| 7,112,324 B1 | 9/2006 | Dorken et al. |
| 7,235,641 B2 | 6/2007 | Kufer et al. |
| 7,575,923 B2 | 8/2009 | Dorken et al. |
| 7,635,472 B2 | 12/2009 | Kufer et al. |
| 7,642,228 B2 | 1/2010 | Carter et al. |
| 7,695,936 B2 | 4/2010 | Carter et al. |
| 7,820,166 B2 | 10/2010 | Lanzavecchia |
| 7,879,985 B2 | 2/2011 | Urso et al. |
| 7,951,917 B1 | 5/2011 | Arathoon et al. |
| 8,007,796 B2 | 8/2011 | Baeuerle et al. |

(Continued)

FOREIGN PATENT DOCUMENTS

| | | |
|---|---|---|
| CA | 2990511 A1 | 12/2016 |
| CN | 102378768 A | 3/2012 |

(Continued)

OTHER PUBLICATIONS

Kim et al., Evidence That the Hinge Region Plays a Role in Maintaining Serum Levels of the Murine IgG1 Molecule, 1995, Molecular Immunology, vol. 32, No. 7, pp. 467-475 (Year: 1995).*
Vaks et al., Design Principles for Bispecific IgGs, Opportunities and Pitfalls of Artificial Disulfide Bonds, 2018, Antibodies, vol. 7, Issue 27, pp. 1-28 (Year: 2018).*
Ahmad et al., scFv Antibody: Principles and Clinical Application, 2012, Clinical and Developmental Immunology, vol. 2012, Article 980250, pp. 1-15 (Year: 2012).*
Weatherill et al., Towards a universal disulphide stabilised single chain Fv format: importance of interchain disulphide bond location and vL-vH orientation, 2012, Protein Engineering, Design, and Selection, vol. 25, No. 7, pp. 321-329 (Year: 2012).*

(Continued)

*Primary Examiner* — Jeffrey Stucker
*Assistant Examiner* — Brittney E Donoghue
(74) *Attorney, Agent, or Firm* — Goodwin Procter LLP

(57) ABSTRACT

Multi-specific binding proteins that bind to and kill human cancer cells expressing epidermal growth factor receptor 2 (HER2 or ErbB2), but does not kill non-cancerous healthy human cells expressing HER2 are described, as well as pharmaceutical compositions and therapeutic methods useful for the treatment of HER2 expressing cancer. The invention also relates to multi-specific binding proteins that trigger CD8+ T cell killing of tumor cells.

6 Claims, 18 Drawing Sheets

Specification includes a Sequence Listing.

(56) References Cited

U.S. PATENT DOCUMENTS

| | | |
|---|---|---|
| 8,076,459 B2 | 12/2011 | Hofmeister et al. |
| 8,101,722 B2 | 1/2012 | Kufer et al. |
| 8,236,308 B2 | 8/2012 | Kischel et al. |
| 8,409,577 B2 | 4/2013 | Thompson et al. |
| 8,518,403 B2 | 8/2013 | Hoffmann et al. |
| 8,591,897 B2 | 11/2013 | Bryant |
| 8,592,562 B2 | 11/2013 | Kannan et al. |
| 8,658,765 B2 | 2/2014 | Martin, Jr. et al. |
| 8,679,785 B2 | 3/2014 | Carter et al. |
| 8,759,494 B2 | 6/2014 | Bachmann et al. |
| 8,784,821 B1 | 7/2014 | Kufer et al. |
| 8,796,420 B2 | 8/2014 | Martin, Jr. et al. |
| 8,840,888 B2 | 9/2014 | Nagorsen et al. |
| 8,931,406 B2 | 1/2015 | Detloff et al. |
| 9,079,969 B2 | 7/2015 | Martin, Jr. et al. |
| 9,102,736 B2 | 8/2015 | Hofmeister et al. |
| 9,127,064 B2 | 9/2015 | Urso et al. |
| 9,150,656 B2 | 10/2015 | Johnson et al. |
| 9,150,663 B2 | 10/2015 | Labrijn et al. |
| 9,200,078 B2 | 12/2015 | Bachmann |
| 9,248,181 B2 | 2/2016 | De Kruif et al. |
| 9,248,182 B2 | 2/2016 | De Kruif et al. |
| 9,273,136 B2 | 3/2016 | Rader et al. |
| 9,334,331 B2 | 5/2016 | Igawa et al. |
| 9,447,185 B2 | 9/2016 | Romagne et al. |
| 9,493,578 B2 | 11/2016 | Lazar et al. |
| 9,562,109 B2 | 2/2017 | Von Kreudenstein et al. |
| 9,587,036 B2 | 3/2017 | Kufer et al. |
| 9,637,557 B2 | 5/2017 | Scheer et al. |
| 9,683,053 B2 | 6/2017 | Blein et al. |
| 9,690,969 B2 | 6/2017 | Okamoto |
| 9,718,893 B2 | 8/2017 | Jung et al. |
| 9,951,145 B2 | 4/2018 | Kim et al. |
| 9,963,513 B2 | 5/2018 | Vu et al. |
| 10,040,853 B2 | 8/2018 | Spies et al. |
| 10,047,167 B2 | 8/2018 | Demarest et al. |
| 10,059,765 B2 | 8/2018 | Velardi et al. |
| 10,377,827 B2 | 8/2019 | Swanson et al. |
| 10,421,807 B2 | 9/2019 | Gonzales et al. |
| 10,526,409 B2 | 1/2020 | Urso et al. |
| 10,767,760 B2 | 9/2020 | Ando |
| 11,084,880 B2 | 8/2021 | Brogdon et al. |
| 11,124,582 B2 | 9/2021 | Ambrogelly et al. |
| 11,787,864 B2 | 10/2023 | Cheung et al. |
| 11,834,506 B2 * | 12/2023 | Chang ............... C07K 16/2803 |
| 11,884,732 B2 * | 1/2024 | Chang ................ A61K 39/395 |
| 11,884,733 B2 * | 1/2024 | Chang .................... A61P 35/00 |
| 11,939,384 B1 | 3/2024 | Chang et al. |
| 2002/0103345 A1 | 8/2002 | Zhu |
| 2002/0193569 A1 | 12/2002 | Hanna |
| 2003/0095965 A1 | 5/2003 | Van Beneden et al. |
| 2004/0038339 A1 | 2/2004 | Kufer et al. |
| 2004/0052783 A1 | 3/2004 | Weiner et al. |
| 2004/0115198 A1 | 6/2004 | Spies et al. |
| 2005/0037002 A1 | 2/2005 | Velardi et al. |
| 2005/0054019 A1 | 3/2005 | Michaud et al. |
| 2005/0058639 A1 | 3/2005 | Gudas et al. |
| 2005/0158307 A1 | 7/2005 | Spies et al. |
| 2005/0244416 A1 | 11/2005 | Jung |
| 2006/0018899 A1 | 1/2006 | Kao et al. |
| 2006/0235201 A1 | 10/2006 | Kischel |
| 2006/0246004 A1 | 11/2006 | Adams et al. |
| 2007/0004909 A1 | 1/2007 | Johnson et al. |
| 2007/0071759 A1 | 3/2007 | Shin et al. |
| 2007/0179086 A1 | 8/2007 | Gliniak et al. |
| 2007/0190063 A1 | 8/2007 | Bahjat et al. |
| 2008/0025975 A1 | 1/2008 | Weiner et al. |
| 2008/0299137 A1 | 12/2008 | Svendsen et al. |
| 2008/0305105 A1 | 12/2008 | Kufer et al. |
| 2009/0142352 A1 | 6/2009 | Jackson et al. |
| 2009/0175867 A1 | 7/2009 | Thompson et al. |
| 2009/0226442 A1 | 9/2009 | Huet et al. |
| 2009/0226466 A1 | 9/2009 | Fong et al. |
| 2009/0252729 A1 | 10/2009 | Farrington et al. |
| 2009/0304693 A1 | 12/2009 | Ghayur et al. |
| 2009/0304696 A1 | 12/2009 | Lawson et al. |
| 2010/0009866 A1 | 1/2010 | Prinz et al. |
| 2010/0055034 A1 | 3/2010 | Martin et al. |
| 2010/0056764 A1 | 3/2010 | Urso et al. |
| 2010/0124764 A1 | 5/2010 | Hufton et al. |
| 2010/0174053 A1 | 7/2010 | Johnson et al. |
| 2010/0178298 A1 | 7/2010 | Lindhofer |
| 2010/0260765 A1 | 10/2010 | Barry et al. |
| 2010/0272718 A1 | 10/2010 | Urso et al. |
| 2010/0286374 A1 | 11/2010 | Kannan et al. |
| 2010/0291112 A1 | 11/2010 | Kellner et al. |
| 2010/0310463 A1 | 12/2010 | Cicortas Gunnarsson et al. |
| 2011/0008335 A1 | 1/2011 | Velardi et al. |
| 2011/0020273 A1 | 1/2011 | Chang et al. |
| 2011/0044980 A1 | 2/2011 | Ghayur et al. |
| 2011/0054151 A1 | 3/2011 | Lazar et al. |
| 2011/0150870 A1 | 6/2011 | Rader et al. |
| 2011/0311535 A1 | 12/2011 | Dranoff et al. |
| 2012/0014957 A1 | 1/2012 | Ghayur et al. |
| 2012/0058082 A1 | 3/2012 | Kaplan et al. |
| 2012/0058906 A1 | 3/2012 | Smider et al. |
| 2012/0093823 A1 | 4/2012 | Van Den Brink et al. |
| 2012/0149876 A1 | 6/2012 | Von Kreudenstein et al. |
| 2012/0171173 A1 | 7/2012 | Ideno et al. |
| 2012/0195900 A1 | 8/2012 | Ghayur et al. |
| 2012/0263722 A1 | 10/2012 | Ghayur et al. |
| 2012/0269723 A1 | 10/2012 | Brinkmann et al. |
| 2012/0294796 A1 | 11/2012 | Johnson et al. |
| 2012/0294857 A1 | 11/2012 | Sentman et al. |
| 2012/0321626 A1 | 12/2012 | Zhou |
| 2012/0328619 A1 | 12/2012 | Fey et al. |
| 2013/0115208 A1 | 5/2013 | Ho et al. |
| 2013/0177555 A1 | 7/2013 | Wilkinson et al. |
| 2013/0209514 A1 | 8/2013 | Gilboa et al. |
| 2013/0216528 A1 | 8/2013 | Cheung et al. |
| 2013/0216544 A1 | 8/2013 | Bachmann |
| 2013/0230525 A1 | 9/2013 | Li et al. |
| 2013/0336977 A1 | 12/2013 | Thompson et al. |
| 2014/0044739 A1 | 2/2014 | Teng et al. |
| 2014/0044770 A1 * | 2/2014 | Yaffe .................. G01N 33/573 424/490 |
| 2014/0072579 A1 | 3/2014 | De Kruif et al. |
| 2014/0072581 A1 | 3/2014 | Dixit et al. |
| 2014/0105889 A1 | 4/2014 | Igawa et al. |
| 2014/0112926 A1 | 4/2014 | Liu et al. |
| 2014/0120096 A1 | 5/2014 | Bakker et al. |
| 2014/0127203 A1 | 5/2014 | Thompson et al. |
| 2014/0140999 A1 | 5/2014 | De Kruif et al. |
| 2014/0141022 A1 | 5/2014 | Thompson et al. |
| 2014/0154250 A1 | 6/2014 | Thompson et al. |
| 2014/0154252 A1 | 6/2014 | Thompson et al. |
| 2014/0199294 A1 | 7/2014 | Mimoto et al. |
| 2014/0234342 A1 | 8/2014 | Narni-Mancinelli et al. |
| 2014/0242077 A1 | 8/2014 | Choi et al. |
| 2014/0271617 A1 | 9/2014 | Igawa et al. |
| 2014/0288275 A1 | 9/2014 | Moore et al. |
| 2014/0294827 A1 | 10/2014 | Gastwirt et al. |
| 2014/0302064 A1 | 10/2014 | Moore |
| 2014/0363426 A1 | 12/2014 | Moore et al. |
| 2014/0364340 A1 | 12/2014 | Vasquez et al. |
| 2014/0377269 A1 | 12/2014 | Mabry et al. |
| 2015/0050269 A1 | 2/2015 | Igawa et al. |
| 2015/0056206 A1 | 2/2015 | Zhou |
| 2015/0079088 A1 | 3/2015 | Lowman et al. |
| 2015/0119555 A1 | 4/2015 | Jung et al. |
| 2015/0166636 A1 | 6/2015 | Igawa et al. |
| 2015/0166654 A1 | 6/2015 | Igawa et al. |
| 2015/0175697 A1 | 6/2015 | Bonvini et al. |
| 2015/0175700 A1 | 6/2015 | Lum et al. |
| 2015/0203591 A1 | 7/2015 | Yancopoulos et al. |
| 2015/0210765 A1 | 7/2015 | Roschke et al. |
| 2015/0259431 A1 | 9/2015 | Stemmer et al. |
| 2015/0259434 A1 | 9/2015 | Johnson et al. |
| 2015/0274838 A1 | 10/2015 | Johnson et al. |
| 2015/0299319 A1 | 10/2015 | Velardi et al. |
| 2015/0307617 A1 | 10/2015 | Du et al. |
| 2015/0307628 A1 | 10/2015 | Kim et al. |
| 2015/0329637 A1 | 11/2015 | Urech et al. |
| 2015/0353636 A1 | 12/2015 | Parren et al. |

(56) References Cited

U.S. PATENT DOCUMENTS

| | | |
|---|---|---|
| 2016/0017038 A1 | 1/2016 | Koenig |
| 2016/0024214 A1 | 1/2016 | Urso et al. |
| 2016/0032009 A1 | 2/2016 | Cheung et al. |
| 2016/0039942 A1 | 2/2016 | Cobbold et al. |
| 2016/0046727 A1 | 2/2016 | Labrijn et al. |
| 2016/0046730 A1 | 2/2016 | Ghayur et al. |
| 2016/0077105 A1 | 3/2016 | Bobrowicz et al. |
| 2016/0090426 A1 | 3/2016 | Zhou et al. |
| 2016/0096892 A1 | 4/2016 | Brogdon et al. |
| 2016/0122432 A1 | 5/2016 | Baty et al. |
| 2016/0159882 A1 | 6/2016 | Landgraf et al. |
| 2016/0159924 A1 | 6/2016 | Padkjaer et al. |
| 2016/0176968 A1 | 6/2016 | Chang et al. |
| 2016/0289341 A1 | 10/2016 | Wu |
| 2016/0326249 A1 | 11/2016 | Ng et al. |
| 2016/0347849 A1 | 12/2016 | Cai et al. |
| 2016/0369002 A1 | 12/2016 | Gauthier et al. |
| 2017/0022291 A1 | 1/2017 | Baruah et al. |
| 2017/0029529 A1 | 2/2017 | Croasdale et al. |
| 2017/0066827 A1 | 3/2017 | Pule et al. |
| 2017/0114141 A1 | 4/2017 | Amann et al. |
| 2017/0233472 A1 | 8/2017 | Barat et al. |
| 2017/0291955 A1 | 10/2017 | Li et al. |
| 2017/0362321 A1 | 12/2017 | Campbell et al. |
| 2017/0368169 A1* | 12/2017 | Loew .................. C07K 14/71 |
| 2017/0369595 A1 | 12/2017 | Brinkmann et al. |
| 2018/0044415 A1 | 2/2018 | Escarpe et al. |
| 2018/0057608 A1 | 3/2018 | Jung et al. |
| 2018/0105594 A1 | 4/2018 | Urso et al. |
| 2018/0105599 A1 | 4/2018 | Cobbold et al. |
| 2018/0118851 A1 | 5/2018 | Comeau et al. |
| 2018/0237519 A1 | 8/2018 | Caligiuri et al. |
| 2018/0237541 A1 | 8/2018 | Kim et al. |
| 2018/0273633 A1 | 9/2018 | Jiang et al. |
| 2018/0312592 A1 | 11/2018 | Junutula et al. |
| 2018/0346600 A1 | 12/2018 | Kim et al. |
| 2019/0048079 A1 | 2/2019 | Spies et al. |
| 2019/0225702 A1 | 7/2019 | Baeuerle et al. |
| 2019/0359716 A1 | 11/2019 | Chang et al. |
| 2019/0375838 A1 | 12/2019 | Chang et al. |
| 2020/0002436 A1 | 1/2020 | Chang et al. |
| 2020/0024353 A1 | 1/2020 | Chang et al. |
| 2020/0048347 A1 | 2/2020 | Miao et al. |
| 2020/0055939 A1 | 2/2020 | Lombana et al. |
| 2020/0095327 A1 | 3/2020 | Chang et al. |
| 2020/0157174 A1 | 5/2020 | Chang et al. |
| 2020/0157226 A1 | 5/2020 | Chang et al. |
| 2020/0157227 A1 | 5/2020 | Chang et al. |
| 2020/0165344 A1 | 5/2020 | Chang et al. |
| 2020/0216544 A1 | 7/2020 | Chang et al. |
| 2020/0231678 A1 | 7/2020 | Chang et al. |
| 2020/0231679 A1 | 7/2020 | Chang et al. |
| 2020/0231700 A1 | 7/2020 | Cheung et al. |
| 2020/0277383 A1 | 9/2020 | Chang et al. |
| 2020/0277384 A1 | 9/2020 | Chang et al. |
| 2020/0376034 A1 | 12/2020 | Chang et al. |
| 2021/0009718 A1 | 1/2021 | Ambrogelly et al. |
| 2021/0032349 A1 | 2/2021 | Dengl et al. |
| 2021/0054082 A1 | 2/2021 | Chang et al. |
| 2021/0070887 A1 | 3/2021 | Ambrogelly et al. |
| 2021/0079102 A1 | 3/2021 | Chang et al. |
| 2021/0101976 A1 | 4/2021 | Chang et al. |
| 2021/0130471 A1 | 5/2021 | Chang et al. |
| 2021/0130474 A1 | 5/2021 | Chang et al. |
| 2021/0130496 A1 | 5/2021 | Chang et al. |
| 2021/0198369 A1 | 7/2021 | Chang et al. |
| 2021/0206859 A1 | 7/2021 | Chang et al. |
| 2021/0214436 A1 | 7/2021 | Chang et al. |
| 2021/0221894 A1 | 7/2021 | Bigelow et al. |
| 2021/0238290 A1 | 8/2021 | Chang et al. |
| 2021/0261668 A1 | 8/2021 | Chang et al. |
| 2021/0292420 A1 | 9/2021 | Chang et al. |
| 2021/0363261 A1 | 11/2021 | Chang et al. |
| 2022/0025037 A1 | 1/2022 | Baruah et al. |
| 2022/0089760 A1 | 3/2022 | Bigelow et al. |
| 2022/0119533 A1 | 4/2022 | Cheung et al. |
| 2022/0119534 A1 | 4/2022 | Baruah et al. |
| 2022/0153848 A1 | 5/2022 | Chang et al. |
| 2022/0195065 A1 | 6/2022 | Chang et al. |
| 2022/0380459 A1 | 12/2022 | Chang et al. |
| 2023/0034186 A1 | 2/2023 | Cuillerot et al. |
| 2023/0203202 A1 | 6/2023 | Bigelow et al. |
| 2023/0227562 A1 | 7/2023 | Chang et al. |
| 2023/0250176 A1 | 8/2023 | Cheung et al. |
| 2023/0257467 A1 | 8/2023 | Cheung et al. |
| 2023/0272041 A1 | 8/2023 | Bigelow et al. |
| 2023/0303702 A1 | 9/2023 | Chang et al. |
| 2023/0357409 A1 | 11/2023 | Chang et al. |
| 2023/0391877 A1 | 12/2023 | Chang et al. |
| 2023/0416402 A1 | 12/2023 | Cuillerot et al. |

FOREIGN PATENT DOCUMENTS

| | | |
|---|---|---|
| CN | 105814084 A | 7/2016 |
| CN | 105906722 A | 8/2016 |
| DE | 102013019352 A1 | 9/2015 |
| EP | 627940 A1 | 12/1994 |
| EP | 845998 A1 | 6/1998 |
| EP | 871673 A1 | 10/1998 |
| EP | 1124568 A1 | 8/2001 |
| EP | 1769000 B1 | 4/2007 |
| EP | 2185595 A1 | 5/2010 |
| EP | 2222706 B2 | 9/2010 |
| EP | 2927321 A1 | 10/2015 |
| EP | 2930188 A1 | 10/2015 |
| EP | 2942629 A1 | 11/2015 |
| EP | 2982380 A1 | 2/2016 |
| EP | 2990416 A1 | 3/2016 |
| KR | 10-2013-0103325 A | 9/2013 |
| KR | 10-2014-0067944 A | 6/2014 |
| RU | 2588668 C2 | 7/2016 |
| RU | 2593720 C2 | 8/2016 |
| WO | WO-1988008854 A1 | 11/1988 |
| WO | WO-1989006544 A1 | 7/1989 |
| WO | WO-1996027011 A1 | 9/1996 |
| WO | WO-2001071005 A2 | 9/2001 |
| WO | WO-2004056873 A1 | 7/2004 |
| WO | WO-2005/003172 A2 | 1/2005 |
| WO | WO-2005/009465 A1 | 2/2005 |
| WO | WO-2005/105849 A1 | 11/2005 |
| WO | WO-2006037960 A2 | 4/2006 |
| WO | WO-2007002905 A1 | 1/2007 |
| WO | WO-2007042573 A2 | 4/2007 |
| WO | WO-2007055926 A1 | 5/2007 |
| WO | WO-2007/097812 A2 | 8/2007 |
| WO | WO-2009/007124 A1 | 1/2009 |
| WO | WO-2009077483 A1 | 6/2009 |
| WO | WO-2009/089004 A1 | 7/2009 |
| WO | WO-2010017103 A2 | 2/2010 |
| WO | WO-2010080124 A2 | 7/2010 |
| WO | WO-2011014659 A2 | 2/2011 |
| WO | WO-2011075636 A2 | 6/2011 |
| WO | WO-2011/109400 A2 | 9/2011 |
| WO | WO-2011/131746 A2 | 10/2011 |
| WO | WO-2011/143545 A1 | 11/2011 |
| WO | WO-2012/006490 A2 | 1/2012 |
| WO | WO-2012/025530 A1 | 3/2012 |
| WO | WO-2012/032080 A1 | 3/2012 |
| WO | WO-2012034039 A2 | 3/2012 |
| WO | WO-2012/045752 A1 | 4/2012 |
| WO | WO-2012/058768 A1 | 5/2012 |
| WO | WO-2012/115241 A1 | 8/2012 |
| WO | WO-2012/125850 A1 | 9/2012 |
| WO | WO-2012/131555 A2 | 10/2012 |
| WO | WO-2012/158818 A2 | 11/2012 |
| WO | WO-2012/162482 A1 | 11/2012 |
| WO | WO-2013013700 A1 | 1/2013 |
| WO | WO-2013036799 A2 | 3/2013 |
| WO | WO-2013092001 A1 | 6/2013 |
| WO | WO-2013192594 A2 | 12/2013 |
| WO | WO-2014/001324 A1 | 1/2014 |
| WO | WO-2014012085 A2 | 1/2014 |
| WO | WO-2014/079000 A1 | 5/2014 |
| WO | WO-2014/084607 A1 | 6/2014 |

(56) References Cited

FOREIGN PATENT DOCUMENTS

| | | |
|---|---|---|
| WO | WO-2014/110601 A1 | 7/2014 |
| WO | WO-2014116051 A1 * | 7/2014 ............ C07K 16/00 |
| WO | WO-2014/124326 A1 | 8/2014 |
| WO | WO-2014/131712 A1 | 9/2014 |
| WO | WO-2014/145806 A2 | 9/2014 |
| WO | WO-2014144763 A2 | 9/2014 |
| WO | WO-2014/159940 A1 | 10/2014 |
| WO | WO-2014/165818 A2 | 10/2014 |
| WO | WO-2014198748 A1 | 12/2014 |
| WO | WO-2015009856 A2 | 1/2015 |
| WO | WO-2015/036606 A1 | 3/2015 |
| WO | WO-2015036582 A2 | 3/2015 |
| WO | WO-2015063187 A1 | 5/2015 |
| WO | WO-2015070061 A1 | 5/2015 |
| WO | WO-2015/077891 A1 | 6/2015 |
| WO | WO-2015089344 A1 | 6/2015 |
| WO | WO-2015095412 A1 | 6/2015 |
| WO | WO-2015095539 A1 | 6/2015 |
| WO | WO-2015/095972 A1 | 7/2015 |
| WO | WO-2015/150447 A1 | 10/2015 |
| WO | WO-2015153765 A1 | 10/2015 |
| WO | WO-2015153912 A1 | 10/2015 |
| WO | WO-2015158636 A1 | 10/2015 |
| WO | WO-2015169781 A1 | 11/2015 |
| WO | WO-2015181282 A1 | 12/2015 |
| WO | WO-2015184203 A1 | 12/2015 |
| WO | WO-2015184207 A1 | 12/2015 |
| WO | WO-2015197582 A1 | 12/2015 |
| WO | WO-2015197593 A1 | 12/2015 |
| WO | WO-2015197598 A2 | 12/2015 |
| WO | WO-2016/001810 A1 | 1/2016 |
| WO | WO-2016011571 A1 | 1/2016 |
| WO | WO-2016023909 A1 | 2/2016 |
| WO | WO-2016025880 A1 | 2/2016 |
| WO | WO-2016028672 A1 | 2/2016 |
| WO | WO-2016/032334 A1 | 3/2016 |
| WO | WO-2016/070959 A1 | 5/2016 |
| WO | WO-2016/090278 A2 | 6/2016 |
| WO | WO-2016097408 A1 | 6/2016 |
| WO | WO-2016100533 A2 | 6/2016 |
| WO | WO-2016109774 A1 | 7/2016 |
| WO | WO-2016115274 A1 | 7/2016 |
| WO | WO-2016122701 A1 | 8/2016 |
| WO | WO-2016134371 A2 | 8/2016 |
| WO | WO-2016/135041 A1 | 9/2016 |
| WO | WO-2016135066 A1 | 9/2016 |
| WO | WO-2016142768 A1 | 9/2016 |
| WO | WO-2016146702 A1 | 9/2016 |
| WO | WO-2016/166139 A1 | 10/2016 |
| WO | WO-2016161390 A1 | 10/2016 |
| WO | WO-2016164369 A2 | 10/2016 |
| WO | WO-2016164637 A1 | 10/2016 |
| WO | WO-2016184592 A1 | 11/2016 |
| WO | WO-2016187220 A2 | 11/2016 |
| WO | WO-2016/201300 A1 | 12/2016 |
| WO | WO-2016191305 A1 | 12/2016 |
| WO | WO-2016196237 A1 | 12/2016 |
| WO | WO-2016201389 A2 | 12/2016 |
| WO | WO-2016207273 A2 | 12/2016 |
| WO | WO-2016207278 A1 | 12/2016 |
| WO | WO-2017/011342 A1 | 1/2017 |
| WO | WO-2017005732 A1 | 1/2017 |
| WO | WO-2017008169 A1 | 1/2017 |
| WO | WO-2017021349 A1 | 2/2017 |
| WO | WO-2017048824 A1 | 3/2017 |
| WO | WO-2017075432 A2 | 5/2017 |
| WO | WO-2017079694 A2 | 5/2017 |
| WO | WO-2017081190 A1 | 5/2017 |
| WO | WO-2017083545 A1 | 5/2017 |
| WO | WO-2017114694 A1 | 7/2017 |
| WO | WO-2017124002 A1 | 7/2017 |
| WO | WO-2017125897 A1 | 7/2017 |
| WO | WO-2017143406 A1 | 8/2017 |
| WO | WO-2017/165464 A1 | 9/2017 |
| WO | WO-2017165683 A1 | 9/2017 |
| WO | WO-2017/180813 A1 | 10/2017 |
| WO | WO-2017177337 A1 | 10/2017 |
| WO | WO-2017211873 A1 | 12/2017 |
| WO | WO-2017218707 A2 | 12/2017 |
| WO | WO-2018/045090 A1 | 3/2018 |
| WO | WO-2018098365 A2 | 5/2018 |
| WO | WO-2018119171 A1 | 6/2018 |
| WO | WO-2018148445 A1 | 8/2018 |
| WO | WO-2018148447 A1 | 8/2018 |
| WO | WO-2018148566 A1 | 8/2018 |
| WO | WO-2018148610 A1 | 8/2018 |
| WO | WO-2018152516 A1 | 8/2018 |
| WO | WO-2018152518 A1 | 8/2018 |
| WO | WO-2018152530 A1 | 8/2018 |
| WO | WO-2018152547 A1 | 8/2018 |
| WO | WO-2018157147 A1 | 8/2018 |
| WO | WO-2018201051 A1 | 11/2018 |
| WO | WO-2018217799 A1 | 11/2018 |
| WO | WO-2018217945 A1 | 11/2018 |
| WO | WO-2018217947 A1 | 11/2018 |
| WO | WO-2019028027 A1 | 2/2019 |
| WO | WO-2019035939 A1 | 2/2019 |
| WO | WO-2019040727 A1 | 2/2019 |
| WO | WO-2019051308 A1 | 3/2019 |
| WO | WO-2019055677 A1 | 3/2019 |
| WO | WO-2019157332 A1 | 8/2019 |
| WO | WO-2019157366 A1 | 8/2019 |
| WO | WO-2019164929 A1 | 8/2019 |
| WO | WO-2019164930 A1 | 8/2019 |
| WO | WO-2019195408 A1 | 10/2019 |
| WO | WO-2019195409 A1 | 10/2019 |
| WO | WO-2019217332 A1 | 11/2019 |
| WO | WO-2019222449 A1 | 11/2019 |
| WO | WO-2019231920 A1 | 12/2019 |
| WO | WO-2020/033587 A1 | 2/2020 |
| WO | WO-2020/033630 A1 | 2/2020 |
| WO | WO-2020/033664 A1 | 2/2020 |
| WO | WO-2020/033702 A1 | 2/2020 |
| WO | WO-2020/086758 A1 | 4/2020 |
| WO | WO-2020/172189 A1 | 8/2020 |
| WO | WO-2021/041878 A1 | 3/2021 |
| WO | WO-2021/076554 A1 | 4/2021 |
| WO | WO-2021/076564 A1 | 4/2021 |
| WO | WO-2021/216916 A1 | 10/2021 |
| WO | WO-2021/226163 A2 | 11/2021 |
| WO | WO-2021/226193 A1 | 11/2021 |
| WO | WO-2022/031935 A1 | 2/2022 |
| WO | WO-2022/031965 A1 | 2/2022 |
| WO | WO-2022/187539 A1 | 9/2022 |
| WO | WO-2023/056243 A1 | 4/2023 |
| WO | WO-2023/056252 A1 | 4/2023 |
| WO | WO-2023/107954 A1 | 6/2023 |
| WO | WO-2023/107956 A1 | 6/2023 |
| WO | WO-2023/154796 A2 | 8/2023 |
| WO | WO-2023/168384 A2 | 9/2023 |

OTHER PUBLICATIONS

Kussie et al., A Single Engineered Amino Acid Substitution Changes Antibody Fine Specificity, 1994, Journal of Immunology, pp. 146-152 (Year: 1994).*

Rudikoff et al., Single amino acid substitution altering antigen-binding specificity, 1982, PNAS, vol. 79, pp. 1979-1983 (Year: 1982).*

Vajdos et al., Comprehensive Functional Maps of the Antigen-binding Site of an Anti-ErbB2 Antibody Obtained with Shotgun Scanning Mutagenesis, 2002, Journal of Molecular Biology, vol. 320, pp. 415-428 (Year: 2002).*

Brown et al., Tolerance to Single, but Not Multiple, Amino Acid Replacements in Antibody VH CDR2, 1996, Journal of Immunology, vol. 156, pp. 3285-3291 (Year: 1996).*

Bostrom, et al. (2009) "Improving Antibody Binding Affinity and Specificity for Therapeutic Development," *Methods and Protocols* 525:353-376.

Bryceson et al. (2006) "Synergy among receptors on resting NK cells for the activation of natural cytotoxicity and cytokine secretion," *Blood* 107(1):159-166.

(56) References Cited

OTHER PUBLICATIONS

Casset et al. (2003) "A peptide mimetic of an anti-CD4 monoclonal antibody by rational design," *Biochemical and Biophysical Research Communications* 307:198-205.
Chen et al. (1995) "Enhancement and destruction of antibody function by somatic mutation: unequal occurrence is controlled by V gene combinatorial associations," *The EMBO Journal* 14(12):2784-2794.
Chen et al. (1999) "Selection and Analysis of an Optimized Anti-VEGF Antibody: Crystal Structure of an Affinity-matured Fab in Complex with Antigen," *J. Mol. Biol.* 293:865-881.
Chen X. et al. (2013) "Fusion protein linkers: property, design and functionality" Advanced drug delivery reviews, 65(10):1357-1369.
Choi et al. (2013) "A Heterodimeric Fc-Based Bispecific Antibody Simultaneously Targeting VEGFR-2 and Met Exhibits Potent Antitumor Activity," *Mol Cancer Ther*, 12(12):2748-2759.
Colman P. M. (1994) "Effects of amino acid sequence changes on antibody-antigen interactions" Research in Immunology 145(1):33-36.
De Pascalis et al. (2002) "Grafting of "Abbreviated" Complementarity-Determining Regions Containing Specificity-Determining Residues Essential for Ligand Contact to Engineer a Less Immunogenic Humanized Monoclonal Antibody," *The Journal of Immunology* 169:3076-3084.
Dickopf et al. (2020) "Format and geometries matter: Structure-based design defines the functionality of bispecific antibodies," *Computational and Structural Biotechnology Journal* 18:1221-1227.
Edwards et al. (2003) "The Remarkable Flexibility of the Human Antibody Repertoire; Isolation of Over One Thousand Different Antibodies to a Single Protein, BLyS," *J. Mol. Biol.* 334:103-118.
Gonzales, et al. (2005) "Minimizing the Immunogenicity of Antibodies for Clinical Application," *Tumour Biol.* 26(1):31-43.
Henry et al. (2017) "Stability-Diversity Tradeoffs Impose Fundamental Constraints on Selection of Synthetic Human $V_H/V_L$ Single-Domain Antibodies from In Vitro Display Libraries," *Frontiers in Immunology*, 8:1-15.
Junttila et al. (2014) "Antitumor Efficacy of a Bispecific Antibody That Targets HER2 and Activates T Cells," *Cancer Research* 74(19):5561-5571.
Kim et al. (2014) "Mutational approaches to improve the biophysical properties of human single-domain antibodies," *Biochimica et Biophysica Acta*, 1844:1983-2001.
Koerner et al. (2015) "Induction of NK and T Cell Immune Responses Against Leukemia Cells by Bispecific NKG2D-CD16 and -CD3 Fusion Proteins," *Blood* 126(23):2558, Abstract 606.
Kranz et al. (1981) "Restricted reassociation of heavy and light chains from hapten-specific monoclonal antibodies," *Pro. Natl. Acad. Sci. USA* 78(9):5807-5811.
Krieg et al. (2005) "Functional Analysis of B and T Lymphocyte Attenuator Engagement on CD4+ and CD8+ T Cells," *The Journal of Immunology* 175(10):6420-6427.
Lamminmäki et al. (2001) "Crystal Structure of a Recombinant Anti-estradiol Fab Fragment in Complex with 17β-Estradiol," *The Journal of Biological Chemistry* 276(39):36687-36694.
Lloyd et al. (2009) "Modelling the human immune response: performance of a 1011 human antibody repertoire against a broad panel of therapeutically relevant antigens," *Protein Engineering, Design and Selection* 22(3):159-168.
Lund et al. (1996) "Multiple interactions of IgG with its core oligosaccharide can modulate recognition by complement and human Fc gamma receptor I and influence the synthesis of its oligosaccharide chains," *J. Immunol* 157:4963-4969.
MacCallum et al. (1996) "Antibody-antigen Interactions: Contact Analysis and Binding Site Topography," *J. Mol. Biol.* 262:732-745.
Maeda Y. et al. (1997) "Engineering of Functional Chimeric Protein G-Vargula Luciferase" Analytical biochemistry, 249(2):147-152.
Morris "Epitope Mapping of Protein Antigens by Competition ELISA," The Protein Protocols Handbook, Totowa, NJ, Humana Press, (Jan. 1, 1996):595-600.

Padlan et al. (1989) "Structure of an antibody-antigen complex: Crystal structure of the HyHEL-10 Fab-lysozyme complex," *Pro. Natl. Acad. Sci. USA* 86:5938-5942.
Pakula et al. (1989) "Genetic Analysis of Protein Stability and Function," *Annu. Rev. Genet.* 23:289-310.
Paul et al. (1993) "Fundamental Immunology," (textbook) 292-295.
Portolano et al. (1993) "Lack of promiscuity in autoantigen-specific H and L chain combinations as revealed by human H and L chain roulette," *J. Immunol.* 15(30):880-887.
Powers et al. (2016) "Abstract 1407: FPA 144, a therapeutic monoclonal antibody targeting the FGFR2b receptor, promotes antibody dependent cell-mediated cytotoxicity and stimulates sensitivity to PD-1 in the 4T1 syngeneic tumor model," *Cancer Research* 4 pages.
Roda-Navarro et al. (2020) "Understanding the Spatial Topology of Artificial Immunological Synapses Assembled in T Cell-Redirecting Strategies: A Major Issue in Cancer Immunotherapy," *Frontiers in Cell and Developmental Biology* 7:1-5.
Rudikoff et al. (1982) "Single amino acid substitution altering antigen-binding specificity," *Pro. Natl. Acad. Sci USA* 79:1979-1983.
Safdari Y. et al. (2013) "Antibody humanization methods-a review and update" Biotechnology and Genetic Engineering Reviews, 29(2):175-186.
Shen J. et al. (2006) "Single variable domain-IgG fusion: a novel recombinant approach to Fc domain-containing bispecific antibodies" Journal of Biological Chemistry, 281(16):10706-10714.
Stamova et al. (2011) "Simultaneous engagement of the activatory receptors NKG2D and CD3 for retargeting of effector cells to CD33-positive malignant cells," *Leukemia* 25:1053-1056.
Stein et al. (2012) "Natural Killer (NK)- and T-Cell Engaging Antibody-Derived Therapeutics," *Antibodies* 1:88-123.
Teplyakov A. et al. (2014) "Antibody modeling assessment II. Structures and models" Proteins: Structure, Function, and Bioinformatics, 82(8):1563-1582.
Torres M. et al. (2008) "The immunoglobulin constant region contributes to affinity and specificity" Trends in immunology, 29(2):91-97.
Vajdos et al. (2002) "Comprehensive Functional Maps of the Antigen-binding Site of an Anti-ErbB2 Antibody Obtained with Shotgun Scanning Mutagenesis," *J. Mol. Biol.* 320:415-428.
Vallera et al. (2016) "IL 15 Trispecific Killer Engagers (TriKE) Make Natural Killer Cells Specific to CD33+ Targets While Also Inducing Persistence, In Vivo Expansion, and Enhanced Function," *Clin Cancer Res*, 22(14):3440-50.
Wu et al. (1999) "Humanization of a Murine Monoclonal Antibody by Simultaneous Optimization of Framework and CDR Residues," *J. Mol. Biol.* 294:151-162.
Xu et al. (2014) "Production of bispecific antibodies in "knobs-into-holes" using a cell-free expression system," mAbs 7(1)231-242.
Yan et al. (2014) "Construction of a synthetic phage-displayed Nanobody library with CDR3 regions randomized by trinucleotide cassettes for diagnostic applications," *Journal of Translational Medicine* 12:343 (12 pages).
Zhang et al. (2021) "Bispecific antibody-mediated redirection of NKG2D-CAR natural killer cells facilitates dual targeting and enhances antitumor activity," *Journal for ImmunoTherapy of Cancer*; 9:e002980. doi:10.1136/jitc-2021-002980.
Affimed, Affimed Enters Into Collaboration With Merck to Evaluate AFM13 in Combination With . . . Retreived < U RL:https ://www.affimed.com/affi med-enters-into-collaboration-with-merck-to-evaluate-afm 13-i n-combination-with-keytruda-pembrolizumab-for-patients-with-hodgkin-lymphoma/>[retrieved on Feb. 1, 2023] Jan. 25, 2016.
Akbar et al. (2021) "A compact vocabulary of paratope-epitope interactions enables predictability of antibody-antigen binding," Cell Reports 34:108856 (21 pages).
Altshuler et al. (2010) "Generation of Recombinant Antibodies and Means for Increasing Their Affinity," *Biochemistry* (Moscow) 75(13):1584-1605.

(56) References Cited

OTHER PUBLICATIONS

Atwell et al. (1989) "Stable Heterodimers from Remodeling the Domain Interface of a Homodimer using a Phage Display Library," J Mol Biol 270:26-35.
Baek et al. (2014) "Construction of a Large Synthetic Human Fab Antibody Library on Yeast Cell Surface by Optimized Yeast Mating," J Microbial Biotechnol 24(3):408-420.
Bartlett et al. (2007) "Lenalidomide and pomalidomide strongly enhance tumor cell killing in vitro during antibody-dependent cellular cytotoxicity (ADCC) mediated by trastuzumab, cetuximab and rituximab," American Society of Clinical Oncology, 25(18S) (19 pages).
Bendayan et al. (1995) "Possibilities of False Immunocytochemical Results Generated by the Use of Monoclonal Antibodies: The Example of the Anti-proinsulin Antibody," *J. Histochem. Cytochem.* 43:881-886.
Berenbaum (1977) "Synergy, additivism and antagonism in immunosuppression," Clin. Exp. Immunol. 28:1-18.
Berenbaum (1989) "What is Synergy?" Pharmacological Reviews 41:93-141.
Bogen et al. (2021) "Design of a Trispecific Checkpoint Inhibitor and Natural Killer Cell Engager Based on a 2+1 Common Light Chain Antibody Architecture," Frontiers in Immunology 12:16 pages.
Boltz (2011) "Bi-specific Aptamers mediating Tumour Cell Lysis," Dissertation, M.Sc. Molekulare Biotechnologie, Technische Universität Darmstadt, pp. 1-133.
Bost et al. (1988) "Antibodies Against a Peptide Sequence Within the HIV Envelope Protein Crossreacts with Human Interleukin-2," *Immunological Investigations* 17(6&7):577-586.
Bowen et al. (2016) "Revisiting the Immunoglobulin Intramolecular Signaling Hypothesis," *Trends Immunol.* 37(11):721-723.
Branca et al. (2018) "Nature Biotechnology's academic spinouts of 2017," Nature Biotechnology 36(4):297-306.
Briney et al. (2019) "Commonality despite exceptional diversity in the baseline human antibody repertoire," Nature 566:393 (19 pages).
Brinkmann et al. (2017) "The making of bispecific antibodies," MABS 9(2):182-212.
Brown et al. (1996) "Tolerance of single, but not multiple, amino acid replacements in antibody VH CDR 2: a means of minimizing B cell wastage from somatic hypermutation?," Journal of Immunology, 156: 3285-3291.
Bruhns et al. (2009) "Specificity and affinity of human FCγ receptors and their polymorphic variants for human IgG subclasses," *Blood* 113(16):3716-3724.
Chan et al. (2010) "Therapeutic antibodies for autoimmunity and inflammation," Nature Reviews 10:301-316.
Choi et al. (2015) "Crystal structures of immunoglobulin Fc heterodimers reveal the molecular basis for heterodimer formation," Molecular Immunology 65(2):377-83.
Choi et al. (2015) "Engineering of Immunoglobulin Fc Heterodimers Using Yeast Surface-Displayed Combinatorial Fc Library Screening," PloS One. Dec. 16, 2015; 10(12);e0145349; pp. 1-20.
Cunningham et al. (1969) "Subgroups of Amino Acid Sequences in the Variable Regions of Immunoglobulin Heavy Chains," Proc Natl Acad Sci USA 64(3):997-1003.
Dahlberg et al. (2015) "Natural Killer Cell-Based Therapies Targeting Cancer: Possible Strategies to Gain and sustain Anti-Tumor Activity" Frontiers In Immunology 6(Article 605):19 pages.
Dasgupta et al. (2005) "Inhibition of NK Cell Activity through TGF-β1 by Down-Regulation of NKG2D in a Murine Model of Head and Neck Cancer," J Immunol 175(8):5541-5550.
Davis et al. (2010) "SEEDbodies: Fusion Proteins Based on Strand-Exchange Engineered Domain (SEED) CH3 Heterodimers in an Fc Analogue Platform for Asymmetric Binders or Immunofusions and Bispecific Antibodies," Protein Eng Des Sel 23(4):195-202.
Demaria et al. (2021) "Natural killer cell engagers in cancer immunotherapy: Next generation of immuno-oncology treatments," Eur. J. Immunol. 51:1934-1942.
El-Amine et al. (2002) "In vivo induction of tolerance by an Ig peptide is not affected by the deletion of FcR or a mutated IgG Fc fragment," *International Immunology* 14(7):761-766.
Elliott et al. (2014) "Antiparallel conformation of knob and hole aglycosylated half-antibody homodimers is mediated by a CH2-CH3 hydrophobic interaction", J. Mol. Biol., 426(9):1947-57.
Feng et al. (2011) "Design, Expression and Characterization of a Soluble Single-Chain Functional Human Neonatal Fc Receptor," Protein Expr Purif 79(1):66-71.
Feng et al., (2020) "NKG2D-Fc fusion protein promotes antitumor immunity through the depletion of immunosuppressive cells," Cancer Immunol. Immunother. 69(10):2147-2155.
Germain et al. (2008) "Redirecting NK cells mediated tumor cell lysis by a new recombinant bifunctional protein," *Protein Engineering, Design & Selection* 21(11):665-672.
Giuliani et al. (2017) "Activation of NK cells and disruption of PD-L1/PD-1 axis: two different ways for lenalidomide to block myeloma progression," Oncotarget 8(14):24031-24044.
Goel et al. (2004) "Plasticity within the Antigen-Combining Site May Manifest as Molecular Mimicry in the Humoral Immune Response," *The Journal of Immunology* 173(12):7358-7367.
Gunasekaran et al. (2010) "Enhancing Antibody Fc Heterodimer Formation through Electrostatic Steering Effects: Applications to Bispecific Molecules and Monovalent IgG," J Biol Chem 285(25):19637-46.
Ha et al. (2016) "Immunoglobulin Fc Heterodimer Platform Technology: From Design to Applications in Therapeutic Antibodies and Proteins," Front Immunol. 7:394, 16 pages.
Han et al. (2018) "Control of triple-negative breast cancer using ex vivo self-enriched, constimulated NKG2D CAR T cells," 11:92 13 pages.
Hasegawa et al. (2017) "Single amino acid substitution in LC-CDR1 induces Russell body phenotype that attenuates cellular protein synthesis through eIF2α phosphorylation and thereby downregulates IgG secretion despite operational secretory pathway traffic," MABS 9(5):854-873.
Herold et al. (2017) "Determinants of the assembly and function of antibody variable domains," Scientific Reports, 7:12276.
Hilpert et al. (2012) "Comprehensive analysis of NKG2D ligand expression and release in leukemia: implications for NKG2D-mediated NK cell responses," J Immunol. 189(3):1360-71.
Hlavacek et al. 1999 "Steric Effects on Multivalent Ligand-Receptor Binding: Exclusion of Ligand Sites by Bound Cell Surface Receptors," *Biophysical Journal* 76:3031-3043.
Holliger et al. (2005) "Engineered antibody fragments and the rise of single domains," Nat Biotechnol 23(9): 1126-36.
Hoseini et al. (2017) "Acute myeloid leukemia targets for bispecific antibodies," Blood Cancer Journal 7(2):e522 (12 pages).
Janeway et al. (1997) Chapter 3, Structure of the Antibody Molecule and Immunoglobulin Genes, *Immunology* Third Edition, Garland Publishing Inc., 3:1-3:11.
Jonnalagadda et al. (2015) "Chimeric Antigen Receptors With Mutated IgG4 Fc Spacer Avoid Fc Receptor Binding and Improve T Cell Persistence and Antitumor Efficacy," *Molecular Therapy* 23(4):757-768.
Jorge Flavio Mendoza Rincón (2014) "El receptor NKG2D en la frontera de la inmunovigilancia y la carcinogénesis," Publicación Científica en Ciencias Biomédicas 2(21):237-43.
Kanyavuz et al. (2019) "Breaking the law: unconventional strategies for antibody diversification," *Nature Reviews Immunology* 19(6):355-368.
Katano et al. (2015) "Predominant Development of Mature and Functional Human NK Cells in a Novel Human IL-2-Producing Transgenic NOG Mouse" J. Immunol. 194(7):3513-3525.
Kaur et al. (2015) "Applications of In Vitro-In Vivo Correlations in Generic Drug Development: Case Studies," *The AAPS Journal* 17(4):1035-1039; doi: 10.1208/s12248-015-9765-1.
Khan et al. (2014) "Adjustable Locks and Flexible Keys: Plasticity of Epitope-Paratope Interactions in Germline Antibodies," J. Immunol 192:5398-5405.

(56) References Cited

OTHER PUBLICATIONS

Kijanka et al. (2013) "Rapid optical imaging of human breast tumour xenografts using anti-HER2 VHHs site-directly conjugated to IRDye 800CW for image-guided surgery," *Eur J Nucl Med Mol Imaging* 40:1718-1729.

Kjellev et al. (2007) "Inhibition of NKG2D receptor function by antibody therapy attenuates transfer-induced colitis in SCID mice," *Eur. J. Immunol.* 37:1397-1406.

Klein et al. (2012) "Progress in overcoming the chain association issue in bispecific; heterodimeric IgG antibodies," mAbs 4(6):653-663.

Kunik, et al. (2012) "Structural consensus among antibodies defines the antigen binding site," *PLoS Comput Biol.* 8(2):e1002388.

Lewis et al. (2014) "Generation of bispecific IgG antibodies by structure-based design of an orthogonal Fab interface," Nat Biotechnol 32(2):191-98.

Lin et al. (2011) "Improved affinity of a chicken single-chain antibody to avian infectious bronchitis virus by site-directed mutagenesis of complementarity-determining region H3," *African Journal of Biotechnology* 10(79):18294-18303.

Lippow et al. (2007) "Computational design of antibody-affinity improvement beyond in vivo maturation," Nature Biotechnology 25(10):1171-1176.

Lo et al. (2021) "Conformational epitope matching and prediction based on protein surface spiral features," BMC Genomics 22(Suppl 2):116 16 pages.

Long et al. (2013) "Controlling NK Cell Responses: Integration of Signals for Activation and Inhibition," Annu Rev Immunol. 2013 ; 31: 10.1146/annurev-immunol-020711-075005.

Maeda et al. (2015) "New antibody modification technology and its application to antibody drugs," Farumashia 51(5):424-428.

Maelig et al. (2016) "NK cells and cancer: you can teach innate cells new tricks", Nature Reviews Cancer, 16(1):7-19.

Mandelboim et al. (1999) "Human CD16 as a lysis receptor mediating direct natural killer cell cytotoxicity," *PNAS USA* 96(10):5640-5644; doi: 10.1073/pnas.96.10.5640.

Mariuzza et al. (1987) "The Structural Basis of Antigen-Antibody Recognition," *Ann. Rev. Biophys. Chem.* 16:139:59.

Marks et al. (2020) "How repertoire data are changing antibody science," J. Biol. Chem. 295(29):9823-9837.

McCarthy et al. (2001) "Altering the fine specificity of an anti-Legionella single chain antibody by a single amino acid insertion," *Journal of Immunological Methods* 251:137-149.

Merchant et al. (1998), "An efficient route to human bispecific IgG," Nature Biotechnology 16, 677-681 doi : 10.1038/nbt0798-677.

Miller et al. (2003) "Design, Construction, and in Vitro Analyses of Multivalent Antibodies," J Immunol 170(9):4854-61.

Miller et al. 2019 "Natural Killer Cells in Cancer Immunotherapy," Ann. Rev. Cancer Biol. 3:77-103.

Mimoto et al. (2014) "Crystal structure of a novel asymmetrically engineered Fc variant with improved affinity for FcγRs," Mo/ Immunol 58(1):132-38.

Moore et al. (2011) "A novel bispecific antibody format enables simultaneous bivalent and monovalent co-engagement of distinct target antigens," mAbs 3:6, 546-557; Nov./Dec. 2011, Landes Bioscience, DOI: 10.4161/mabs.3.6.18123.

Muda et al. (2011) "Therapeutic assessment of SEED: a new engineered antibody platform designed to generate mono- and bispecific antibodies," Protein Eng Des Se/ 24(5):447-54.

Muller et al. (2015) "Trastuzumab emtansine (T-DM1) renders HER2+ breast cancer highly susceptible to CTLA-4/PD-1 blockade," Sci. Transl. Med. 7(315):1-14.

Muntasell et al. (2017) "Interplay between Natural Killer Cells and Anti-HER2 Antibodies: Perspectives for Breast Cancer Immunotherapy," *Front. Immunol.* 8:1544, doi: 10.3389/fimmu.2017.01544, 15 pages.

Muntasell et al. (2017) "Targeting NK-cell checkpoints for cancer immunotherapy," Current Opinion in Immunology 45:73-81.

Parsons et al. (2016) "NKG2D Acts as a Co-Receptor for Natural Killer Cell-Mediated Anti-HIV-1 Antibody-Dependent Cellular Cytotoxicity," AIDS Research and Human Retroviruses 32(10-11) 1089-1096.

Piche-Nicholas et al. (2018) "Changes in complementarity-determining regions significantly alter IgG binding to the neonatal Fc receptor (FcRn) and pharmacokinetics," *MABS* 10(1)81-94.

Poosaria et al. (2017) "Computational de novo Design of Antibodies binding to a Peptide with High Affinity," 114(6):1331-1342.

Rabia et al. (2018) "Understanding and overcoming trade-offs between antibody affinity, specificity, stability and solubility" Biochem Eng J. 137:365-374.

Raulet (2003) "Roles of the NKG2D immunoreceptor and its ligands," *Nature: Reviews Immunology* 3:781-790; doi: 10.1038/nri1199.

Ridgway et al. (1996) "'Knobs-into-Holes' engineering of antibody Ch3 domains for heavy chain heterodimerization," Protein Engineering 9(7):617-21.

Roell et al. (2017) "An Introduction to Terminology and Methoodology of Chemical Synergy—Perspectives from Across Disciplines," *Frontiers in Pharmacology: Cancer Molecular Targets and Therapeutics* 8:1-11.

Rosano et al. (2014) "Recombinant protein expression in *Escherichia coli*: advances and challenges" Frontiers in Microbiology 5(172):17 pages.

Sazinsky et al. (2008) "Aglycosylated immunoglobulin $G_1$ variants productively engage activating Fc receptors," *Proceedings of the National Academy of Sciences* 105(51)20167-20172.

Schroeder et al. (2010) "Structure and Function of Immunoglobulins," *J Allergy Clin Immunol* 125:S41-S52 (24 pages).

Shum et al. (2002) "Conservation and Variation in Human and Common Chimpanzee CD94 and NKG2 Genes," *The Journal of Immunology* 168:240-252.

Siena et al. (2010) "Reduced Incidence of Infusion-Related Reactions in Metastatic Colorectal Cancer During Treatment With Cetuximab Plus Irinotecan With Combined Corticosteroid and Antihistamine Premedication," *Cancer* 116(7):1827-1837.

Singer et al. (1998) "Genes and Genomes," Moscow, "Mir" 1:63-64.

Sondermann et al. (2000) "The 3.2-Å crystal structure of the human IgG1 Fc fragment-Fc[gamma]RIII complex," Nature 406(6793):267-273.

Spiess et al. (2015) "Alternative molecular formats and therapeutic applications for bispecific antibodies," Molecular Immunology 67:95-106.

Strop et al. (2012) "Generating Bispecific Human IgG1 and IgG2 Antibodies from Any Antibody Pair," J Mol Biol 420:204-19.

Sulea et al. (2018) "Application of Assisted Design of Antibody and Protein Therapeutics (ADAPT) improves efficacy of a *Clostridium difficile* toxin A single-domain antibody," 8:2260 11 pages.

Tallarida (2000) "Drug Synergism and Dose Effect Analysis," Ed. Chapman & Hall pp. 1-71.

Thakur et al. (2018) "Bispecific antibody based therapeutics: Strengths and challenges," Blood Review 32:339-347.

Trivedi et al. (2017) "Clinical pharmacology and translational aspects of bispecific antibodies," Clin. Transl. Sci., 10:147-162.

Vajda et al. (2021) "Progress toward improved understanding of antibody maturation," Current Opinion in Structural Biology 67:226-231.

Van de Winkel et al. (1993) "Human IgG Fc receptor heterogeneity: molecular aspects and clinical implications," Immunology Today 14(5):215-221.

Vidarsson et al. (2014) "IgG subclasses and allotypes: from structure to effector functions," Front. Immunol. 5:520, 17 pages.

Von Kreudenstein et al. (2013) "Improving Biophysical Properties of a Bispecific Antibody Scaffold to Aid Developability: Quality by Molecular Design," mAbs 5(5):646-54.

Von Kreudenstein et al. (2014), "Protein Engineering and the Use of Molecular Modeling and Simulation: The Case of Heterodimeric Fc Engineering," Methods 65(1):77-94.

Wang et al. (2018) "IgG Fc engineering to modulate antibody effector functions," Protein Cell 9(1):63-73.

(56) References Cited

OTHER PUBLICATIONS

Ward et al. (1989) "Binding activities of a epertoire of single immunoglobulin variable domains secreted from *Escherichia coli*," *Nature* 341:544-546.

Wark et al. (2006) "Latest technologies for the enhancement of antibody affinity", *Advanced Drug Delivery Reviews* 58(5-6):657-670.

Watanabe et al. (2014) NKG2D functions as an activating receptor on natural killer cells in the common marmoset (*Callithrix jacchus*) International Immunology 26(11):597-606.

Watzl et al. (2010) "Signal Transduction During Activation and Inhibition of Natural Killer Cells", Curr Protoc Immunol., 90(1):11.9B1-11.9B.17.

Wensveen et al. (2018) "NKG2D: A Master Regulator of Immune Cell Responsiveness," *Frontiers in Immunology* 9(Article 411):8 pages.

Whalen et al. (2023) "Engaging natural killer cells for cancer therapy via NKG2D, CD16A and other receptors," 15(1) 15 pages.

Wikipedia: "Trifunctional antibody Jan. 2, 2018",, Jan. 2, 2018 (Jan. 2, 2018), pp. 1-4, XP093016568, Retrieved from the Internet: URL:https://en.wikipedia.org/w/index.php?title=Trifunctional antibody8 oldid=818265015.

Wranik et al. (2012) "LUZ-Y, a novel platform for the mammalian cell production of full-length IgG-bispecific antibodies," J Biol Chem 287(52):43331-9.

Wu et al. (2011), "Lenalidomide enhances antibody-dependent cellular cytotoxicity of solid tumor cells in vitro: influence of host immune and tumor markers," Cancer Immunology, Immunotherapy, Springer, 60(1):61-73.

Xie et al. (2005) "A new format of bispecific antibody: highly efficient heterodimerization, expression and tumor cell lysis," J Immunol Methods 296(1):95-101.

Xie et al. (2015) "VEGFR2 targeted antibody fused with MICA stimulates NKG2D mediated immunosurveillance and exhibits potent anti-tumor activity against breast cancer," Oncotarget 7(13):16455-16471.

Yang et al. (2017) "Bispecific Antibodies as a Development Platform for New Concepts and Treatment Strategies" Int. J. Mol. Sci. 18(48) 21 pages.

Yang et al. (2017) "Enhancing NK cell-mediated cytotoxicity to cisplatin-resistant lung cancer cells via MEK/Erk signaling inhibition," Nature Scientific Reports, 7:7958 (13 pages).

Zhou et al. (1995) "Characterization of human homologue of 4-1BB and its ligand," Immunology Letters 45:67-73.

Ahmad et al. (2012) "scFv antibody: principles and clinical application," *Clinical and Developmental Immunology* 2012:1-16.

Averdam et al. (2009) "A Novel System of Polymorphic and Diverse NK Cell Receptors in Primates," *PLoS Genetics* 5(10):e1000688.

Busfield et al. (2014) "Targeting of acute myeloid leukemia in vitro and in vivo with an anti-CD123 mAb engineered for optimal ADCC," *Leukemia* 28(11): 2213-2221.

Cai et al. (2014) "Autonomous Stimulation of Cancer Cell Plasticity by the Human NKG2D Lymphocyte Receptor Coexpressed with Its Ligands on Cancer Cells," *PLOS ONE* 9(10):e108942.

Cho et al. (2010) "Delivery of NKG2D Ligand Using an Anti-HER2 Antibody-NKG2D Ligand Fusion Protein Results in an Enhanced Innate and Adaptive Antitumor Response," *Cancer Research* 70(24):10121-10130.

Chu, S. et al. (2014) "Immunotherapy with Long-Lived Anti-CD123 x Anti-CD3 Bispecific Antibodies Stimulates Potent T Cell-Mediated Killing of Human AML Cell Lines and of CD123+ Cells in Monkeys: A Potential Therapy for Acute Myelogenous Leukemia 11," *Blood* 124(21):2316.

Ding et al. (2018) "Fusion Proteins of NKG2D/NKG2DL in Cancer Immunotherapy," *International Journal of Molecular Sciences* 19(1):177.

Felices et al. (2016) "Generation of BiKEs and TriKEs to Improve NK cell-Mediated Targeting of Tumor Cells," Natural Killer Cells: Methods and Protocols, Methods in Molecular Biology 1441:333-346.

Gantke et al. (2016) "Trispecific Antibodies for Selective CD16A-Directed NK-Cell Engagement in Multiple Myeloma," Blood 128(22):4513.

Gantke et al. (2017) "Trispecific antibodies for CD16A-directed NK cell engagement and dual-targeting of tumor cells," Protein Engineering, Design & Selection 38(9):673-684.

Gauthier et al. (2019) "Multifunctional Natural Killer Cell Engagers Targeting NKp46 Trigger Protective Tumor Immunity," Cell 177(7):1701-1713.

Germain et al. (2005) "MHC Class I-Related Chain a Conjugated to Antitumor antibodies Can Sensitize Tumor Cells to Specific Lysis by Natural Killer Cells," *Clinical Cancer Research* US 11(20):7516-7522.

Glas et al. (1997) "Analysis of rearranged immunoglobulin heavy chain variable region genes obtained from a bone marrow transplant (BMT) recipient," *Clinical & Experimental Immunology* 107(2):372-380.

Gleason et al. (2012) "Bispecific and Trispecific Killer Cell Engagers Directly Activate Human NK Cells through CD16 Signaling and Induce Cytotoxicity and Cytokine Production," *Molecular Cancer Therapeutics* 11(12):2674-2684.

Gleason et al. (2014) "CD16xCD33 bispecific killer cell engager (BiKE) activates NK cells against primary MDS and MDSC CD33+ targets," *Blood* 123(19):3016-3026.

Gooden et al. (2012) "Infiltrating CTLs are bothered by HLA-E on tumors," OncoImmunology, 1(1):92-93.

Hezareh et al. (2001) "Effector Function Activities of a Panel of Mutants of a Broadly Neutralizing Antibody against Human Immunodeficiency Virus Type 1," *Journal of Virology* 75(24):12161-12168.

Jachimowicz et al. (2011) "Induction of In Vitro and In Vivo NK Cell Cytotoxicity Using High-Avidity Immunoligands Targeting Prostate-Specific Membrane Antigen in Prostate Carcinoma," *Mol Cancer Thera*, 10(6):1036-1045.

Kellner et al. (2012) "Fusion proteins between ligands for NKG2D and CD20-directed single-chain variable fragments sensitize lymphoma cells for natural killer cell-mediated lysis and enhance antibody-dependent cellular cytotoxicity," *Leukemia* 26:830-834.

Kellner et al. (2013) "Promoting natural killer cell functions by recombinant immunoligands mimicking an induced self phenotype," *Oncoimmunology* 2(6):e24481.

Kellner et al. (2016) "Enhancing natural killer cell-mediated lysis of lymphoma cells by combining therapeutic antibodies with CD20-specific immunoligands engaging NKG2D or NKp30," *OncoImmunology* 5(1):e1058459-1-e1058459-12.

Kluge et al. (2017) "EGFR/CD16A TandAbs are efficacious NK-cell engagers with favorable biological properties which potently kill EGFR(+) tumors with and without Ras mutation," Cancer Research 77(13 Suppl.):Abstract 3641.

Kwong et al. (2008) "Generation, affinity maturation, and characterization of a human anti-human NKG2D monoclonal antibody with dual antagonistic and agonistic activity," *Journal of Molecular Biology* 384(5):1143-1156.

Lin et al. (2013) "CD4+ NKG2D+ T cells induce NKG2D down-regulation in natural killer cells in CD86-RAE-1 E transgenic mice," *Immunology* 141(3):401-415.

Liu et al. (2017) "Fc engineering for Developing Therapeutic Bispecific Antibodies and Novel Scaffolds," *Frontiers in Immunology* 8(38):1-15.

Madlener et al. (2010) "A Bispecific Protein Targeting the NKG2D Receptor on Natural Killer Cells: In Vitro and In Vivo activity of ULBP2-CEA," *Blood* 116(21):2095.

McWilliams, et al. (2016) "Targeting the Tumor Evasion Interaction of NKG2A and Its Ligand HLA-E Increases Natural-Killer Cell Activity in Chronic Lymphocytic Leukemia," Blood 1289-1291.

Morvan et al. (2016). "NK cells and cancer: you can teach innate cells new tricks" *Nat Rev Cancer* 16(1):7-19.

Myers et al. (2021) "Exploring the NK cell platform for cancer immunotherapy," Nature Reviews Clinical Oncology 18(2):85-100.

(56) References Cited

OTHER PUBLICATIONS

Nagasaki et al. (2014) "Interleukin-6 released by colon cancer-associated fibroblasts is critical for tumour angiogenesis: anti-interleukin-6 receptor antibody suppressed angiogenesis and inhibited tumour-stroma interaction," *British Journal of Cancer* 110(2):469-478.

Nie et al. (2020) "Biology drives the discovery of bispecific antibodies as innovative therapeutics," Antibody Therapeutics 3(1):18-62.

Petricevic et al. (2013) "Trastuzumab mediates antibody-dependent cell-mediated cytotoxicity and phagocytosis to the same extent in both adjuvant and metastatic HER2/neu breast cancer patients," *Journal of Translational Medicine* 11(307).

Raab et al. (2014) "Fc-Optimized NKG2D-Fc Constructs Induce NK Cell Antibody-Dependent Cellular Cytotoxicity Against Breast Cancer Cells Independently of HER2/neu Expression Status," *Journal of Immunology* 193(8):4261-72.

Romee et al. (2013) "NK cell CD16 surface expression and function is regulated by a disintegrin and metalloprotease-17 (ADAM17)," *Blood* 121(18):3599-608.

Rothe et al. (2013) "The Bispecific Immunoligand ULBP2-aCEA Redirects Natural Killer Cells to Tumor Cells and Reveals Potent Anti-Tumor Activity Against Colon Carcinoma," *Int. J. Cancer* 134(12):2829-2840.

Schuster et al. (2015) "Immunotherapy with the trifunctional anti-CD20 x anti-CD3 antibody FBTA05 (Lymphomun) in paediatric high-risk patients with recurrent CD20-positive B cell malignancies," *British Journal of Haematology* 169(1):90-102.

Smits et al. (2016) "Designing multivalent proteins based on natural killer cell receptors and their ligands as immunotherapy for cancer," *Expert Opinion on Biological Therapy* 16(9):1105-1112.

Spear et al. (2013) "NKG2D ligands as therapeutic targets," *Cancer Immunology* 13:8.

Steigerwald et al. (2009) "Human IgG1 antibodies antagonizing activating receptor NKG2D on natural killer cells," *mAbs* 1(2):115-127.

Steinbacher et al. (2015) "An Fc-optimized NKG2D-immunoglobulin G fusion protein for induction of natural killer cell reactivity against leukemia," *International Journal of Cancer* 136(5):1073-1084.

Strong (2002) "Asymmetric ligand recognition by the activating natural killer cell receptor NKG2D, a symmetric homodimer," *Molecular Immunology* 38(14):1029-1037.

Tay et al. (2016) "TriKEs and BiKEs join CARs on the cancer immunotherapy highway," *Human Vaccines & Immunotherapeutics* 12(11):2790-2796.

Vaks et al. (2018) "Design Principles for Bispecific IgGs, Opportunities and Pitfalls of Artificial Disulfide Bonds," *Antibodies* 7(27):1-28.

Von Strandmann et al. (2006) "A novel bispecific protein (ULBP2-BB4) targeting the NKG2D receptor on natural killer (NK) cells and CD138 activates NK cells and has potent antitumor activity against human multiple myeloma in vitro and in vivo," *Blood* 107(5):1955-1962.

Vyas et al. (2016) "Mono- and dual-targeting triplebodies activate natural killer cells and have anti-tumor activity in vitro and in vivo against chronic lymphocytic leukemia," Oncoimmunology 5(9):p. e1211220.

Wang et al. (2016) "A bispecific protein rG7S-MICA recruits natural killer cells and enhances NKG2D-mediated immunosurveillance against hepatocellular carcinoma," *Cancer Letters* 372(2):166-178.

Weiss-Steider et al. (2011) "Expression of MICA, MICB and NKG2D in human leukemic myelomonocytic and cervical cancer cells," *Journal of Experimental & Clinical Cancer Research* 30(1):37.

Written Opinion for International Application No. PCT/US2019/045561 dated Nov. 8, 2019.

Xu et al. (2019) "A VEGFR2-MICA bispecific antibody activates tumor-infiltrating lymphocytes and exhibits potent anti-tumor efficacy in mice," *Cancer Immunology Immunotherapy* 68(9):1429-1441.

Yeap et al. (2016) "CD16 is indispensable for antibody dependent cellular cytotoxicity by human monocytes," *Scientific Reports* 6:34310.

Young et al. (1995) "Thermal stabilization of a single-chain Fv antibody fragment by introduction of a disulphide bond," *FEBS Letters* 377(2):135-139.

Absolute Antibody, 2023, Anti-NKG2D [ADI-27749 (A49)] Standard Size Ab03079-3.0, 1 page.

Bryceson et al. (2006) "Activation, coactivation, and costimulation of resting human natural killer cells Immunological Reviews," 214:73-91.

Chen et al. (2017) "Targeting FLT3 by Chimeric Antigen Receptor T Cells for the Treatment of Acute Myeloid Leukemia," Leukemia 31(8):1830-1834.

Davis et al. (2017) "Natural killer cells unleashed: Checkpoint receptor blockade and BIKE/TriKE utilization in NK-mediated anti-tumor immunotherapy," Seminars in Immunology 31:64-75.

Epling-Burnette et al. (2004) "Dysregulated NK receptor expression in patients with lymphoproliferative disease of granularlymphocytes," Blood 13(9):3431-3439.

Eruslanov et al. (2013) "Expansion of CCR8+ Inflammatory Myeloid Cells in Cancer Patients with Urothelial and Renal Carcinomas," *Clinical Cancer Research* 19(7):1670-1680.

Liu et al. (2020) "Fc-Engineering for Modulated Effector Functions—Improving Antibodies for Cancer Treatment," Antibodies 9(64):34 pages.

Modi et al. (2022) "Trastuzumab Deruxtecan in Previously Treated HER2-Low Advanced Breast Cancer," N Engl J Med 387(1):9-20.

Nersesian et al.(2020) "N K cell infiltration is associated with improved overall survival in solid cancers: A systematic review and meta-analysis," Translational Oncology 14 (20 pages).

Novus Biologicals, 2015, "CD-16: Find me on macrophages, neutrophils and NK cells," https://www.novusbio.com/antibody-news/antibodies/cd16-find-me-on-macrophages-neutrophils-and-nk-cells.

Plitas et al. (2016) "Regulatory T Cells Exhibit Distinct Features in Human Breast Cancer," *Immunity* 45(5):1122-1134.

Raynaud et al. (2021) "Anti-NKG2D single domain-based antibodies for the modulation of anti-tumor immune response," Oncoimmunology 10(1):e1854529-1-e1854529-14.

Stallard (2016) "New Approach Could Boost Immunotherapy for Breast Cancer," Memorial Sloan Kettering Cancer Center 1-5.

* cited by examiner scFv-Fab format scFv-KiH format

MULTI-SPECIFIC BINDING PROTEINS THAT BIND HER2, NKG2D, AND CD16, AND METHODS OF USE

CROSS-REFERENCE TO RELATED APPLICATIONS

This application is a U.S. national stage application, filed under 35 U.S.C. § 371, of International Application No. PCT/US2019/045561, filed on Aug. 7, 2019, which claims the benefit of and priority to U.S. Provisional Patent Application No. 62/716,259, filed on Aug. 8, 2018, the disclosure of each of which is hereby incorporated by reference in its entirety for all purposes.

SEQUENCE LISTING

The instant application contains a Sequence Listing which has been submitted electronically in ASCII format and is hereby incorporated by reference in its entirety. Said ASCII copy, created on Aug. 26, 2024, is named DFY-057WOUS_ST25.txt and is 208,716 bytes in size.

FIELD OF THE INVENTION

The invention relates to multi-specific binding proteins that bind to NKG2D, CD16, and epidermal growth factor receptor 2 (HER2 or ErbB2). These multi-specific binding proteins are useful for killing human cancer cells expressing Her2 without significant cytotoxicity to non-cancerous healthy human cells expressing HER2.

BACKGROUND

Cancer continues to be a significant health problem despite the substantial research efforts and scientific advances reported in the literature for treating this disease. Some of the most frequently diagnosed cancers include prostate cancer, breast cancer, and lung cancer. Prostate cancer is the most common form of cancer in men. Breast cancer remains a leading cause of death in women. Current treatment options for these cancers are not effective for all patients and/or can have substantial adverse side effects. Other types of cancer also remain challenging to treat using existing therapeutic options.

Cancer immunotherapies are desirable because they are highly specific and can facilitate destruction of cancer cells using the patient's own immune system. Fusion proteins such as bi-specific T-cell engagers are cancer immunotherapies described in the literature that bind to tumor cells and T-cells to facilitate destruction of tumor cells. Antibodies that bind to certain tumor-associated antigens and to certain immune cells have been described in the literature. See, e.g., WO 2016/134371 and WO 2015/095412.

Natural killer (NK) cells are a component of the innate immune system and make up approximately 15% of circulating lymphocytes. NK cells infiltrate virtually all tissues and were originally characterized by their ability to kill tumor cells effectively without the need for prior sensitization. Activated NK cells kill target cells by means similar to cytotoxic T cells—i.e., via cytolytic granules that contain perforin and granzymes as well as via death receptor pathways. Activated NK cells also secrete inflammatory cytokines such as IFN-γ and chemokines that promote the recruitment of other leukocytes to the target tissue.

NK cells respond to signals through a variety of activating and inhibitory receptors on their surface. For example, when NK cells encounter healthy self-cells, their activity is inhibited through activation of the killer-cell immunoglobulin-like receptors (KIRs). Alternatively, when NK cells encounter foreign cells or cancer cells, they are activated via their activating receptors (e.g., NKG2D, NCRs, DNAM1). NK cells are also activated by the constant region of some immunoglobulins through CD16 receptors on their surface. The overall sensitivity of NK cells to activation depends on the sum of stimulatory and inhibitory signals.

HER2 (ErbB2) is a transmembrane glycoprotein, which belongs to the epidermal growth factor receptor family. It is a receptor tyrosine kinase and regulates cell survival, proliferation, and growth. HER2 plays an important role in human malignancies. The ERBB2 gene is amplified or overexpressed in approximately 30% of human breast cancers. Patients with HER2-overexpressing breast cancer have substantially lower overall survival rates and shorter disease-free intervals than patients whose cancer does not overexpress HER2. Moreover, overexpression of HER2 leads to increased breast cancer metastasis. Over-expression of HER2 is also known to occur in many other cancer types, including breast, ovarian, esophageal, bladder and gastric cancer, salivary duct carcinoma, adenocarcinoma of the lung and aggressive forms of uterine cancer, such as uterine serous endometrial carcinoma.

SUMMARY

The invention relates to multi-specific binding proteins that bind to and kill human cancer cells expressing epidermal growth factor receptor 2 (HER2 or ErbB2). The invention provides multi-specific binding proteins that bind to HER2 on a cancer cell and to the NKG2D receptor and CD16 receptor on natural killer cells. Such proteins can engage more than one kind of NK activating receptor, and may block the binding of natural ligands to NKG2D. In certain embodiments, the proteins can agonize NK cells in humans, and in other species such as rodents and cynomolgus monkeys. In certain embodiments, the proteins can stimulate T cells in humans, and in other species such as human, rodents and cynomolgus monkeys. Various aspects and embodiments of the invention are described in further detail below.

In one aspect, the present invention provides a protein (e.g., a multi-specific binding protein) comprising: (a) a first antigen-binding site comprising an Fab fragment that binds NKG2D; (b) a second antigen-binding site comprising a single-chain variable fragment (scFv) that binds HER2; and (c) an antibody Fc domain or a portion thereof sufficient to bind CD16, or a third antigen-binding site that binds CD16.

In certain embodiments, the scFv is linked to the antibody Fc domain or a portion thereof sufficient to bind CD16, or the third antigen-binding site that binds CD16, via a hinge comprising Ala-Ser. In certain embodiments, the scFv is linked to the antibody Fc domain.

In certain embodiments, the scFv comprises a heavy chain variable domain and a light chain variable domain. In certain embodiments, the heavy chain variable domain of the scFv forms a disulfide bridge with the light chain variable domain of the scFv. In certain embodiments, the disulfide bridge is formed between C44 of the heavy chain variable domain and C100 of the light chain variable domain.

In certain embodiments, the light chain variable domain of the scFv is linked to the heavy chain variable domain of the scFv via a flexible linker. In certain embodiments, the flexible linker comprises the amino acid sequence of SEQ ID NO:143. In certain embodiments, the flexible linker consists of the amino acid sequence of SEQ ID NO: 143. In certain embodiments, the light chain variable domain is positioned to the N-terminus or C-terminus to the heavy chain variable domain. In certain embodiments, the light chain variable domain is positioned to the N-terminus of the heavy chain variable domain.

In certain embodiments, the Fab fragment is linked to the antibody Fc domain or a portion thereof sufficient to bind CD16, or the third antigen-binding site that binds CD16.

In certain embodiments, the first antigen-binding site that binds NKG2D comprises a heavy chain variable domain comprising complementarity-determining region 1 (CDR1), complementarity-determining region 2 (CDR2), and complementarity-determining region 3 (CDR3) sequences represented by the amino acid sequences of SEQ ID NOs: 168, 96, and 169, respectively; and a light chain variable domain comprising CDR1, CDR2, and CDR3 sequences represented by the amino acid sequences of SEQ ID NOs: 99, 100, and 101, respectively. In certain embodiments, the first antigen-binding site that binds NKG2D comprises a heavy chain variable domain comprising CDR1, CDR2, and CDR3 sequences represented by the amino acid sequences of SEQ ID NOs: 95, 96, and 97, respectively; and a light chain variable domain comprising CDR1, CDR2, and CDR3 sequences represented by the amino acid sequences of SEQ ID NOs: 99, 100, and 101, respectively.

In certain embodiments, a protein of the present invention comprising a first antigen-binding that binds NKG2D, comprises:

(a) a heavy chain variable domain comprising complementarity-determining region 1 (CDR1), complementarity-determining region 2 (CDR2), and complementarity-determining region 3 (CDR3) sequences represented by the amino acid sequences of SEQ ID NOs: 168, 96, and 169, respectively; and a light chain variable domain comprising CDR1, CDR2, and CDR3 sequences represented by the amino acid sequences of SEQ ID NOs: 99, 100, and 101, respectively;

(b) a heavy chain variable domain comprising CDR1, CDR2, and CDR3 sequences represented by the amino acid sequences of SEQ ID NOs: 168, 96, and 173, respectively; and a light chain variable domain comprising CDR1, CDR2, and CDR3 sequences represented by the amino acid sequences of SEQ ID NOs: 99, 100, and 101, respectively;

(c) a heavy chain variable domain comprising CDR1, CDR2, and CDR3 sequences represented by the amino acid sequences of SEQ ID NOs: 95, 96, and 97, respectively; and a light chain variable domain comprising CDR1, CDR2, and CDR3 sequences represented by the amino acid sequences of SEQ ID NOs: 99, 100, and 101, respectively;

(d) a heavy chain variable domain comprising CDR1, CDR2, and CDR3 sequences represented by the amino acid sequences of SEQ ID NOs: 166, 88, and 167, respectively; and a light chain variable domain comprising CDR1, CDR2, and CDR3 sequences represented by the amino acid sequences of SEQ ID NOs: 91, 92, and 93, respectively;

(e) a heavy chain variable domain comprising CDR1, CDR2, and CDR3 sequences represented by the amino acid sequences of SEQ ID NOs: 162, 72, and 170, respectively; and a light chain variable domain comprising CDR1, CDR2, and CDR3 sequences represented by the amino acid sequences of SEQ ID NOs: 107, 108, and 109, respectively;

(f) a heavy chain variable domain comprising CDR1, CDR2, and CDR3 sequences represented by the amino acid sequences of SEQ ID NOs: 162, 72, and 163, respectively; and a light chain variable domain comprising CDR1, CDR2, and CDR3 sequences represented by the amino acid sequences of SEQ ID NOs: 75, 76, and 77, respectively;

(g) a heavy chain variable domain comprising CDR1, CDR2, and CDR3 sequences represented by the amino acid sequences of SEQ ID NOs: 164, 80, and 165, respectively; and a light chain variable domain comprising CDR1, CDR2, and CDR3 sequences represented by the amino acid sequences of SEQ ID NOs: 75, 76, and 85, respectively;

(h) a heavy chain variable domain comprising CDR1, CDR2, and CDR3 sequences represented by the amino acid sequences of SEQ ID NOs: 168, 96, and 176, respectively; and a light chain variable domain comprising CDR1, CDR2, and CDR3 sequences represented by the amino acid sequences of SEQ ID NOs: 99, 100, and 101, respectively;

(i) a heavy chain variable domain comprising CDR1, CDR2, and CDR3 sequences represented by the amino acid sequences of SEQ ID NOs: 168, 96, and 179, respectively; and a light chain variable domain comprising CDR1, CDR2, and CDR3 sequences represented by the amino acid sequences of SEQ ID NOs: 99, 100, and 101, respectively;

(j) a heavy chain variable domain comprising CDR1, CDR2, and CDR3 sequences represented by the amino acid sequences of SEQ ID NOs: 168, 96, and 182, respectively; and a light chain variable domain comprising CDR1, CDR2, and CDR3 sequences represented by the amino acid sequences of SEQ ID NOs: 99, 100, and 101, respectively;

(k) a heavy chain variable domain comprising CDR1, CDR2, and CDR3 sequences represented by the amino acid sequences of SEQ ID NOs: 168, 96, and 185, respectively; and a light chain variable domain comprising CDR1, CDR2, and CDR3 sequences represented by the amino acid sequences of SEQ ID NOs: 99, 100, and 101, respectively; or (1) a heavy chain variable domain comprising CDR1, CDR2, and CDR3 sequences represented by the amino acid sequences of SEQ ID NOs: 168, 96, and 188, respectively; and a light chain variable domain comprising CDR1, CDR2, and CDR3 sequences represented by the amino acid sequences of SEQ ID NOs: 99, 100, and 101, respectively; and a second antigen-binding site comprising an scFv that binds HER2, comprises: (a) a heavy chain variable domain comprising CDR1, CDR2, and CDR3 sequences represented by the amino acid sequences of SEQ ID NOs: 115, 116, and 117, respectively, and a light chain variable domain comprising CDR1, CDR2, and CDR3 sequences represented by the amino acid sequences of SEQ ID NOs: 119, 120, and 121, respectively;

(b) a heavy chain variable domain comprising CDR1, CDR2, and CDR3 sequences represented by the amino acid sequences of SEQ ID NOs: 123, 124, and 125, respectively, and a light chain variable domain comprising CDR1, CDR2, and CDR3 sequences represented by the amino acid sequences of SEQ ID NOs: 127, 128, and 129, respectively; or (c) a heavy chain variable domain comprising CDR1, CDR2, and CDR3 sequences represented by the amino acid sequences of SEQ ID NOs: 131, 132, and 133, respectively, and a light chain variable domain comprising CDR1, CDR2, and CDR3 sequences represented by the amino acid sequences of SEQ ID NOs: 135, 136, and 137, respectively.

In some embodiments, the first antigen-binding site comprises a heavy chain variable domain related to SEQ ID NO:94 and a light chain variable domain related to SEQ ID NO: 98. For example, the heavy chain variable domain of the first antigen-binding site can be at least 90% (e.g., 90%, 91%, 92%, 93%, 94%, 95%, 96%, 97%, 98%, 99%, or 100%) identical to SEQ ID NO:94, and/or incorporate amino acid sequences identical to the CDR1 (SEQ ID NO:95 or 168), CDR2 (SEQ ID NO:96), and CDR3 (SEQ ID NO:97 or 169) sequences of SEQ ID NO:94. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:98, and/or incorporate amino acid sequences identical to the CDR1 (SEQ ID NO:99), CDR2 (SEQ ID NO:100), and CDR3 (SEQ ID NO: 101) sequences of SEQ ID NO:98.

In some embodiments, the first antigen-binding site comprises a heavy chain variable domain related to SEQ ID NO:144 and a light chain variable domain related to SEQ ID NO: 98. For example, the heavy chain variable domain of the first antigen-binding site can be at least 90% (e.g., 90%, 91%, 92%, 93%, 94%, 95%, 96%, 97%, 98%, 99%, or 100%) identical to SEQ ID NO: 144, and/or incorporate amino acid sequences identical to the CDR1 (SEQ ID NO:95 or 168), CDR2 (SEQ ID NO:96), and CDR3 (SEQ ID NO:172 or 173) sequences of SEQ ID NO: 144. Similarly, the light chain variable domain of the second identical to the CDR1 (SEQ ID NO:99), CDR2 (SEQ ID NO: 100), and CDR3 (SEQ ID NO: 101) sequences of SEQ ID NO:98.

In some embodiments, the first antigen-binding site comprises a heavy chain variable domain related to SEQ ID NO:174 and a light chain variable domain related to SEQ ID NO: 98. For example, the heavy chain variable domain of the first antigen-binding site can be at least 90% (e.g., 90%, 91%, 92%, 93%, 94%, 95%, 96%, 97%, 98%, 99%, or 100%) identical to SEQ ID NO: 174, and/or incorporate amino acid sequences identical to the CDR1 (SEQ ID NO:95 or 168), CDR2 (SEQ ID NO:96), and CDR3 (SEQ ID NO:175 or 176) sequences of SEQ ID NO: 174. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:98, and/or incorporate amino acid sequences identical to the CDR1 (SEQ ID NO:99), CDR2 (SEQ ID NO:100), and CDR3 (SEQ ID NO: 101) sequences of SEQ ID NO:98.

In some embodiments, the first antigen-binding site comprises a heavy chain variable domain related to SEQ ID NO:177 and a light chain variable domain related to SEQ ID NO: 98. For example, the heavy chain variable domain of the first antigen-binding site can be at least 90% (e.g., 90%, 91%, 92%, 93%, 94%, 95%, 96%, 97%, 98%, 99%, or 100%) identical to SEQ ID NO: 177, and/or incorporate amino acid sequences identical to the CDR1 (SEQ ID NO:95 or 168), CDR2 (SEQ ID NO:96), and CDR3 (SEQ ID NO:178 or 179) sequences of SEQ ID NO: 177. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:98, and/or incorporate amino acid sequences identical to the CDR1 (SEQ ID NO:99), CDR2 (SEQ ID NO:100), and CDR3 (SEQ ID NO: 101) sequences of SEQ ID NO:98.

In some embodiments, the first antigen-binding site comprises a heavy chain variable domain related to SEQ ID NO:180 and a light chain variable domain related to SEQ ID NO: 98. For example, the heavy chain variable domain of the first antigen-binding site can be at least 90% (e.g., 90%, 91%, 92%, 93%, 94%, 95%, 96%, 97%, 98%, 99%, or 100%) identical to SEQ ID NO: 180, and/or incorporate amino acid sequences identical to the CDR1 (SEQ ID NO:95 or 168), CDR2 (SEQ ID NO:96), and CDR3 (SEQ ID NO:181 or 182) sequences of SEQ ID NO: 180. Similarly, the light chain variable domain of the second identical to the CDR1 (SEQ ID NO:99), CDR2 (SEQ ID NO: 100), and CDR3 (SEQ ID NO: 101) sequences of SEQ ID NO:98.

In some embodiments, the first antigen-binding site comprises a heavy chain variable domain related to SEQ ID NO:183 and a light chain variable domain related to SEQ ID NO: 98. For example, the heavy chain variable domain of the first antigen-binding site can be at least 90% (e.g., 90%, 91%, 92%, 93%, 94%, 95%, 96%, 97%, 98%, 99%, or 100%) identical to SEQ ID NO: 183, and/or incorporate amino acid sequences identical to the CDR1 (SEQ ID NO:95 or 168), CDR2 (SEQ ID NO:96), and CDR3 (SEQ ID NO:184 or 185) sequences of SEQ ID NO: 183. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:98, and/or incorporate amino acid sequences identical to the CDR1 (SEQ ID NO:99), CDR2 (SEQ ID NO:100), and CDR3 (SEQ ID NO: 101) sequences of SEQ ID NO:98.

In some embodiments, the first antigen-binding site comprises a heavy chain variable domain related to SEQ ID NO:186 and a light chain variable domain related to SEQ ID NO: 98. For example, the heavy chain variable domain of the first antigen-binding site can be at least 90% (e.g., 90%, 91%, 92%, 93%, 94%, 95%, 96%, 97%, 98%, 99%, or 100%) identical to SEQ ID NO: 186, and/or incorporate amino acid sequences identical to the CDR1 (SEQ ID NO:95 or 168), CDR2 (SEQ ID NO:96), and CDR3 (SEQ ID NO:187 or 188) sequences of SEQ ID NO: 186. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:98, and/or incorporate amino acid sequences identical to the CDR1 (SEQ ID NO:99), CDR2 (SEQ ID NO:100), and CDR3 (SEQ ID NO: 101) sequences of SEQ ID NO:98.

In some embodiments, the first antigen-binding site comprises a heavy chain variable domain related to SEQ ID NO:86 and a light chain variable domain related to SEQ ID NO: 90. For example, the heavy chain variable domain of the first antigen-binding site can be at least 90% (e.g., 90%, 91%, 92%, 93%, 94%, 95%, 96%, 97%, 98%, 99%, or 100%) identical to SEQ ID NO:86, and/or incorporate amino acid sequences identical to the CDR1 (SEQ ID NO:87 or 166), CDR2 (SEQ ID NO:88), and CDR3 (SEQ ID NO:89 or 167) sequences of SEQ ID NO:86. Similarly, the light chain variable domain of the second 98%, 99%, or 100%) identical to SEQ ID NO:90, and/or incorporate amino acid sequences identical to the CDR1 (SEQ ID NO:91), CDR2 (SEQ ID NO:92), and CDR3 (SEQ ID NO: 93) sequences of SEQ ID NO:90.

In some embodiments, the first antigen-binding site comprises a heavy chain variable domain related to SEQ ID NO:

102 and a light chain variable domain related to SEQ ID NO: 106. For example, the heavy chain variable domain of the first antigen-binding site can be at least 90% (e.g., 90%, 91%, 92%, 93%, 94%, 95%, 96%, 97%, 98%, 99%, or 100%) identical to SEQ ID NO: 102, and/or incorporate amino acid sequences identical to the CDR1 (SEQ ID NO:71 or 162), CDR2 (SEQ ID NO:72), and CDR3 (SEQ ID NO:105 or 170) sequences of SEQ ID NO: 102. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:106, and/or incorporate amino acid sequences identical to the CDR1 (SEQ ID NO:107), CDR2 (SEQ ID NO:108), and CDR3 (SEQ ID NO: 109) sequences of SEQ ID NO:106.

In some embodiments, the first antigen-binding site comprises a heavy chain variable domain related to SEQ ID NO:70 and a light chain variable domain related to SEQ ID NO: 74. For example, the heavy chain variable domain of the first antigen-binding site can be at least 90% (e.g., 90%, 91%, 92%, 93%, 94%, 95%, 96%, 97%, 98%, 99%, or 100%) identical to SEQ ID NO:70, and/or incorporate amino acid sequences identical to the CDR1 (SEQ ID NO:71 or 162), CDR2 (SEQ ID NO:72), and CDR3 (SEQ ID NO:73 or 163) sequences of SEQ ID NO:70. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:74, and/or incorporate amino acid sequences identical to the CDR1 (SEQ ID NO:75), CDR2 (SEQ ID NO:76), and CDR3 (SEQ ID NO: 77) sequences of SEQ ID NO:74.

In some embodiments, the first antigen-binding site comprises a heavy chain variable domain related to SEQ ID NO:70 and a light chain variable domain related to SEQ ID NO: 74. For example, the heavy chain variable domain of the first antigen-binding site can be at least 90% (e.g., 90%, 91%, 92%, 93%, 94%, 95%, 96%, 97%, 98%, 99%, or 100%) identical to SEQ ID NO:70, and/or incorporate amino acid sequences identical to the CDR1 (SEQ ID NO:71 or 162), CDR2 (SEQ ID NO:72), and CDR3 (SEQ ID NO:73 or 163) sequences of SEQ ID NO:70. Similarly, the light chain variable domain of the second 98%, 99%, or 100%) identical to SEQ ID NO:74, and/or incorporate amino acid sequences identical to the CDR1 (SEQ ID NO:75), CDR2 (SEQ ID NO:76), and CDR3 (SEQ ID NO: 77) sequences of SEQ ID NO:74.

In some embodiments, the first antigen-binding site comprises a heavy chain variable domain related to SEQ ID NO:78 and a light chain variable domain related to SEQ ID NO: 82. For example, the heavy chain variable domain of the first antigen-binding site can be at least 90% (e.g., 90%, 91%, 92%, 93%, 94%, 95%, 96%, 97%, 98%, 99%, or 100%) identical to SEQ ID NO:78, and/or incorporate amino acid sequences identical to the CDR1 (SEQ ID NO:79 or 164), CDR2 (SEQ ID NO:80), and CDR3 (SEQ ID NO:81 or 165) sequences of SEQ ID NO:78. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:82, and/or incorporate amino acid sequences identical to the CDR1 (SEQ ID NO:75), CDR2 (SEQ ID NO:76), and CDR3 (SEQ ID NO: 77) sequences of SEQ ID NO:82.

In certain embodiments, the first antigen-binding site binds to NKG2D with a $K_D$ of 2 nM to 120 nM, as measured by surface plasmon resonance. In certain embodiments, the protein binds to NKG2D with a $K_D$ of 2 nM to 120 nM, as measured by surface plasmon resonance.

In some embodiments, the second antigen-binding site binding to HER2 comprises a heavy chain variable domain related to SEQ ID NO:195 and a light chain variable domain related to SEQ ID NO:196. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:195, and/or incorporate amino acid sequences identical to the CDR1 (SEQ ID NO:115), CDR2 (SEQ ID NO:116), and CDR3 (SEQ ID NO:117) sequences of SEQ ID NO:195. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO: 196, and/or incorporate amino acid sequences identical to the CDR1 (SEQ ID NO:119), CDR2 (SEQ ID NO:120), and CDR3 (SEQ ID NO: 121) sequences of SEQ ID NO:196. In some embodiments, the second antigen-binding site binding to HER2 comprises an scFv comprising the amino acid sequence of SEQ ID NO:139.

Alternatively, the second antigen-binding site binding to HER2 comprises a heavy chain variable domain related to SEQ ID NO:197 and a light chain variable domain related to SEQ ID NO:198. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:197, and/or incorporate amino acid sequences identical to the CDR1 (SEQ ID NO:123), CDR2 (SEQ ID NO:124), and CDR3 (SEQ ID NO: 125) sequences of SEQ ID NO: 197. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:198, and/or incorporate amino acid sequences identical to the CDR1 (SEQ ID NO:127), CDR2 (SEQ ID NO:128), and CDR3 (SEQ ID NO:129) sequences of SEQ ID NO:198. In some embodiments, the second antigen-binding site binding to HER2 comprises an scFv comprising the amino acid sequence of SEQ ID NO: 189.

Alternatively, the second antigen-binding site binding to HER2 comprises a heavy chain variable domain related to SEQ ID NO:199 and a light chain variable domain related to SEQ ID NO:200. For example, the heavy chain variable domain of the second antigen-binding site can be at least 90% (e.g., 90%, 91%, 92%, 93%, 94%, 95%, 96%, 97%, 98%, 99%, or 100%) identical to SEQ ID NO:199, and/or incorporate amino acid sequences identical to the CDR1 (SEQ ID NO:131), CDR2 (SEQ ID NO:132), and CDR3 (SEQ ID NO: 133) sequences of SEQ ID NO: 199. Similarly, the light chain variable domain of the second antigen-binding site can be at least 90% (e.g., 90%, 91%, 92%, 93%, 94%, 95%, 96%, 97%, 98%, 99%, or 100%) identical to SEQ ID NO:200, and/or incorporate amino acid sequences identical to the CDR1 (SEQ ID NO:135), CDR2 (SEQ ID NO:136), and CDR3 (SEQ ID NO:137) sequences of SEQ ID NO:200. In some embodiments, the second antigen-binding site binding to HER2 comprises an scFv comprising the amino acid sequence of SEQ ID NO: 171.

In certain embodiments, the antibody Fc domain comprises hinge and CH2 domains of a human IgG1 antibody. In certain embodiments, the antibody Fc domain comprises an amino acid sequence at least 90% identical to amino acids 234-332 of a human IgG1 antibody.

In certain embodiments, the antibody Fc domain comprises an Fc domain comprising an amino acid sequence at least 90% identical to the Fc domain of human IgG1 and differs at one or more positions selected from the group consisting of Q347, Y349, T350, L351, S354, E356, E357, K360, Q362, S364, T366, L368, K370, N390, K392, T394, D399, S400, D401, F405, Y407, K409, T411, K439.

In certain embodiments, the antibody Fc domain comprises an Fc domain of a human IgG1 comprising Q347R, D399V, and F405T substitutions, e.g., in an Fc domain linked to an scFv. In certain embodiments, the antibody Fc domain comprises an Fc domain of a human IgG1 comprising K360E and K409W substitutions, e.g., in an Fc domain linked to an Fab fragment.

In certain embodiments, the antibody Fc domain comprises an Fc domain of a human IgG1 comprising a T366W substitution, e.g., in an Fc domain linked to an Fab fragment. In certain embodiments, the antibody Fc domain comprises an Fc domain of a human IgG1 comprising T366S, L368A, and Y407V substitutions, e.g., in an Fc domain linked to an scFv.

In certain embodiments, the protein comprises a sequence of SEQ ID NO:141, SEQ ID NO: 145, SEQ ID NO:147, SEQ ID NO: 194, SEQ ID NO:155, or SEQ ID NO: 148.

In certain embodiments, this sequence represents the heavy chain portion of the Fab fragment linked to the antibody Fc domain.

In certain embodiments, the protein comprises a sequence of SEQ ID NO: 140 or SEQ ID NO:146. In certain embodiments, this sequence represents the scFv linked to the antibody Fc domain.

In another aspect, the instant disclosure provides a protein (e.g., a multi-specific binding protein) comprising: (a) a first polypeptide comprising an amino acid sequence at least 90% (e.g., 90%, 91%, 92%, 93%, 94%, 95%, 96%, 97%, 98%, 99%, or 100%) identical to SEQ ID NO:141; (b) a second polypeptide comprising an amino acid sequence at least 90% (e.g., 90%, 91%, 92%, 93%, 94%, 95%, 96%, 97%, 98%, 99%, or 100%) identical to SEQ ID NO:140, SEQ ID NO: 190, or SEQ ID NO: 192; and (c) a third polypeptide comprising an amino acid sequence at least 90% (e.g., 90%, 91%, 92%, 93%, 94%, 95%, 96%, 97%, 98%, 99%, or 100%) identical to SEQ ID NO:142. In certain embodiments, the second polypeptide comprises an amino acid sequence at least 90% (e.g., 90%, 91%, 92%, 93%, 94%, 95%, 96%, 97%, 98%, 99%, or 100%) identical to SEQ ID NO:140.

In another aspect, the instant disclosure provides a protein (e.g., a multi-specific binding protein) comprising: (a) a first polypeptide comprising an amino acid sequence at least 95% (e.g., 95%, 96%, 97%, 98%, 99%, or 100%) identical to SEQ ID NO: 141; (b) a second polypeptide comprising an amino acid sequence at least 95% (e.g., 95%, 96%, 97%, 98%, 99%, or 100%) identical to SEQ ID NO:140, SEQ ID NO: 190, or SEQ ID NO: 192; and (c) a third polypeptide comprising an amino acid sequence at least 95% (e.g., 95%, 96%, 97%, 98%, 99%, or 100%) identical to SEQ ID NO:142. In certain embodiments, the second polypeptide comprises an amino acid sequence at least 95% (e.g., 95%, 96%, 97%, 98%, 99%, or 100%) identical to SEQ ID NO:140.

In another aspect, the instant disclosure provides a protein (e.g., a multi-specific binding protein) comprising: (a) a first polypeptide comprising the amino acid sequence of SEQ ID NO:141; (b) a second polypeptide comprising the amino acid sequence of SEQ ID NO: 140, SEQ ID NO:190, or SEQ ID NO: 192; and (c) a third polypeptide comprising the amino acid sequence of SEQ ID NO:142. In certain embodiments, the protein comprises (a) a first polypeptide comprising the amino acid sequence of SEQ ID NO: 141; (b) a second polypeptide comprising the amino acid sequence of SEQ ID NO:140; and (c) a third polypeptide comprising the amino acid sequence of SEQ ID NO:142.

In another aspect, the instant disclosure provides a formulation comprising a protein disclosed herein and a pharmaceutically acceptable carrier.

In another aspect, the instant disclosure provides a cell comprising one or more nucleic acids expressing a protein disclosed herein.

In another aspect, the instant disclosure provides a method of directly and/or indirectly enhancing tumor cell death, the method comprising exposing a tumor and natural killer cells to a protein disclosed herein.

In another aspect, the instant disclosure provides a method of treating cancer, wherein the method comprises administering a protein or a formulation disclosed herein to a patient in need thereof. In certain embodiments, the cancer is selected from the group consisting of breast cancer, thyroid cancer, gastric cancer, renal cell carcinoma, adenocarcinoma of the lung, prostate cancer, cholangiocarcinoma, uterine cancer, pancreatic cancer, colorectal cancer, ovarian cancer, cervical cancer, head and neck cancer, lung squamous, mesothelioma, liver cancer, mesothelioma, sarcoma, and gall bladder cancer.

BRIEF DESCRIPTION OF THE DRAWINGS

FIG. 8A shows that HER2-Targeted TriNKETs show minimal binding to NK cells in human blood; FIG. 8B shows that HER2-Targeted TriNKETs show minimal binding to CD8+ T cells; FIG. 8C shows that HER2-Targeted TriNKETs show minimal binding to CD4+ T cells; FIG. 8D shows that HER2-Targeted TriNKETs show minimal binding to B cells; FIG. 8E shows that HER2-Targeted TriNKETs show minimal binding to monocytes; and FIG. 8F shows that HER2-Targeted TriNKETs show minimal binding to granulocytes (Dash-dotted line-secondary control; dashed line-Trastuzumab; Solid line-HER2-F3'-TriNKET-A49).

FIG. 13A shows enhanced killing of SkBr-3 tumor cells in short-term co-cultures by A49-F3'-TriNKET-Trastuzumab. HER2-targeting A49-F3'-TriNKET-Trastuzumab triggered dose-dependent lysis of SkBr-3 target cells by IL-15 stimulated CD8+ T cell. FIG. 13B shows that 67 nM of HER2-targeting TriNKET triggered lysis of SkBr-3 target cells by IL-2 stimulated CD8+ T cell. Dotted line indicates the effect with only CD8+ T cells co-cultured with SkBr-3 tumor cells (untreated).

FIG. 15A shows the level of binding as percentage values of median fluorescence intensity (MFI) relative to the maximum MFI observed with the cells incubated with 670 nM of TriNKET. FIG. 15B shows the level of binding as fold over background (FOB) values of MFI relative to the background MFI observed with the cells incubated with the secondary antibody only.

FIG. 16A shows the level of binding as percentage values of median fluorescence intensity (MFI) relative to the maximum MFI observed with the cells incubated with 670 nM of TriNKET. FIG. 16B shows the level of binding as fold over background (FOB) values of MFI relative to the background MFI observed with the cells incubated with the secondary antibody only.

FIG. 16A shows the level of binding as percentage values of median fluorescence intensity (MFI) relative to the maximum MFI observed with the cells incubated with 670 nM of TriNKET. FIG. 16B shows the level of binding as fold over background (FOB) values of MFI relative to the background MFI observed with the cells incubated with the secondary antibody only.

DETAILED DESCRIPTION

Figure 1:
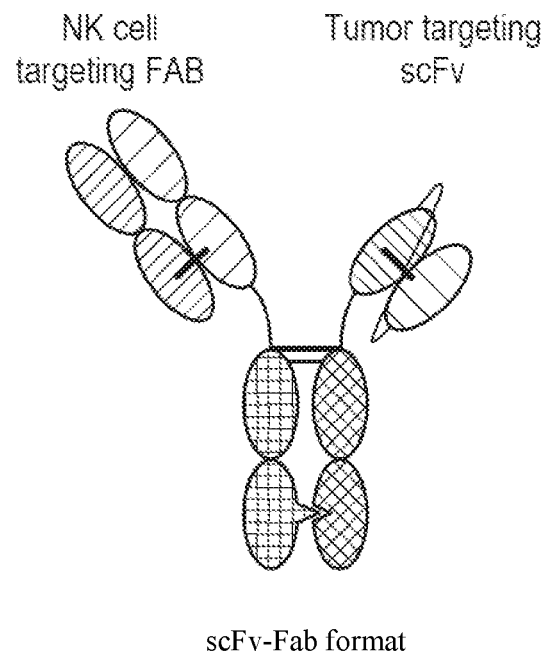
FIG. 1 illustrates a trispecific antibody (TriNKET) that contains an HER2-binding scFv, a NKG2D-targeting Fab, and a heterodimerized antibody constant region/domain ("CD domain") that binds CD16 (scFv-Fab format). In an exemplary embodiment, the Fc domain linked to the Fab fragment comprises mutations of K360E and K409W and the Fc domain linked to the scFv comprises matching mutations Q347R, D399V, and F405T for forming an Fc heterodimer (shown as a triangular lock-and-key format in the Fc domains in FIG. 1). The antibody format is referred herein as F3'-TriNKET. In another exemplary embodiment, the Fc domain linked to the Fab fragment comprises the mutations of Q347R, D399V, and F405T, and the Fc domain linked to the scFv comprises matching mutations K360E and K409W for forming a heterodimer.

The invention provides multi-specific binding proteins that bind HER2 on a cancer cell and the NKG2D receptor and CD16 receptor on natural killer cells, pharmaceutical compositions comprising such multi-specific binding proteins, and therapeutic methods using such multi-specific proteins and pharmaceutical compositions, including for the treatment of cancer. Various aspects of the invention are set forth below in sections; however, aspects of the invention described in one particular section are not to be limited to any particular section.

To facilitate an understanding of the present invention, a number of terms and phrases are defined below.

The terms "a" and "an" as used herein mean "one or more" and include the plural unless the context is inappropriate.

As used herein, the term "antigen-binding site" refers to the part of the immunoglobulin molecule that participates in antigen binding. In human antibodies, the antigen-binding site is formed by amino acid residues of the N-terminal variable ("V") regions of the heavy ("H") and light ("L")

chains. Three highly divergent stretches within the V regions of the heavy and light chains are referred to as "hypervariable regions" which are interposed between more conserved flanking stretches known as "framework regions," or "FR." Thus the term "FR" refers to amino acid sequences which are naturally found between and adjacent to hypervariable regions in immunoglobulins. In a human antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." In certain animals, such as camels and cartilaginous fish, the antigen-binding site is formed by a single antibody chain providing a "single domain antibody." Antigen-binding sites can exist in an intact antibody, in an antigen-binding fragment of an antibody that retains the antigen-binding surface, or in a recombinant polypeptide such as an scFv, using a peptide linker to connect the heavy chain variable domain to the light chain variable domain in a single polypeptide. All the amino acid positions in heavy or light chain variable regions disclosed herein are numbered according to Kabat numbering.

The term "tumor-associated antigen" as used herein means any antigen including but not limited to a protein, glycoprotein, ganglioside, carbohydrate, or lipid that is associated with cancer. Such an antigen can be expressed on malignant cells or in the tumor microenvironment, such as on tumor-associated blood vessels, extracellular matrix, mesenchymal stroma, or immune infiltrates.

The CDRs of an antigen-binding site can be determined by the methods described in Kabat et al., J. Biol. Chem. 252, 6609-6616 (1977) and Kabat et al., Sequences of protein of immunological interest. (1991), Chothia et al., J. Mol. Biol. 196:901-917 (1987), and MacCallum et al., J. Mol. Biol. 262:732-745 (1996). The CDRs determined under these definitions typically include overlapping or subsets of amino acid residues when compared against each other. In certain embodiments, the term "CDR" is a CDR as defined by MacCallum et al., J. Mol. Biol. 262:732-745 (1996) and Martin A., Protein Sequence and Structure Analysis of Antibody Variable Domains, in Antibody Engineering, Kontermann and Dubel, eds., Chapter 31, pp. 422-439, Springer-Verlag, Berlin (2001). In certain embodiments, the term "CDR" is a CDR as defined by Kabat et al., J. Biol. Chem. 252, 6609-6616 (1977) and Kabat et al., Sequences of protein of immunological interest. (1991). In certain embodiments, heavy chain CDRs and light chain CDRs of an antibody are defined using different conventions. For example, in certain embodiments, the heavy chain CDRs are defined according to MacCallum (supra), and the light CDRs are defined according to Kabat (supra). CDRH1, CDRH2 and CDRH3 denote the heavy chain CDRs, and CDRL1, CDRL2 and CDRL3 denote the light chain CDRs.

As used herein, the terms "subject" and "patient" refer to an organism to be treated by the methods and compositions described herein. Such organisms preferably include, but are not limited to, mammals (e.g., murines, simians, equines, bovines, porcines, canines, felines, and the like), and more preferably include humans.

As used herein, the term "effective amount" refers to the amount of a compound (e.g., a compound of the present invention) sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, PA [1975].

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Exemplary acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Exemplary bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Exemplary salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

I. Proteins

The invention provides multi-specific binding proteins that bind HER2 on a cancer cell and the NKG2D receptor and CD16 receptor on natural killer cells to activate the natural killer cell. The multi-specific binding proteins are useful in the pharmaceutical compositions and therapeutic methods described herein. Binding of the multi-specific binding protein to the NKG2D receptor and CD16 receptor on natural killer cell enhances the activity of the natural killer cell toward destruction of a cancer cell. Binding of the multi-specific binding protein to HER2 on a cancer cell brings the cancer cell into proximity with the natural killer cell, which facilitates direct and indirect destruction of the cancer cell by the natural killer cell. Further description of exemplary multi-specific binding proteins is provided below.

The first component of the multi-specific binding proteins binds to NKG2D receptor-expressing cells, which can include but are not limited to NK cells, NKT cells, γδ T cells and $CD8^+\alpha\beta$ T cells. Upon NKG2D binding, the multi-specific binding proteins may block natural ligands, such as ULBP6 and MICA, from binding to NKG2D and activating NK cells.

The second component of the multi-specific binding proteins binds to HER2-expressing cells, which can include but are limited to breast, ovarian, esophageal, bladder and gastric cancer, salivary duct carcinoma, adenocarcinoma of the lung and aggressive forms of uterine cancer, such as uterine serous endometrial carcinoma.

The third component for the multi-specific binding proteins binds to cells expressing CD16, an Fc receptor on the surface of leukocytes including natural killer cells, macrophages, neutrophils, eosinophils, mast cells, and follicular dendritic cells.

The multi-specific binding proteins described herein can take various formats. For example, one format involves a heterodimeric, multi-specific antibody including a first immunoglobulin heavy chain, a second immunoglobulin heavy chain and an immunoglobulin light chain (FIG. 1). The first immunoglobulin heavy chain includes a first Fc (hinge-CH2-CH3) domain fused via either a linker or an antibody hinge to an Fab fragment composed of a heavy chain portion comprising a heavy chain variable domain and a heavy chain CH1 domain, and a light chain portion comprising a light chain variable domain and a light chain constant domain (CL), wherein the heavy chain and light chain portions of the Fab fragment pair and bind NKG2D. The second immunoglobulin heavy chain includes a second Fc (hinge-CH2-CH3) domain fused via either a linker or an antibody hinge to a single-chain variable fragment (scFv) composed of a heavy chain variable domain and light chain variable domain which pair and bind the HER2 antigen.

In some embodiments, the single-chain variable fragment (scFv) described above is linked to the antibody constant domain via a hinge sequence. In some embodiments, the hinge comprises amino acids Ala-Ser. In some other embodiments, the hinge comprises amino acids Ala-Ser and Thr-Lys-Gly. The hinge sequence can provide flexibility of binding to the target antigen, and balance between flexibility and optimal geometry.

In some embodiments, the single-chain variable fragment (scFv) described above includes a heavy chain variable domain and a light chain variable domain. In some embodiments, the heavy chain variable domain forms a disulfide bridge with the light chain variable domain to enhance stability of the scFv. For example, a disulfide bridge can be formed between the C44 residue of the heavy chain variable domain and the C100 residue of the light chain variable domain, the amino acid positions numbered under Kabat. In some embodiments, the heavy chain variable domain is linked to the light chain variable domain via a flexible linker. Any suitable linker can be used, for example, the $(G_4S)_4$ linker (SEQ ID NO: 143). In some embodiments of the scFv, the heavy chain variable domain is positioned at the N-terminus of the light chain variable domain. In some embodiments of the scFv, the heavy chain variable domain is positioned at the C terminus of the light chain variable domain.

Figure 2:
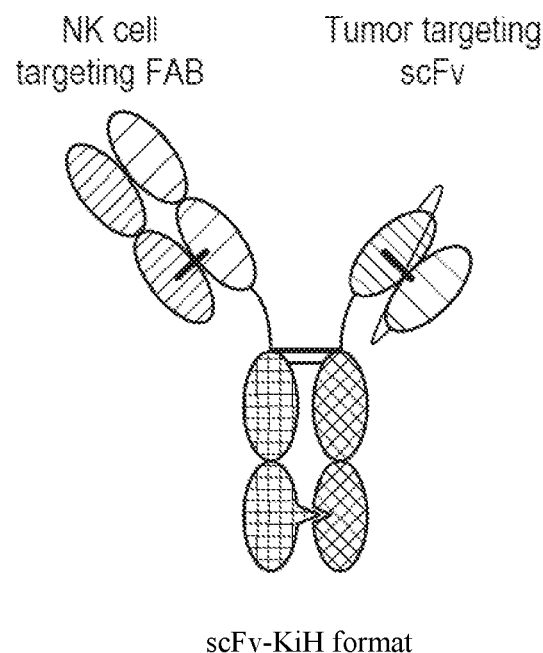
FIG. 2 is a representation of a "knob-in-hole" (KiH) TriNKET, which includes an scFv that binds HER2 linked to an Fc domain via a hinge comprising Ala-Ser, and an NKG2D-binding Fab fragment including (a) a heavy chain portion comprising a heavy chain variable domain and a CH1 domain connected to an Fc domain, and (b) a light chain portion comprising a light chain variable domain and a CL domain. In an exemplary embodiment, the Fc domain linked to the Fab fragment comprises a knob mutation T366W, and the Fc domain linked to the scFv comprises matching "hole" mutations T366S, L368A, Y407V (shown as a triangular lock-and-key format in the Fc domains in FIG. 2). In an exemplary embodiment, the Fc domain linked to the Fab fragment comprises knob mutations T366S, L368A, Y407V, and the Fc domain linked to the scFv comprises a "hole" mutation T366W.

The multi-specific binding proteins described herein can further include one or more additional antigen-binding sites. The additional antigen-binding site(s) may be fused to the C-terminus of the constant region CH2 domain or to the C-terminus of the constant region CH3 domain, optionally via a linker sequence. In certain embodiments, the additional antigen-binding site(s) takes the form of a single-chain variable region (scFv) that is optionally disulfide-stabilized, resulting in a tetravalent or trivalent multi-specific binding protein. For example, a multi-specific binding protein includes an NKG2D-binding site, a HER2-binding site, a third antigen-binding site that binds a tumor-associated antigen, and an antibody constant region or a portion thereof sufficient to bind CD16, or a fourth antigen-binding site that binds CD16. Any one of these antigen-binding sites can either take the form of an Fab or an scFv, such as the scFv described above. In some embodiments, the third antigen-binding site binds a different tumor-associated antigen from HER2. In some embodiments, the third antigen-binding site binds to the same tumor-associated antigen HER2, and the exemplary formats are shown in FIGS. 2C and 2D. Accordingly, the multi-specific binding proteins can provide bivalent engagement of HER2. Bivalent engagement of HER2 by the multi-specific proteins can stabilize the HER2 on cancer cell surface, and enhance cytotoxicity of NK cells towards the cancer cells. Bivalent engagement of HER2 by the multi-specific proteins can confer stronger binding of the multi-specific proteins to the cancer cells, thereby facilitating stronger cytotoxic response of NK cells towards the cancer cells, especially towards cancer cells expressing a low level of HER2.

Within the Fc domain, CD16 binding is mediated by the hinge region and the CH2 domain. For example, within human IgG1, the interaction with CD16 is primarily focused on amino acid residues Asp 265-Glu 269, Asn 297-Thr 299, Ala 327-Ile 332, Leu 234-Ser 239, and carbohydrate residue N-acetyl-D-glucosamine in the CH2 domain (see, Sondermann et al., Nature, 406 (6793): 267-273). Based on the known domains, mutations can be selected to enhance or reduce the binding affinity to CD16, such as by using phage-displayed libraries or yeast surface-displayed cDNA libraries, or can be designed based on the known three-dimensional structure of the interaction.

In some embodiments, the antibody constant domain comprises a CH2 domain and a CH3 domain of an IgG antibody, for example, a human IgG1 antibody. In some embodiments, mutations are introduced in the antibody constant domain to enable heterodimerization with another antibody constant domain. For example, if the antibody constant domain is derived from the constant domain of a human IgG1, the antibody constant domain can comprise an amino acid sequence at least 90% identical to amino acids 234-332 of a human IgG1 antibody, and differs at one or more positions selected from the group consisting of Q347, Y349, L351, S354, E356, E357, K360, Q362, S364, T366, L368, K370, N390, K392, T394, D399, S400, D401, F405, Y407, K409, T411, and K439. All the amino acid positions in an Fc domain or hinge region disclosed herein are numbered according to EU numbering.

In some embodiments, the antibody constant domain can comprise an amino acid sequence at least 90% identical to amino acids 234-332 of a human IgG1 antibody, and differs by one or more substitutions selected from the group consisting of Q347E, Q347R, Y349S, Y349K, Y349T, Y349D, Y349E, Y349C, L351K, L351D, L351Y, S354C, E356K, E357Q, E357L, E357W, K360E, K360W, Q362E, S364K, S364E, S364H, S364D, T366V, T366I, T366L, T366M, T366K, T366W, T366S, L368E, L368A, L368D, K370S, N390D, N390E, K392L, K392M, K392V, K392F, K392D, K392E, T394F, D399R, D399K, D399V, S400K, S400R, D401K, F405A, F405T, Y407A, Y407I, Y407V, K409F, K409W, K409D, T411D, T411E, K439D, and K439E.

Individual components of the multi-specific binding proteins are described in more detail below.

NKG2D-Binding Site

Upon binding to the NKG2D receptor and CD16 receptor on natural killer cells, and a tumor-associated antigen on cancer cells, the multi-specific binding proteins can engage more than one kind of NK-activating receptor, and may block the binding of natural ligands to NKG2D. In certain embodiments, the proteins can agonize NK cells in humans. In some embodiments, the proteins can agonize NK cells in humans and in other species such as rodents and cynomolgus monkeys.

Table 1 lists peptide sequences of heavy chain variable domains and light chain variable domains that, in combination, can bind to NKG2D. In some embodiments, the heavy chain variable domain and the light chain variable domain are arranged in Fab format. In some embodiments, the heavy chain variable domain and the light chain variable domain are fused together to from an scFv.

The NKG2D binding domains listed in Table 1 can vary in their binding affinity to NKG2D, nevertheless, they all activate human NK cells.

Unless indicated otherwise, the CDR sequences provided in Table 1 are determined under Kabat.

TABLE 1

| Clones | Heavy chain variable region amino acid sequence | Light chain variable region amino acid sequence |
|---|---|---|
| ADI-27705 | QVQLQQWGAGLLKPSETLSLTCA VYGGSFSGYYWSWIRQPPGKGLE WIGEIDHSGSTNYNPSLKSRVTISV DTSKNQFSLKLSSVTAADTAVYYC ARARGPWSFDPWGQGTLVTVSS (SEQ ID NO: 1) CDR1 (SEQ ID NO: 3) - GSFSGYYWS CDR2 (SEQ ID NO: 4) - EIDHSGSTNYNPSLKS CDR3 (SEQ ID NO: 5) - ARARGPWSFDP | DIQMTQSPSTLSASVGDRVTI TCRASQSISSWLAWYQQKPG KAPKLLIYKASSLESGVPSRF SGSGSGTEFTLTISSLQPDDFA TYYCQQYNSYPITFGGGTKV EIK (SEQ ID NO: 2) |
| ADI-27724 | QVQLQQWGAGLLKPSETLSLTCA VYGGSFSGYYWSWIRQPPGKGLE WIGEIDHSGSTNYNPSLKSRVTISV DTSKNQFSLKLSSVTAADTAVYYC ARARGPWSFDPWGQGTLVTVSS (SEQ ID NO: 6) | EIVLTQSPGTLSLSPGERATLS CRASQSVSSSYLAWYQQKPG QAPRLLIYGASSRATGIPDRES GSGSGTDFTLTISRLEPEDFA VYYCQQYGSSPITFGGGTKV EIK (SEQ ID NO: 7) |
| ADI-27740 (A40) | QVQLQQWGAGLLKPSETLSLTCA VYGGSFSGYYWSWIRQPPGKGLE WIGEIDHSGSTNYNPSLKSRVTISV DTSKNQFSLKLSSVTAADTAVYYC ARARGPWSFDPWGQGTLVTVSS (SEQ ID NO: 8) | DIQMTQSPSTLSASVGDRVTI TCRASQSIGSWLAWYQQKPG KAPKLLIYKASSLESGVPSRF SGSGSGTEFTLTISSLQPDDFA TYYCQQYHSFYTFGGGTKVE IK (SEQ ID NO: 9) |
| ADI-27741 | QVQLQQWGAGLLKPSETLSLTCA VYGGSFSGYYWSWIRQPPGKGLE WIGEIDHSGSTNYNPSLKSRVTISV DTSKNQFSLKLSSVTAADTAVYYC ARARGPWSFDPWGQGTLVTVSS (SEQ ID NO: 10) | DIQMTQSPSTLSASVGDRVTI TCRASQSIGSWLAWYQQKPG KAPKLLIYKASSLESGVPSRF SGSGSGTEFTLTISSLQPDDFA TYYCQQSNSYYTFGGGTKVE IK (SEQ ID NO: 11) |
| ADI-27743 | QVQLQQWGAGLLKPSETLSLTCA VYGGSFSGYYWSWIRQPPGKGLE WIGEIDHSGSTNYNPSLKSRVTISV DTSKNQFSLKLSSVTAADTAVYYC ARARGPWSFDPWGQGTLVTVSS (SEQ ID NO: 12) | DIQMTQSPSTLSASVGDRVTI TCRASQSISSWLAWYQQKPG KAPKLLIYKASSLESGVPSRF SGSGSGTEFTLTISSLQPDDFA TYYCQQYNSYPTFGGGTKVE IK (SEQ ID NO: 13) |

TABLE 1-continued

| Clones | Heavy chain variable region amino acid sequence | Light chain variable region amino acid sequence |
|---|---|---|
| ADI-28153 | QVQLQQWGAGLLKPSETLSLTCA VYGGSFSGYYWSWIRQPPGKGLE WIGEIDHSGSTNYNPSLKSRVTISV DTSKNQFSLKLSSVTAADTAVYYC ARARGPWGFDPWGQGTLVTVSS (SEQ ID NO: 14) | ELQMTQSPSSLSASVGDRVTI TCRTSQSISSYLNWYQQKPG QPPKLLIYWASTRESGVPDRF SGSGSGTDFTLTISSLQPEDSA TYYCQQSYDIPYTFGQGTKL EIK (SEQ ID NO: 15) |
| ADI-28226 (C26) | QVQLQQWGAGLLKPSETLSLTCA VYGGSFSGYYWSWIRQPPGKGLE WIGEIDHSGSTNYNPSLKSRVTISV DTSKNQFSLKLSSVTAADTAVYYC ARARGPWSFDPWGQGTLVTVSS (SEQ ID NO: 16) | DIQMTQSPSTLSASVGDRVTI TCRASQSISSWLAWYQQKPG KAPKLLIYKASSLESGVPSRF SGSGSGTEFTLTISSLQPDDFA TYYCQQYGSFPITFGGGTKVE IK (SEQ ID NO: 17) |
| ADI-28154 | QVQLQQWGAGLLKPSETLSLTCA VYGGSFSGYYWSWIRQPPGKGLE WIGEIDHSGSTNYNPSLKSRVTISV DTSKNQFSLKLSSVTAADTAVYYC ARARGPWSFDPWGQGTLVTVSS (SEQ ID NO: 18) | DIQMTQSPSTLSASVGDRVTI TCRASQSISSWLAWYQQKPG KAPKLLIYKASSLESGVPSRF SGSGSGTDFTLTISSLQPDDFA TYYCQQSKEVPWTFGQGTK VEIK (SEQ ID NO: 19) |
| ADI-29399 | QVQLQQWGAGLLKPSETLSLTCA VYGGSFSGYYWSWIRQPPGKGLE WIGEIDHSGSTNYNPSLKSRVTISV DTSKNQFSLKLSSVTAADTAVYYC ARARGPWSFDPWGQGTLVTVSS (SEQ ID NO: 20) | DIQMTQSPSTLSASVGDRVTI TCRASQSISSWLAWYQQKPG KAPKLLIYKASSLESGVPSRF SGSGSGTEFTLTISSLQPDDFA TYYCQQYNSFPTFGGGTKVEI K (SEQ ID NO: 21) |
| ADI-29401 | QVQLQQWGAGLLKPSETLSLTCA VYGGSFSGYYWSWIRQPPGKGLE WIGEIDHSGSTNYNPSLKSRVTISV DTSKNQFSLKLSSVTAADTAVYYC ARARGPWSFDPWGQGTLVTVSS (SEQ ID NO: 22) | DIQMTQSPSTLSASVGDRVTI TCRASQSIGSWLAWYQQKPG KAPKLLIYKASSLESGVPSRF SGSGSGTEFTLTISSLQPDDFA TYYCQQYDIYPTFGGGTKVEI K (SEQ ID NO: 23) |
| ADI-29403 | QVQLQQWGAGLLKPSETLSLTCA VYGGSFSGYYWSWIRQPPGKGLE WIGEIDHSGSTNYNPSLKSRVTISV DTSKNQFSLKLSSVTAADTAVYYC ARARGPWSFDPWGQGTLVTVSS (SEQ ID NO: 24) | DIQMTQSPSTLSASVGDRVTI TCRASQSISSWLAWYQQKPG KAPKLLIYKASSLESGVPSRF SGSGSGTEFTLTISSLQPDDFA TYYCQQYDSYPTFGGGTKVE IK (SEQ ID NO: 25) |
| ADI-29405 | QVQLQQWGAGLLKPSETLSLTCA VYGGSFSGYYWSWIRQPPGKGLE WIGEIDHSGSTNYNPSLKSRVTISV DTSKNQFSLKLSSVTAADTAVYYC ARARGPWSFDPWGQGTLVTVSS (SEQ ID NO: 26) | DIQMTQSPSTLSASVGDRVTI TCRASQSISSWLAWYQQKPG KAPKLLIYKASSLESGVPSRF SGSGSGTEFTLTISSLQPDDFA TYYCQQYGSFPTFGGGTKVEI K (SEQ ID NO: 27) |
| ADI-29407 | QVQLQQWGAGLLKPSETLSLTCA VYGGSFSGYYWSWIRQPPGKGLE WIGEIDHSGSTNYNPSLKSRVTISV DTSKNQFSLKLSSVTAADTAVYYC ARARGPWSFDPWGQGTLVTVSS (SEQ ID NO: 28) | DIQMTQSPSTLSASVGDRVTI TCRASQSISSWLAWYQQKPG KAPKLLIYKASSLESGVPSRF SGSGSGTEFTLTISSLQPDDFA TYYCQQYQSFPTFGGGTKVEI K (SEQ ID NO: 29) |
| ADI-29419 | QVQLQQWGAGLLKPSETLSLTCA VYGGSFSGYYWSWIRQPPGKGLE WIGEIDHSGSTNYNPSLKSRVTISV DTSKNQFSLKLSSVTAADTAVYYC ARARGPWSFDPWGQGTLVTVSS (SEQ ID NO: 30) | DIQMTQSPSTLSASVGDRVTI TCRASQSISSWLAWYQQKPG KAPKLLIYKASSLESGVPSRF SGSGSGTEFTLTISSLQPDDFA TYYCQQYSSFSTFGGGTKVEI K (SEQ ID NO: 31) |
| ADI-29421 | QVQLQQWGAGLLKPSETLSLTCA VYGGSFSGYYWSWIRQPPGKGLE WIGEIDHSGSTNYNPSLKSRVTISV DTSKNQFSLKLSSVTAADTAVYYC | DIQMTQSPSTLSASVGDRVTI TCRASQSISSWLAWYQQKPG KAPKLLIYKASSLESGVPSRF SGSGSGTEFTLTISSLQPDDFA |

TABLE 1-continued

| Clones | Heavy chain variable region amino acid sequence | Light chain variable region amino acid sequence |
|---|---|---|
| | ARARGPWSFDPWGQGTLVTVSS (SEQ ID NO: 32) | TYYCQQYESYSTFGGGTKVEIK (SEQ ID NO: 33) |
| ADI-29424 | QVQLQQWGAGLLKPSETLSLTCAVYGGSFSGYYWSWIRQPPGKGLEWIGEIDHSGSTNYNPSLKSRVTISVDTSKNQFSLKLSSVTAADTAVYYCARARGPWSFDPWGQGTLVTVSS (SEQ ID NO: 34) | DIQMTQSPSTLSASVGDRVTITCRASQSISSWLAWYQQKPGKAPKLLIYKASSLESGVPSRFSGSGSGTEFTLTISSLQPDDFATYYCQQYDSFITFGGGTKVEIK (SEQ ID NO: 35) |
| ADI-29425 | QVQLQQWGAGLLKPSETLSLTCAVYGGSFSGYYWSWIRQPPGKGLEWIGEIDHSGSTNYNPSLKSRVTISVDTSKNQFSLKLSSVTAADTAVYYCARARGPWSFDPWGQGTLVTVSS (SEQ ID NO: 36) | DIQMTQSPSTLSASVGDRVTITCRASQSISSWLAWYQQKPGKAPKLLIYKASSLESGVPSRFSGSGSGTEFTLTISSLQPDDFATYYCQQYQSYPTFGGGTKVEIK (SEQ ID NO: 37) |
| ADI-29426 | QVQLQQWGAGLLKPSETLSLTCAVYGGSFSGYYWSWIRQPPGKGLEWIGEIDHSGSTNYNPSLKSRVTISVDTSKNQFSLKLSSVTAADTAVYYCARARGPWSFDPWGQGTLVTVSS (SEQ ID NO: 38) | DIQMTQSPSTLSASVGDRVTITCRASQSIGSWLAWYQQKPGKAPKLLIYKASSLESGVPSRFSGSGSGTEFTLTISSLQPDDFATYYCQQYHSFPTFGGGTKVEIK (SEQ ID NO: 39) |
| ADI-29429 | QVQLQQWGAGLLKPSETLSLTCAVYGGSFSGYYWSWIRQPPGKGLEWIGEIDHSGSTNYNPSLKSRVTISVDTSKNQFSLKLSSVTAADTAVYYCARARGPWSFDPWGQGTLVTVSS (SEQ ID NO: 40) | DIQMTQSPSTLSASVGDRVTITCRASQSIGSWLAWYQQKPGKAPKLLIYKASSLESGVPSRFSGSGSGTEFTLTISSLQPDDFATYYCQQYELYSYTFGGGTKVEIK (SEQ ID NO: 41) |
| ADI-29447 (F47) | QVQLQQWGAGLLKPSETLSLTCAVYGGSFSGYYWSWIRQPPGKGLEWIGEIDHSGSTNYNPSLKSRVTISVDTSKNQFSLKLSSVTAADTAVYYCARARGPWSFDPWGQGTLVTVSS (SEQ ID NO: 42) | DIQMTQSPSTLSASVGDRVTITCRASQSISSWLAWYQQKPGKAPKLLIYKASSLESGVPSRFSGSGSGTEFTLTISSLQPDDFATYYCQQYDTFITFGGGTKVEIK (SEQ ID NO: 43) |
| ADI-27727 | QVQLVQSGAEVKKPGSSVKVSCKASGGTFSSYAISWVRQAPGQGLEWMGGIIPIFGTANYAQKFQGRVTITADESTSTAYMELSSLRSEDTAVYYCARGDSSIRHAYYYYGMDVWGQGTTVTVSS (SEQ ID NO: 44) CDR1 (SEQ ID NO: 45) - GTFSSYAIS (non-Kabat) or SYAIS (SEQ ID NO: 158) CDR2 (SEQ ID NO: 46) - GIIPIFGTANYAQKFQG CDR3 (SEQ ID NO: 47) - ARGDSSIRHAYYYYGMDV (non-Kabat) or GDSSIRHAYYYYGMDV (SEQ ID NO: 159) | DIVMTQSPDSLAVSLGERATINCKSSQSVLYSSNNKNYLAWYQQKPGQPPKLLIYWASTRESGVPDRFSGSGSGTDFTLTISSLQAEDVAVYYCQQYYSTPITFGGGTKVEIK (SEQ ID NO: 48) CDR1 (SEQ ID NO: 49) - KSSQSVLYSSNNKNYLA CDR2 (SEQ ID NO: 50) - WASTRES CDR3 (SEQ ID NO: 51) - QQYYSTPIT |
| ADI-29443 (F43) | QLQLQESGPGLVKPSETLSLTCTVSGGSISSSSYYWGWIRQPPGKGLEWIGSIYYSGSTYYNPSLKSRVTISVDTSKNQFSLKLSSVTAADTAVYYCARGSDRFHPYFDYWGQGTLVTVSS (SEQ ID NO: 52) CDR1 (SEQ ID NO: 53) - GSISSSSYYWG (non-Kabat) or SSSYYWG (SEQ ID NO: 160) CDR2 (SEQ ID NO: 54) - SIYYSGSTYYNPSLKS CDR3 (SEQ ID NO: 55) - ARGSDRFHPYFDY (non-Kabat) or GSDRFHPYFDY (SEQ ID NO: 161) | EIVLTQSPATLSLSPGERATLSCRASQSVSRYLAWYQQKPGQAPRLLIYDASNRATGIPARFSGSGSGTDFTLTISSLEPEDFAVYYCQQFDTWPPTFGGGTKVEIK (SEQ ID NO: 56) CDR1 (SEQ ID NO: 57) - RASQSVSRYLA CDR2 (SEQ ID NO: 58) - DASNRAT CDR3 (SEQ ID NO: 59) - QQFDTWPPT |

TABLE 1-continued

| Clones | Heavy chain variable region amino acid sequence | Light chain variable region amino acid sequence |
|---|---|---|
| ADI-29404 (F04) | QVQLQQWGAGLLKPSETLSLTCA VYGGSFSGYYWSWIRQPPGKGLE WIGEIDHSGSTNYNPSLKSRVTISV DTSKNQFSLKLSSVTAADTAVYYC ARARGPWSFDPWGQGTLVTVSS (SEQ ID NO: 60) | DIQMTQSPSTLSASVGDRVTI TCRASQSISSWLAWYQQKPG KAPKLLIYKASSLESGVPSRF SGSGSGTEFTLTISSLQPDDFA TYYCEQYDSYPTFGGGTKVE IK (SEQ ID NO: 61) |
| ADI-28200 | QVQLVQSGAEVKKPGSSVKVSCK ASGGTESSYAISWVRQAPGQGLE WMGGIIPIFGTANYAQKFQGRVTI TADESTSTAYMELSSLRSEDTAVY YCARRGRKASGSFYYYYGMDVW GQGTTVTVSS (SEQ ID NO: 62) CDR1 (SEQ ID NO: 63) - GTFSSYAIS (non-Kabat) or SYAIS (SEQ ID NO: 158) CDR2 (SEQ ID NO: 64) - GIIPIFGTANYAQKFQG CDR3 (SEQ ID NO: 65) - ARRGRKASGSFYYYYGMDV | DIVMTQSPDSLAVSLGERATI NCESSQSLLNSGNQKNYLTW YQQKPGQPPKPLIYWASTRES GVPDRFSGSGSGTDFTLTISSL QAEDVAVYYCQNDYSYPYT FGQGTKLEIK (SEQ ID NO: 66) CDR1 (SEQ ID NO: 67) - ESSQSLLNSGNQKNYLT CDR2 (SEQ ID NO: 68) - WASTRES CDR3 (SEQ ID NO: 69) - QNDYSYPYT |
| ADI-29379 (E79) | QVQLVQSGAEVKKPGASVKVSCK ASGYTFTSYYMHWVRQAPGQGLE WMGIINPSGGSTSYAQKFQGRVT MTRDTSTSTVYMELSSLRSEDTAV YYCARGAPNYGDTTHDYYYMDV WGKGTTVTVSS (SEQ ID NO: 70) CDR1 (SEQ ID NO: 71) - YTFTSYYMH (non-Kabat) or SYYMH (SEQ ID NO: 162) CDR2 (SEQ ID NO: 72) - IINPSGGSTSYAQKFQG CDR3 (SEQ ID NO: 73) - ARGAPNYGDTTHDYYYMDV (non-Kabat) or GAPNYGDTTHDYYYMDV (SEQ ID NO: 163) | EIVMTQSPATLSVSPGERATL SCRASQSVSSNLAWYQQKPG QAPRLLIYGASTRATGIPARF SGSGSGTEFTLTISSLQSEDFA VYYCQQYDDWPFTFGGGTK VEIK (SEQ ID NO: 74) CDR1 (SEQ ID NO: 75) - RASQSVSSNLA CDR2 (SEQ ID NO: 76) - GASTRAT CDR3 (SEQ ID NO: 77) - QQYDDWPFT |
| ADI-29463 (F63) | QVQLVQSGAEVKKPGASVKVSCK ASGYTFTGYYMHWVRQAPGQGL EWMGWINPNSGGTNYAQKFQGR VTMTRDTSISTAYMELSRLRSDDT AVYYCARDTGEYYDTDDHGMDV WGQGTTVTVSS (SEQ ID NO: 78) CDR1 (SEQ ID NO: 79) - YTFTGYYMH (non-Kabat) or GYYMH (SEQ ID NO: 164) CDR2 (SEQ ID NO: 80) - WINPNSGGTNYAQKFQG CDR3 (SEQ ID NO: 81) - ARDTGEYYDTDDHGMDV (non-Kabat) or DTGEYYDTDDHGMDV (SEQ ID NO: 165) | EIVLTQSPGTLSLSPGERATLS CRASQSVSSNLAWYQQKPGQ APRLLIYGASTRATGIPARFS GSGSGTEFTLTISSLQSEDFAV YYCQQDDYWPPTFGGGTKV EIK (SEQ ID NO: 82) CDR1 (SEQ ID NO: 75) - RASQSVSSNLA CDR2 (SEQ ID NO: 76) - GASTRAT CDR3 (SEQ ID NO: 85) - QQDDYWPPT |
| ADI-27744 (A44) | EVQLLESGGGLVQPGGSLRLSCAA SGFTFSSYAMSWVRQAPGKGLEW VSAISGSGGSTYYADSVKGRFTISR DNSKNTLYLQMNSLRAEDTAVYY CAKDGGYYDSGAGDYWGQGTLV TVSS (SEQ ID NO: 86) CDR1 (SEQ ID NO: 87) - FTFSSYAMS (non-Kabat) or SYAMS (SEQ ID NO: 166) CDR2 (SEQ ID NO: 88) - AISGSGGSTYYADSVKG CDR3 (SEQ ID NO: 89) - AKDGGYYDSGAGDY (non-Kabat) or DGGYYDSGAGDY (SEQ ID NO: 167) | DIQMTQSPSSVSASVGDRVTI TCRASQGIDSWLAWYQQKP GKAPKLLIYAASSLQSGVPSR FSGSGSGTDFTLTISSLQPEDF ATYYCQQGVSYPRTFGGGTK VEIK (SEQ ID NO: 90) CDR1 (SEQ ID NO: 91) - RASQGIDSWLA CDR2 (SEQ ID NO: 92) - AASSLQS CDR3 (SEQ ID NO: 93) - QQGVSYPRT |
| ADI-27749 (A49) | EVQLVESGGGLVKPGGSLRLSCAA SGFTFSSYSMNWVRQAPGKGLEW VSSISSSSSYIYYADSVKGRFTISRD | DIQMTQSPSSVSASVGDRVTI TCRASQGISSWLAWYQQKPG KAPKLLIYAASSLQSGVPSRF |

TABLE 1-continued

| Clones | Heavy chain variable region amino acid sequence | Light chain variable region amino acid sequence |
|---|---|---|
| | NAKNSLYLQMNSLRAEDTAVYYC ARGAPMGAAAGWFDPWGQGTLV TVSS<br>(SEQ ID NO: 94)<br>CDR1 (SEQ ID NO: 95) - FTFSSYSMN (non-Kabat) or SYSMN (SEQ ID NO: 168)<br>CDR2 (SEQ ID NO: 96) - SISSSSSYIYYADSVKG<br>CDR3 (SEQ ID NO: 97) - ARGAPMGAAAGWFDP (non-Kabat) or GAPMGAAAGWFDP (SEQ ID NO: 169) | SGSGSGTDFTLTISSLQPEDFA TYYCQQGVSFPRTFGGGTKV EIK<br>(SEQ ID NO: 98)<br>CDR1 (SEQ ID NO: 99) - RASQGISSWLA<br>CDR2 (SEQ ID NO: 100) - AASSLQS<br>CDR3 (SEQ ID NO: 101) - QQGVSFPRT |
| ADI-29378 (E78) | QVQLVQSGAEVKKPGASVKVSCK ASGYTFTSYYMHWVRQAPGQGLE WMGIINPSGGSTSYAQKFQGRVT MTRDTSTSTVYMELSSLRSEDTAV YYCAREGAGFAYGMDYYYMDV WGKGTTVTVSS<br>(SEQ ID NO: 102)<br>CDR1 (SEQ ID NO: 71) - YTFTSYYMH (non-Kabat) or SYYMH (SEQ ID NO: 162)<br>CDR2 (SEQ ID NO: 72) - IINPSGGSTSYAQKFQG<br>CDR3 (SEQ ID NO: 105) - AREGAGFAYGMDYYYMDV (non-Kabat) or EGAGFAYGMDYYYMDV (SEQ ID NO: 170) | EIVLTQSPATLSLSPGERATLS CRASQSVSSYLAWYQQKPGQ APRLLIYDASNRATGIPARFS GSGSGTDFTLTISSLEPEDFAV YYCQQSDNWPFTFGGGTKVE IK<br>(SEQ ID NO: 106)<br>CDR1 (SEQ ID NO: 107) - RASQSVSSYLA<br>CDR2 (SEQ ID NO: 108) - DASNRAT<br>CDR3 (SEQ ID NO: 109) - QQSDNWPFT |
| A49MI | EVQLVESGGGLVKPGGSLRLSCAA SGFTFSSYSMNWVRQAPGKGLEW VSSISSSSSYIYYADSVKGRFTISRD NAKNSLYLQMNSLRAEDTAVYYC ARGAPIGAAAGWFDPWGQGTLVT VSS<br>(SEQ ID NO: 144)<br>CDR1 (SEQ ID NO: 95) - FTFSSYSMN (non-Kabat) or SYSMN (SEQ ID NO: 168)<br>CDR2 (SEQ ID NO: 96) - SISSSSSYIYYADSVKG<br>CDR3: (non-Kabat) ARGAPIGAAAGWFDP (SEQ ID NO: 172) or GAPIGAAAGWFDP (SEQ ID NO: 173) | DIQMTQSPSSVSASVGDRVTI TCRASQGISSWLAWYQQKPG KAPKLLIYAASSLQSGVPSRF SGSGSGTDFTLTISSLQPEDFA TYYCQQGVSFPRTFGGGTKV EIK<br>(SEQ ID NO: 98)<br>CDR1 (SEQ ID NO: 99) - RASQGISSWLA<br>CDR2 (SEQ ID NO: 100) - AASSLQS<br>CDR3 (SEQ ID NO: 101) - QQGVSFPRT |
| A49MQ | EVQLVESGGGLVKPGGSLRLSCAA SGFTFSSYSMNWVRQAPGKGLEW VSSISSSSSYIYYADSVKGRFTISRD NAKNSLYLQMNSLRAEDTAVYYC ARGAPQGAAAGWFDPWGQGTLV TVSS<br>(SEQ ID NO: 174)<br>CDR1 (SEQ ID NO: 95) - FTFSSYSMN (non-Kabat) or SYSMN (SEQ ID NO: 168)<br>CDR2 (SEQ ID NO: 96) - SISSSSSYIYYADSVKG<br>CDR3 (non-Kabat) (SEQ ID NO: 175) ARGAPQGAAAGWFDP or CDR3 (SEQ ID NO: 176) - GAPQGAAAGWFDP | DIQMTQSPSSVSASVGDRVTI TCRASQGISSWLAWYQQKPG KAPKLLIYAASSLQSGVPSRF SGSGSGTDFTLTISSLQPEDFA TYYCQQGVSFPRTFGGGTKV EIK<br>(SEQ ID NO: 98)<br>CDR1 (SEQ ID NO: 99) - RASQGISSWLA<br>CDR2 (SEQ ID NO: 100) - AASSLQS<br>CDR3 (SEQ ID NO: 101) - QQGVSFPRT |
| A49ML | EVQLVESGGGLVKPGGSLRLSCAA SGFTFSSYSMNWVRQAPGKGLEW VSSISSSSSYIYYADSVKGRFTISRD NAKNSLYLQMNSLRAEDTAVYYC ARGAPLGAAAGWFDPWGQGTLV TVSS<br>(SEQ ID NO: 177)<br>CDR1 (SEQ ID NO: 95) - FTFSSYSMN (non-Kabat) or SYSMN (SEQ ID NO: 168)<br>CDR2 (SEQ ID NO: 96) - | DIQMTQSPSSVSASVGDRVTI TCRASQGISSWLAWYQQKPG KAPKLLIYAASSLQSGVPSRF SGSGSGTDFTLTISSLQPEDFA TYYCQQGVSFPRTFGGGTKV EIK<br>(SEQ ID NO: 98)<br>CDR1 (SEQ ID NO: 99) - RASQGISSWLA<br>CDR2 (SEQ ID NO: 100) - AASSLQS |

TABLE 1-continued

| Clones | Heavy chain variable region amino acid sequence | Light chain variable region amino acid sequence |
|---|---|---|
| | SISSSSSYIYYADSVKG<br>CDR3 (non-Kabat) (SEQ ID NO: 178) - ARGAPLGAAAGWFDP or CDR3 (SEQ ID NO: 179) - GAPLGAAAGWFDP | CDR3 (SEQ ID NO: 101) - QQGVSFPRT |
| A49MF | EVQLVESGGGLVKPGGSLRLSCAA SGFTFSSYSMNWVRQAPGKGLEW VSSISSSSSYIYYADSVKGRFTISRD NAKNSLYLQMNSLRAEDTAVYYC ARGAPFGAAAGWFDPWGQGTLV TVSS<br>(SEQ ID NO: 180)<br>CDR1 (SEQ ID NO: 95) - FTFSSYSMN (non-Kabat) or SYSMN (SEQ ID NO: 168)<br>CDR2 (SEQ ID NO: 96) - SISSSSSYIYYADSVKG<br>CDR3 (non-Kabat) (SEQ ID NO: 181) - ARGAPFGAAAGWFDP or CDR3 (SEQ ID NO: 182) - GAPFGAAAGWFDP | DIQMTQSPSSVSASVGDRVTI TCRASQGISSWLAWYQQKPG KAPKLLIYAASSLQSGVPSRF SGSGSGTDFTLTISSLQPEDFA TYYCQQGVSFPRTFGGGTKV EIK<br>(SEQ ID NO: 98)<br>CDR1 (SEQ ID NO: 99) - RASQGISSWLA<br>CDR2 (SEQ ID NO: 100) - AASSLQS CDR3 (SEQ ID NO: 101) - QQGVSFPRT |
| A49MV | EVQLVESGGGLVKPGGSLRLSCAA SGFTFSSYSMNWVRQAPGKGLEW VSSISSSSSYIYYADSVKGRFTISRD NAKNSLYLQMNSLRAEDTAVYYC ARGAPVGAAAGWFDPWGQGTLV TVSS<br>(SEQ ID NO: 183)<br>CDR1 (SEQ ID NO: 95) -<br><br>FTFSSYSMN (non-Kabat) or SYSMN (SEQ ID NO: 168)<br>CDR2 (SEQ ID NO: 96) - SISSSSSYIYYADSVKG<br>CDR3 (non-Kabat) (SEQ ID NO: 184) - ARGAPVGAAAGWFDP or CDR3 (SEQ ID NO: 185) - GAPVGAAAGWFDP | DIQMTQSPSSVSASVGDRVTI TCRASQGISSWLAWYQQKPG KAPKLLIYAASSLQSGVPSRF SGSGSGTDFTLTISSLQPEDFA TYYCQQGVSFPRTFGGGTKV EIK<br>(SEQ ID NO: 98)<br>CDR1 (SEQ ID NO: 99) - RASQGISSWLA<br>CDR2 (SEQ ID NO: 100) - AASSLQS<br>CDR3 (SEQ ID NO: 101) - QQGVSFPRT |
| A49-consensus | EVQLVESGGGLVKPGGSLRLSCAA SGFTFSSYSMNWVRQAPGKGLEW VSSISSSSSYIYYADSVKGRFTISRD NAKNSLYLQMNSLRAEDTAVYYC ARGAPXGAAAGWFDPWGQGTLV TVSS, wherein X is M, L, I, V, Q, or F<br>(SEQ ID NO: 186)<br>CDR1 (SEQ ID NO: 95) - FTFSSYSMN (non-Kabat) or SYSMN (SEQ ID NO: 168)<br>CDR2 (SEQ ID NO: 96) - SISSSSSYIYYADSVKG<br>CDR3 (non-Kabat) (SEQ ID NO: 187) - ARGAPXGAAAGWFDP or CDR3 (SEQ ID NO: 188) - GAPXGAAAGWFDP, wherein X is M, L, I, V, Q, or F | DIQMTQSPSSVSASVGDRVTI TCRASQGISSWLAWYQQKPG KAPKLLIYAASSLQSGVPSRF SGSGSGTDFTLTISSLQPEDFA TYYCQQGVSFPRTFGGGTKV EIK<br>(SEQ ID NO: 98)<br>CDR1 (SEQ ID NO: 99) - RASQGISSWLA<br>CDR2 (SEQ ID NO: 100) - AASSLQS<br>CDR3 (SEQ ID NO: 101) - QQGVSFPRT |

Alternatively, a heavy chain variable domain represented by SEQ ID NO:110 can be paired with a light chain variable domain represented by SEQ ID NO:111 to form an antigen-binding site that can bind to NKG2D, as illustrated in U.S. Pat. No. 9,273,136.

SEQ ID NO: 110
QVQLVESGGGLVKPGGSLRLSCAASGFTFSSYGMHWVRQAPGKGLEWVA
FIRYDGSNKYYADSVKGRFTISRDNSKNTLYLQMNSLRAEDTAVYYCAK
DRGLGDGTYFDYWGQGTTVTVSS

-continued

SEQ ID NO: 111
QSALTQPASVSGSPGQSITISCSGSSSNIGNNAVNWYQQLPGKAPKLLI
YYDDLLPSGVSDRFSGSKSGTSAFLAISGLQSEDEADYYCAAWDDSLNG
PVFGGGTKLTVL

Alternatively, a heavy chain variable domain represented by SEQ ID NO:112 can be paired with a light chain variable domain represented by SEQ ID NO:113 to form an antigen-binding site that can bind to NKG2D, as illustrated in U.S. Pat. No. 7,879,985.

SEQ ID NO: 112
QVHLQESGPGLVKPSETLSLTCTVSDDSISSYYWSWIRQPPGKGLEWIG
HISYSGSANYNPSLKSRVTISVDTSKNQFSLKLSSVTAADTAVYYCANW
DDAFNIWGQGTMVTVSS

SEQ ID NO: 113
EIVLTQSPGTLSLSPGERATLSCRASQSVSSSYLAWYQQKPGQAPRLLI
YGASSRATGIPDRFSGSGSGTDFTLTISRLEPEDFAVYYCQQYGSSPWT
FGQGTKVEIK

The multi-specific binding proteins can bind to NKG2D-expressing cells, which include but are not limited to NK cells, γδ T cells and CD8$^+$ αβ T cells. Upon NKG2D binding, the multi-specific binding proteins may block natural ligands, such as ULBP6 and MICA, from binding to NKG2D and activating NK cells.

The multi-specific binding proteins binds to cells expressing CD16, an Fc receptor on the surface of leukocytes including natural killer cells, macrophages, neutrophils, eosinophils, mast cells, and follicular dendritic cells. A protein of the present disclosure binds to NKG2D with an affinity of $K_D$ of 2 nM to 120 nM, e.g., 2 nM to 110 nM, 2 nM to 100 nM, 2 nM to 90 nM, 2 nM to 80 nM, 2 nM to 70 nM, 2 nM to 60 nM, 2 nM to 50 nM, 2 nM to 40 nM, 2 nM to 30 nM, 2 nM to 20 nM, 2 nM to 10 nM, about 15 nM, about 14 nM, about 13 nM, about 12 nM, about 11 nM, about 10 nM, about 9 nM, about 8 nM, about 7 nM, about 6 nM, about 5 nM, about 4.5 nM, about 4 nM, about 3.5 nM, about 3 nM, about 2.5 nM, about 2 nM, about 1.5 nM, about 1 nM, between about 0.5 nM to about 1 nM, about 1 nM to about 2 nM, about 2 nM to 3 nM, about 3 nM to 4 nM, about 4 nM to about 5 nM, about 5 nM to about 6 nM, about 6 nM to about 7 nM, about 7 nM to about 8 nM, about 8 nM to about 9 nM, about 9 nM to about 10 nM, about 1 nM to about 10 nM, about 2 nM to about 10 nM, about 3 nM to about 10 nM, about 4 nM to about 10 nM, about 5 nM to about 10 nM, about 6 nM to about 10 nM, about 7 nM to about 10 nM, or about 8 nM to about 10 nM. In some embodiments, NKG2D-binding sites bind to NKG2D with a $K_D$ of 10 to 62 nM.

HER2-Binding Site

The HER2-binding site of the multi-specific binding protein disclosed herein comprises a heavy chain variable domain and a light chain variable domain fused together to from an scFv.

Table 2 lists peptide sequences of heavy chain variable domains and light chain variable domains that, in combination, can bind to HER2.

TABLE 2

| Clones | Heavy chain variable domain amino acid sequence | Light chain variable domain amino acid sequence |
| --- | --- | --- |
| Trastuzumab | EVQLVESGGGLVQPGGSLRLSCA ASGFNIKDTYIHWVRQAPGKGLE WVARIYPTNGYTRYADSVKGRF TISADTSKNTAYLQMNSLRAEDT AVYYCSRWGGDGFYAMDYWG QGTLVTVSS (SEQ ID NO: 114) CDR1(SEQ ID NO: 115) - GFNIKDT CDR2 (SEQ ID NO: 116) - YPTNGY CDR3 (SEQ ID NO: 117) - WGGDGFYAMDY | DIQMTQSPSSLSASVGDRVTITCR ASQDVNTAVAWYQQKPGKAPK LLIYSASFLYSGVPSRFSGSRSGT DFTLTISSLQPEDFATYYCQQHY TTPPTFGQGTKVEIK (SEQ ID NO: 118) CDR1(SEQ ID NO: 119) - QDVNTAVA CDR2 (SEQ ID NO: 120) - SASFLYS CDR3 (SEQ ID NO: 121) - QQHYTTPPT |
| Trastuzumab (VH and VL in scFv construct) | EVQLVESGGGLVQPGGSLRLSCA ASGFNIKDTYIHWVRQAPGKCLE WVARIYPTNGYTRYADSVKGRF TISADTSKNTAYLQMNSLRAEDT AVYYCSRWGGDGFYAMDYWG QGTLVTVSS (SEQ ID NO: 195) CDR1 (SEQ ID NO: 115) - GFNIKDT CDR2 (SEQ ID NO: 116) - YPTNGY CDR3 (SEQ ID NO: 117) - WGGDGFYAMDY | DIQMTQSPSSLSASVGDRVTITCR ASQDVNTAVAWYQQKPGKAPK LLIYSASFLYSGVPSRFSGSRSGT DFTLTISSLQPEDFATYYCQQHY TTPPTFGCGTKVEIK (SEQ ID NO: 196) CDR1(SEQ ID NO: 119) - QDVNTAVA CDR2 (SEQ ID NO: 120) - SASFLYS CDR3 (SEQ ID NO: 121) - QQHYTTPPT |
| Trastuzumab-scFv | DIQMTQSPSSLSASVGDRVTITCRASQDVNTAVAWYQQKPGKAPKLL IYSASFLYSGVPSRFSGSRSGTDFTLTISSLQPEDFATYYCQQHYTTPPT FGCGTKVEIKGGGGSGGGGSGGGGSGGGGSEVQLVESGGGLVQPGG SLRLSCAASGFNIKDTYIHWVRQAPGKCLEWVARIYPTNGYTRYADS VKGRFTISADTSKNTAYLQMNSLRAEDTAVYYCSRWGGDGFYAMD YWGQGTLVTVSS (SEQ ID NO: 139) | |
| Pertuzumab | EVQLVESGGGLVQPGGSLRLSCA ASGFTFTDYTMDWVRQAPGKGL EWVADVNPNSGGSIYNQRFKGR FTLSVDRSKNTLYLQMNSLRAED TAVYYCARNLGPSFYFDYWGQG TLVTVSSA (SEQ ID NO: 122) CDR1 (SEQ ID NO: 123) - GFTFTDY CDR2 (SEQ ID NO: 124) - NPNSGG CDR3 (SEQ ID NO: 125) - NLGPSFYFDY | DIQMTQSPSSLSASVGDRVTITCK ASQDVSIGVAWYQQKPGKAPKL LIYSASYRYTGVPSRFSGSGSGTD FTLTISSLQPEDFATYYCQQYYIY PYTFGQGTKVEIKR (SEQ ID NO: 126) CDR1 (SEQ ID NO: 127) - QDVSIGVA CDR2 (SEQ ID NO: 128) - SASYRYT CDR3 (SEQ ID NO: 129) - QQYYIYPYT |

TABLE 2-continued

| Clones | Heavy chain variable domain amino acid sequence | Light chain variable domain amino acid sequence |
|---|---|---|
| Pertuzumab (VH and VL in scFv construct) | EVQLVESGGGLVQPGGSLRLSCA ASGFTFTDYTMDWVRQAPGKCL EWVADVNPNSGGSIYNQRFKGR FTLSVDRSKNTLYLQMNSLRAED TAVYYCARNLGPSFYFDYWGQG TLVTVSSA (SEQ ID NO: 197) CDR1 (SEQ ID NO: 123) - GFTFTDY CDR2 (SEQ ID NO: 124) - NPNSGG CDR3 (SEQ ID NO: 125) - NLGPSFYFDY | DIQMTQSPSSLSASVGDRVTITCK ASQDVSIGVAWYQQKPGKAPKL LIYSASYRYTGVPSRFSGSGSGTD FTLTISSLQPEDFATYYCQQYYIY PYTFGCGTKVEIKR (SEQ ID NO: 198) CDR1 (SEQ ID NO: 127) - QDVSIGVA CDR2 (SEQ ID NO: 128) - SASYRYT CDR3 (SEQ ID NO: 129) - QQYYIYPYT |
| Pertuzumab scFv | DIQMTQSPSSLSASVGDRVTITCKASQDVSIGVAWYQQKPGKAPKLLI YSASYRYTGVPSRFSGSGSGTDFTLTISSLQPEDFATYYCQQYYIYPYT FGCGTKVEIKRGGGGSGGGGSGGGGSGGGGSEVQLVESGGGLVQPG GSLRLSCAASGFTFTDYTMDWVRQAPGKCLEWVADVNPNSGGSIYN QRFKGRFTLSVDRSKNTLYLQMNSLRAEDTAVYYCARNLGPSFYFDY WGQGTLVTVSSA (SEQ ID NO: 189) | |
| MGAH22 (US 8,802,093) | QVQLQQSGPELVKPGASLKLSCT ASGFNIKDTYIHWVKQRPEQGLE WIGRIYPTNGYTRYDPKFQDKAT ITADTSSNTAYLQVSRLTSEDTA VYYCSRWGGDGFYAMDYWGQ GASVTVSS (SEQ ID NO: 130) CDR1 (SEQ ID NO: 131) - GFNIKDT CDR2 (SEQ ID NO: 132) - YPTNGY CDR3 (SEQ ID NO: 133) - WGGDGFYAMDY | DIVMTQSHKFMSTSVGDRVSITC KASQDVNTAVAWYQQKPGHSP KLLIYSASFRYTGVPDRFTGSRSG TDFTFTISSVQAEDLAVYYCQQH YTTPPTFGGGTKVEIK (SEQ ID NO: 134) CDR1 (SEQ ID NO: 135) - QDVNTAVA CDR2 (SEQ ID NO: 136) - SASFRYT CDR3 (SEQ ID NO: 137) - QQHYTTPPT |
| MGAH22 (VH and VL in scFv construct) | QVQLQQSGPELVKPGASLKLSCT ASGFNIKDTYIHWVKQRPEQCLE WIGRIYPTNGYTRYDPKFQDKAT ITADTSSNTAYLQVSRLTSEDTA VYYCSRWGGDGFYAMDYWGQ GASVTVSSA (SEQ ID NO: 199) CDR1 (SEQ ID NO: 131) - GFNIKDT CDR2 (SEQ ID NO: 132) - YPTNGY CDR3 (SEQ ID NO: 133) - WGGDGFYAMDY | DIVMTQSHKFMSTSVGDRVSITC KASQDVNTAVAWYQQKPGHSP KLLIYSASFRYTGVPDRFTGSRSG TDFTFTISSVQAEDLAVYYCQQH YTTPPTFGCGTKVEIKR (SEQ ID NO: 200) CDR1 (SEQ ID NO: 135) - QDVNTAVA CDR2 (SEQ ID NO: 136) - SASFRYT CDR3 (SEQ ID NO: 137) - QQHYTTPPT |
| MGAH22 scFv | DIVMTQSHKFMSTSVGDRVSITCKASQDVNTAVAWYQQKPGHSPKL LIYSASFRYTGVPDRFTGSRSGTDFTFTISSVQAEDLAVYYCQQHYTTP PTFGCGTKVEIKRGGGGSGGGGSGGGGSGGGGSQVQLQQSGPELVKP GASLKLSCTASGFNIKDTYIHWVKQRPEQCLEWIGRIYPTNGYTRYDP KFQDKATITADTSSNTAYLQVSRLTSEDTAVYYCSRWGGDGFYAMD YWGQGASVTVSSA (SEQ ID NO: 171) | |

Alternatively, novel antigen-binding sites that can bind to HER2 can be identified by screening for binding to the amino acid sequence defined by SEQ ID NO: 138 or a mature extracellular fragment thereof.

(SEQ ID NO: 138)
MELAALCRWGLLLALLPPGAASTQVCTGTDMKLRLPASPETHLDMLRHL

YQGCQVVQGNLELTYLPTNASLSFLQDIQEVQGYVLIAHNQVRQVPLQR

LRIVRGTQLFEDNYALAVLDNGDPLNNTTPVTGASPGGLRELQLRSLTE

ILKGGVLIQRNPQLCYQDTILWKDIFHKNNQLALTLIDTNRSRACHPCS

PMCKGSRCWGESSEDCQSLTRTVCAGGCARCKGPLPTDCCHEQCAAGCT

GPKHSDCLACLHFNHSGICELHCPALVTYNTDTFESMPNPEGRYTFGAS

CVTACPYNYLSTDVGSCTLVCPLHNQEVTAEDGTQRCEKCSKPCARVCY

GLGMEHLREVRAVTSANIQEFAGCKKIFGSLAFLPESFDGDPASNTAPL

QPEQLQVFETLEEITGYLYISAWPDSLPDLSVFQNLQVIRGRILHNGAY

SLTLQGLGISWLGLRSLRELGSGLALIHHNTHLCFVHTVPWDQLFRNPH

QALLHTANRPEDECVGEGLACHQLCARGHCWGPGPTQCVNCSQFLRGQE

CVEECRVLQGLPREYVNARHCLPCHPECQPQNGSVTCFGPEADQCVACA

HYKDPPFCVARCPSGVKPDLSYMPIWKFPDEEGACQPCPINCTHSCVDL

DDKGCPAEQRASPLTSIISAVVGILLVVVLGVVFGILIKRRQQKIRKYT

MRRLLQETELVEPLTPSGAMPNQAQMRILKETELRKVKVLGSGAFGTVY

KGIWIPDGENVKIPVAIKVLRENTSPKANKEILDEAYVMAGVGSPYVSR

-continued

LLGICLTSTVQLVTQLMPYGCLLDHVRENRGRLGSQDLLNWCMQIAKGM

SYLEDVRLVHRDLAARNVLVKSPNHVKITDFGLARLLDIDETEYHADGG

KVPIKWMALESILRRRFTHQSDVWSYGVTVWELMTFGAKPYDGIPAREI

PDLLEKGERLPQPPICTIDVYMIMVKCWMIDSECRPRFRELVSEFSRMA

RDPQRFVVIQNEDLGPASPLDSTFYRSLLEDDDMGDLVDAEEYLVPQQG

FFCPDPAPGAGGMVHHRHRSSSTRSGGGDLTLGLEPSEEEAPRSPLAPS

EGAGSDVFDGDLGMGAAKGLQSLPTHDPSPLQRYSEDPTVPLPSETDGY

VAPLTCSPQPEYVNQPDVRPQPPSPREGPLPAARPAGATLERPKTLSPG

KNGVVKDVFAFGGAVENPEYLTPQGGAAPQPHPPPAFSPAFDNLYYWDQ

DPPERGAPPSTFKGTPTAENPEYLGLDVPV.

The VH and VL of the scFv can be positioned in various orientations. In certain embodiments, the VL is positioned N-terminal to the VH. In certain embodiments, the VL is positioned C-terminal to the VH.

The VH and VL of the scFv can be connected via a linker, e.g., a peptide linker. In certain embodiments, the peptide linker is a flexible linker. Regarding the amino acid composition of the linker, peptides are selected with properties that confer flexibility, do not interfere with the structure and function of the other domains of the proteins of the present invention, and resist cleavage from proteases. For example, glycine and serine residues generally provide protease resistance. In certain embodiments, the VL is positioned N-terminal to the VH and is connected to the VH via a linker.

The length of the linker (e.g., flexible linker) can be "short," e.g., 0, 1, 2, 3, 4, 5, 6, 7, 8, 9, 10, 11 or 12 amino acid residues, or "long," e.g., at least 13 amino acid residues. In certain embodiments, the linker is 10-50, 10-40, 10-30, 10-25, 10-20, 15-50, 15-40, 15-30, 15-25, 15-20, 20-50, 20-40, 20-30, or 20-25 amino acid residues in length.

In certain embodiments, the linker comprises or consists of a $(GS)_n$ (SEQ ID NO: 204), $(GGS)_n$ (SEQ ID NO:205), $(GGGS)_n$ (SEQ ID NO:206), $(GGSG)_n$ (SEQ ID NO: 207), $(GGSGG)_n$ (SEQ ID NO:208), and $(GGGGS)_n$ (SEQ ID NO:209) sequence, wherein n is 1, 2, 3, 4, 5, 6, 7, 8, 9, 10, 11, 12, 13, 14, 15, 16, 17, 18, 19, or 20. In certain embodiments, the linker comprises or consists of an amino acid sequence selected from SEQ ID NO: 143, SEQ ID NO:201, SEQ ID NO:202, SEQ ID NO: 103, SEQ ID NO:104, SEQ ID NO: 83, SEQ ID NO:84, SEQ ID NO:150, SEQ ID NO:152, and SEQ ID NO: 154, as listed in Table 3. In certain embodiments, the linker is a $(G_4S)_4$ (SEQ ID NO:143) linker consisting of the sequence of SEQ ID NO:143.

TABLE 3

| SEQ ID | Amino Acid Sequence |
|---|---|
| SEQ ID NO: 201 | GSGSGSGSGSGSGSGSGS |
| SEQ ID NO: 202 | GGSGGSGGSGGSGGSGGSGGSGGSGGSGGS |
| SEQ ID NO: 103 | GGGSGGGSGGGSGGGSGGGSGGGSGGGSG GGSGGGSGGGS |
| SEQ ID NO: 104 | GGSGGGSGGGSGGGSGGGSGGGSGGGSGG GSGGGSGGGSG |

TABLE 3-continued

| SEQ ID | Amino Acid Sequence |
|---|---|
| SEQ ID NO: 83 | GGSGGGGSGGGGSGGGGSGGGGSGGGGSG GGSGGGGSGGGGSGGGGSGG |
| SEQ ID NO: 84 | GGGGSGGGGSGGGGSGGGGSGGGGSGGGG SGGGGSGGGGSGGGGSGGGGS |
| SEQ ID NO: 143 | GGGGSGGGGSGGGGSGGGGS |
| SEQ ID NO: 150 | GGGGSGGGGSGGGGS |
| SEQ ID NO: 152 | GGGGSGGGGSGGGGSGGGGSGGGGSGGGG SGGGGSGGGGSGGGGSGGGGSGGGGSGGG GSGGGGSGGGGSGGGGSGGGGSGGGGSGG GGSGGGGSGGGGS |
| SEQ ID NO: 154 | GGSGGGGSGGGGSGGGGSGGGGSGGGGSG GGSGGGGSGGGGSGGGGSGGGGSGGGGS GGGGSGGGGSGGGGSGGGGSGGGGSGGGG SGGGGSGGGGSGG |

Fc Domain

Within the Fc domain, CD16 binding is mediated by the hinge region and the CH2 domain. For example, within human IgG1, the interaction with CD16 is primarily focused on amino acid residues Asp 265-Glu 269, Asn 297-Thr 299, Ala 327-Ile 332, Leu 234-Ser 239, and carbohydrate residue N-acetyl-D-glucosamine in the CH2 domain (see, Sondermann et al, Nature, 406 (6793): 267-273). Based on the known domains, mutations can be selected to enhance or reduce the binding affinity to CD16, such as by using phage-displayed libraries or yeast surface-displayed cDNA libraries, or can be designed based on the known three-dimensional structure of the interaction.

The assembly of heterodimeric antibody heavy chains can be accomplished by expressing two different antibody heavy chain sequences in the same cell, which may lead to the assembly of homodimers of each antibody heavy chain as well as assembly of heterodimers. Promoting the preferential assembly of heterodimers can be accomplished by incorporating different mutations in the CH3 domain of each antibody heavy chain constant region as shown in U.S. Ser. No. 13/494,870, U.S. Ser. No. 16/028,850, U.S. Ser. No. 11/533,709, U.S. Ser. No. 12/875,015, U.S. Ser. No. 13/289,934, U.S. Ser. No. 14/773,418, U.S. Ser. No. 12/811,207, U.S. Ser. No. 13/866,756, U.S. Ser. No. 14/647,480, and U.S. Ser. No. 14/830,336. For example, mutations can be made in the CH3 domain based on human IgG1 and incorporating distinct pairs of amino acid substitutions within a first polypeptide and a second polypeptide that allow these two chains to selectively heterodimerize with each other. The positions of amino acid substitutions illustrated below are all numbered according to the EU index as in Kabat.

In one scenario, an amino acid substitution in the first polypeptide replaces the original amino acid with a larger amino acid, selected from arginine (R), phenylalanine (F), tyrosine (Y) or tryptophan (W), and at least one amino acid substitution in the second polypeptide replaces the original amino acid(s) with a smaller amino acid(s), chosen from alanine (A), serine(S), threonine (T), or valine (V), such that the larger amino acid substitution (a protuberance) fits into the surface of the smaller amino acid substitutions (a cavity). For example, one polypeptide can incorporate a T366W substitution, and the other can incorporate three substitutions including T366S, L368A, and Y407V.

An antibody heavy chain variable domain of the invention can optionally be coupled to an amino acid sequence at least 90% identical to an antibody constant region, such as an IgG constant region including hinge, CH2 and CH3 domains with or without CH1 domain. In some embodiments, the amino acid sequence of the constant region is at least 90% identical to a human antibody constant region, such as a human IgG1 constant region, an IgG2 constant region, IgG3 constant region, or IgG4 constant region. In some other embodiments, the amino acid sequence of the constant region is at least 90% identical to an antibody constant region from another mammal, such as rabbit, dog, cat, mouse, or horse. One or more mutations can be incorporated into the constant region as compared to human IgG1 constant region, for example at Q347, Y349, L351, S354, E356, E357, K360, Q362, S364, T366, L368, K370, N390, K392, T394, D399, S400, D401, F405, Y407, K409, T411 and/or K439. Exemplary substitutions include, for example, Q347E, Q347R, Y349S, Y349K, Y349T, Y349D, Y349E, Y349C, T350V, L351K, L351D, L351Y, S354C, E356K, E357Q, E357L, E357W, K360E, K360W, Q362E, S364K, S364E, S364H, S364D, T366V, T366I, T366L, T366M, T366K, T366W, T366S, L368E, L368A, L368D, K370S, N390D, N390E, K392L, K392M, K392V, K392F, K392D, K392E, T394F, T394W, D399R, D399K, D399V, S400K, S400R, D401K, F405A, F405T, Y407A, Y407I, Y407V, K409F, K409W, K409D, T411D, T411E, K439D, and K439E.

In certain embodiments, mutations that can be incorporated into the CH1 of a human IgG1 constant region may be at amino acid V125, F126, P127, T135, T139, A140, F170, P171, and/or V173. In certain embodiments, mutations that can be incorporated into the Cκ of a human IgG1 constant region may be at amino acid E123, F116, S176, V163, S174, and/or T164.

Amino acid substitutions could be selected from the following sets of substitutions shown in Table 4.

TABLE 4

| | First Polypeptide | Second Polypeptide |
|---|---|---|
| Set 1 | S364E/F405A | Y349K/T394F |
| Set 2 | S364H/D401K | Y349T/T411E |
| Set 3 | S364H/T394F | Y349T/F405A |
| Set 4 | S364E/T394F | Y349K/F405A |
| Set 5 | S364E/T411E | Y349K/D401K |
| Set 6 | S364D/T394F | Y349K/F405A |
| Set 7 | S364H/F405A | Y349T/T394F |
| Set 8 | S364K/E357Q | L368D/K370S |
| Set 9 | L368D/K370S | S364K |
| Set 10 | L368E/K370S | S364K |
| Set 11 | K360E/Q362E | D401K |
| Set 12 | L368D/K370S | S364K/E357L |
| Set 13 | K370S | S364K/E357Q |
| Set 14 | F405L | K409R |
| Set 15 | K409R | F405L |

Alternatively, amino acid substitutions could be selected from the following sets of substitutions shown in Table 5.

TABLE 5

| | First Polypeptide | Second Polypeptide |
|---|---|---|
| Set 1 | K409W | D399V/F405T |
| Set 2 | Y349S | E357W |
| Set 3 | K360E | Q347R |
| Set 4 | K360E/K409W | Q347R/D399V/F405T |
| Set 5 | Q347E/K360E/K409W | Q347R/D399V/F405T |
| Set 6 | Y349S/K409W | E357W/D399V/F405T |

Alternatively, amino acid substitutions could be selected from the following set of substitutions shown in Table 6.

TABLE 6

| | First Polypeptide | Second Polypeptide |
|---|---|---|
| Set 1 | T366K/L351K | L351D/L368E |
| Set 2 | T366K/L351K | L351D/Y349E |
| Set 3 | T366K/L351K | L351D/Y349D |
| Set 4 | T366K/L351K | L351D/Y349E/L368E |
| Set 5 | T366K/L351K | L351D/Y349D/L368E |
| Set 6 | E356K/D399K | K392D/K409D |

Alternatively, at least one amino acid substitution in each polypeptide chain could be selected from Table 7.

TABLE 7

| First Polypeptide | Second Polypeptide |
|---|---|
| L351Y, D399R, D399K, S400K, S400R, Y407A, Y407I, Y407V | T366V, T366I, T366L, T366M, N390D, N390E, K392L, K392M, K392V, K392F K392D, K392E, K409F, K409W, T411D and T411E |

Alternatively, at least one amino acid substitutions could be selected from the following set of substitutions in Table 8, where the position(s) indicated in the First Polypeptide column is replaced by any known negatively-charged amino acid, and the position(s) indicated in the Second Polypeptide Column is replaced by any known positively-charged amino acid.

TABLE 8

| First Polypeptide | Second Polypeptide |
|---|---|
| K392, K370, K409, or K439 | D399, E356, or E357 |

Alternatively, at least one amino acid substitutions could be selected from the following set of in Table 9, where the position(s) indicated in the First Polypeptide column is replaced by any known positively-charged amino acid, and the position(s) indicated in the Second Polypeptide Column is replaced by any known negatively-charged amino acid.

TABLE 9

| First Polypeptide | Second Polypeptide |
|---|---|
| D399, E356, or E357 | K409, K439, K370, or K392 |

Alternatively, amino acid substitutions could be selected from the following set in Table 10.

TABLE 10

| First Polypeptide | Second Polypeptide |
|---|---|
| T350V, L351Y, F405A, and Y407V | T350V, T366L, K392L, and T394W |

Alternatively, or in addition, the structural stability of a hetero-multimeric protein may be increased by introducing S354C on either of the first or second polypeptide chain, and Y349C on the opposing polypeptide chain, which forms an artificial disulfide bridge within the interface of the two polypeptides.

In some embodiments, the amino acid sequence of one polypeptide chain of the antibody constant region differs from the amino acid sequence of an IgG1 constant region at position T366, and wherein the amino acid sequence of the other polypeptide chain of the antibody constant region differs from the amino acid sequence of an IgG1 constant region at one or more positions selected from the group consisting of T366, L368 and Y407.

In some embodiments, the amino acid sequence of one polypeptide chain of the antibody constant region differs from the amino acid sequence of an IgG1 constant region at one or more positions selected from the group consisting of T366, L368 and Y407, and wherein the amino acid sequence of the other polypeptide chain of the antibody constant region differs from the amino acid sequence of an IgG1 constant region at position T366.

In some embodiments, the amino acid sequence of one polypeptide chain of the antibody constant region differs from the amino acid sequence of an IgG1 constant region at one or more positions selected from the group consisting of E357, K360, Q362, S364, L368, K370, T394, D401, F405, and T411 and wherein the amino acid sequence of the other polypeptide chain of the antibody constant region differs from the amino acid sequence of an IgG1 constant region at one or more positions selected from the group consisting of Y349, E357, S364, L368, K370, T394, D401, F405 and T411.

In some embodiments, the amino acid sequence of one polypeptide chain of the antibody constant region differs from the amino acid sequence of an IgG1 constant region at one or more positions selected from the group consisting of Y349, E357, S364, L368, K370, T394, D401, F405 and T411 and wherein the amino acid sequence of the other polypeptide chain of the antibody constant region differs from the amino acid sequence of an IgG1 constant region at one or more positions selected from the group consisting of E357, K360, Q362, S364, L368, K370, T394, D401, F405, and T411.

In some embodiments, the amino acid sequence of one polypeptide chain of the antibody constant region differs from the amino acid sequence of an IgG1 constant region at one or more positions selected from the group consisting of L351, D399, S400 and Y407 and wherein the amino acid sequence of the other polypeptide chain of the antibody constant region differs from the amino acid sequence of an IgG1 constant region at one or more positions selected from the group consisting of T366, N390, K392, K409 and T411.

In some embodiments, the amino acid sequence of one polypeptide chain of the antibody constant region differs from the amino acid sequence of an IgG1 constant region at one or more positions selected from the group consisting of T366, N390, K392, K409 and T411 and wherein the amino acid sequence of the other polypeptide chain of the antibody constant region differs from the amino acid sequence of an IgG1 constant region at one or more positions selected from the group consisting of L351, D399, S400 and Y407.

In some embodiments, the amino acid sequence of one polypeptide chain of the antibody constant region differs from the amino acid sequence of an IgG1 constant region at one or more positions selected from the group consisting of Q347, Y349, K360, and K409, and wherein the amino acid sequence of the other polypeptide chain of the antibody constant region differs from the amino acid sequence of an IgG1 constant region at one or more positions selected from the group consisting of Q347, E357, D399 and F405.

In some embodiments, the amino acid sequence of one polypeptide chain of the antibody constant region differs from the amino acid sequence of an IgG1 constant region at one or more positions selected from the group consisting of Q347, E357, D399 and F405, and wherein the amino acid sequence of the other polypeptide chain of the antibody constant region differs from the amino acid sequence of an IgG1 constant region at one or more positions selected from the group consisting of Y349, K360, Q347 and K409.

In some embodiments, the amino acid sequence of one polypeptide chain of the antibody constant region differs from the amino acid sequence of an IgG1 constant region at one or more positions selected from the group consisting of K370, K392, K409 and K439, and wherein the amino acid sequence of the other polypeptide chain of the antibody constant region differs from the amino acid sequence of an IgG1 constant region at one or more positions selected from the group consisting of D356, E357 and D399.

In some embodiments, the amino acid sequence of one polypeptide chain of the antibody constant region differs from the amino acid sequence of an IgG1 constant region at one or more positions selected from the group consisting of D356, E357 and D399, and wherein the amino acid sequence of the other polypeptide chain of the antibody constant region differs from the amino acid sequence of an IgG1 constant region at one or more positions selected from the group consisting of K370, K392, K409 and K439.

In some embodiments, the amino acid sequence of one polypeptide chain of the antibody constant region differs from the amino acid sequence of an IgG1 constant region at one or more positions selected from the group consisting of L351, E356, T366 and D399, and wherein the amino acid sequence of the other polypeptide chain of the antibody constant region differs from the amino acid sequence of an IgG1 constant region at one or more positions selected from the group consisting of Y349, L351, L368, K392 and K409.

In some embodiments, the amino acid sequence of one polypeptide chain of the antibody constant region differs from the amino acid sequence of an IgG1 constant region at one or more positions selected from the group consisting of Y349, L351, L368, K392 and K409, and wherein the amino acid sequence of the other polypeptide chain of the antibody constant region differs from the amino acid sequence of an IgG1 constant region at one or more positions selected from the group consisting of L351, E356, T366 and D399.

In some embodiments, the amino acid sequence of one polypeptide chain of the antibody constant region differs from the amino acid sequence of an IgG1 constant region by an S354C substitution and wherein the amino acid sequence of the other polypeptide chain of the antibody constant region differs from the amino acid sequence of an IgG1 constant region by a Y349C substitution.

In some embodiments, the amino acid sequence of one polypeptide chain of the antibody constant region differs from the amino acid sequence of an IgG1 constant region by a Y349C substitution and wherein the amino acid sequence of the other polypeptide chain of the antibody constant region differs from the amino acid sequence of an IgG1 constant region by an S354C substitution.

In some embodiments, the amino acid sequence of one polypeptide chain of the antibody constant region differs from the amino acid sequence of an IgG1 constant region by K360E and K409W substitutions and wherein the amino acid sequence of the other polypeptide chain of the antibody constant region differs from the amino acid sequence of an IgG1 constant region by Q347R, D399V and F405T substitutions.

In some embodiments, the amino acid sequence of one polypeptide chain of the antibody constant region differs from the amino acid sequence of an IgG1 constant region by Q347R, D399V and F405T substitutions and wherein the amino acid sequence of the other polypeptide chain of the antibody constant region differs from the amino acid sequence of an IgG1 constant region by K360E and K409W substitutions.

In some embodiments, the amino acid sequence of one polypeptide chain of the antibody constant region differs from the amino acid sequence of an IgG1 constant region by a T366W substitutions and wherein the amino acid sequence of the other polypeptide chain of the antibody constant region differs from the amino acid sequence of an IgG1 constant region by T366S, T368A, and Y407V substitutions.

In some embodiments, the amino acid sequence of one polypeptide chain of the antibody constant region differs from the amino acid sequence of an IgG1 constant region by T366S, T368A, and Y407V substitutions and wherein the amino acid sequence of the other polypeptide chain of the antibody constant region differs from the amino acid sequence of an IgG1 constant region by a T366W substitution.

In some embodiments, the amino acid sequence of one polypeptide chain of the antibody constant region differs from the amino acid sequence of an IgG1 constant region by T350V, L351Y, F405A, and Y407V substitutions and wherein the amino acid sequence of the other polypeptide chain of the antibody constant region differs from the amino acid sequence of an IgG1 constant region by T350V, T366L, K392L, and T394W substitutions.

In some embodiments, the amino acid sequence of one polypeptide chain of the antibody constant region differs from the amino acid sequence of an IgG1 constant region by T350V, T366L, K392L, and T394W substitutions and wherein the amino acid sequence of the other polypeptide chain of the antibody constant region differs from the amino acid sequence of an IgG1 constant region by T350V, L351Y, F405A, and Y407V substitutions.

Certain proteins described in the present disclosure have an Fc domain, which comprises one or more mutations that reduce the ability of the Fc sequence to induce antibody-dependent cellular cytotoxicity (ADCC) and/or antibody-dependent cellular phagocytosis (ADCP). At least one mutation is located in the regions including amino acid positions 232-239, 265-270, 296-299, and 325-332 (see Want et al., Protein Cell (2018) 9 (1): 63-73). The mutations may include an amino acid substitution (relative to wild-type human IgG1) at one or more positions 233, 234, 235, 297, and 329. The one or more mutations may include E233P; L234A; L235A; N297A, N297Q, N297G, or N297D; and/or P329A, P329G, or P329R relative to wild-type human IgG1. The one or more mutations may include L234A and L235A relative to wild-type human IgG1. Alternatively, the one or more mutations may include L234A, L235A, and P329A relative to wild-type human IgG1. The mutation may be present on each of the two polypeptide chains of the Fc domain.

Exemplary Multi-Specific Binding Proteins

Listed below are examples of TriNKETs comprising a HER2-binding scFv and an NKG2D-binding Fab each linked to an antibody constant region, wherein the antibody constant regions include mutations that enable heterodimerization of two Fc chains. The scFv comprises a heavy chain variable domain (VH) and a light chain variable domain (VL) derived from an anti-HER2 antibody (e.g., trastuzumab), and further comprises substitution of Cys for the amino acid residues at position 100 of VL and position 44 of VH, thereby facilitating formation of a disulfide bridge between the VH and VL of the scFv. The VL is linked N-terminal to the VH via a $(G_4S)_4$ linker (SEQ ID NO:143), and the VH is linked N-terminal to an Fc via an Ala-Ser linker. The Ala-Ser linker is included at the elbow hinge region sequence to balance between flexibility and optimal geometry. In certain embodiments, an additional sequence Thr-Lys-Gly can be added N-terminal or C-terminal to the Ala-Ser sequence at the hinge. As used herein to describe these exemplary TriNKETs, Fc includes an antibody hinge, CH2, and CH3.

Accordingly, each of the TriNKETs described below comprises the following three polypeptide chains:

Chain A, comprising from N-terminus to C-terminus: VH of an NKG2D-binding Fab, CH1, and Fc;

Chain B, comprising from N-terminus to C-terminus: VL of a HER2-binding scFv, $(G_4S)_4$ linker (SEQ ID NO:143), VH of the HER2-binding scFv, Ala-Ser linker, and Fc; and Chain C, comprising from N-terminus to C-terminus: VL of the NKG2D-binding Fab, and CL.

The amino acid sequences of the exemplary TriNKETs are summarized in Table 11.

TABLE 11

| TriNKET Construct | NKG2D Binding Fab | HER2 Binding scFv | Human IgG1 Fc | Chain A | Chain B | Chain C |
|---|---|---|---|---|---|---|
| A49-F3'-TriNKET-Trastuzumab | A49 | Trastuzumab | EW-RVT | SEQ ID NO: 141 | SEQ ID NO: 140 | SEQ ID NO: 142 |
| A49-F3'-KiH-TriNKET-Trastuzumab | A49 | Trastuzumab | KIH | SEQ ID NO: 147 | SEQ ID NO: 146 | SEQ ID NO: 142 |
| A49-F3'-TriNKET-Pertuzumab | A49 | Pertuzumab | EW-RVT | SEQ ID NO: 141 | SEQ ID NO: 190 | SEQ ID NO: 142 |
| A49-F3'-KiH-TriNKET-Pertuzumab | A49 | Pertuzumab | KIH | SEQ ID NO: 147 | SEQ ID NO: 191 | SEQ ID NO: 142 |
| A49-F3'-TriNKET-MGAH22 | A49 | MGAH22 | EW-RVT | SEQ ID NO: 141 | SEQ ID NO: 192 | SEQ ID NO: 142 |
| A49-F3'-KiH-TriNKET-MGAH22 | A49 | MGAH22 | KIH | SEQ ID NO: 147 | SEQ ID NO: 193 | SEQ ID NO: 142 |
| A49MI-F3'-TriNKET-Trastuzumab | A49MI | Trastuzumab | EW-RVT | SEQ ID NO: 145 | SEQ ID NO: 140 | SEQ ID NO: 142 |
| A49MI-F3'-KiH-TriNKET-Trastuzumab | A49MI | Trastuzumab | KIH | SEQ ID NO: 194 | SEQ ID NO: 146 | SEQ ID NO: 142 |
| A49MI-F3'-TriNKET-Pertuzumab | A49MI | Pertuzumab | EW-RVT | SEQ ID NO: 145 | SEQ ID NO: 190 | SEQ ID NO: 142 |
| A49MI-F3'-KiH-TriNKET-Pertuzumab | A49MI | Pertuzumab | KIH | SEQ ID NO: 194 | SEQ ID NO: 191 | SEQ ID NO: 142 |
| A49MI-F3'-TriNKET-MGAH22 | A49MI | MGAH22 | EW-RVT | SEQ ID NO: 145 | SEQ ID NO: 192 | SEQ ID NO: 142 |

TABLE 11-continued

| TriNKET Construct | NKG2D Binding Fab | HER2 Binding scFv | Human IgG1 Fc | Chain A | Chain B | Chain C |
|---|---|---|---|---|---|---|
| A49MI-F3'-KiH-TriNKET-MGAH22 | A49MI | MGAH22 | KIH | SEQ ID NO: 194 | SEQ ID NO: 193 | SEQ ID NO: 142 |
| A44-F3'-TriNKET-Trastuzumab | A44 | Trastuzumab | EW-RVT | SEQ ID NO: 155 | SEQ ID NO: 140 | SEQ ID NO: 149 |
| A44-F3'-KiH-TriNKET-Trastuzumab | A44 | Trastuzumab | KIH | SEQ ID NO: 148 | SEQ ID NO: 146 | SEQ ID NO: 149 |
| A44-F3'-TriNKET-Pertuzumab | A44 | Pertuzumab | EW-RVT | SEQ ID NO: 155 | SEQ ID NO: 190 | SEQ ID NO: 149 |
| A44-F3'-KiH-TriNKET-Pertuzumab | A44 | Pertuzumab | KIH | SEQ ID NO: 148 | SEQ ID NO: 191 | SEQ ID NO: 149 |
| A44-F3'-TriNKET-MGAH22 | A44 | MGAH22 | EW-RVT | SEQ ID NO: 155 | SEQ ID NO: 192 | SEQ ID NO: 149 |
| A44-F3'-KiH-TriNKET-MGAH22 | A44 | MGAH22 | KIH | SEQ ID NO: 148 | SEQ ID NO: 193 | SEQ ID NO: 149 |

In certain embodiments, the multi-specific binding protein of the present disclosure comprises a first polypeptide chain, a second polypeptide chain, and a third polypeptide chain, wherein the first, second, and third polypeptide chains comprise the amino acid sequences of Chain A, Chain B, and Chain C, respectively, of a TriNKET disclosed in Table 11. In certain embodiments, the first, second, and third polypeptide chains consist of the amino acid sequences of Chain A, Chain B, and Chain C, respectively, of a TriNKET disclosed in Table 11.

In an exemplary embodiment, the Fc domain linked to the NKG2D-binding Fab fragment comprises the mutations of Q347R, D399V, and F405T, and the Fc domain linked to the HER2 scFv comprises matching mutations K360E and K409W for forming a heterodimer. In another exemplary embodiment, the Fc domain linked to the NKG2D-binding Fab fragment comprises knob mutations T366S, L368A, and Y407V, and the Fc domain linked to the HER2-binding scFv comprises a "hole" mutation T366W. In an exemplary embodiment, the Fc domain linked to the NKG2D-binding Fab fragment includes an S354C substitution in the CH3 domain, which forms a disulfide bond with a Y349C substitution on the Fc linked to the HER2-binding scFv.

Specific TriNKETs and their polypeptide chains are described in more detail below. In the amino acid sequences, $(G_4S)_4$ (SEQ ID NO: 143) and Ala-Ser linkers are bold-underlined: Cys residues in scFv that form disulfide bridges are bold-italic-underlined: Fc heterodimerization mutations are bold-underlined; and CDR sequences under Kabat are underlined.

For example, a TriNKET of the present disclosure is A49-F3'-TriNKET-Trastuzumab. A49-F3'-TriNKET-Trastuzumab includes a single-chain variable fragment (scFv) (SEQ ID NO:139) derived from trastuzumab that binds HER2, linked via a hinge comprising Ala-Ser to an Fc domain; and an NKG2D-binding Fab fragment derived from A49 including a heavy chain portion comprising a heavy chain variable domain (SEQ ID NO: 94) and a CH1 domain, and a light chain portion comprising a light chain variable domain (SEQ ID NO:98) and a light chain constant domain, wherein the heavy chain variable domain is connected to the CH1 domain, and the CH1 domain is connected to the Fc domain. A49-F3'-TriNKET-Trastuzumab includes three polypeptides, having the sequences of SEQ ID NO: 140, SEQ ID NO:141, and SEQ ID NO: 142.

SEQ ID NO:140 represents the full sequence of the HER2-binding scFv linked to an Fc domain via a hinge comprising Ala-Ser (scFv-Fc). The Fc domain linked to the scFv includes Q347R, D399V, and F405T substitutions for heterodimerization and an S354C substitution for forming a disulfide bond with a Y349C substitution in SEQ ID NO: 141 as described below. The scFv (SEQ ID NO:139) includes a heavy chain variable domain of trastuzumab connected to the N-terminus of a light chain variable domain of trastuzumab via a $(G_4S)_4$ linker (SEQ ID NO:143), the scFv represented as VL-$(G_4S)_4$-VH ("$(G_4S)_4$" is represented by SEQ ID NO:143). The heavy and the light variable domains of the scFv are also connected through a disulfide bridge between C100 of VL and C44 of VH, as a result of Q100C and G44C substitutions in the VL and VH, respectively.

Trastuzumab scFv (SEQ ID NO: 139)
DIQMTQSPSSLSASVGDRVTITCRASQDVNTAVAWYQQKPGKAPKLLIY
SASFLYSGVPSRFSGSRSGTDFTLTISSLQPEDFATYYCQQHYTTPPTF
G*C*GTKVEIKGGGGSGGGGSGGGGSGGGGSEVQLVESGGGLVQPGGSLRL
SCAASGFNIKDTYIHWVRQAPGK*C*LEWVARIYPTNGYTRYADSVKGRFT
ISADTSKNTAYLQMNSLRAEDTAVYYCSRWGGDGFYAMDYWGQGTLVTV
SS Trastuzumab scFv-Fc (RVT)

(SEQ ID NO: 140)
DIQMTQSPSSLSASVGDRVTITCRASQDVNTAVAWYQQKPGKAPKLLIY
SASFLYSGVPSRFSGSRSGTDFTLTISSLQPEDFATYYCQQHYTTPPTF
G*C*GTKVEIKGGGGSGGGGSGGGGSGGGGSEVQLVESGGGLVQPGGSLRL
SCAASGFNIKDTYIHWVRQAPGK*C*LEWVARIYPTNGYTRYADSVKGRFT
ISADTSKNTAYLQMNSLRAEDTAVYYCSRWGGDGFYAMDYWGQGTLVTV
SSASDKTHTCPPCPAPELLGGPSVFLFPPKPKDTLMISRTPEVTCVVVD
VSHEDPEVKENWYVDGVEVHNAKTKPREEQYNSTYRVVSVLTVLHQDWL
NGKEYKCKVSNKALPAPIEKTISKAKGQPREPRVYTLPPCRDELTKNQV
SLTCLVKGFYPSDIAVEWESNGQPENNYKTTPPVLVSDGSFTLYSKLTV
DKSRWQQGNVFSCSVMHEALHNHYTQKSLSLSPG

SEQ ID NO:141 represents the heavy chain portion of the Fab fragment, which comprises a heavy chain variable domain (SEQ ID NO:94) of an NKG2D-binding site and a CH1 domain, connected to an Fc domain. The Fc domain in SEQ ID NO:141 includes a Y349C substitution in the CH3 domain, which forms a disulfide bond with an S354C substitution on the Fc linked to the HER2-binding scFv (SEQ ID NO: 140). In SEQ ID NO: 141, the Fc domain also includes K360E and K409W substitutions for heterodimerization with the Fc in SEQ ID NO:140.

A49 VH (SEQ ID NO: 94)
EVQLVESGGGLVKPGGSLRLSCAASGFTFSSYSMNWVRQAPGKGLEWVS
SISSSSSYIYYADSVKGRFTISRDNAKNSLYLQMNSLRAEDTAVYYCAR
GAPMGAAAGWFDPWGQGTLVTVSS

A49 VH-CH1-Fc (EW)

(SEQ ID NO: 141)
EVQLVESGGGLVKPGGSLRLSCAASGFTFSSYSMNWVRQAPGKGLEWVS
SISSSSSYIYYADSVKGRFTISRDNAKNSLYLQMNSLRAEDTAVYYCAR
GAPMGAAAGWFDPWGQGTLVTVSSASTKGPSVFPLAPSSKSTSGGTAAL
GCLVKDYFPEPVTVSWNSGALTSGVHTFPAVLQSSGLYSLSSVVTVPSS
SLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKT

-continued
KPREEQYNSTYRVVSVLTVLHQDWLNGKEYKCKVSNKALPAPIEKTISK
AKGQPREPQVCTLPPSRDELTENQVSLTCLVKGFYPSDIAVEWESNGQP
ENNYKTTPPVLDSDGSFFLYSWLTVDKSRWQQGNVFSCSVMHEALHNHY
TQKSLSLSPG SEQ ID NO: 142 represents the light chain portion of the Fab fragment comprising a light chain variable domain (SEQ ID NO:98) of an NKG2D-binding site and a light chain constant domain.

A49 VL
(SEQ ID NO: 98)
DIQMTQSPSSVSASVGDRVTITCRASQGISSWLAWYQQKPGKAPKLLIY
AASSLQSGVPSRFSGSGSGTDFTLTISSLQPEDFATYYCQQGVSFPRTF
GGGTKVEIK

A49 VL-LC
(SEQ ID NO: 142)
DIQMTQSPSSVSASVGDRVTITCRASQGISSWLAWYQQKPGKAPKLLIY
AASSLQSGVPSRFSGSGSGTDFTLTISSLQPEDFATYYCQQGVSFPRTF
GGGTKVEIKRTVAAPSPPSDEQLKSGTASVVCLLNNFYPREAKVQWKVD
NALQSGNSQESVTEQDSKDSTYSLSSTLTLSKADYEKHKVYACEVTHQG
LSSPVTKSFNRGEC

Another TriNKET of the present disclosure is A49MI-F3'-TriNKET-Trastuzumab. A49MI-F3'-TriNKET-Trastuzumab includes the same Her2-binding scFv (SEQ ID NO:139) as in A49-F3'-TriNKET-Trastuzumab linked via a hinge comprising Ala-Ser to an Fc domain; and an NKG2D-binding Fab fragment derived from A49MI including a heavy chain portion comprising a heavy chain variable domain (SEQ ID NO:144) and a CH1 domain, and a light chain portion comprising a light chain variable domain (SEQ ID NO:98) and a light chain constant domain, wherein the heavy chain variable domain is connected to the CH1 domain, and the CH1 domain is connected to the Fc domain. A49MI-F3'-TriNKET-Trastuzumab includes three polypeptides, having the sequences of SEQ ID NO: 140 (as in A49-F3'-TriNKET-Trastuzumab), SEQ ID NO: 145, and SEQ ID NO:142 (as in A49-F3'-TriNKET-Trastuzumab).

SEQ ID NO:145 represents a heavy chain portion of the Fab fragment, which comprises a heavy chain variable domain (SEQ ID NO:144) of an NKG2D-binding site and a CH1 domain, connected to an Fc domain. In SEQ ID NO:144, wherein a methionine in the CDR3 of SEQ ID NO:94 has been substituted by isoleucine (M→I substitution; shown within a third bracket [ ] in SEQ ID NO:144 and SEQ ID NO: 145). The Fc domain in SEQ ID NO: 145 includes a Y349C substitution in the CH3 domain, which forms a disulfide bond with an S354C substitution in the Fc linked to the HER2-binding scFv (SEQ ID NO:140). In SEQ ID NO:145, the Fc domain also includes K360E and K409W substitutions.

A49MI VH
(SEQ ID NO: 144)
EVQLVESGGGLVKPGGSLRLSCAASGFTFSSYSMNWVRQAPGKGLEWVS
SISSSSSYIYYADSVKGRFTISRDNAKNSLYLQMNSLRAEDTAVYYCAR
GAP[I]GAAAGWEDPWGQGTLVTVSS

A49MI VH-CH1-Fc (EW)
(SEQ ID NO: 145)
EVQLVESGGGLVKPGGSLRLSCAASGFTFSSYSMNWVRQAPGKGLEWVS
SISSSSSYIYYADSVKGRFTISRDNAKNSLYLQMNSLRAEDTAVYYCAR
GAP[I]GAAAGWFDPWGQGTLVTVSSASTKGPSVFPLAPSSKSTSGGTA
ALGCLVKDYFPEPVTVSWNSGALTSGVHTFPAVLQSSGLYSLSSVVTVP
SSSLGTQTYICNVNHKPSNTKVDKKVEPKSCDKTHTCPPCPAPELLGGP
SVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTI

-continued
SKAKGQPREPQVCTLPPSRDELTENQVSLTCLVKGFYPSDIAVEWESNG
QPENNYKTTPPVLDSDGSFFLYSWLTVDKSRWQQGNVFSCSVMHEALHN
HYTQKSLSLSPG Another TriNKET of the present disclosure is A49-F3'-KiH-TriNKET-Trastuzumab. KiH refers to the knobs-into-holes (KiH) Fc technology, which involves engineering of the CH3 domains to create either a "knob" or a "hole" in each heavy chain to promote heterodimerization. The concept behind the KiH Fc technology was to introduce a "knob" in one CH3 domain (CH3A) by substitution of a small residue with a bulky one (e.g., T366WCH3A in EU numbering). To accommodate the "knob," a complementary "hole" surface was created on the other CH3 domain (CH3B) by replacing the closest neighboring residues to the knob with smaller ones (e.g., T366S/L368A/Y407V$_{CH3B}$). The "hole" mutation was optimized by structured-guided phage library screening (Atwell S, Ridgway J B, Wells J A, Carter P., Stable heterodimers from remodeling the domain interface of a homodimer using a phage display library, *J. Mol. Biol.* (1997) 270 (1): 26-35). X-ray crystal structures of KiH Fc variants (Elliott J M, Ultsch M, Lee J, Tong R, Takeda K, Spiess C, et al., Antiparallel conformation of knob and hole aglycosylated half-antibody homodimers is mediated by a CH2-CH3 hydrophobic interaction. *J. Mol. Biol.* (2014) 426 (9): 1947-57; Mimoto F, Kadono S, Katada H, Igawa T, Kamikawa T, Hattori K. Crystal structure of a novel asymmetrically engineered Fc variant with improved affinity for FcγRs. *Mol. Immunol.* (2014) 58 (1): 132-8) demonstrated that heterodimerization is thermodynamically favored by hydrophobic interactions driven by steric complementarity at the inter-CH3 domain core interface, whereas the knob-knob and the hole-hole interfaces do not favor homodimerization owing to steric hindrance and disruption of the favorable interactions, respectively.

A49-F3'-KiH-TriNKET-Trastuzumab includes the same Her2-binding scFv (SEQ ID NO: 139) as in A49-F3'-TriNKET-Trastuzumab linked via a hinge comprising Ala-Ser to an Fc domain comprising the "hole" substitutions of T366S, L368A, and Y407V; and the same NKG2D-binding Fab fragment as in A49-F3'-TriNKET-Trastuzumab, the CH1 domain of which is connected to an Fc domain comprising the "knob" substitution of T366W. A49-F3'-KiH-TriNKET-Trastuzumab includes three polypeptides, having the sequences of SEQ ID NO: 146, SEQ ID NO:147, and SEQ ID NO: 142 (as in A49-F3'-TriNKET-Trastuzumab).

SEQ ID NO: 146 represents the full sequence of the HER2-binding scFv (SEQ ID NO: 139) linked to an Fc domain via a hinge comprising Ala-Ser (scFv-Fc). The Fc domain linked to the scFv includes T366S, L368A, and Y407V substitutions for heterodimerization and an S354C substitution for forming a disulfide bond with a Y349C substitution in SEQ ID NO: 147 as described below.

Trastuzumab scFv-Fc (KiH)
(SEQ ID NO: 146)
DIQMTQSPSSLSASVGDRVTITCRASQDVNTAVAWYQQKPGKAPKLLIY

SASFLYSGVPSRFSGSRSGTDFTLTISSLOPEDFATYYCQQHYTTPPTF

GCGTKVEIKGGGGSGGGGSGGGGSGGGGSEVQLVESGGGLVQPGGSLRL

SCAASGFNIKDTYIHWVRQAPGKCLEWVARIYPTNGYTRYADSVKGRFT

ISADTSKNTAYLQMNSLRAEDTAVYYCSRWGGDGFYAMDYWGQGTLVTV

SSASDKTHTCPPCPAPELLGGPSVFLFPPKPKDTLMISRTPEVTCVVVD

-continued
VSHEDPEVKFNWYVDGVEVHNAKTKPREEQYNSTYRVVSVLTVLHQDWL

NGKEYKCKVSNKALPAPIEKTISKAKGQPREPQVCTLPPSRDELTKNQV

SLSCAVKGFYPSDIAVEWESNGQPENNYKTTPPVLDSDGSFFLVSKLTV

DKSRWQQGNVFSCSVMHEALHNHYTQKSLSLSPG

SEQ ID NO:147 represents the heavy chain portion of a Fab fragment, which comprises a heavy chain variable domain (SEQ ID NO:94) of an NKG2D-binding site derived from A49 and a CH1 domain, connected to an Fc domain. The Fc domain in SEQ ID NO: 147 includes an S354C substitution, which forms a disulfide bond with a Y349C substitution in the CH3 domain of the Fc linked to the HER2-binding scFv (SEQ ID NO: 146). In SEQ ID NO:147, the Fc domain also includes a T366W substitution.

A49 VH-CH1-Fc (KiH)
(SEQ ID NO: 147)
EVQLVESGGGLVKPGGSLRLSCAASGFTFSSYSMNWVRQAPGKGLEWVS

SISSSSSYIYYADSVKGRFTISRDNAKNSLYLQMNSLRAEDTAVYYCAR

GAPMGAAAGWFDPWGQGTLVTVSSASTKGPSVFPLAPSSKSTSGGTAAL

GCLVKDYFPEPVTVSWNSGALTSGVHTFPAVLQSSGLYSLSSVVTVPSS

SLGTQTYICNVNHKPSNTKVDKKVEPKSCDKTHTCPPCPAPELLGGPSV

FLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISK

AKGQPREPQVYTLPPCRDELTKNQVSLWCLVKGFYPSDIAVEWESNGQP

ENNYKTTPPVLDSDGSFFLYSKLTVDKSRWQQGNVFSCSVMHEALHNHY

TQKSLSLSPG

Another TriNKET of the present disclosure is A49MI-F3'-KiH-TriNKET-Trastuzumab. A49MI-F3'-KiH-TriNKET-Trastuzumab includes the same Her2-binding scFv (SEQ ID NO:139) as in A49-F3'-TriNKET-Trastuzumab linked via a hinge comprising Ala-Ser to an Fc domain comprising the "hole" substitutions of T366S, L368A, and Y407V; and the same NKG2D-binding Fab fragment as in A49MI-F3'-TriNKET-Trastuzumab, the CH1 domain of which is connected to an Fc domain comprising the "knob" substitution of T366W. A49MI-F3'-KiH-TriNKET-Trastuzumab includes three polypeptides, having the sequences of SEQ ID NO: 146 (as in A49-F3'-KiH-TriNKET-Trastuzumab), SEQ ID NO: 194, and SEQ ID NO: 142 (as in A49-F3'-TriNKET-Trastuzumab).

SEQ ID NO:194 represents the heavy chain portion of a Fab fragment, which comprises a heavy chain variable domain (SEQ ID NO: 144) of an NKG2D-binding site derived from A49MI and a CH1 domain, connected to an Fc domain. The Fc domain in SEQ ID NO: 194 includes an S354C substitution, which forms a disulfide bond with a Y349C substitution in the CH3 domain of the Fc linked to the HER2-binding scFv (SEQ ID NO: 146). In SEQ ID NO:194, the Fc domain also includes a T366W substitution.

A49MI VH-CH1-Fc (KiH)
(SEQ ID NO: 194)
EVQLVESGGGLVKPGGSLRLSCAASGFTFSSYSMNWVRQAPGKGLEWVS

SISSSSSYIYYADSVKGRFTISRDNAKNSLYLQMNSLRAEDTAVYYCAR

-continued
GAPIGAAAGWFDPWGQGTLVTVSSASTKGPSVFPLAPSSKSTSGGTAAL

GCLVKDYFPEPVTVSWNSGALTSGVHTFPAVLQSSGLYSLSSVVTVPSS

SLGTQTYICNVNHKPSNTKVDKKVEPKSCDKTHTCPPCPAPELLGGPSV

FLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISK

AKGQPREPQVYTLPPCRDELTKNQVSLWCLVKGFYPSDIAVEWESNGQP

ENNYKTTPPVLDSDGSFFLYSKLTVDKSRWQQGNVFSCSVMHEALHNHY

TQKSLSLSPG

Another exemplary TriNKET of the present disclosure is A44-F3'-TriNKET-Trastuzumab. A44-F3'-TriNKET-Trastuzumab includes the same Her2-binding scFv (SEQ ID NO: 139) as in A49-F3'-TriNKET-Trastuzumab linked via a hinge comprising Ala-Ser to an Fc domain; and an NKG2D-binding Fab fragment derived from A44 including a heavy chain portion comprising a heavy chain variable domain (SEQ ID NO:86) and a CH1 domain, and a light chain portion comprising a light chain variable domain (SEQ ID NO:90) and a light chain constant domain, wherein the heavy chain variable domain is connected to the CH1 domain, and the CH1 domain is connected to the Fc domain. A44-F3'-TriNKET-Trastuzumab includes three polypeptides, having the sequences of SEQ ID NO: 140 (as in A49-F3'-TriNKET-Trastuzumab), SEQ ID NO: 155, and SEQ ID NO:149.

SEQ ID NO:155 represents a heavy chain variable domain (SEQ ID NO:86) of an NKG2D-binding site derived from A44, connected to an Fc domain. The Fc domain in SEQ ID NO: 155 includes a Y349C substitution in the CH3 domain, which forms a disulfide bond with an S354C substitution on the Fc linked to the HER2-binding scFv (SEQ ID NO:140). In SEQ ID NO:155, the Fc domain also includes K360E and K409W substitutions.

A44 VH
(SEQ ID NO: 86)
EVQLLESGGGLVQPGGSLRLSCAASGFTFSSYAMSWVRQAPGKGLEWVS

AISGSGGSTYYADSVKGRFTISRDNSKNTLYLQMNSLRAEDTAVYYCAK

DGGYYDSGAGDYWGQGTLVTVSS

A44 VH-CH1-Fc (EW)
(SEQ ID NO: 155)
EVQLLESGGGLVQPGGSLRLSCAASGFTFSSYAMSWVRQAPGKGLEWVS

AISGSGGSTYYADSVKGRFTISRDNSKNTLYLQMNSLRAEDTAVYYCAK

DGGYYDSGAGDYWGQGTLVTVSSASTKGPSVFPLAPSSKSTSGGTAALG

CLVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSVF

LFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKA

KGQPREPQVCTLPPSRDELTENQVSLTCLVKGFYPSDIAVEWESNGQPE

NNYKTTPPVLDSDGSFFLYSWLTVDKSRWQQGNVFSCSVMHEALHNHYT

QKSLSLSPG

SEQ ID NO:149 represents the light chain portion of the Fab fragment comprising a light chain variable domain (SEQ ID NO:90) of an NKG2D-binding site and a light chain constant domain.

A44 VL
(SEQ ID NO: 90)
DIQMTQSPSSVSASVGDRVTITCRASQGIDSWLAWYQQKPGKAPKLLIY

AASSLQSGVPSRFSGSGSGTDFTLTISSLQPEDFATYYCQQGVSYPRTF

GGGTKVEIK

A44 VL-CL (SEQ ID NO: 149)
DIQMTQSPSSVSASVGDRVTITCRASQGIDSWLAWYQQKPGKAPKLLIY
AASSLQSGVPSRFSGSGSGTDFTLTISSLQPEDFATYYCQQGVSYPRTF
GGGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGEC

Another exemplary TriNKET of the present disclosure is A44-F3'-KiH-TriNKET-Trastuzumab. A44-F3'-KiH-TriNKET-Trastuzumab includes the same Her2-binding scFv (SEQ ID NO:139) as in A49-F3'-TriNKET-Trastuzumab linked via a hinge comprising Ala-Ser to an Fc domain comprising the "hole" substitutions of T366S, L368A, and Y407V; and the same NKG2D-binding Fab fragment as in A44-F3'-TriNKET-Trastuzumab, the CH1 domain of which is connected to an Fc domain comprising the "knob" substitution of T366W. A44-F3'-KiH-TriNKET-Trastuzumab includes three polypeptides, having the sequences of SEQ ID NO: 146 (as in A49-F3'-KiH-TriNKET-Trastuzumab), SEQ ID NO: 148, and SEQ ID NO:149 (as in A44-F3'-TriNKET-Trastuzumab).

SEQ ID NO:148 represents a heavy chain variable domain (SEQ ID NO:86) of an NKG2D-binding site derived from A44, connected to an Fc domain. The Fc domain in SEQ ID NO:148 includes a Y349C substitution in the CH3 domain, which forms a disulfide bond with an S354C substitution on the Fc linked to the HER2-binding scFv (SEQ ID NO: 146). In SEQ ID NO:148, the Fc domain also includes a T366W substitution.

A44 VH-CH1-Fc (KiH)

(SEQ ID NO: 148)
EVQLLESGGGLVQPGGSLRLSCAASGFTFSSYAMSWVRQAPGKGLEWVS

AISGSGGSTYYADSVKGRFTISRDNSKNTLYLQMNSLRAEDTAVYYCAK

DGGYYDSGAGDYWGQGTLVTVSSASTKGPSVFPLAPSSKSTSGGTAALG

CLVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSVF

LFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKA

KGQPREPQVYTLPPCRDELTKNQVSLWCLVKGFYPSDIAVEWESNGQPE

NNYKTTPPVLDSDGSFFLYSKLTVDKSRWQQGNVFSCSVMHEALHNHYT

QKSLSLSPG

Another TriNKET of the present disclosure is A49-F3'-TriNKET-Pertuzumab. A49-F3'-TriNKET-Pertuzumab includes an scFv (SEQ ID NO:189) derived from pertuzumab that binds HER2, linked via a hinge comprising Ala-Ser to an Fc domain; and and the same NKG2D-binding Fab fragment as in A49-F3'-TriNKET-Trastuzumab, the CH1 domain of which is connected to an Fc domain. The Fc domain linked to the scFv includes Q347R, D399V, and F405T substitutions, and the Fc domain linked to the Fab fragment includes K360E and K409W substitutions. A49-F3'-TriNKET-Pertuzumab includes three polypeptides, having the sequences of SEQ ID NO: 190, SEQ ID NO: 141 (as in A49-F3'-TriNKET-Trastuzumab), and SEQ ID NO:142 (as in A49-F3'-TriNKET-Trastuzumab).

SEQ ID NO:190 represents the full sequence of the HER2-binding scFv linked to an Fc domain via a hinge comprising Ala-Ser (scFv-Fc). The Fc domain linked to the scFv includes Q347R, D399V, and F405T substitutions for heterodimerization and an S354C substitution for forming a disulfide bond with a Y349C substitution in SEQ ID NO:141 as described above. The scFv (SEQ ID NO:189) includes a heavy chain variable domain of pertuzumab connected to the N-terminus of a light chain variable domain of pertuzumab via a $(G_4S)_4$ linker (SEQ ID NO:143), the scFv represented as VL-$(G_4S)_4$-VH ("$(G_4S)_4$" is represented by SEQ ID NO: 143). The heavy and the light variable domains of the scFv are also connected through a disulfide bridge between C100 of VL and C44 of VH, as a result of Q100C and G44C substitutions in the VL and VH, respectively.

Pertuzumab scFv (SEQ ID NO: 189)
DIQMTQSPSSLSASVGDRVTITCKASQDVSIGVAWYQQKPGKAPKLLIY
SASYRYTGVPSRFSGSGSGTDFTLTISSLQPEDFATYYCQQYYIYPYTF
GCGTKVEIKRGGGGSGGGGSGGGGSGGGGSEVQLVESGGGLVQPGGSLR
LSCAASGFTFTDYTMDWVRQAPGKCLEWVADVNPNSGGSIYNQRFKGRF
TLSVDRSKNTLYLQMNSLRAEDTAVYYCARNLGPSFYFDYWGQGTLVTV
SSA Pertuzumab scFv-Fc (SEQ ID NO: 190)
DIQMTQSPSSLSASVGDRVTITCKASQDVSIGVAWYQQKPGKAPKLLIY
SASYRYTGVPSRFSGSGSGTDFTLTISSLQPEDFATYYCQQYYIYPYTF
GCGTKVEIKRGGGGSGGGGSGGGGSGGGGSEVQLVESGGGLVQPGGSLR
LSCAASGFTFTDYTMDWVRQAPGKCLEWVADVNPNSGGSIYNQRFKGRF
TLSVDRSKNTLYLQMNSLRAEDTAVYYCARNLGPSFYFDYWGQGTLVTV
SSAASDKTHTCPPCPAPELLGGPSVFLFPPKPKDTLMISRTPEVTCVVV
DVSHEDPEVKENWYVDGVEVHNAKTKPREEQYNSTYRVVSVLTVLHQDW
LNGKEYKCKVSNKALPAPIEKTISKAKGQPREPRVYTLPPCRDELTKNQ
VSLTCLVKGFYPSDIAVEWESNGQPENNYKTTPPVLVSDGSFTLYSKLT
VDKSRWQQGNVFSCSVMHEALHNHYTQKSLSLSPG Another exemplary TriNKET of the present disclosure is A49MI-F3'-TriNKET-Pertuzumab. A49MI-F3'-TriNKET-Pertuzumab includes the same Her2-binding scFv (SEQ ID NO: 189) as in A49-F3'-TriNKET-Pertuzumab linked via a hinge comprising Ala-Ser to an Fc domain; and the same NKG2D-binding Fab fragment as in A49MI-F3'-TriNKET-Trastuzumab, the CH1 domain of which is connected to an Fc domain. The Fc domain linked to the scFv includes Q347R, D399V, and F405T substitutions, and the Fc domain linked to the Fab fragment includes K360E and K409W substitutions. A49MI-F3'-TriNKET-Pertuzumab includes three polypeptides, having the sequences of SEQ ID NO:190 (as in A49-F3'-KiH-TriNKET-Pertuzumab), SEQ ID NO:145 (as in A49MI-F3'-TriNKET-Trastuzumab), and SEQ ID NO: 142 (as in A49-F3'-TriNKET-Trastuzumab).

Another exemplary TriNKET of the present disclosure is A49-F3'-KiH-TriNKET-Pertuzumab. A49-F3'-KiH-TriNKET-Pertuzumab includes the same Her2-binding scFv (SEQ ID NO:189) as in A49-F3'-TriNKET-Pertuzumab linked via a hinge comprising Ala-Ser to an Fc domain; and the same NKG2D-binding Fab fragment as in A49-F3'-TriNKET-Trastuzumab, the CH1 domain of which is connected to an Fc domain. The Fc domain linked to the scFv includes the "hole" substitutions of T366S, L368A, and Y407V, and the Fc domain linked to the Fab fragment includes the "knob" substitution of T366W. A49-F3'-KiH-TriNKET-Pertuzumab includes three polypeptides, having the sequences of SEQ ID NO: 191, SEQ ID NO: 147 (as in A49-F3'-KiH-TriNKET-Trastuzumab), and SEQ ID NO: 142 (as in A49-F3'-TriNKET-Trastuzumab).

SEQ ID NO: 191 represents the full sequence of the HER2-binding scFv (SEQ ID NO: 189) linked to an Fc domain via a hinge comprising Ala-Ser (scFv-Fc). The Fc domain linked to the scFv includes T366S, L368A, and Y407V substitutions for heterodimerization and an S354C substitution for forming a disulfide bond with a Y349C substitution in SEQ ID NO: 191 as described above.

```
Pertuzumab scFv-Fc (KiH)
                                        (SEQ ID NO: 191)
DIQMTQSPSSLSASVGDRVTITCKASQDVSIGVAWYQQKPGKAPKLLIY

SASYRYTGVPSRFSGSGSGTDFTLTISSLOPEDFATYYCQQYYIYPYTF

GCGTKVEIKRGGGGSGGGGGGGGSGGGGSEVQLVESGGGLVQPGGSLRL

SCAASGFTFTDYTMDWVRQAPGKCLEWVADVNPNSGGSIYNQRFKGRFT

LSVDRSKNTLYLQMNSLRAEDTAVYYCARNLGPSFYFDYWGQGTLVTVS

SAASDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWL

NGKEYKCKVSNKALPAPIEKTISKAKGQPREPQVCTLPPSRDELTKNQV

SLSCAVKGFYPSDIAVEWESNGQPENNYKTTPPVLDSDGSFFLVSKLTV

DKSRWQQGNVFSCSVMHEALHNHYTQKSLSLSPG
```

Another exemplary TriNKET of the present disclosure is A49MI-F3'-KiH-TriNKET-Pertuzumab. A49MI-F3'-KiH-TriNKET-Pertuzumab includes the same Her2-binding scFv (SEQ ID NO:189) as in A49-F3'-TriNKET-Pertuzumab linked via a hinge comprising Ala-Ser to an Fc domain; and the same NKG2D-binding Fab fragment as in A49MI-F3'-TriNKET-Trastuzumab, the CH1 domain of which is connected to an Fc domain. The Fc domain linked to the scFv includes the "hole" substitutions of T366S, L368A, and Y407V, and the Fc domain linked to the Fab fragment includes the "knob" substitution of T366W. A49MI-F3'-KiH-TriNKET-Pertuzumab includes three polypeptides, having the sequences of SEQ ID NO: 191 (as in A49-F3'-KiH-TriNKET-Pertuzumab), SEQ ID NO:194 (as in A49MI-F3'-KiH-TriNKET-Trastuzumab), and SEQ ID NO:142 (as in A49-F3'-TriNKET-Trastuzumab).

Another exemplary TriNKET of the present disclosure is A44-F3'-TriNKET-Pertuzumab. A44-F3'-TriNKET-Pertuzumab includes the same Her2-binding scFv (SEQ ID NO: 189) as in A49-F3'-TriNKET-Pertuzumab linked via a hinge comprising Ala-Ser to an Fc domain; and the same NKG2D-binding Fab fragment as in A44-F3'-TriNKET-Trastuzumab, the CH1 domain of which is connected to an Fc domain. The Fc domain linked to the scFv includes Q347R, D399V, and F405T substitutions, and the Fc domain linked to the Fab fragment includes K360E and K409W substitutions. A44-F3'-TriNKET-Pertuzumab includes three polypeptides, having the sequences of SEQ ID NO: 190 (as in A49-F3'-KiH-TriNKET-Pertuzumab), SEQ ID NO:155 (as in A44-F3'-TriNKET-Trastuzumab), and SEQ ID NO: 149 (as in A44-F3'-TriNKET-Trastuzumab).

Another exemplary TriNKET of the present disclosure is A44-F3'-KiH-TriNKET-Pertuzumab. A44-F3'-KiH-TriNKET-Pertuzumab includes the same Her2-binding scFv (SEQ ID NO:189) as in A49-F3'-TriNKET-Pertuzumab linked via a hinge comprising Ala-Ser to an Fc domain; and the same NKG2D-binding Fab fragment as in A44-F3'-TriNKET-Trastuzumab, the CH1 domain of which is connected to an Fc domain. The Fc domain linked to the scFv includes the "hole" substitutions of T366S, L368A, and Y407V, and the Fc domain linked to the Fab fragment includes the "knob" substitution of T366W. A44-F3'-KiH-TriNKET-Pertuzumab includes three polypeptides, having the sequences of SEQ ID NO: 191 (as in A49-F3'-KiH-TriNKET-Pertuzumab), SEQ ID NO: 148 (as in A44-F3'-KiH-TriNKET-Trastuzumab), and SEQ ID NO: 149 (as in A44-F3'-TriNKET-Trastuzumab).

Another TriNKET of the present disclosure is A49-F3'-TriNKET-MGAH22. A49-F3'-TriNKET-MGAH22 includes an scFv (SEQ ID NO: 171) derived from MGAH22 that binds HER2, linked via a hinge comprising Ala-Ser to an Fc domain; and the same NKG2D-binding Fab fragment as in A49-F3'-TriNKET-Trastuzumab, the CH1 domain of which is connected to an Fc domain. The Fc domain linked to the scFv includes Q347R, D399V, and F405T substitutions, and the Fc domain linked to the Fab fragment includes K360E and K409W substitutions. A49-F3'-TriNKET-MGAH22 includes three polypeptides, having the sequences of SEQ ID NO: 192, SEQ ID NO: 141 (as in A49-F3'-TriNKET-Trastuzumab), and SEQ ID NO: 142 (as in A49-F3'-TriNKET-Trastuzumab).

SEQ ID NO: 192 represents the full sequence of the HER2-binding scFv linked to an Fc domain via a hinge comprising Ala-Ser (scFv-Fc). The Fc domain linked to the scFv includes Q347R, D399V, and F405T substitutions for heterodimerization and an S354C substitution for forming a disulfide bond with a Y349C substitution in SEQ ID NO:141 as described above. The scFv (SEQ ID NO:171) includes a heavy chain variable domain of pertuzumab connected to the N-terminus of a light chain variable domain of pertuzumab via a (G$_4$S)$_4$ linker (SEQ ID NO:143), the scFv represented as VL-(G$_4$S)$_4$-VH ("(G$_4$S)$_4$" is represented by SEQ ID NO: 143). The heavy and the light variable domains of the scFv are also connected through a disulfide bridge between C100 of VL and C44 of VH, as a result of G100C and G44C substitutions in the VL and VH, respectively.

```
MGAH22 scFv
                                        (SEQ ID NO: 171)
DIVMTQSHKFMSTSVGDRVSITCKASQDVNTAVAWYQQKPGHSPKLLIY
SASFRYTGVPDRFTGSRSGTDFTFTISSVQAEDLAVYYCQQHYTTPPTF
GCGTKVEIKRGGGGSGGGGSGGGGSGGGGSQVQLQQSGPELVKPGASLK
LSCTASGFNIKDTYIHWVKQRPEQCLEWIGRIYPTNGYTRYDPKFQDKA
TITADTSSNTAYLQVSRLTSEDTAVYYCSRWGGDGFYAMDYWGQGASVT
VSSA

MGAH22 scFv-Fc
                                        (SEQ ID NO: 192)
DIVMTQSHKFMSTSVGDRVSITCKASQDVNTAVAWYQQKPGHSPKLLIY
SASFRYTGVPDRFTGSRSGTDFTFTISSVQAEDLAVYYCQQHYTTPPTF
GCGTKVEIKRGGGGSGGGGSGGGGSGGGGSQVQLQQSGPELVKPGASLK
LSCTASGFNIKDTYIHWVKQRPEQCLEWIGRIYPTNGYTRYDPKFQDKA
TITADTSSNTAYLQVSRLTSEDTAVYYCSRWGGDGFYAMDYWGQGASVT
VSSAASDKTHTCPPCPAPELLGGPSVFLFPPKPKDTLMISRTPEVTCVV
VDVSHEDPEVKFNWYVDGVEVHNAKTKPREEQYNSTYRVVSVLTVLHQD
WLNGKEYKCKVSNKALPAPIEKTISKAKGQPREPRVYTLPPCRDELTKN
QVSLTCLVKGFYPSDIAVEWESNGQPENNYKTTPPVLVSDGSFTLYSKL
TVDKSRWQQGNVFSCSVMHEALHNHYTQKSLSLSPG
```

Another TriNKET of the present disclosure is A49MI-F3'-TriNKET-MGAH22. A49MI-F3'-TriNKET-MGAH22 includes the same Her2-binding scFv (SEQ ID NO:171) as in A49-F3'-TriNKET-MGAH22 linked via a hinge comprising Ala-Ser to an Fc domain; and the same NKG2D-binding Fab fragment as in A49MI-F3'-TriNKET-Trastuzumab, the CH1 domain of which is connected to an Fc domain. The Fc domain linked to the scFv includes Q347R, D399V, and F405T substitutions, and the Fc domain linked to the Fab fragment includes K360E and K409W substitutions. A49MI-F3'-KiH-TriNKET-MGAH22 includes three polypeptides, having the sequences of SEQ ID NO: 192 (as in A49-F3'-TriNKET-MGAH22), SEQ ID NO: 145 (as in A49MI-F3'-TriNKET-Trastuzumab), and SEQ ID NO: 142 (as in A49-F3'-TriNKET-Trastuzumab).

Another TriNKET of the present disclosure is A49-F3'-KiH-TriNKET-MGAH22. A49-F3'-KiH-TriNKET-MGAH22 includes the same Her2-binding scFv (SEQ ID NO: 171) as in A49-F3'-TriNKET-MGAH22 linked via a hinge comprising Ala-Ser to an Fc domain; and the same NKG2D-binding Fab fragment as in A49-F3'-TriNKET-Trastuzumab, the CH1 domain of which is connected to an Fc domain. The Fc domain linked to the scFv includes the "hole" substitutions of T366S, L368A, and Y407V, and the Fc domain linked to the Fab fragment includes the "knob" substitution of T366W. A49-F3'-KiH-TriNKET-MGAH22 includes three polypeptides, having the sequences of SEQ ID NO: 193, SEQ ID NO: 147 (as in A49-F3'-KiH-TriNKET-Trastuzumab), and SEQ ID NO: 142 (as in A49-F3'-TriNKET-Trastuzumab).

SEQ ID NO: 193 represents the full sequence of the HER2-binding scFv (SEQ ID NO: 171) linked to an Fc domain via a hinge comprising Ala-Ser (scFv-Fc). The Fc domain linked to the scFv includes T366S, L368A, and Y407V substitutions for heterodimerization and an S354C substitution for forming a disulfide bond with a Y349C substitution in SEQ ID NO: 147 as described above.

MGAH22 scFv-Fc (KiH)
(SEQ ID NO: 193)
DIVMTQSHKFMSTSVGDRVSITCKAS<u>QDVNTAVAWY</u>QQKPGHSPKLLIY

<u>SASFRYTGVPDRFTGSRSGTDFTFTISSVQAEDLAVYYC<u>QQHYTTPPTF</u>

G<u>C</u>GTKVEIKRGGGGSGGGGSGGGGSGGGGSQVQLQQSGPELVKPGASLK

LSCTASG<u>FNIKDTYIHWVKQRPEQ<u>C</u>LEWIGRI<u>YPTNGY</u>TRYDPKFQDKA

TITADTSSNTAYLQVSRLTSEDTAVYYC<u>SRWGGDGFYAMDY</u>WGQGASVT

VSSAASDKTHTCPPCPAPELLGGPSVFLFPPKPKDTLMISRTPEVTCVV

VDVSHEDPEVKFNWYVDGVEVHNAKTKPREEQYNSTYRVVSVLTVLHQD

WLNGKEYKCKVSNKALPAPIEKTISKAKGQPREPQV<u>C</u>TLPPSRDELTKN

QVSL<u>SC</u>AVKGFYPSDIAVEWESNGQPENNYKTTPPVLDSDGSFFL<u>V</u>SKL

TVDKSRWQQGNVFSCSVMHEALHNHYTQKSLSLSPG

Another exemplary TriNKET of the present disclosure is A49MI-F3'-KiH-TriNKET-MGAH22. A49MI-F3'-KiH-TriNKET-MGAH22 includes the same Her2-binding scFv (SEQ ID NO:171) as in A49-F3'-TriNKET-MGAH22 linked via a hinge comprising Ala-Ser to an Fc domain; and the same NKG2D-binding Fab fragment as in A49MI-F3'-TriNKET-Trastuzumab, the CH1 domain of which is connected to an Fc domain. The Fc domain linked to the scFv includes the "hole" substitutions of T366S, L368A, and Y407V, and the Fc domain linked to the Fab fragment includes the "knob" substitution of T366W. A49MI-F3'-KiH-TriNKET-MGAH22 includes three polypeptides, having the sequences of SEQ ID NO: 193 (as in A49-F3'-KiH-TriNKET-MGAH22), SEQ ID NO: 194 (as in A49MI-F3'-KiH-TriNKET-Trastuzumab), and SEQ ID NO: 142 (as in A49-F3'-TriNKET-Trastuzumab).

Another exemplary TriNKET of the present disclosure is A44-F3'-TriNKET-MGAH22. A44-F3'-TriNKET-MGAH22 includes the same Her2-binding scFv (SEQ ID NO: 171) as in A49-F3'-TriNKET-MGAH22 linked via a hinge comprising Ala-Ser to an Fc domain; and the same NKG2D-binding Fab fragment as in A44-F3'-TriNKET-Trastuzumab, the CH1 domain of which is connected to an Fc domain. The Fc domain linked to the scFv includes Q347R, D399V, and F405T substitutions, and the Fc domain linked to the Fab fragment includes K360E and K409W substitutions. A44-F3'-TriNKET-MGAH22 includes three polypeptides, having the sequences of SEQ ID NO: 192 (as in A49-F3'-TriNKET-MGAH22), SEQ ID NO: 155 (as in A44-F3'-TriNKET-Trastuzumab), and SEQ ID NO:149 (as in A44-F3'-TriNKET-Trastuzumab).

Another exemplary TriNKET of the present disclosure is A44-F3'-KiH-TriNKET-MGAH22. A44-F3'-KiH-TriNKET-MGAH22 includes the same Her2-binding scFv (SEQ ID NO:171) as in A49-F3'-TriNKET-MGAH22 linked via a hinge comprising Ala-Ser to an Fc domain; and the same NKG2D-binding Fab fragment as in A44-F3'-TriNKET-Trastuzumab, the CH1 domain of which is connected to an Fc domain. The Fc domain linked to the scFv includes the "hole" substitutions of T366S, L368A, and Y407V, and the Fc domain linked to the Fab fragment includes the "knob" substitution of T366W. A44-F3'-KiH-TriNKET-MGAH22 includes three polypeptides, having the sequences of SEQ ID NO: 193 (as in A49-F3'-KiH-TriNKET-MGAH22), SEQ ID NO: 148 (as in A44-F3'-KiH-TriNKET-Trastuzumab), and SEQ ID NO:149 (as in A44-F3'-TriNKET-Trastuzumab).

In a certain embodiment, a TriNKET of the present disclosure is identical to one of the exemplary TriNKETs described above that includes the EW-RVT Fc mutations, except that the Fc domain linked to the NKG2D-binding Fab fragment comprises the substitutions of Q347R, D399V, and F405T, and the Fc domain linked to the HER2-binding scFv comprises matching substitutions K360E and K409W for forming a heterodimer. In certain embodiments, a TriNKET of the present disclosure is identical to one of the exemplary TriNKETs described above that includes the KiH Fc mutations, except that the Fc domain linked to the NKG2D-binding Fab fragment comprises the "hole" substitutions of T366S, L368A, and Y407V, and the Fc domain linked to the HER2-binding scFv comprises the "knob" substitution of T366W for forming a heterodimer.

In certain embodiments, a TriNKET of the present disclosure is identical to one of the exemplary TriNKETs described above, except that the Fc domain linked to the NKG2D-binding Fab fragment includes an S354C substitution in the CH3 domain, and the Fc domain linked to the HER2-binding scFv includes a matching Y349C substitution in the CH3 domain for forming a disulfide bond.

A skilled person in the art would appreciate that during production and/or storage of proteins, N-terminal glutamate (E) or glutamine (Q) can be cyclized to form a lactam (e.g., spontaneously or catalyzed by an enzyme present during production and/or storage). Accordingly, in some embodiments where the N-terminal residue of an amino acid sequence of a polypeptide is E or Q, a corresponding amino acid sequence with the E or Q replaced with pyroglutamate is also contemplated herein.

A skilled person in the art would also appreciate that during protein production and/or storage, the C-terminal lysine (K) of a protein can be removed (e.g., spontaneously or catalyzed by an enzyme present during production and/or storage). Such removal of K is often observed with proteins that comprise an Fc domain at its C-terminus. Accordingly, in some embodiments where the C-terminal residue of an amino acid sequence of a polypeptide (e.g., an Fc domain sequence) is K, a corresponding amino acid sequence with the K removed is also contemplated herein.

The multi-specific proteins described above can be made using recombinant DNA technology well known to a skilled person in the art. For example, a first nucleic acid sequence encoding the first immunoglobulin heavy chain can be cloned into a first expression vector; a second nucleic acid sequence encoding the second immunoglobulin heavy chain can be cloned into a second expression vector; a third nucleic acid sequence encoding the immunoglobulin light chain can be cloned into a third expression vector; and the first, second, and third expression vectors can be stably transfected together into host cells to produce the multimeric proteins.

To achieve the highest yield of the multi-specific protein, different ratios of the first, second, and third expression vector can be explored to determine the optimal ratio for transfection into the host cells. After transfection, single clones can be isolated for cell bank generation using methods known in the art, such as limited dilution, ELISA, FACS, microscopy, or Clonepix.

Clones can be cultured under conditions suitable for bio-reactor scale-up and maintained expression of the multi-specific protein. The multi-specific proteins can be isolated and purified using methods known in the art including centrifugation, depth filtration, cell lysis, homogenization, freeze-thawing, affinity purification, gel filtration, ion exchange chromatography, hydrophobic interaction exchange chromatography, and mixed-mode chromatography.

II. Characteristics of the Multi-Specific Proteins

In certain embodiments, a multi-specific binding protein of the present disclosure, e.g., A49-F3'-TriNKET-Trastuzumab, which include an NKG2D-binding Fab fragment and a HER2-binding scFv domain, bind to cells expressing low levels of HER2 at a level higher than a monoclonal antibody having the same HER2-binding domain. For example, the multi-specific binding proteins that include an NKG2D-binding Fab domain and a HER2-binding svFv domain derived from trastuzumab, e.g., A49-F3'-TriNKET-Trastuzumab, can bind to low-HER2 expressing cells at a level higher than trastuzumab.

Moreover, the multi-specific binding proteins described herein are more effective in reducing tumor growth and killing cancer cells. For example, a multi-specific binding protein of the present disclosure that targets HER2-expressing tumor/cancer cells is more effective than trastuzumab. A TriNKET of the present disclosure A49-F3'-TriNKET-Trastuzumab (comprising an HER2-binding scFv (SEQ ID NO:139) linked to an Fc domain via a hinge comprising Ala-Ser (scFv-Fc represented by SEQ ID NO:140); and an NKG2D-binding Fab fragment including a heavy chain portion comprising a heavy chain variable domain of ADI-27749 (A49) (SEQ ID NO:94) and a CH1 domain, and a light chain portion comprising a light chain variable domain (SEQ ID NO:98) and a light chain constant domain, where the heavy chain variable domain is connected to the CH1, and the CH1 domain is connected to the Fc domain (heavy chain portion represented as VH-CH1-Fc, amino acid sequence set forth in SEQ ID NO:141)) is effective in promoting NK-mediated cell lysis of a human cancer cell line with low level of HER2 expression (HER2+), while trastuzumab shows little activity against this cell line. Moreover, A49-F3'-TriNKET-Trastuzumab has superior NK-mediated cell lysis of a human cancer cell line with higher expression than the HER2+ cell line (HER2++) compared to trastuzumab. And even against a human cancer cell line with the highest level of HER2 expression (compared to HER+ and HER2++ cell lines) (HER2+++), A49-F3'-TriNKET-Trastuzumab has superior NK-mediated cell lysis compared to trastuzumab.

In some embodiments, the multi-specific binding proteins described herein including an NKG2D-binding domain (e.g., A49-F3'-TriNKET-Trastuzumab, A49MI-F3'-TriNKET-Trastuzumab, A49-F3'-KiH-TriNKET-Trastuzumab, A44-F3'-TriNKET-Trastuzumab) delay progression of the tumor more effectively than monoclonal antibodies that include the same tumor antigen-binding domain. In some embodiments, the multi-specific binding proteins including an NKG2D-binding domain (e.g., A49-F3'-TriNKET-Trastuzumab, A49MI-F3'-TriNKET-Trastuzumab, A49-F3'-KiH-TriNKET-Trastuzumab, A44-F3'-TriNKET-Trastuzumab) are more effective against cancer metastases than monoclonal antibodies that include the same tumor antigen-binding domain.

The multi-specific binding proteins described herein including an NKG2D-binding domain (e.g., A49-F3'-TriNKET-Trastuzumab, A49MI-F3'-TriNKET-Trastuzumab, A49-F3'-KiH-TriNKET-Trastuzumab, A44-F3'-TriNKET-Trastuzumab) bind to non-cancerous human cells (e.g., human cardiomyocytes) to a similar extent as binding to HER2++ cancer cells (medium level expression). However, despite the comparable binding, the multi-specific binding proteins do not induce NK-mediated killing of healthy non-cancerous human cells (e.g., human cardiomyocytes).

Figure 13A:
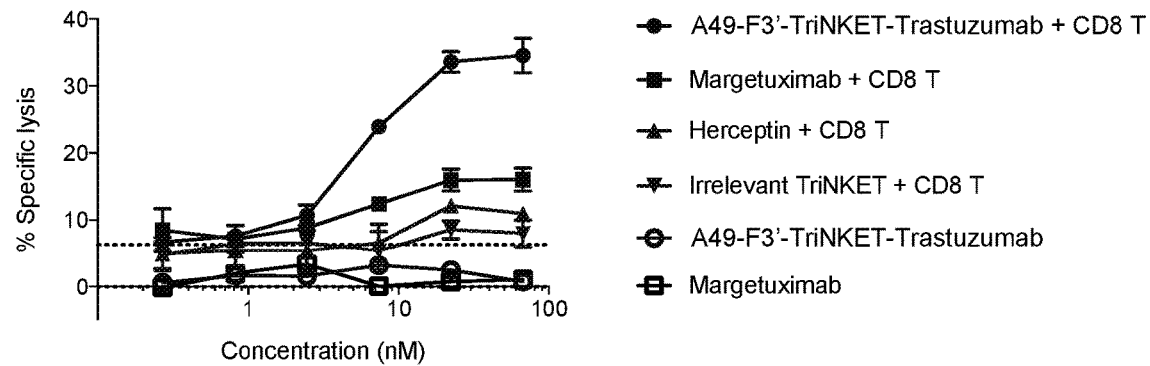
FIGS. 13A to 13B are graphs showing cytotoxic activity of CD8+ T cells in the presence of A49-F3'-TriNKET-Trastuzumab, after culturing with IL-15.
Figure 13B:
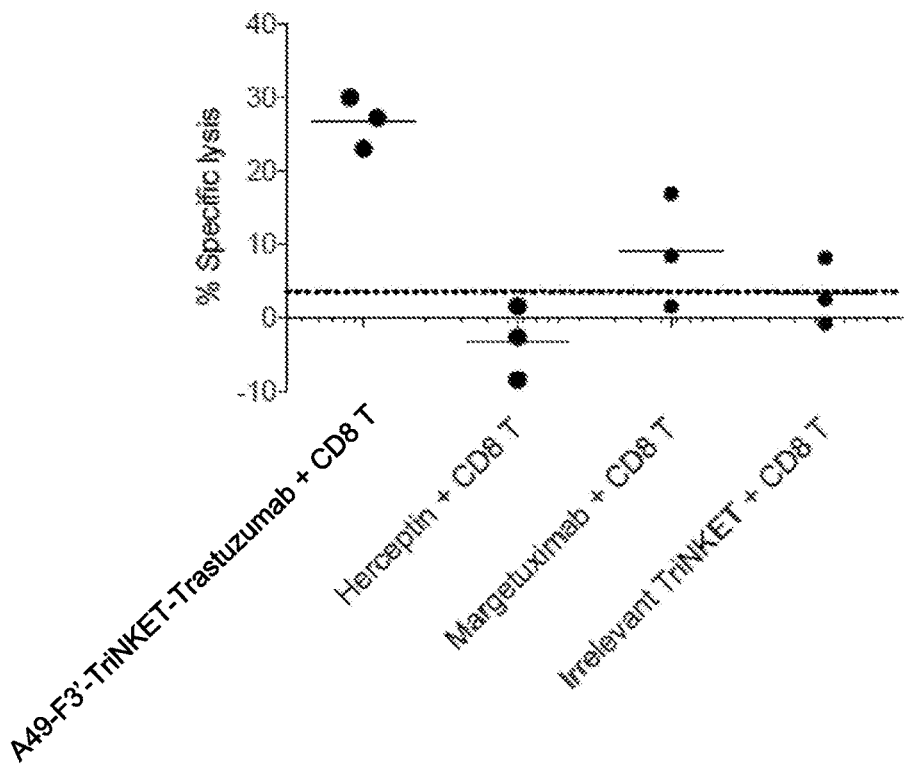

The multi-specific binding proteins described herein including an NKG2D-binding domain (e.g., A49-F3'-TriNKET-Trastuzumab, A49MI-F3'-TriNKET-Trastuzumab, A49-F3'-KiH-TriNKET-Trastuzumab, A44-F3'-TriNKET-Trastuzumab) trigger CD8+ T cell lysis of Tumor-Associated Antigen positive (TAA+) tumor cells. For example, A49-F3'-TriNKET-Trastuzumab enhances the cytotoxic activity of human primary CD8+ T cells after culture with IL-15 in a dose-dependent manner (FIG. 13A). A49-F3'-TriNKET-Trastuzumab also enhances the cytotoxic activity of human primary CD8+ T cells after culture with IL-2 (FIG. 13B). In contrast, anti-HER2 monoclonal antibodies margetuximab or trastuzumab does not have similar effects.

Margetuximab (also called MGAH22) is an Fc-optimized monoclonal antibody that binds HER2. The heavy chain variable domain of margetuximab is represented by SEQ ID NO: 130, and the light chain variable domain of margetuximab is represented by SEQ ID NO: 134. Margetuximab includes F243L, R292P, Y300L, and P396L substitutions in the Fc domain, which are designed to be ADCC enhancing mutations. The heavy chain and light chain sequences are provided in SEQ ID NO:151 and SEQ ID NO:153, respectively. The F243L, R292P, Y300L, and P396L substitutions are bold-underlined.

```
MGAH22 heavy chain
                                        (SEQ ID NO: 151)
QVQLQQSGPELVKPGASLKLSCTASGFNIKDTYIHWVKQRPEQGLEWIG
RIYPTNGYTRYDPKFQDKATITADTSSNTAYLQVSRLTSEDTAVYYCSR
WGGDGFYAMDYWGQGASVTVSSASTKGPSVFPLAPSSKSTSGGTAALGC
LVKDYFPEPVTVSWNSGALTSGVHTFPAVLQSSGLYSLSSVVTVPSSSL
GTQTYICNVNHKPSNTKVDKRVEPKSCDKTHTCPPCPAPELVGGPSVFL
LPPKPKDTLMISRTPEVTCVVVDVSHEDPEVKFNWYVDGVEVHNAKTKP
PEEQYNSTLRVVSVLTVLHQDWLNGKEYKCKVSNKALPAPIEKTISKAK
GQPREPQVYTLPPSRDELTKNQVSLTCLVKGFYPSDIAVEWESNGQPEN
NYKTTPLVLDSDGSFFLYSKLTVDKSRWQQGNVFSCSVMHEALHNHYTQ
KSLSLSPGK MGAH22 light chain
                                        (SEQ ID NO: 153)
DIVMTQSHKFMSTSVGDRVSITCKASQDVNTAVAWYQQKPGHSPKLLIY
SASFRYTGVPDRFTGSRSGTDFTFTISSVQAEDLAVYYCQQHYTTPPTF
GGGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGEC
```

Figure 19:
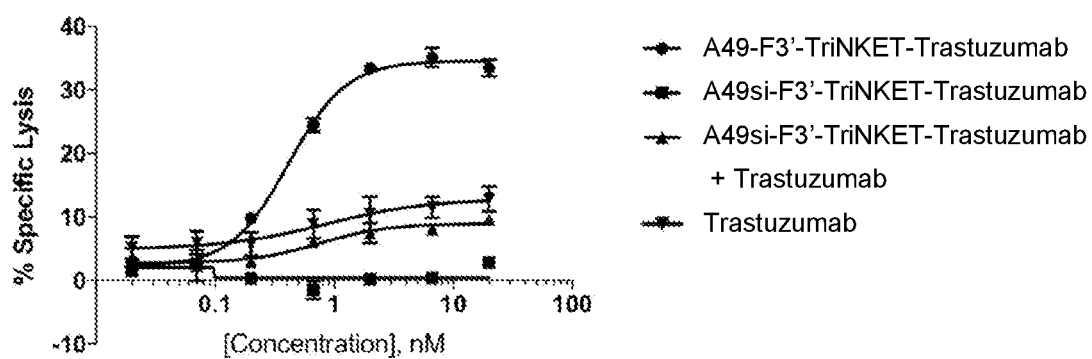
FIG. 19 shows TriNKETs are more potent and effective in mediating NK-cell killing of 786-O target cells than the combination of Fc-silent TriNKET and trastuzumab.

Compared to several HER2-targeted TriNKETs, A49-F3'-TriNKET-Trastuzumab shows weak binding to cells expressing NKG2D. The multi-specific binding proteins described herein including an NKG2D-binding domain (e.g., A49-F3'-TriNKET-Trastuzumab) exhibit a significant advantage in potency and maximum lysis of target cells compared to the combination of Fc-silent TriNKET ("A49si-F3'-TriNKET-Trastuzumab"; the amino acid sequence of the constant region has L234A, L235A, and P329G (LALAPG) mutations, which reduce effector functions of the Fc), and trastuzumab, when the target cells were HER2+ (786-O cells) (FIG. 19) or HER2++ (H661 cells) (FIG. 20), suggesting A49-F3'-TriNKET-Trastuzumab can mediate robust effector cell dependent killing of cancer cells expressing HER2.

Accordingly, compared to monoclonal antibodies, the multi-specific binding proteins described herein (e.g., A49-F3'-TriNKET-Trastuzumab) are advantageous in treating HER2-expressing cancers.

III. Therapeutic Applications

The invention provides methods for treating cancer using a multi-specific binding protein described herein and/or a pharmaceutical composition described herein. The methods may be used to treat a variety of cancers which express HER2 by administering to a patient in need thereof a therapeutically effective amount of a multi-specific binding protein described herein.

The therapeutic method can be characterized according to the cancer to be treated. For example, in certain embodiments, the cancer is breast, ovarian, esophageal, bladder or gastric cancer, salivary duct carcinoma, salivary duct carcinomas, adenocarcinoma of the lung or aggressive forms of uterine cancer, such as uterine serous endometrial carcinoma.

In certain other embodiments, the cancer is brain cancer, breast cancer, cervical cancer, colon cancer, colorectal cancer, endometrial cancer, esophageal cancer, leukemia, lung cancer, liver cancer, melanoma, ovarian cancer, pancreatic cancer, rectal cancer, renal cancer, stomach cancer, testicular cancer, or uterine cancer. In yet other embodiments, the cancer is a squamous cell carcinoma, adenocarcinoma, small cell carcinoma, melanoma, neuroblastoma, sarcoma (e.g., an angiosarcoma or chondrosarcoma), larynx cancer, parotid cancer, bilary tract cancer, thyroid cancer, acral lentiginous melanoma, actinic keratoses, acute lymphocytic leukemia, acute myeloid leukemia, adenoid cystic carcinoma, adenomas, adenosarcoma, adenosquamous carcinoma, anal canal cancer, anal cancer, anorectum cancer, astrocytic tumor, bartholin gland carcinoma, basal cell carcinoma, biliary cancer, bone cancer, bone marrow cancer, bronchial cancer, bronchial gland cancer, carcinoid, cholangiocarcinoma, chondosarcoma, choriod plexus papilloma/carcinoma, chronic lymphocytic leukemia, chronic myeloid leukemia, clear cell carcinoma, connective tissue cancer, cystadenoma, digestive system cancer, duodenum cancer, endocrine system cancer, endodermal sinus tumor, endometrial hyperplasia, endometrial stromal sarcoma, endometrioid adenocarcinoma, endothelial cell cancer, ependymal cancer, epithelial cell cancer, Ewing's sarcoma, eye and orbit cancer, female genital cancer, focal nodular hyperplasia, gallbladder cancer, gastric antrum cancer, gastric fundus cancer, gastrinoma, glioblastoma, glucagonoma, heart cancer, hemangiblastomas, hemangioendothelioma, hemangiomas, hepatic adenoma, hepatic adenomatosis, hepatobiliary cancer, hepatocellular carcinoma, Hodgkin's disease, ileum cancer, insulinoma, intaepithelial neoplasia, interepithelial squamous cell neoplasia, intrahepatic bile duct cancer, invasive squamous cell carcinoma, jejunum cancer, joint cancer, Kaposi's sarcoma, pelvic cancer, large cell carcinoma, large intestine cancer, leiomyosarcoma, lentigo maligna melanomas, lymphoma, male genital cancer, malignant melanoma, malignant mesothelial tumors, medulloblastoma, medulloepithelioma, meningeal cancer, mesothelial cancer, metastatic carcinoma, mouth cancer, mucoepidermoid carcinoma, multiple myeloma, muscle cancer, nasal tract cancer, nervous system cancer, neuroepithelial adenocarcinoma nodular melanoma, non-epithelial skin cancer, non-Hodgkin's lymphoma, oat cell carcinoma, oligodendroglial cancer, oral cavity cancer, osteosarcoma, papillary serous adenocarcinoma, penile cancer, pharynx cancer, pituitary tumors, plasmacytoma, pseudosarcoma, pulmonary blastoma, rectal cancer, renal cell carcinoma, respiratory system cancer, retinoblastoma, rhabdomyosarcoma, sarcoma, serous carcinoma, sinus cancer, skin cancer, small cell carcinoma, small intestine cancer, smooth muscle cancer, soft tissue cancer, somatostatin-secreting tumor, spine cancer, squamous cell carcinoma, striated muscle cancer, submesothelial cancer, superficial spreading melanoma, T cell leukemia, tongue cancer, undifferentiated carcinoma, ureter cancer, urethra cancer, urinary bladder cancer, urinary system cancer, uterine cervix cancer, uterine corpus cancer, uveal melanoma, vaginal cancer, verrucous carcinoma, VIPoma, vulva cancer, well-differentiated carcinoma, or Wilms tumor.

In certain other embodiments, the cancer is non-Hodgkin's lymphoma, such as a B-cell lymphoma or a T-cell lymphoma. In certain embodiments, the non-Hodgkin's lymphoma is a B-cell lymphoma, such as a diffuse large B-cell lymphoma, primary mediastinal B-cell lymphoma, follicular lymphoma, small lymphocytic lymphoma, mantle cell lymphoma, marginal zone B-cell lymphoma, extranodal marginal zone B-cell lymphoma, nodal marginal zone B-cell lymphoma, splenic marginal zone B-cell lymphoma, Burkitt lymphoma, lymphoplasmacytic lymphoma, hairy cell leukemia, or primary central nervous system (CNS) lymphoma. In certain other embodiments, the non-Hodgkin's lymphoma is a T-cell lymphoma, such as a precursor T-lymphoblastic lymphoma, peripheral T-cell lymphoma, cutaneous T-cell lymphoma, angioimmunoblastic T-cell lymphoma, extranodal natural killer/T-cell lymphoma, enteropathy type T-cell lymphoma, subcutaneous panniculitis-like T-cell lymphoma, anaplastic large cell lymphoma, or peripheral T-cell lymphoma.

In certain other embodiments, the cancer is breast cancer, thyroid cancer, gastric cancer, renal cell carcinoma, adenocarcinoma of the lung, prostate cancer, cholangiocarcinoma, uterine cancer, pancreatic cancer, colorectal cancer, ovarian cancer, cervical cancer, head and neck cancer, lung squamous, mesothelioma, liver cancer, sarcoma, and gall bladder cancer.

The cancer to be treated can be characterized according to the presence of a particular antigen expressed on the surface of the cancer cell. In certain embodiments, the cancer cell can express one or more of the following in addition to HER2: CD2, CD19, CD20, CD30, CD38, CD40, CD52, CD70, EGFR/ERBB1, IGFIR, HER3/ERBB3, HER4/ERBB4, MUC1, cMET, SLAMF7, PSCA, MICA, MICB, TRAILR1, TRAILR2, MAGE-A3, B7.1, B7.2, CTLA4, and PD1.

IV. Combination Therapy

Another aspect of the invention provides for combination therapy. A multi-specific binding protein described herein can be used in combination with additional therapeutic agents to treat cancer.

Exemplary therapeutic agents that may be used as part of a combination therapy in treating cancer, include, for example, radiation, mitomycin, tretinoin, ribomustin, gemcitabine, vincristine, etoposide, cladribine, mitobronitol, methotrexate, doxorubicin, carboquone, pentostatin, nitracrine, zinostatin, cetrorelix, letrozole, raltitrexed, daunorubicin, fadrozole, fotemustine, thymalfasin, sobuzoxane, nedaplatin, cytarabine, bicalutamide, vinorelbine, vesnarinone, aminoglutethimide, amsacrine, proglumide, elliptinium acetate, ketanserin, doxifluridine, etretinate, isotretinoin, streptozocin, nimustine, vindesine, flutamide, drogenil, butocin, carmofur, razoxane, sizofilan, carboplatin, mitolactol, tegafur, ifosfamide, prednimustine, picibanil, levamisole, teniposide, improsulfan, enocitabine, lisuride, oxymetholone, tamoxifen, progesterone, mepitiostane, epitiostanol, formestane, interferon-alpha, interferon-2 alpha, interferon-beta, interferon-gamma (IFN-γ), colony stimulating factor-1, colony stimulating factor-2, denileukin diftitox, interleukin-2, luteinizing hormone releasing factor and variations of the aforementioned agents that may exhibit differential binding to its cognate receptor, or increased or decreased serum half-life.

An additional class of agents that may be used as part of a combination therapy in treating cancer is immune checkpoint inhibitors. Exemplary immune checkpoint inhibitors include agents that inhibit one or more of (i) cytotoxic T lymphocyte-associated antigen 4 (CTLA4), (ii) programmed cell death protein 1 (PD1), (iii) PDL1, (iv) LAG3, (v) B7-H3, (vi) B7-H4, and (vii) TIM3. The CTLA4 inhibitor ipilimumab has been approved by the United States Food and Drug Administration for treating melanoma.

Yet other agents that may be used as part of a combination therapy in treating cancer are monoclonal antibody agents that target non-checkpoint targets (e.g., herceptin) and non-cytotoxic agents (e.g., tyrosine-kinase inhibitors).

Yet other categories of anti-cancer agents include, for example: (i) an inhibitor selected from an ALK Inhibitor, an ATR Inhibitor, an A2A Antagonist, a Base Excision Repair Inhibitor, a Bcr-Abl Tyrosine Kinase Inhibitor, a Bruton's Tyrosine Kinase Inhibitor, a CDC7 Inhibitor, a CHK1 Inhibitor, a Cyclin-Dependent Kinase Inhibitor, a DNA-PK Inhibitor, an Inhibitor of both DNA-PK and mTOR, a DNMT1 Inhibitor, a DNMT1 Inhibitor plus 2-chloro-deoxyadenosine, an HDAC Inhibitor, a Hedgehog Signaling Pathway Inhibitor, an IDO Inhibitor, a JAK Inhibitor, a mTOR Inhibitor, a MEK Inhibitor, a MELK Inhibitor, a MTH1 Inhibitor, a PARP Inhibitor, a Phosphoinositide 3-Kinase Inhibitor, an Inhibitor of both PARPI and DHODH, a Proteasome Inhibitor, a Topoisomerase-II Inhibitor, a Tyrosine Kinase Inhibitor, a VEGFR Inhibitor, and a WEE1 Inhibitor; (ii) an agonist of OX40, CD137, CD40, GITR, CD27, HVEM, TNFRSF25, or ICOS; and (iii) a cytokine selected from IL-12, IL-15, GM-CSF, and G-CSF.

Proteins of the invention can also be used as an adjunct to surgical removal of the primary lesion.

The amount of multi-specific binding protein and additional therapeutic agent and the relative timing of administration may be selected in order to achieve a desired combined therapeutic effect. For example, when administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. Further, for example, a multi-specific binding protein may be administered during a time when the additional therapeutic agent(s) exerts its prophylactic or therapeutic effect, or vice versa.

V. Pharmaceutical Compositions

The present disclosure also features pharmaceutical compositions that contain a therapeutically effective amount of a protein described herein. The composition can be formulated for use in a variety of drug delivery systems. One or more physiologically acceptable excipients or carriers can also be included in the composition for proper formulation. Suitable formulations for use in the present disclosure are found in Remington's Pharmaceutical Sciences, Mack Publishing Company, Philadelphia, Pa., 17th ed., 1985. For a brief review of methods for drug delivery, see, e.g., Langer (Science 249:1527-1533, 1990).

The intravenous drug delivery formulation of the present disclosure may be contained in a bag, a pen, or a syringe. In certain embodiments, the bag may be connected to a channel comprising a tube and/or a needle. In certain embodiments, the formulation may be a lyophilized formulation or a liquid formulation. In certain embodiments, the formulation may freeze-dried (lyophilized) and contained in 12 to 60 vials. In certain embodiments, the formulation may be freeze-dried and 45 mg of the freeze-dried formulation may be contained in one vial. In certain embodiments, the about 40 mg—about 100 mg of freeze-dried formulation may be contained in one vial. In certain embodiments, freeze dried formulation from 12, 27, or 45 vials are combined to obtained a therapeutic dose of the protein in the intravenous drug formulation. In certain embodiments, the formulation may be a liquid formulation and stored as about 250 mg/vial to about 1000 mg/vial. In certain embodiments, the formulation may be a liquid formulation and stored as about 600 mg/vial. In certain embodiments, the formulation may be a liquid formulation and stored as about 250 mg/vial.

The protein could exist in a liquid aqueous pharmaceutical formulation including a therapeutically effective amount of the protein in a buffered solution forming a formulation.

These compositions may be sterilized by conventional sterilization techniques, or may be sterile filtered. The resulting aqueous solutions may be packaged for use as-is, or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the above-mentioned agent or agents. The composition in solid form can also be packaged in a container for a flexible quantity.

In certain embodiments, the present disclosure provides a formulation with an extended shelf life including the protein of the present disclosure, in combination with mannitol, citric acid monohydrate, sodium citrate, disodium phosphate dihydrate, sodium dihydrogen phosphate dihydrate, sodium chloride, polysorbate 80, water, and sodium hydroxide.

In certain embodiments, an aqueous formulation is prepared including the protein of the present disclosure in a pH-buffered solution. The buffer of this invention may have a pH ranging from about 4 to about 8, e.g., from about 4.5 to about 6.0, or from about 4.8 to about 5.5, or may have a pH of about 5.0 to about 5.2. Ranges intermediate to the above recited pH's are also intended to be part of this disclosure. For example, ranges of values using a combination of any of the above recited values as upper and/or lower limits are intended to be included. Examples of buffers that will control the pH within this range include acetate (e.g., sodium acetate), succinate (such as sodium succinate), gluconate, histidine, citrate and other organic acid buffers.

In certain embodiments, the formulation includes a buffer system which contains citrate and phosphate to maintain the pH in a range of about 4 to about 8. In certain embodiments the pH range may be from about 4.5 to about 6.0, or from about pH 4.8 to about 5.5, or in a pH range of about 5.0 to about 5.2. In certain embodiments, the buffer system includes citric acid monohydrate, sodium citrate, disodium phosphate dihydrate, and/or sodium dihydrogen phosphate dihydrate. In certain embodiments, the buffer system includes about 1.3 mg/mL of citric acid (e.g., 1.305 mg/mL), about 0.3 mg/mL of sodium citrate (e.g., 0.305 mg/mL), about 1.5 mg/mL of disodium phosphate dihydrate (e.g., 1.53 mg/mL), about 0.9 mg/mL of sodium dihydrogen phosphate dihydrate (e.g., 0.86), and about 6.2 mg/mL of sodium chloride (e.g., 6.165 mg/mL). In certain embodiments, the buffer system includes about 1 to 1.5 mg/mL of citric acid, about 0.25 to 0.5 mg/mL of sodium citrate, about 1.25 to 1.75 mg/mL of disodium phosphate dihydrate, about 0.7 to 1.1 mg/mL of sodium dihydrogen phosphate dihydrate, and about 6.0 to 6.4 mg/mL of sodium chloride. In certain embodiments, the pH of the formulation is adjusted with sodium hydroxide.

A polyol, which acts as a tonicifier and may stabilize the antibody, may also be included in the formulation. The polyol is added to the formulation in an amount which may vary with respect to the desired isotonicity of the formulation. In certain embodiments, the aqueous formulation may be isotonic. The amount of polyol added may also be altered with respect to the molecular weight of the polyol. For example, a lower amount of a monosaccharide (e.g., mannitol) may be added, compared to a disaccharide (such as trehalose). In certain embodiments, the polyol which may be used in the formulation as a tonicity agent is mannitol. In certain embodiments, the mannitol concentration may be about 5 to about 20 mg/mL. In certain embodiments, the concentration of mannitol may be about 7.5 to 15 mg/mL. In certain embodiments, the concentration of mannitol may be about 10 to 14 mg/mL. In certain embodiments, the concentration of mannitol may be about 12 mg/mL. In certain embodiments, the polyol sorbitol may be included in the formulation.

A detergent or surfactant may also be added to the formulation. Exemplary detergents include nonionic detergents such as polysorbates (e.g., polysorbates 20, 80 etc.) or poloxamers (e.g., poloxamer 188). The amount of detergent added is such that it reduces aggregation of the formulated antibody and/or minimizes the formation of particulates in the formulation and/or reduces adsorption. In certain embodiments, the formulation may include a surfactant which is a polysorbate. In certain embodiments, the formulation may contain the detergent polysorbate 80 or Tween 80. Tween 80 is a term used to describe polyoxyethylene (20) sorbitanmonooleate (see Fiedler, Lexikon der Hifsstoffe, Editio Cantor Verlag Aulendorf, 4th ed., 1996). In certain embodiments, the formulation may contain between about 0.1 mg/mL and about 10 mg/mL of polysorbate 80, or between about 0.5 mg/mL and about 5 mg/mL. In certain embodiments, about 0.1% polysorbate 80 may be added in the formulation.

In embodiments, the protein product of the present disclosure is formulated as a liquid formulation. The liquid formulation may be presented at about a 10 mg/mL concentration in either a USP/Ph Eur type I 50R vial closed with a rubber stopper and sealed with an aluminum crimp seal closure. The stopper may be made of elastomer complying with USP and Ph Eur. In certain embodiments vials may be filled with about 61.2 mL of the protein product solution in order to allow an extractable volume of about 60 mL. In certain embodiments, the liquid formulation may be diluted with about 0.9% saline solution.

In certain embodiments, the liquid formulation of the disclosure may be prepared as a 10 mg/mL concentration solution in combination with a sugar at stabilizing levels. In certain embodiments the liquid formulation may be prepared in an aqueous carrier. In certain embodiments, a stabilizer may be added in an amount no greater than that which may result in a viscosity undesirable or unsuitable for intravenous administration. In certain embodiments, the sugar may be disaccharides, e.g., sucrose. In certain embodiments, the liquid formulation may also include one or more of a buffering agent, a surfactant, and a preservative.

In certain embodiments, the pH of the liquid formulation may be set by addition of a pharmaceutically acceptable acid and/or base. In certain embodiments, the pharmaceutically acceptable acid may be hydrochloric acid. In certain embodiments, the base may be sodium hydroxide.

In addition to aggregation, deamidation is a common product variant of peptides and proteins that may occur during fermentation, harvest/cell clarification, purification, drug substance/drug product storage and during sample analysis. Deamidation is the loss of $NH_3$ from a protein forming a succinimide intermediate that can undergo hydrolysis. The succinimide intermediate results in a 17 dalton mass decrease of the parent peptide. The subsequent hydrolysis results in an 18 dalton mass increase. Isolation of the succinimide intermediate is difficult due to instability under aqueous conditions. As such, deamidation is typically detectable as 1 dalton mass increase. Deamidation of an asparagine results in either aspartic or isoaspartic acid. The parameters affecting the rate of deamidation include pH, temperature, solvent dielectric constant, ionic strength, primary sequence, local polypeptide conformation and tertiary structure. The amino acid residues adjacent to Asn in the peptide chain affect deamidation rates. Gly and Ser following an Asn in protein sequences results in a higher susceptibility to deamidation.

In certain embodiments, the liquid formulation of the present disclosure may be preserved under conditions of pH and humidity to prevent deamination of the protein product.

The aqueous carrier of interest herein is one which is pharmaceutically acceptable (safe and non-toxic for administration to a human) and is useful for the preparation of a liquid formulation. Illustrative carriers include sterile water for injection (SWFI), bacteriostatic water for injection (BWFI), a pH buffered solution (e.g., phosphate-buffered saline), sterile saline solution, Ringer's solution or dextrose solution.

A preservative may be optionally added to the formulations herein to reduce bacterial action. The addition of a preservative may, for example, facilitate the production of a multi-use (multiple-dose) formulation.

Intravenous (IV) formulations may be the preferred administration route in particular instances, such as when a patient is in the hospital after transplantation receiving all drugs via the IV route. In certain embodiments, the liquid formulation is diluted with 0.9% Sodium Chloride solution before administration. In certain embodiments, the diluted drug product for injection is isotonic and suitable for administration by intravenous infusion.

In certain embodiments, a salt or buffer components may be added in an amount of about 10 mM to 200 mM. The salts and/or buffers are pharmaceutically acceptable and are derived from various known acids (inorganic and organic) with "base forming" metals or amines. In certain embodiments, the buffer may be phosphate buffer. In certain embodiments, the buffer may be glycinate, carbonate, citrate buffers, in which case, sodium, potassium or ammonium ions can serve as counterion.

A preservative may be optionally added to the formulations herein to reduce bacterial action. The addition of a preservative may, for example, facilitate the production of a multi-use (multiple-dose) formulation.

The aqueous carrier of interest herein is one which is pharmaceutically acceptable (safe and non-toxic for administration to a human) and is useful for the preparation of a liquid formulation. Illustrative carriers include sterile water for injection (SWFI), bacteriostatic water for injection (BWFI), a pH buffered solution (e.g., phosphate-buffered saline), sterile saline solution, Ringer's solution or dextrose solution.

The protein of the present disclosure could exist in a lyophilized formulation including the proteins and a lyoprotectant. The lyoprotectant may be sugar, e.g., disaccharides. In certain embodiments, the lyoprotectant may be sucrose or maltose. The lyophilized formulation may also include one or more of a buffering agent, a surfactant, a bulking agent, and/or a preservative.

The amount of sucrose or maltose useful for stabilization of the lyophilized drug product may be in a weight ratio of at least 1:2 protein to sucrose or maltose. In certain embodiments, the protein to sucrose or maltose weight ratio may be of from 1:2 to 1:5.

In certain embodiments, the pH of the formulation, prior to lyophilization, may be set by addition of a pharmaceutically acceptable acid and/or base. In certain embodiments the pharmaceutically acceptable acid may be hydrochloric acid. In certain embodiments, the pharmaceutically acceptable base may be sodium hydroxide.

Before lyophilization, the pH of the solution containing the protein of the present disclosure may be adjusted between 6 to 8. In certain embodiments, the pH range for the lyophilized drug product may be from 7 to 8.

In certain embodiments, a salt or buffer components may be added in an amount of 10 mM-200 mM. The salts and/or buffers are pharmaceutically acceptable and are derived from various known acids (inorganic and organic) with "base forming" metals or amines. In certain embodiments, the buffer may be phosphate buffer. In certain embodiments, the buffer may be glycinate, carbonate, citrate buffers, in which case, sodium, potassium or ammonium ions can serve as counterion.

In certain embodiments, a "bulking agent" may be added. A "bulking agent" is a compound which adds mass to a lyophilized mixture and contributes to the physical structure of the lyophilized cake (e.g., facilitates the production of an essentially uniform lyophilized cake which maintains an open pore structure). Illustrative bulking agents include mannitol, glycine, polyethylene glycol and sorbitol. The lyophilized formulations of the present invention may contain such bulking agents.

A preservative may be optionally added to the formulations herein to reduce bacterial action. The addition of a preservative may, for example, facilitate the production of a multi-use (multiple-dose) formulation.

In certain embodiments, the lyophilized drug product may be constituted with an aqueous carrier. The aqueous carrier of interest herein is one which is pharmaceutically acceptable (e.g., safe and non-toxic for administration to a human) and is useful for the preparation of a liquid formulation, after lyophilization. Illustrative diluents include sterile water for injection (SWFI), bacteriostatic water for injection (BWFI), a pH buffered solution (e.g., phosphate-buffered saline), sterile saline solution, Ringer's solution or dextrose solution.

In certain embodiments, the lyophilized drug product of the current disclosure is reconstituted with either Sterile Water for Injection, USP (SWFI) or about 0.9% Sodium Chloride Injection, USP. During reconstitution, the lyophilized powder dissolves into a solution.

In certain embodiments, the lyophilized protein product of the instant disclosure is constituted to about 4.5 mL water for injection and diluted with 0.9% saline solution (sodium chloride solution).

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The specific dose can be a uniform dose for each patient, for example, 50 to 5000 mg of protein. Alternatively, a patient's dose can be tailored to the approximate body weight or surface area of the patient. Other factors in determining the appropriate dosage can include the disease or condition to be treated or prevented, the severity of the disease, the route of administration, and the age, sex and medical condition of the patient. Further refinement of the calculations necessary to determine the appropriate dosage for treatment is routinely made by those skilled in the art, especially in light of the dosage information and assays disclosed herein. The dosage can also be determined through the use of known assays for determining dosages used in conjunction with appropriate dose-response data. An individual patient's dosage can be adjusted as the progress of the disease is monitored. Blood levels of the targetable construct or complex in a patient can be measured to see if the dosage needs to be adjusted to reach or maintain an effective concentration. Pharmacogenomics may be used to determine which targetable constructs and/or complexes, and dosages thereof, are most likely to be effective for a given individual (Schmitz et al., *Clinica Chimica Acta* 308:43-53, 2001; Steimer et al., *Clinica Chimica Acta* 308:33-41, 2001).

In general, dosages based on body weight are from about 0.01 µg to about 100 mg per kg of body weight, such as about 0.01 µg to about 100 mg/kg of body weight, about 0.01 µg to about 50 mg/kg of body weight, about 0.01 µg to about 10 mg/kg of body weight, about 0.01 µg to about 1 mg/kg of body weight, about 0.01 µg to about 100 µg/kg of body weight, about 0.01 µg to about 50 µg/kg of body weight, about 0.01 µg to about 10 µg/kg of body weight, about 0.01 µg to about 1 µg/kg of body weight, about 0.01 µg to about 0.1 µg/kg of body weight, about 0.1 µg to about 100 mg/kg of body weight, about 0.1 µg to about 50 mg/kg of body weight, about 0.1 µg to about 10 mg/kg of body weight, about 0.1 µg to about 1 mg/kg of body weight, about 0.1 µg to about 100 µg/kg of body weight, about 0.1 µg to about 10 µg/kg of body weight, about 0.1 µg to about 1 µg/kg of body weight, about 1 µg to about 100 mg/kg of body weight, about 1 µg to about 50 mg/kg of body weight, about 1 µg to about 10 mg/kg of body weight, about 1 µg to about 1 mg/kg of body weight, about 1 µg to about 100 µg/kg of body weight, about 1 µg to about 50 µg/kg of body weight, about 1 µg to about 10 µg/kg of body weight, about 10 µg to about 100 mg/kg of body weight, about 10 µg to about 50 mg/kg of body weight, about 10 µg to about 10 mg/kg of body weight, about 10 µg to about 1 mg/kg of body weight, about 10 µg to about 100 µg/kg of body weight, about 10 µg to about 50 µg/kg of body weight, about 50 µg to about 100 mg/kg of body weight, about 50 μg to about 50 mg/kg of body weight, about 50 μg to about 10 mg/kg of body weight, about 50 μg to about 1 mg/kg of body weight, about 50 μg to about 100 μg/kg of body weight, about 100 μg to about 100 mg/kg of body weight, about 100 μg to about 50 mg/kg of body weight, about 100 μg to about 10 mg/kg of body weight, about 100 μg to about 1 mg/kg of body weight, about 1 mg to about 100 mg/kg of body weight, about 1 mg to about 50 mg/kg of body weight, about 1 mg to about 10 mg/kg of body weight, about 10 mg to about 100 mg/kg of body weight, about 10 mg to about 50 mg/kg of body weight, about 50 mg to about 100 mg/kg of body weight.

Doses may be given once or more times daily, weekly, monthly or yearly, or even once every 2 to 20 years. Persons of ordinary skill in the art can easily estimate repetition rates for dosing based on measured residence times and concentrations of the targetable construct or complex in bodily fluids or tissues. Administration of the present invention could be intravenous, intraarterial, intraperitoneal, intramuscular, subcutaneous, intrapleural, intrathecal, intracavitary, by perfusion through a catheter or by direct intralesional injection.

This may be administered once or more times daily, once or more times weekly, once or more times monthly, and once or more times annually.

The description above describes multiple aspects and embodiments of the invention. The patent application specifically contemplates all combinations and permutations of the aspects and embodiments.

EXAMPLES

The invention now being generally described, will be more readily understood by reference to the following examples, which are included merely for purposes of illustration of certain aspects and embodiments of the present invention, and is not intended to limit the invention.

Example 1—Primary Human NK Cell Cytotoxicity Assay

Peripheral blood mononuclear cells (PBMCs) were isolated from human peripheral blood buffy coats using density gradient centrifugation. Isolated PBMCs were washed and prepared for NK cell isolation. NK cells were isolated using a negative selection technique with magnetic beads, purity of isolated NK cells was typically >90% CD3 CD56+. Isolated NK cells were rested overnight, rested NK cells were used the following day in cytotoxicity assays.

DELFIA Cytotoxicity Assay:

Human cancer cell lines expressing HER2 were harvested from culture, cells were washed with HBS, and were resuspended in growth media at $10^6$/mL for labeling with BATDA reagent (Perkin Elmer AD0116). Manufacturer instructions were followed for labeling of the target cells. After labeling cells were washed 3× with HBS, and were resuspended at $0.5$-$1.0\times10^5$/mL in culture media. To prepare the background wells an aliquot of the labeled cells was put aside, and the cells were spun out of the media. 100 μl of the media were carefully added to wells in triplicate to avoid disturbing the pelleted cells. 100 μl of BATDA labeled cells were added to each well of the 96-well plate. Wells were saved for spontaneous release from target cells, and wells were prepared for max lysis of target cells by addition of 1% Triton-X. Monoclonal antibodies or a TriNKET against HER2 (A49-F3'-TriNKET-Trastuzumab (comprising an HER2-binding scFv (SEQ ID NO:139) linked to an Fc domain via a hinge comprising Ala-Ser (scFv-Fc represented by SEQ ID NO:140); and an NKG2D-binding Fab fragment including a heavy chain portion comprising a heavy chain variable domain of ADI-27749 (A49) (SEQ ID NO:94) and a CH1 domain, and a light chain portion comprising a light chain variable domain (SEQ ID NO:98) and a light chain constant domain, where the heavy chain variable domain is connected to the CH1, and the CH1 domain is connected to the Fc domain (heavy chain portion represented as VH-CH1-Fc, amino acid sequence set forth in SEQ ID NO:141))) were diluted in culture media, and 50 μl of diluted mAb or the TriNKET were added to each well. Rested NK cells were harvested from culture, cells were washed, and were resuspended at $10^5$-$2.0\times10^6$/mL in culture media depending on the desired E:T ratio. 50 μl of NK cells were added to each well of the plate to make a total of 200 μl culture volume. The plate was incubated at 37° C. with 5% CO2 for 2-3 hours before developing the assay.

After culturing for 2-3 hours, the plate was removed from the incubator and the cells were pelleted by centrifugation at 200 g for 5 minutes. 20 μl of culture supernatant was transferred to a clean microplate provided from the manufacturer, 200 μl of room temperature europium solution was added to each well. The plate was protected from the light and incubated on a plate shaker at 250 rpm for 15 minutes. Plate was read using either Victor 3 or SpectraMax i3X instruments. % Specific lysis was calculated as follows: % Specific lysis= ((Experimental release-Spontaneous release)/(Maximum release-Spontaneous release))*100%.

Long Term Human PBMC Cytotoxicity Assay:

SkBr-3 cells stably expressing NucLight Green were generated using IncuCyte NucLight Green Reagent (catalog #4475). NucLight Green expressing cells were selected in puromycin to obtain a homogenous population. SkBr-3-NucLight Green cells were maintained in growth media containing puromycin before use in assays. SkBr-3-NucLight Green target cells were prepared as follows for cytotoxicity assays.

NucLight Green expressing cells were harvested from culture, and were washed to remove residual selection antibiotic, cells were resuspended in fresh culture media and seeded into a 96 well flat bottom plate. The plate was placed in the IncuCyte S3 overnight to monitor cell attachment and growth. The next day human PBMCs were isolated using density gradient centrifugation, and A49-F3'-TriNKET-Trastuzumab or mAb dilutions were prepared in primary cell culture media. Diluted A49-F3'-TriNKET-Trastuzumab and mAbs were added to SkBr-3-NucLight Green cells, followed by freshly isolated PBMCs. The plate was then returned to the IncuCyte S3.

Image collection was setup on the IncuCyte S3. Images for the phase and green channels were collected every hour, with 2 images per well. Image analysis was done using the IncuCyte S3 software. Masks for the green channel were created to count the number of SkBr-3 tumor cells. Percent growth was calculated as follows: % Growth=((Green object count time X)/(green object count time zero))*100%.

Figure 3:
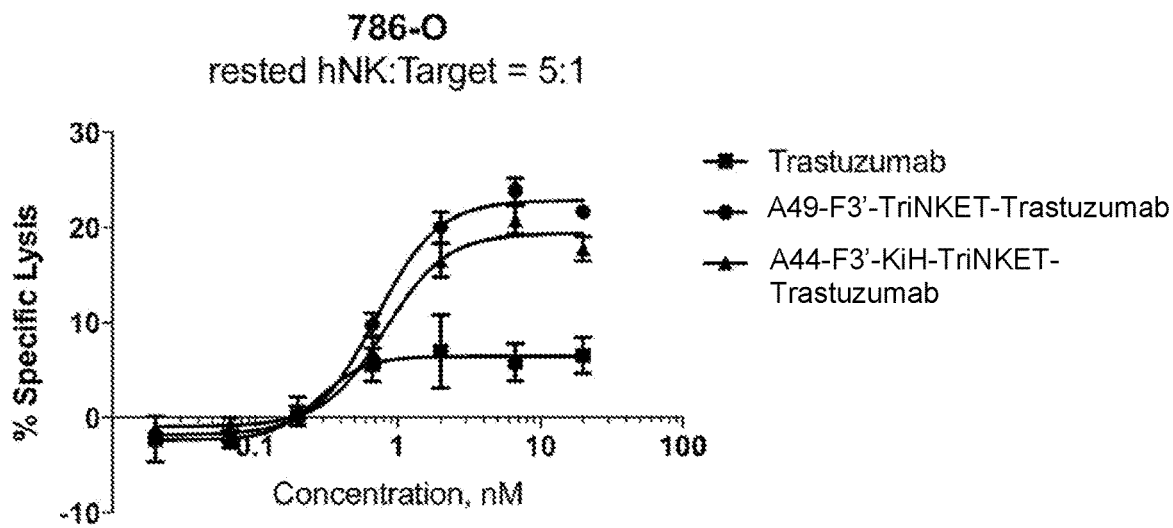
FIG. 3 are line graphs demonstrating HER2-targeted TriNKETs are more potent than trastuzumab on a HER2+ (low) cell line.
Figure 4:
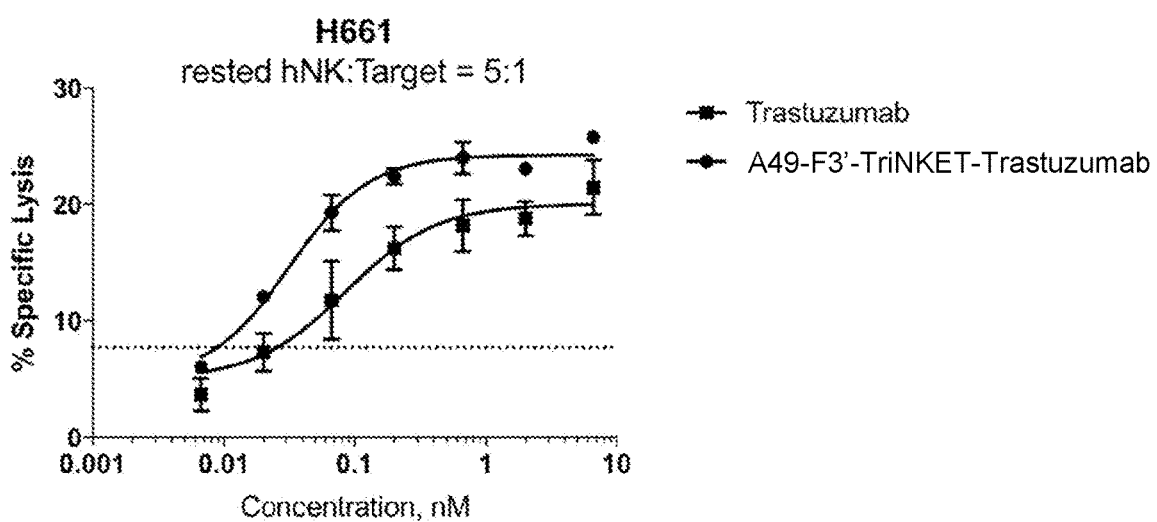
FIG. 4 are line graphs demonstrating HER2-targeted TriNKETs are more potent than trastuzumab on a HER2++ cell line.
Figure 5:
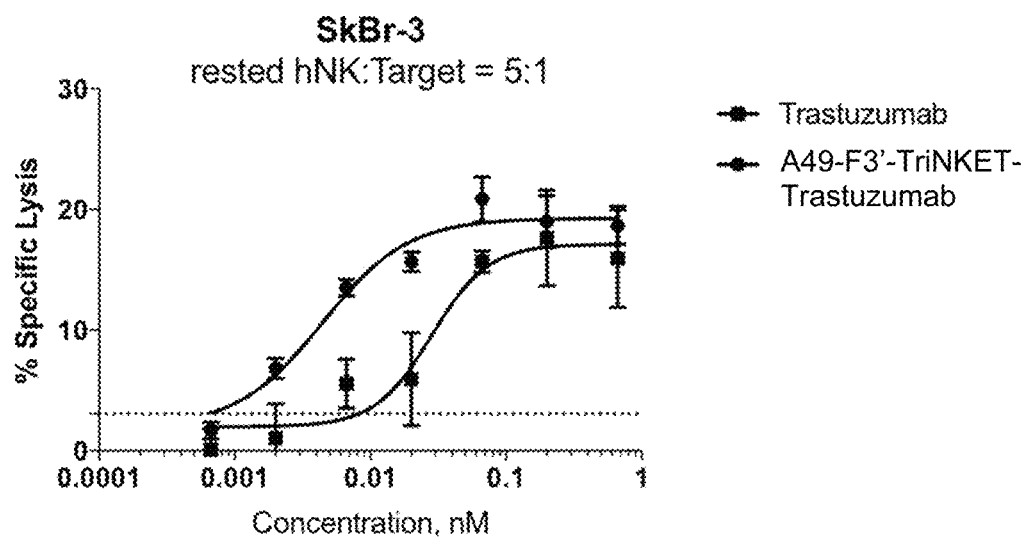
FIG. 5 are line graphs demonstrating HER2-targeted TriNKETs are more potent than trastuzumab on a HER2+++ cell line.

FIG. 3, FIG. 4, and FIG. 5 show TriNKET-mediated killing of three cell lines with different levels of HER2 expression. TriNKETs provided more potent, and higher maximal killing against all HER2-positive cells lines compared to the anti-HER2 monoclonal antibody trastuzumab.

FIG. 3 shows NK-mediated cell lysis of the HER2 1+ human cancer cell line 786-O. trastuzumab shows little activity against HER2 1+ cell lines, increasing specific lysis slightly higher than background killing. However, A49-F3'-TriNKET-Trastuzumab (comprising an HER2-binding scFv (SEQ ID NO:139) linked to an Fc domain via a hinge comprising Ala-Ser (scFv-Fc represented by SEQ ID NO:140); and an NKG2D-binding Fab fragment including a heavy chain portion comprising a heavy chain variable domain of ADI-27749 (A49) (SEQ ID NO:94) and a CH1 domain, and a light chain portion comprising a light chain variable domain (SEQ ID NO:98) and a light chain constant domain, where the heavy chain variable domain is connected to the CH1 domain, and the CH1 domain is connected to the Fc domain (heavy chain portion represented as VH-CH1-Fc, amino acid sequence set forth in SEQ ID NO:141)), and A44-F3'-KiH-TriNKET-Trastuzumab (comprising an HER2-binding scFv comprising SEQ ID NO:139, linked to an Fc domain via a hinge comprising Ala-Ser (scFv-Fc represented by SEQ ID NO:146), and an NKG2D-binding Fab fragment including a heavy chain portion comprising a heavy chain variable domain of ADI-27744 (A44) (SEQ ID NO:86) and a CH1 domain, and a light chain portion comprising a light chain variable domain (SEQ ID NO:90) and a light chain constant domain, where the heavy chain variable domain is connected to the CH1 domain, and the CH1 domain is connected to the Fc domain (heavy chain portion represented as VH-CH1-Fc, amino acid sequence set forth in SEQ ID NO:148)) were more effective at targeting 786-O cells, showing greater specific lysis than monoclonal antibody.

FIG. 4 demonstrates NK-mediated cell lysis of the human cancer cell line H661 with higher level of HER2 expression that the 786-O cell line (denoted as HER2++). Compared to the 786-O cell line, trastuzumab showed improved killing against higher levels of HER2 expressed on H661 target cells. Despite improved lysis mediated by trastuzumab, A49-F3'-TriNKET-Trastuzumab still showed superior lysis of H661 target cells for both potency and maximal killing.

FIG. 5 shows NK-mediated cell lysis of the cancer cell line SkBr-3 with the highest level of HER2 expression among the three cell lines tested (denoted as HER2+++). Trastuzumab showed increased potency against SkBr-3 cells compared to HER2+ and HER2++ cell lines, but A49-F3'-TriNKET-Trastuzumab still showed superior potency and maximal killing.

Figure 6:
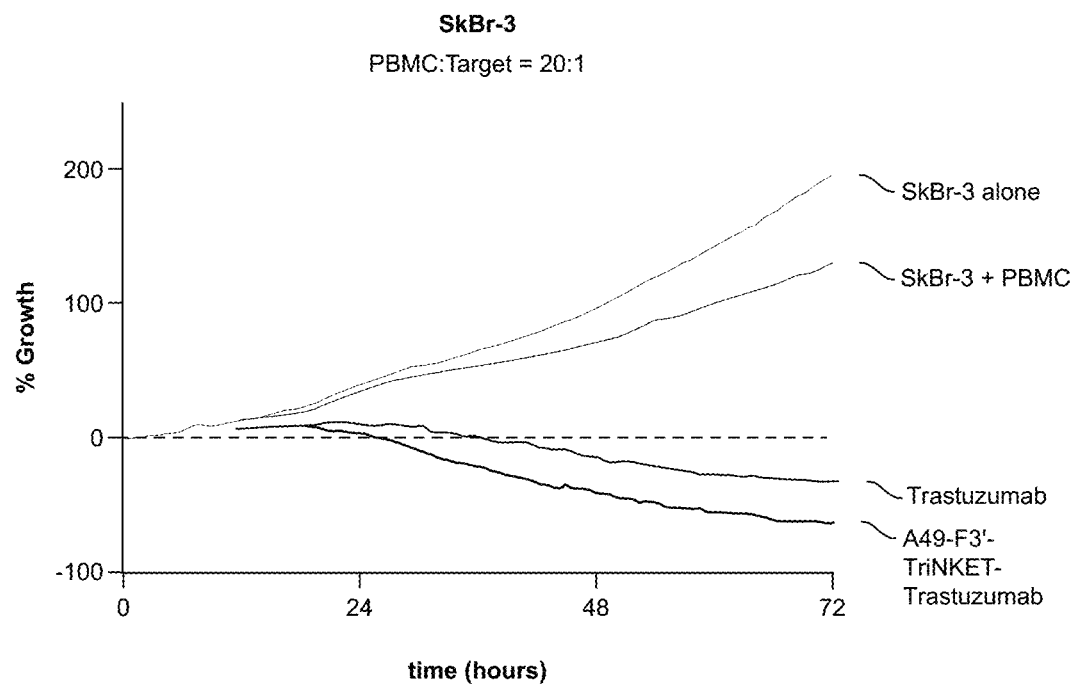
FIG. 6 shows HER2-targeted TriNKETs outperform trastuzumab in a long-term killing assay.
Figure 7:
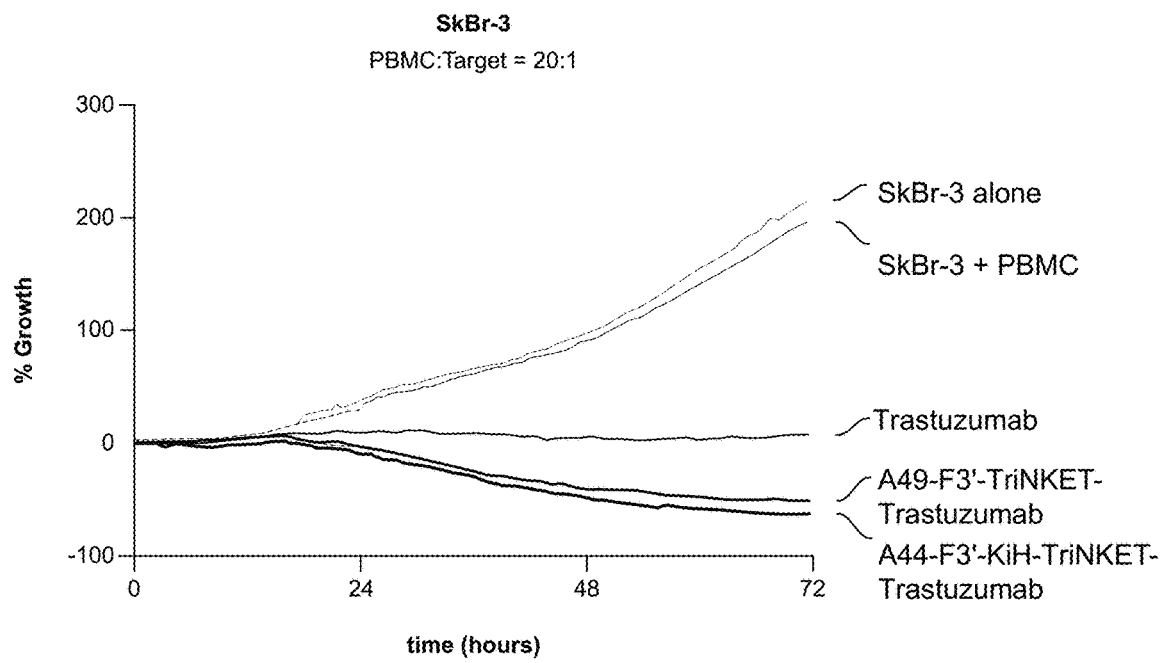
FIG. 7 shows HER2-targeted TriNKETs outperform trastuzumab in a long-term killing assay.
Figure 8A:
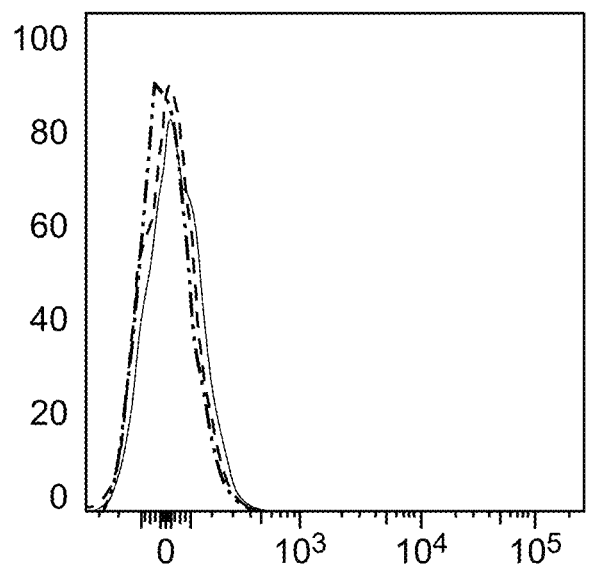
FIGS. 8A to 8F are FACS showing that HER2-Targeted TriNKETs show minimal binding to immune cells in human blood.
Figure 8B:
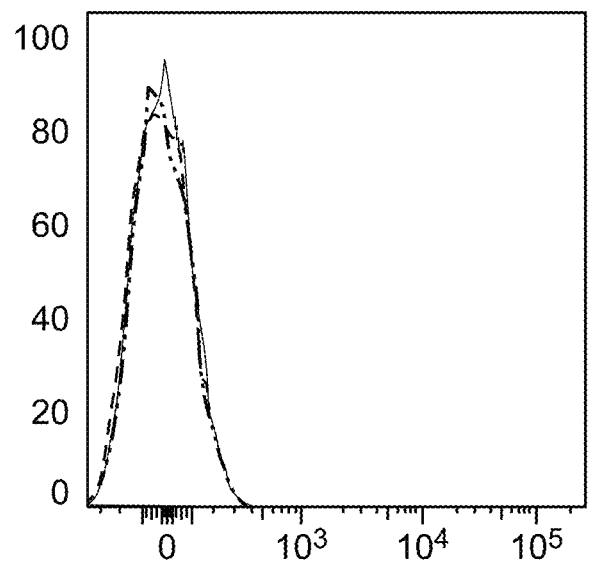
Figure 8C:
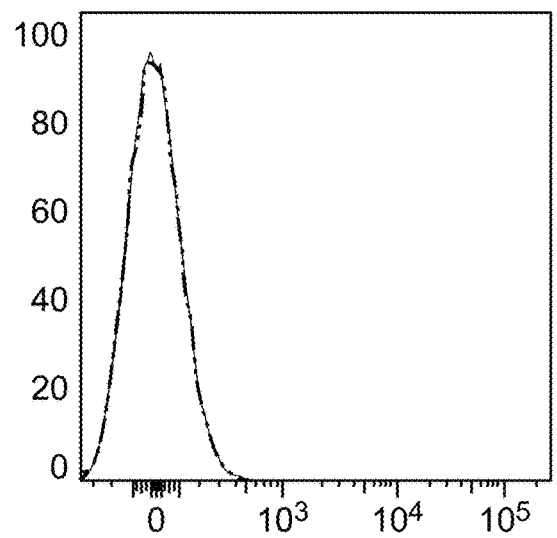
Figure 8D:
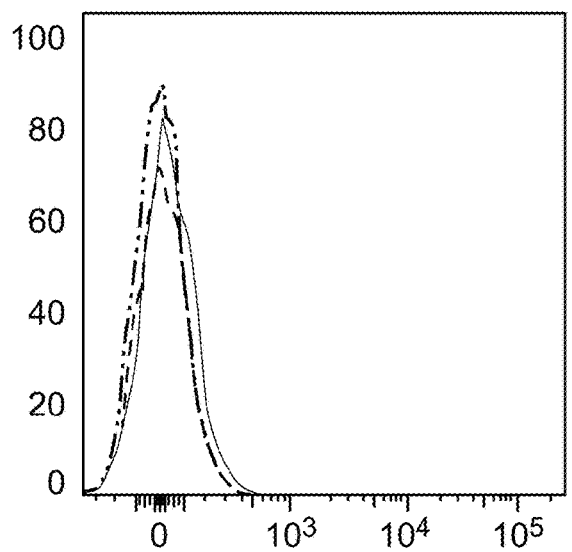
Figure 8E:
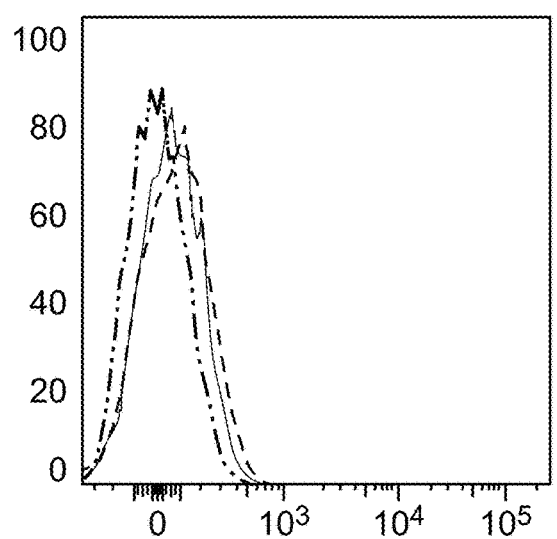
Figure 8F:
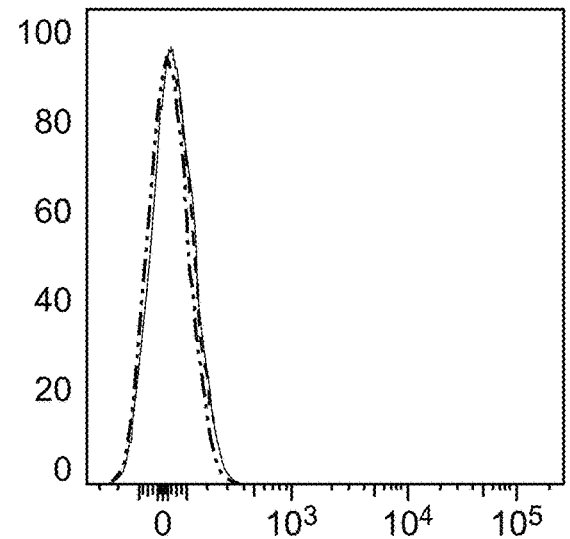

FIG. 6 and FIG. 7 show the effect of TriNKET or mAb on 72-hour co-cultures of human PBMCs and SkBr-3 HER2+ target cells. SkBr-3 cells proliferated about 3-fold over a 72-hour period when cultured without effector PBMCs. Donor variability was evident in effector PBMCs. When PBMCs were added to SkBr-3 cultures, growth of the target SkBr-3 cells was nominally reduced (FIG. 6). In another experiment, the addition of PBMC effector cells had negligible effect on SkBr-3 cell growth (FIG. 7). When trastuzumab was added to the co-culture, the effector PBMCs had an increased ability to lyse target SkBr-3 cells, indicated as a decrease in % growth in FIG. 6 and FIG. 7. When A49-F3'-TriNKET-Trastuzumab (FIG. 6 and FIG. 7) and A44-F3'-KiH-TriNKET-Trastuzumab (FIG. 7) were added to the co-culture, the effector PBMCs were even more effective in lysing SkBr-3 target cells compared to trastuzumab, resulting in a faster and more complete reduction in SkBr-3 cells.

Example 2—Binding of TriNKETs in Human Whole Blood

100 µl of heparinized human whole blood was added to each tube/well. Trispecific-binding proteins (TriNKETs) or monoclonal Ab (mAb) was added directly into whole blood, and samples were incubated at room temperature for 20 minutes. For detection of unlabeled TriNKETs/mAbs, blood was washed 3× following incubation with TriNKET. Directly labeled immunophenotyping mAbs and secondary antibody specific to trastuzumab were added to samples. After a 20 minute incubation, 2 mL of 1×RBC lysis/fixation solution was added to each sample for 15 minutes at room temperature (RT), samples were then washed to remove red blood cells (RBCs). After washing, the samples were resuspended for FACS analysis.

Binding of the A49-F3'-TriNKET-Trastuzumab was compared to trastuzumab and secondary antibody control samples. FIGS. 8A-8F show binding of A49-F3'-TriNKET-Trastuzumab (an NKG2D-binding domain from clone ADI-27749; and an HER2-binding scFv comprising SEQ ID NO:139, derived from trastuzumab monoclonal antibody) in whole human blood. A49-F3'-TriNKET-Trastuzumab binding in human whole blood was the same as trastuzumab. A49-F3'-TriNKET-Trastuzumab and trastuzumab demonstrated minimal binding to all populations of immune cells in blood. Small shifts were observed for trastuzumab and A49-F3'-TriNKET-Trastuzumab in both B cell and monocyte populations compared to secondary control samples. Binding observed on B cells and monocytes can likely be attributed to FcR interactions, rather than being Fab specific.

Example 3—Assessment of A49-F3'-TriNKET-Trastuzumab Binding to Human Cardiomyocytes Versus Human Cancer Cells Expressing Different Levels of HER2

Human cardiomyocytes differentiated from induced pluripotent stem cells (Cellular Dynamics/Fuji Film), 786-O, H661 and SKBR3 cancer cells were used to evaluate binding of A49-F3'-TriNKET-Trastuzumab to these cells. The human renal cell carcinoma cell line 786-O expresses low levels of HER2, the human lung cancer cell line H661 expresses moderate levels of HER2, while the human breast cancer cell line SKBR3 expresses high levels of HER2. TriNKETs were diluted to 3.8e-4 to 100 g/mL, and the dilutions were used as primary antibody stain. Binding of the TriNKET was detected using a fluorophore-conjugated anti-human IgG secondary antibody. Cells were analyzed by flow cytometry. Binding fluorescence intensity (MFI) to cells expressing HER2 was normalized to cells stained with a control (non-specific) TriNKET to obtain fold over background (FOB) values.

Human PBMC Cytotoxicity Assay

PBMCs were isolated from human peripheral blood buffy coats using density gradient centrifugation. SKBR3 target cells were labeled with BacMam 3.0 NucLight Green (#4622) to allow for tracking of the target cells. The manufacturer's protocol was followed for labeling of SKBR3 target cells. Human cardiomyocytes were unlabeled. Monoclonal antibodies or TriNKETs were diluted into culture media. 50 µl of TriNKETs and human PBMCs were added to wells of a 96-well plate already containing target cells, 50 µl of complete culture media was added for a total of 200 µl culture volume.

Image collection was setup on the IncuCyte S3. Image analysis was done using the IncuCyte S3 software. Masks for the green channel was created to count the number of tumor cells. Confluency of cardiomyocytes in the phase channel was used to assess cell viability and calculate % killing.

Figure 9:
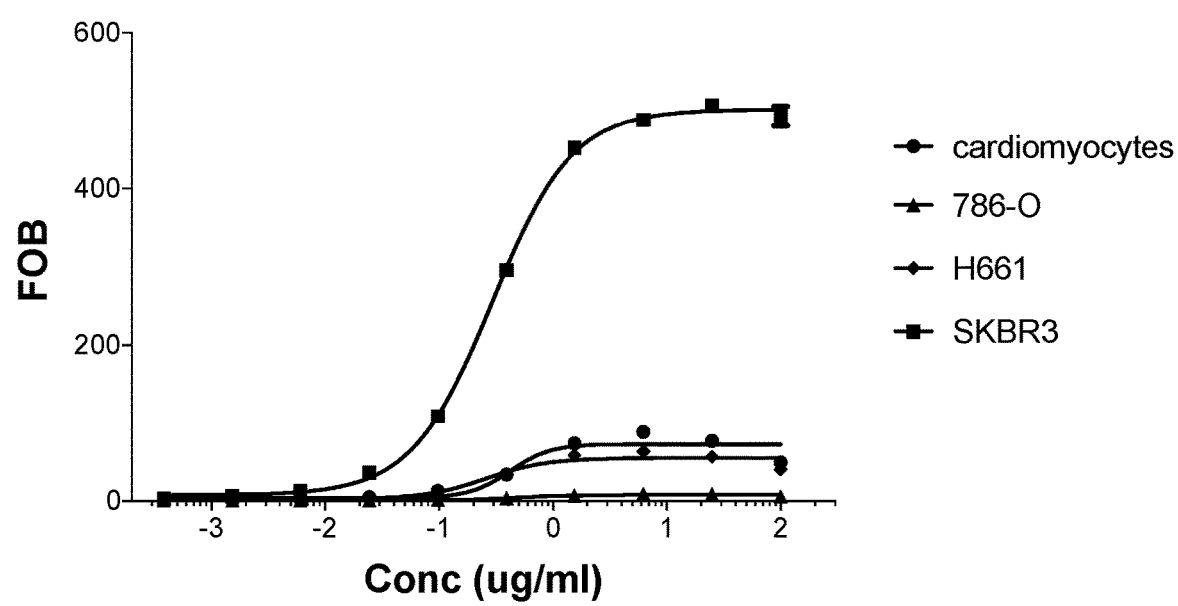
FIG. 9 are line graphs demonstrating binding of A49-F3'-TriNKET-Trastuzumab to human cardiomyocytes, SKBR3, H661 and 786-O cancer cells.

A49-F3'-TriNKET-Trastuzumab binds to human cardiomyocytes to similar extent as binding to H661 cells. FIG. 9 shows binding of A49-F3'-TriNKET-Trastuzumab to human cardiomyocytes, SKBR3, H661 and 786-O cancer cells, where the binding to cardiomyocytes is similar to H661 cells (medium HER2 surface expression levels).

Primary Human PBMC Cytotoxicity Assay

FIGS. 10A-10B and FIGS. 11A-11B show killing of SKBR3 cells by human PBMCs in the presence of A49-F3'-TriNKET-Trastuzumab, whereas viability of cardiomyocytes are minimally affected.

Figure 10A:
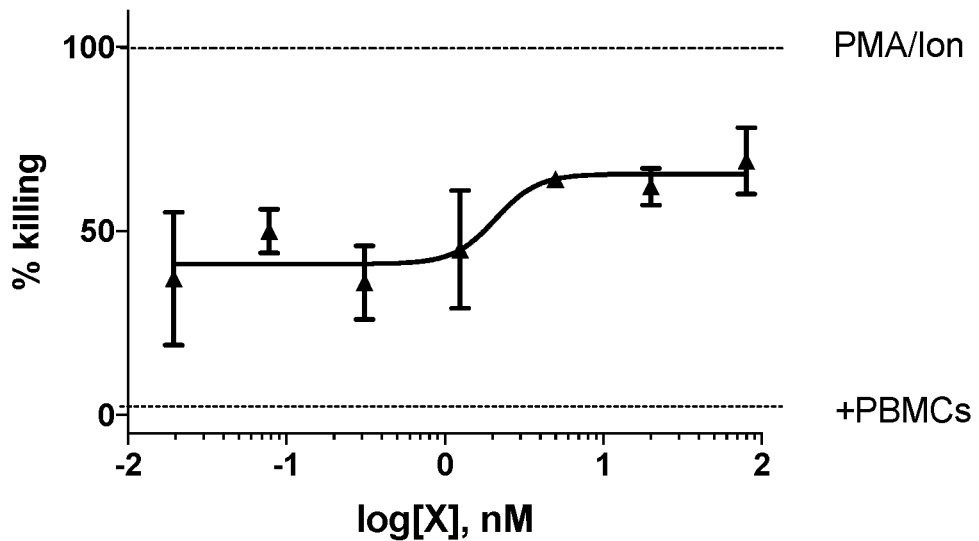
FIG. 10A shows that A49-F3'-TriNKET-Trastuzumab-mediated human PBMC killing of SKBR3 cancer after 3 days in co-culture at PBMC to target cell ratio (E:T) of 1:1.
Figure 10B:
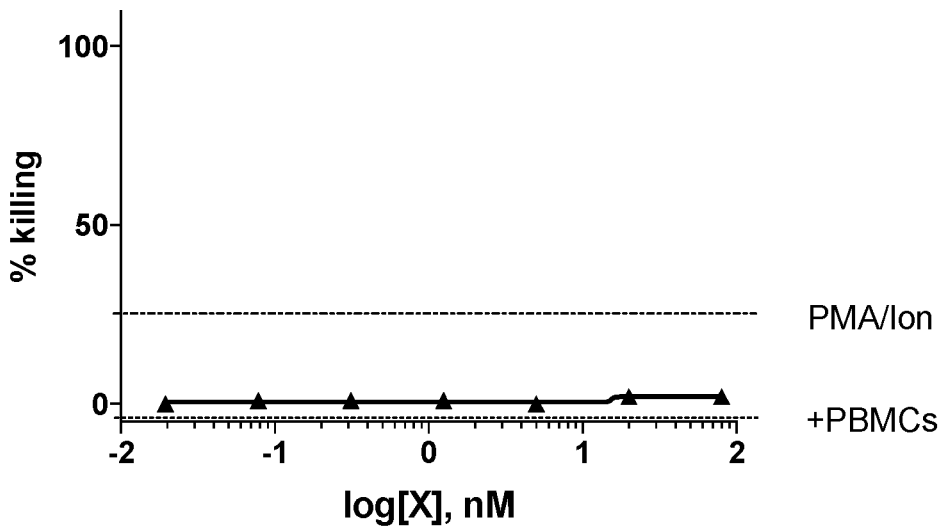
FIG. 10B shows that A49-F3'-TriNKET-Trastuzumab does not kill non-malignant healthy cardiomyocytes even after 3 days in co-culture at PBMC to target cell ratio (E:T) of 1:1.

FIG. 10A shows A49-F3'-TriNKET-Trastuzumab-mediated human PBMC killing of SKBR3 cancer cells; FIG. 10B shows that A49-F3'-TriNKET-Trastuzumab did not kill non-malignant healthy cardiomyocytes after 3 days in co-culture at PBMC to target cell ratio (E:T) of 1:1.

Figure 11A:
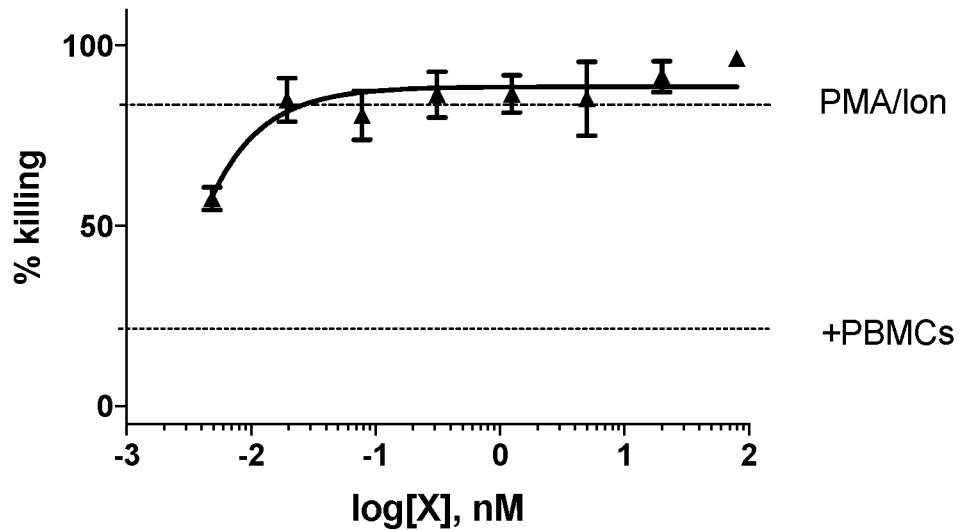
FIG. 11A shows A49-F3'-TriNKET-Trastuzumab-mediated human PBMC killing of SKBR3 cancer cells after 3 days in co-culture at PBMC to target cell ratio (E:T) of 20:1.
Figure 11B:
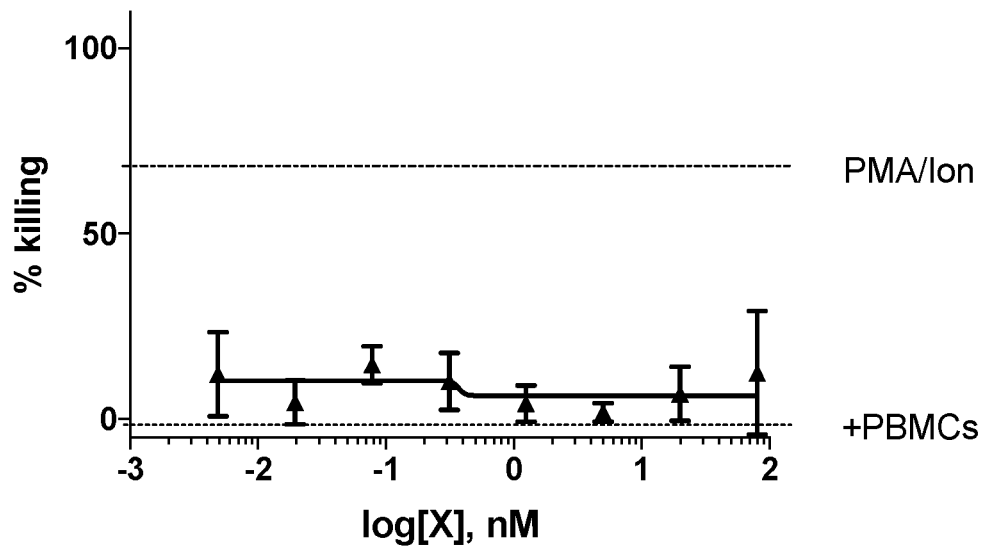
FIG. 11B shows that A49-F3'-TriNKET-Trastuzumab does not kill non-malignant healthy cardiomyocytes even after 3 days in co-culture at PBMC to target cell ratio (E:T) of 20:1.

FIG. 11A shows A49-F3'-TriNKET-Trastuzumab-mediated human PBMC killing of SKBR3 cancer cells; FIG. 11B shows that A49-F3'-TriNKET-Trastuzumab did not kill non-malignant healthy cardiomyocytes after 3 days in co-culture at E:T of 20:1.

Example 4—TriNKETs Trigger CD8+ T Cell Lysis of TAA+ Tumor Cells

Primary Human CD8 T Cell Cytotoxicity Assay: Primary Human CD8 Effector T Cell Generation Human PBMCs were isolated from human peripheral blood buffy coats using density gradient centrifugation. Isolated PBMCs were stimulated with 1 µg/mL Concanavalin A (ConA) at 37° C. for 18 hours. Then ConA was removed and cultured with 25 unit/mL IL-2 at 37° C. for 4 days. CD8+ T cells were purified using a negative selection technique with magnetic beads, then cultured in media containing 25 unit/mL IL-2 or 10 ng/ml IL-15 at 37° C. for 8-10 days.

Primary Human CD8 Effector T Cell Characterization

Human effector CD8+ T cells generated above were analyzed by flow cytometry for CD8+ T cell purity as well as NKG2D and CD16 expression. Cells were stained with fluorophore conjugated antibodies against CD3, CD8, NKG2D, CD16, and analyzed by flow cytometry.

Short-Term CD8 Effector T Cell DELFIA Cytotoxicity Assay

Human cancer cell line SkBr-3 expressing a target of interest, HER2, was harvested from culture. Cells were washed and resuspended in growth media at $10^6$/mL for labeling with BATDA reagent (Perkin Elmer AD0116). Manufacturer instructions were followed for labeling of the target cells. After labeling cells were washed three times with HBS, and were resuspended at $0.5 \times 10^5$/mL in culture media. 100 µl of BATDA labeled cells were added to each well of the 96-well plate. Wells were saved for spontaneous release from target cells, and wells were prepared for max lysis of target cells by addition of 1% Triton-X.

Monoclonal antibodies, TriNKETs and controls were diluted in culture media; 50 µl of diluted mAb/TriNKET were added to each well. CD8 effector T cells were harvested from culture, washed, and resuspended at $5 \times 10^6$/mL in culture media (E:T ratio=50:1). Then 50 µl of CD8 T cells were added to each well of the plate to make a total of 200 µl culture volume. The plate was incubated at 37° C. with 5% $CO_2$ for 3.5 hours before developing the assay. After incubation, the plate was removed from the incubator and the cells were pelleted by centrifugation at 500 g for 5 minutes. Then 20 µl of culture supernatant were transferred to a clean microplate provided from the manufacturer, 200 µl of room temperature europium solution were added to each well. The plate was protected from the light and incubated on a plate shaker at 250 rpm for 15 minutes. The plate was read using either Victor 3 or SpectraMax i3X instruments. % Specific lysis was calculated as follows: % Specific lysis= ((Experimental release-Spontaneous release)/(Maximum release-Spontaneous release))*100%.

Long-Term CD8 Effector T Cell Incucyte Cytotoxicity Assay

Human cancer cell line SkBr-3 expressing a target of interest, HER2, was labeled with BacMam 3.0 NucLight Green (#4622) to allow for tracking of the target cells. SkBr-3 target cells were harvested from culture, washed, resuspended in growth media, and plated at 5,000/well in a 96-well plate. The plate was incubated at 37° C. with 5% $CO_2$ overnight. Monoclonal antibodies, TriNKETs and controls were diluted in culture media; 50 µl of diluted mAb or TriNKET were added to each well. CD8 effector T cells were harvested from culture, washed, and resuspended at $1 \times 10^6$/mL in culture media (E:T ratio=10:1). Then 50 µl of CD8+ T cells were added to each well of the plate to make a total of 200 µl culture volume. The plate was incubated at 37° C. with 5% $CO_2$ for up to 7 days. Image collection was setup on the IncuCyte S3. Images for the phase and green channels were collected every hour, with 2 images per well. Image analysis was done using the IncuCyte S3 software. Green object count/well was used to measure the number of live tumor cells.

Characterization of CD8 T Effector Cells Used in Cytotoxicity Assay

Figure 12C:
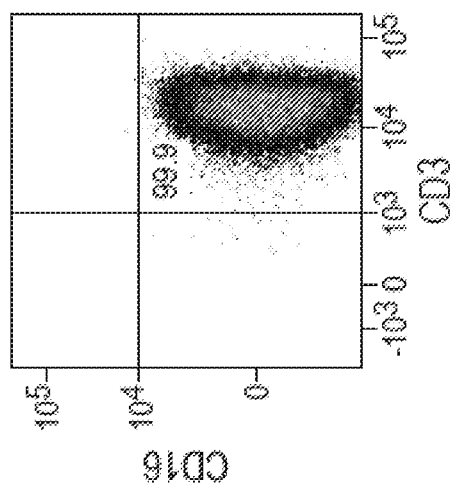
FIGS. 12A to 12B show that CD8+ T cells generated with conA stimulation and cultured with IL-15 were of high purity (99% of CD3+CD8+ cells) (FIG. 12A), and all expressed NKG2D (FIG. 12B), but not CD16 (FIG. 12C).
Figure 12B:
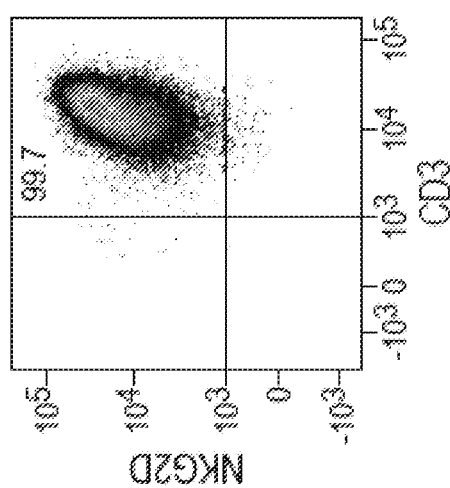
Figure 12A:
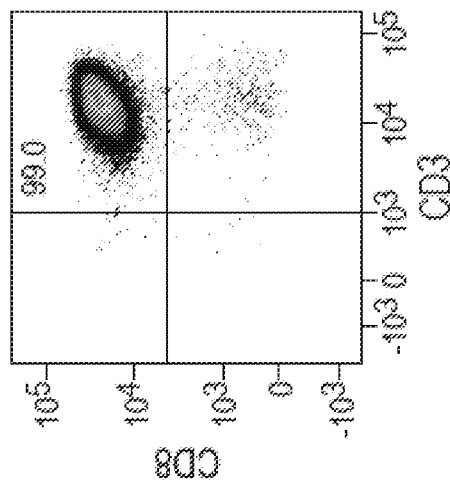

CD8+ T cells generated with conA stimulation and cultured with IL-15 were of high purity (99% of CD3+CD8+ cells), and all expressed NKG2D but not CD16 (FIGS. 12A-12C). Similar results are observed with CD8+ T cells generated with IL-2 culture.

Short-Term CD8 Effector T Cell DELFIA Cytotoxicity Assay

The effect of A49-F3'-TriNKET-Trastuzumab on the cytotoxic activity of human primary CD8+ T cells after culture with IL-15 was assayed. A49-F3'-TriNKET-Trastuzumab enhanced the cytotoxic activity of human primary CD8+ T cells after culture with IL-15 in a dose-dependent manner (FIG. 13A). A49-F3'-TriNKET-Trastuzumab also enhanced the cytotoxic activity of human primary CD8+ T cells after culture with IL-2 (FIG. 13B). Margetuximab or Herceptin did not show the effects observed with A49-F3'-TriNKET-Trastuzumab.

Long-Term CD8 Effector T Cell Incucyte Cytotoxicity Assay

Figure 14A:
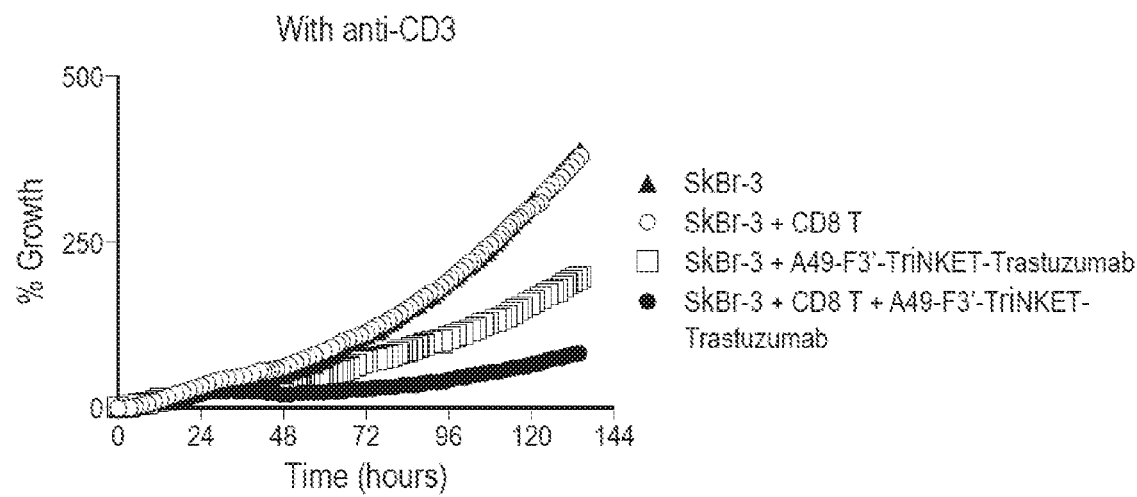
FIG. 14A shows percent growth levels of SkBr-3 cells cultured alone, co-cultured with CD8+ T cells, co-cultured with CD8+ T cells and A49-F3'-TriNKET-Trastuzumab, each in the presence of anti-CD3.
Figure 14B:
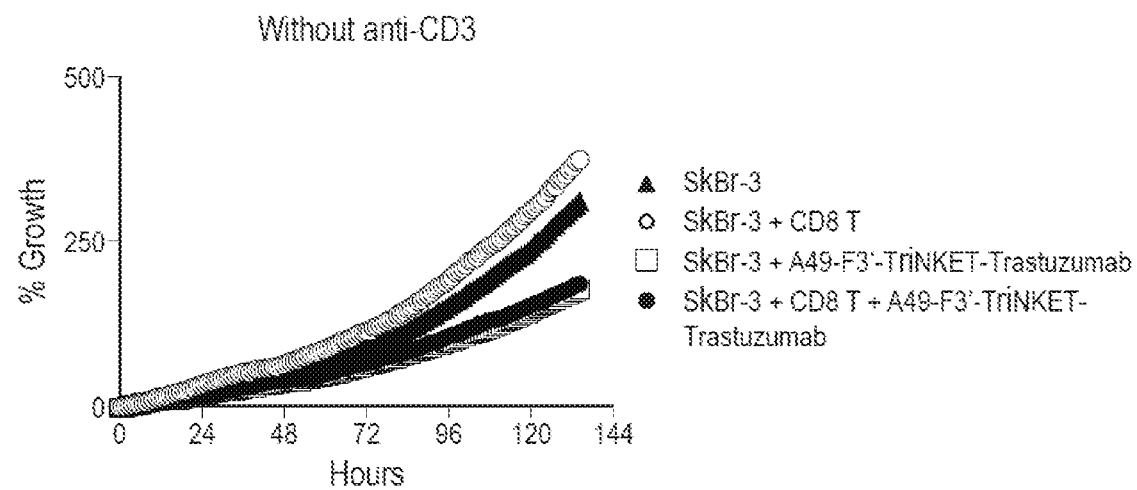
FIG. 14B shows percent growth level of SkBr-3 cells cultured alone, co-cultured with CD8+ T cells, co-cultured with CD8+ T cells and A49-F3'-TriNKET-Trastuzumab, each in the absence of anti-CD3.

SkBr-3 cells cultured alone or co-cultured with CD8+ T cells proliferated in the culture (FIG. 14A). When the cells were treated with A49-F3'-TriNKET-Trastuzumab, the growth of SkBr-3 showed some inhibition due to HER2 signal blockade (FIG. 14A). In the presence of anti-CD3 antibody (mIgG1 antibody cross-linked with F(ab') 2 to anti-mIgG1) (FIG. 14A), adding A49-F3'-TriNKET-Trastuzumab to the co-culture of SkBr-3 cells and CD8 T cells showed much more inhibition of tumor cell growth than A49-F3'-TriNKET-Trastuzumab alone, indicating that A49-F3'-TriNKET-Trastuzumab enhances CD8+ T cell cytotoxicity activity. When T cells were not activated by anti-CD3, the addition of CD8+ T cells did not further inhibit cell growth, indicating that the ability of A49-F3'-TriNKET-Trastuzumab to enhance CD8+ T cell cytotoxicity is dependent on T cell activation by anti-CD3 (FIG. 14B).

Example 5—Assessment of TriNKET Binding to Cell Expressed Human Cancer Antigens TriNKET Binding Assay Human cancer cell lines expressing HER2 were used to assess tumor antigen binding of a TriNKET (A49-F3'-TriNKET-Trastuzumab) and monoclonal antibodies. The human renal cell carcinoma cell line 786-O expressed low levels of HER2, the human lung cancer cell line NCI-H661 expressed moderate levels of HER2, and the human breast cancer cell line SkBr-3 expressed high levels of HER2. All three cell lines were used to assess their binding affinity to TriNKET. TriNKETs were diluted in a series of concentrations, and were incubated with the respective cells.

Binding of the TriNKET (A49-F3'-TriNKET-Trastuzumab) to the cells was detected using a fluorophore conjugated to an anti-human IgG secondary antibody, and the cells were analyzed by flow cytometry. The level of binding at each concentration of the TriNKET (A49-F3'-TriNKET-Trastuzumab) was calculated as a percentage value of median fluorescence intensity (MFI) of the cells relative to the maximum MFI observed with the cells incubated with 670 nM of TriNKET. Alternatively, the level of binding at each concentration of TriNKET was calculated as a fold over background (FOB) value of MFI of the cells relative to the background MFI observed with the cells incubated with the secondary antibody only. Trastuzumab was used as a control in place of TriNKET in each experiment.

As shown in FIGS. 15A-15B, 16A-16B, and 17A-17B, the TriNKET (A49-F3'-TriNKET-Trastuzumab) and trastuzumab exhibited the most potent binding to the SkBr-3 cells (FIG. 15A), which had a high expression level of HER2 (HER+++). The binding affinity of the HER2-targeted TriNKET and trastuzumab to the NCI-H661, which had a moderate expression level of HER2 (HER2++), was similar (FIG. 16A) to but slightly higher than the binding affinity to the 786-O cells (FIG. 17A), which had a low expression level of HER2 (HER2+). This result suggested that the affinity of the HER2-targeted TriNKET and trastuzumab to HER2-expressing cells generally correlated with the expression level of HER2 on the cells.

Figure 15A:
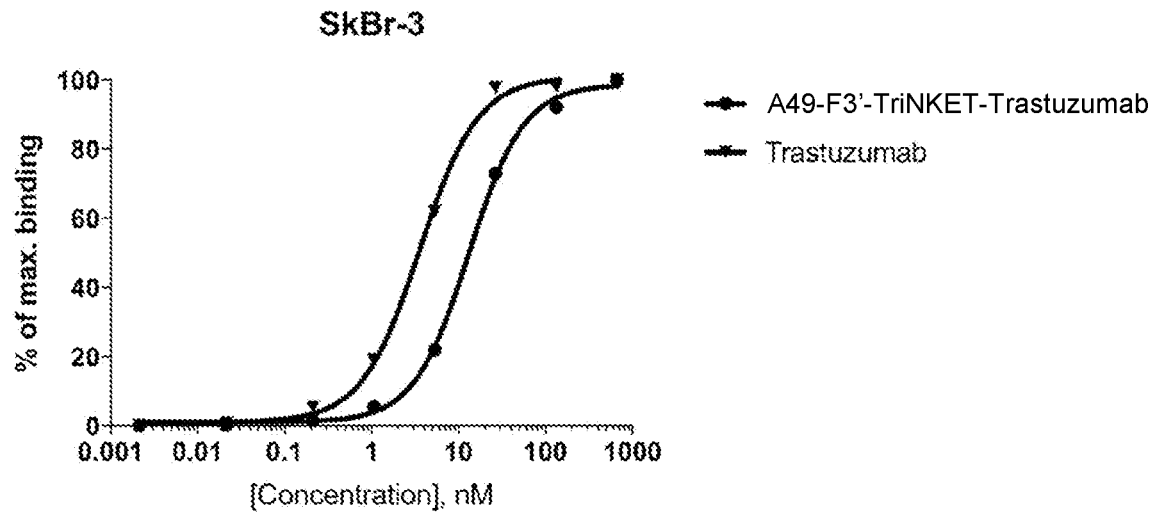
FIGS. 15A to 15B show TriNKET binding to SkBr-3 cell line that has a high level of HER2 expression, as measured by flow cytometry of SkBr-3 cells incubated with a series of concentrations of TriNKET or trastuzumab and a secondary antibody conjugated with a fluorophore.
Figure 15B:
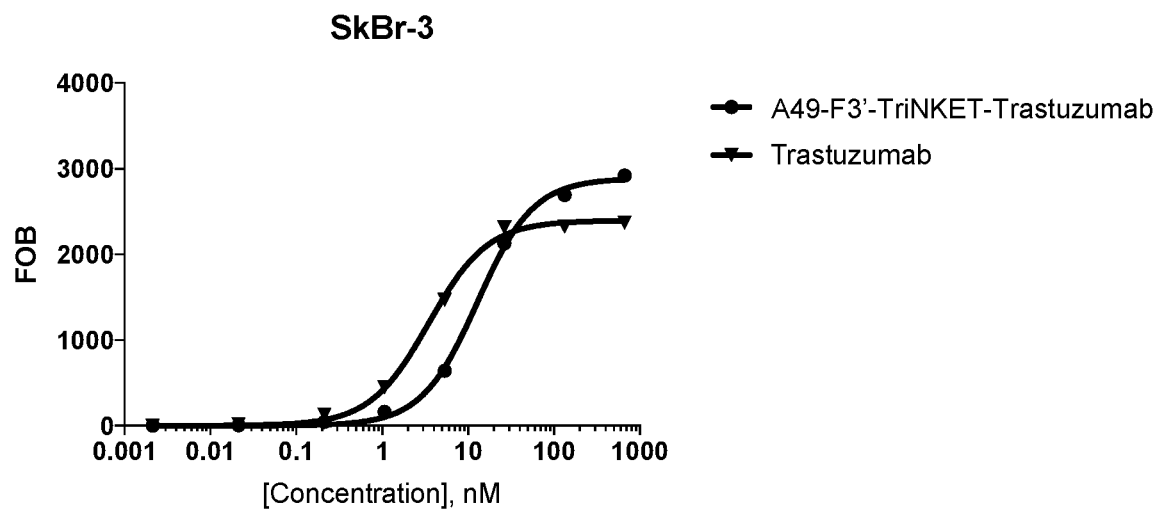
Figure 16A:
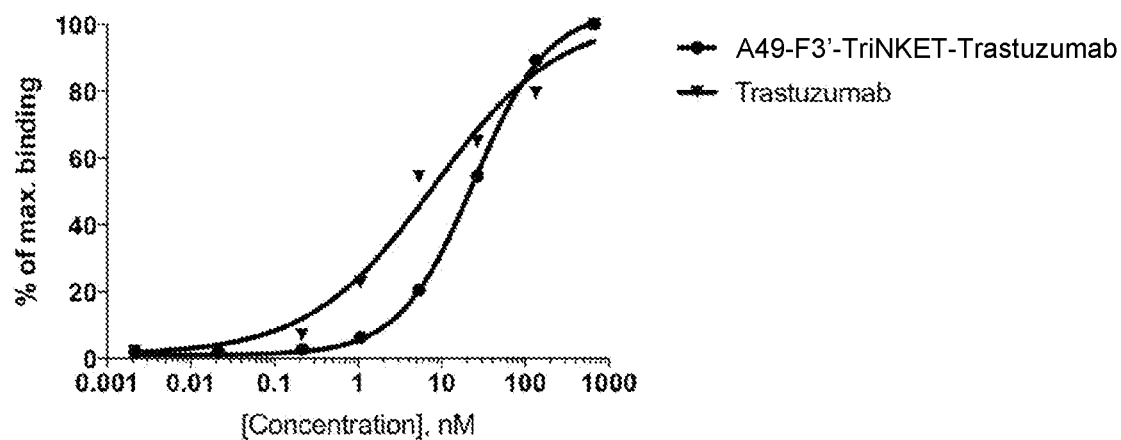
FIGS. 16A to 16B show TriNKET binding to NCI-H661 cell line that has a moderate level of HER2 expression, as measured by flow cytometry of NCI-H661 cells incubated with a series of concentrations of TriNKET or trastuzumab and a secondary antibody conjugated with a fluorophore.
Figure 16B:
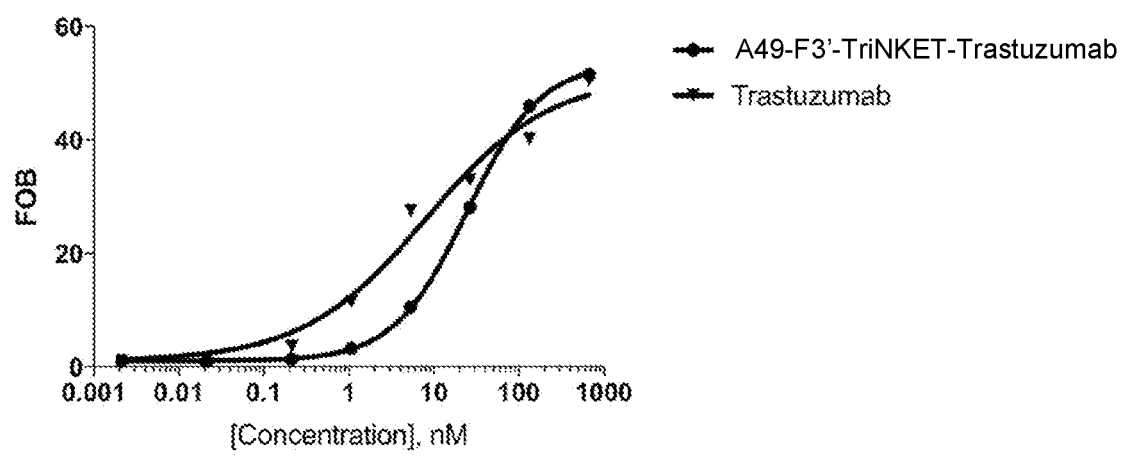
Figure 17A:
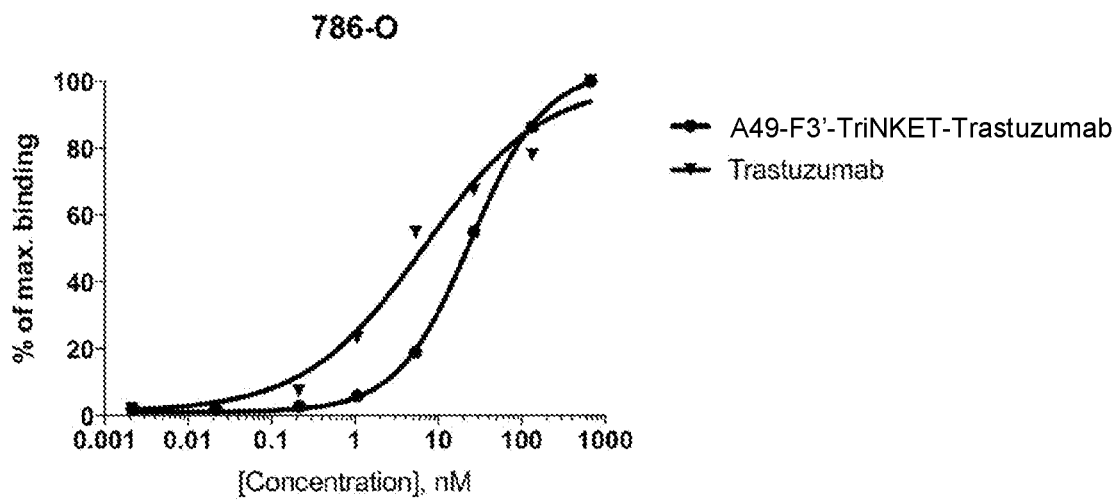
FIGS. 17A to 17B show TriNKET binding to 786-O cell line that has a low level of HER2 expression, as measured by flow cytometry of 786-O cells incubated with a series of concentrations of TriNKET or trastuzumab and a secondary antibody conjugated with a fluorophore.
Figure 17B:
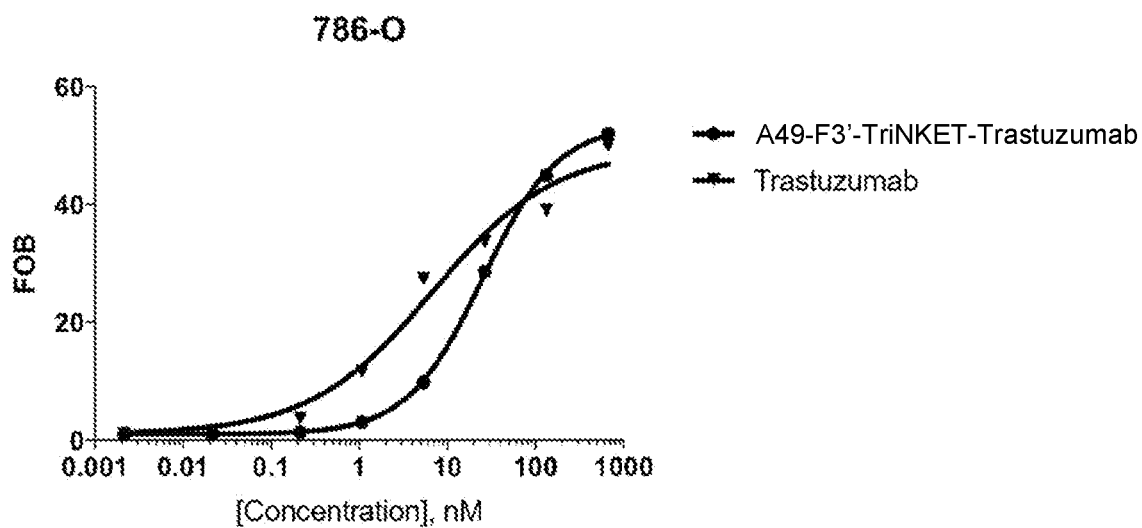

Trastuzumab showed a higher binding affinity than the TriNKET (A49-F3'-TriNKET-Trastuzumab) with each of the three cell lines (SkBr-3 (FIG. 15A), NCI-H661 (FIG. 16A), and 786-O (FIG. 17A)). However, when expressed as fold over background (FOB) values, the maximum binding of the TriNKET to each of the three cell lines was greater than the maximum binding of trastuzumab (SkBr-3 (FIG. 15B), NCI-H661 (FIG. 16B), and 786-O (FIG. 17B)). The difference was especially significant with the SkBr-3 cells, which had a high HER2 expression level (FIG. 15B).

Figure 18A:
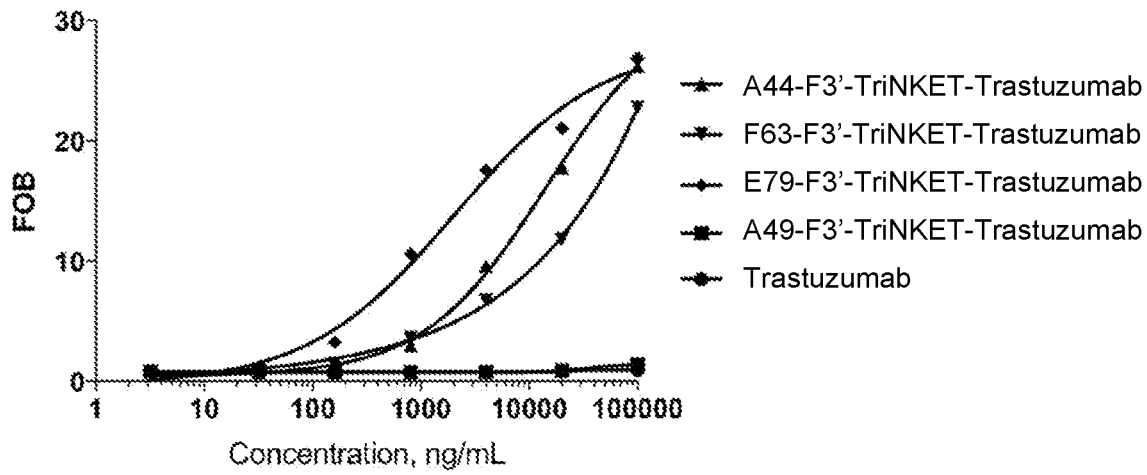
FIGS. 18A to 18B show HER2-targeted TriNKETs binding to hNKG2D-expressing EL4 cells, as measured by flow cytometry of EL4 cells incubated with a series of concentrations of TriNKETs or trastuzumab and a secondary antibody conjugated with a fluorophore. The levels of binding are shown as fold over background (FOB) values of MFI relative to the background MFI observed with the cells incubated with the secondary antibody only.
Figure 18B:
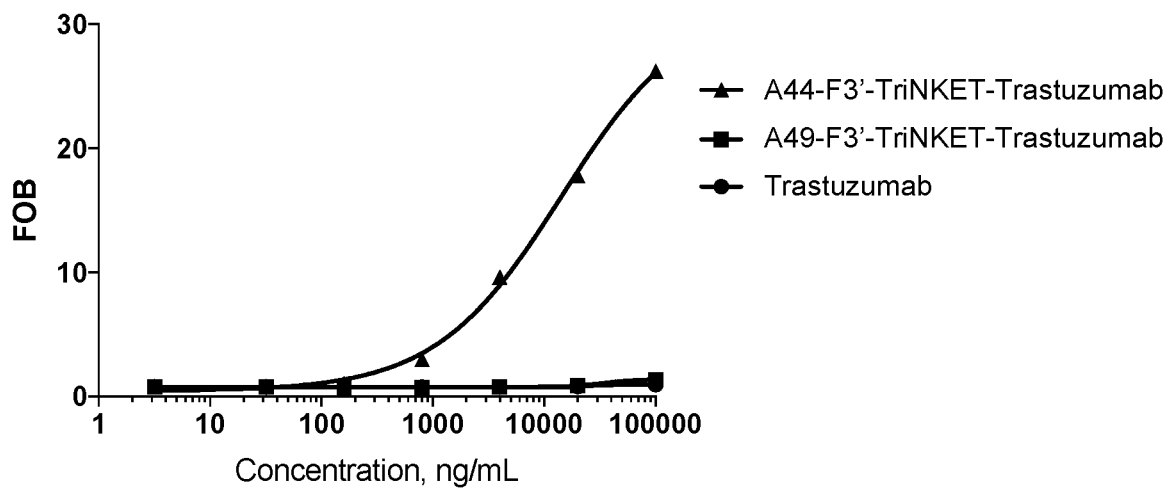

The affinity of TriNKETs to EL4 cells that express NKG2D was measured by a similar method. As shown in FIGS. 18A-18B, different NKG2D targeting domains used in the TriNKET resulted in different levels of binding to NKG2D expressed on EL4 cells. TriNKETs of clones A44, F63, and E79 bound to NKG2D strongly (FIG. 18A and FIG. 18B), whereas a TriNKET of clone A49 bound to NKG2D weakly (FIG. 18A and FIG. 18B).

Primary Human NK Cell Cytotoxicity Assay

PBMCs were isolated from human peripheral blood buffy coats using density gradient centrifugation and were washed. NK cells were isolated from the PBMCs using a negative selection technique with magnetic beads. Typically, with this technique, more than 90% of the harvested cells were CD3-CD56+. The isolated NK cells were rested overnight. Rested NK cells were used the following day in cytotoxicity assays.

DELFIA Cytotoxicity Assay

Human cancer cell lines expressing a target of interest were harvested from culture. The cells were washed with HBS, and were resuspended in growth media at $10^6$ cells/mL for labeling with BATDA reagent (Perkin Elmer AD0116). Manufacturer instructions were followed for labeling of the target cells. After labeling, the cells were washed three times with HBS, and were resuspended at $0.5-1.0\times10^5$/mL in culture media. 100 µl of BATDA labeled cells were added to each well of the 96-well plate. Trastuzumab and A49-F3'-TriNKET-Trastuzumab was diluted in culture media, and 50 µl of diluted trastuzumab and A49-F3'-TriNKET-Trastuzumab were added, respectively, to each of their corresponding wells for the experiment. Rested and/or activated NK cells were harvested from culture. The cells were washed and resuspended at $10^5-2.0\times10^6$/mL in culture media depending on the desired E:T ratio. 50 µl of NK cells were added to each well of the plate to make a total of 200 µl culture volume. To measure the spontaneous release of the BATDA hydrolysis product (e.g., due to spontaneous cell death), no NK cell, mAb, or TriNKET was added to the target cells. To measure the maximum release of the BATDA hydrolysis product, the target cells were lysed by addition of 1% Triton-X. The plate was incubated at 37° C. with 5% $CO_2$ for 2-3 hours.

After culturing for 2-3 hours, the plate was removed from the incubator and the cells were pelleted by centrifugation at 200 g for 5 minutes. 20 µl of culture supernatant were transferred to a clean microplate provided from the manufacturer, and 200 µl of room temperature europium solution were added to each well. The plate was protected from light and incubated on a plate shaker at 250 rpm for 15 minutes. Fluorescence levels were read using either Victor 3 or SpectraMax i3X instruments.

The percentage of specific lysis was calculated as: % Specific lysis=(Experimental release-Spontaneous release)/(Maximum release-Spontaneous release)*100%

Figure 20:
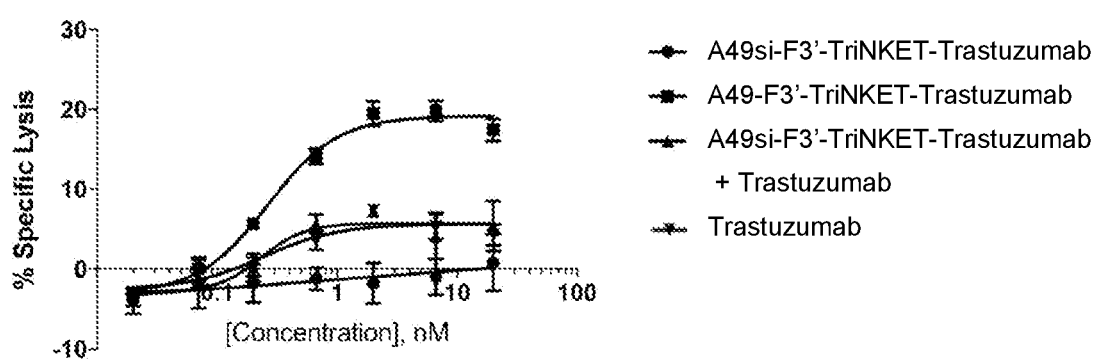
FIG. 20 shows TriNKETs are more potent and effective in mediating NK-cell killing of H661 target cells than the combination of Fc-silent TriNKET and trastuzumab.

To mimic the binding properties of TriNKETs on separate molecules, bispecific antibody engaging NKG2D and HER2 was combined with trastuzumab, and compared to the TriNKET containing all three binding domains on one molecule. Accordingly, 786-O and H661 target cells were incubated with isolated NK cells in the presence of HER2-targeted TriNKET, trastuzumab, Fc-silent TriNKET (comprising SEQ ID NO: 156 and SEQ ID NO: 157, both of which include L234A, L235A, and P329G (LALAPG) substitutions in the Fc domain (shown within a third-bracket [ ])), or the combination of Fc-silent TriNKET and trastuzumab. Remarkably, TriNKET exhibited a significant advantage in potency and maximum lysis of target cells compared to the combination of Fc-silent TriNKET and trastuzumab, when the target cells were 786-O cells (FIG. 19) or H661 cells (FIG. 20).

```
scFv-Fc
(Includes L234A, L235A, and P329G (LALAPG)
substitutions (shown within a third-bracket []))
                                        (SEQ ID NO: 156)
DIQMTQSPSSLSASVGDRVTITCRASQDVNTAVAWYQQKPGKAPKLLIY
SASFLYSGVPSRFSGSRSGTDFTLTISSLQPEDFATYYCQQHYTTPPTF
GCGTKVEIKGGGGSGGGGSGGGGSGGGGSEVQLVESGGGLVQPGGSLRL
SCAASGFNIKDTYIHWVRQAPGKCLEWVARIYPTNGYTRYADSVKGRFT
ISADTSKNTAYLQMNSLRAEDTAVYYCSRWGGDGFYAMDYWGQGTLVTV
SSASDKTHTCPPCPAPE[AA]GGPSVFLFPPKPKDTLMISRTPEVTCVV
```

-continued
VDVSHEDPEVKFNWYVDGVEVHNAKTKPREEQYNSTYRVVSVLTVLHQD
WLNGKEYKCKVSNKAL[G]APIEKTISKAKGQPREPRVYTLPPCRDELT
KNQVSLTCLVKGFYPSDIAVEWESNGQPENNYKTTPPVLVSDGSFTLYS
KLTVDKSRWQQGNVFSCSVMHEALHNHYTQKSLSLSPG Whole chain VH-CH1-Fc
(Includes L234A, L235A, and P329G (LALAPG)
substitutions (shown within a third-bracket []))
(SEQ ID NO: 157)
EVQLVESGGGLVKPGGSLRLSCAASGFTFSSYSMNWVRQAPGKGLEWVS
SISSSSSYIYYADSVKGRFTISRDNAKNSLYLQMNSLRAEDTAVYYCAR
GAPMGAAAGWFDPWGQGTLVTVSSASTKGPSVFPLAPSSKSTSGGTAAL
GCLVKDYFPEPVTVSWNSGALTSGVHTFPAVLQSSGLYSLSSVVTVPSS
SLGTQTYICNVNHKPSNTKVDKKVEPKSCDKTHTCPPCPAPE[AA]GGP
SVFLFPPKPKDTLMISRTPEVTCVVVDVSHEDPEVKFNWYVDGVEVHNA
KTKPREEQYNSTYRVVSVLTVLHQDWLNGKEYKCKVSNKAL[G]APIEK
TISKAKGQPREPQVCTLPPSRDELTENQVSLTCLVKGFYPSDIAVEWES
NGQPENNYKTTPPVLDSDGSFFLYSWLTVDKSRWQQGNVFSCSVMHEAL
HNHYTQKSLSLSPG Example 6—Variants of ADI-27749 and TriNKETs Containing the Variants As described above, ADI-27749 (A49) contains, inter alia, a heavy chain CDR3 having the amino acid sequence of GAPMGAAAGWFDP (SEQ ID NO:169). The Met at position 102 of SEQ ID NO:94 (i.e., at position 4 of this CDR3 sequence) may be replaced by Gln, Leu, Ile, Phe, or Val, thereby generating NKG2D-binding sites A49MQ, A49ML, A49MI, A49MF, and A49MV, respectively, having the corresponding heavy chain variable region, light chain variable region, and CDR sequences provided in Table 1.

Binding of A49-F3'-TriNKET-Trastuzumab ("TriNKET A") and a mutant form of TriNKET A having a substitution of Ile for the Met ("TriNKET A*") to a fusion protein of human NKG2D and murine Fc ("mFc-hNKG2D") was characterized by surface plasmon resonance (SPR) at 37° C. Steady state affinity fit was utilized to obtain the equilibrium affinity data. The equilibrium affinity constants were calculated, and data from two independent experiments for TriNKET A* and the independent experiments for TriNKET A were averaged.

TABLE 12

| Capture | Analyte | Steady State Affinity $K_D$ (M) |
|---|---|---|
| mFc-hNKG2D | TriNKET A* | $5.09 \times 10^{-7}$ |
| mFc-hNKG2D | TriNKET A* | $4.54 \times 10^{-7}$ |
| Average | | $4.81 \times 10^{-7}$ |
| mFc-hNKG2D | TriNKET A | $3.70 \times 10^{-7}$ |
| mFc-hNKG2D | TriNKET A | $3.28 \times 10^{-7}$ |
| mFc-hNKG2D | TriNKET A | $3.13 \times 10^{-7}$ |
| Average ± stdev | | $(3.37 \pm 0.30) \times 10^{-7}$ |

As shown in Table 12, the equilibrium affinity constant ($K_D$) obtained from the affinity fit was very similar between the replicates, which suggested a high confidence in the measured parameters. The $K_D$ values indicated that the M102 variant has less than 2-fold reduced affinity for human NKG2D compared to TriNKET A. The $K_D$ for TriNKET A* was $(4.81+0.39) \times 10^{-7}$ M, while the $K_D$ for TriNKET A was $(3.37+0.30) \times 10^{-7}$ M (calculated from the affinity fit). These $K_D$ values suggested that the M102 mutation had only a minor effect on the binding of an A49-containing TriNKET to human NKG2D.

Additionally, the effect of the M102 mutation on the potency of TriNKETs was assessed in a cytotoxicity assay. Briefly, KHYG-1 cells expressing the high-affinity variant of CD16a (158V) were generated through retroviral transduction. Following transduction, cells were selected in puromycin-containing growth media to generate a selected population of KHYG-1-CD16V cells. The selected population was maintained in media containing 10 ng/mL human IL-2. To prepare the KHYG-1-CD16V cells for use as effectors in cytotoxicity assays, the cells were harvested from culture, pelleted, washed three times in culture media without IL-2, and resuspended in culture media without IL-2 and rested for 24 hours.

To measure the activity of TriNKET A and TriNKET A*, human cancer cell line SKBR-3 expressing the tumor antigen HER2 were selected as target cells. SKBR-3 expressing HER2 were harvested from culture. The cells were washed with Hepes Buffered Saline (HBS), and were resuspended in growth media at $10^6$ cells/mL for labeling with BATDA (hydrophobic esterified form of TDA (bis(acetoxymethyl) 2,2': 6',2"-terpyridine-6,6"-dicarboxylate) reagent (Perkin Elmer C136-100) (BATDA diffuses through the cell membrane of viable cells, and is hydrolyzed by intracellular esterases resulting in accumulation of membrane permeable TDA inside target cells. After incubation of the target cells with the effector cells, the TDA released from lysed cells into the supernatant is chelated with Eu3+, and the NK cell activity is quantified by measuring the intense fluorescence of the EuTDA chelate formed. (See see Blomberg et al. *J. Immunol. Methods* (1996) 193 (2): 199-206)). Manufacturer instructions were followed for labeling of the target cells. After labeling, the cells were washed three times with HBS and were resuspended at $0.5 \times 10^5$ cells/mL in culture media. 100 µl of BATDA labeled cells were added to each well of a 96-well plate.

TriNKETs were serially diluted in culture media, and 50 µl of a diluted TriNKET were added to each well. Rested NK cells were harvested from culture, washed, and resuspended at $1.0 \times 10^6$ cells/mL in culture media. 50 µl of NK cells were added to each well of the plate to attain a desired E:T ratio of 10:1 and to make a total of 200 µl culture volume in each well. The plate was incubated at 37° C. with 5% $CO_2$ for 2-3 hours.

After culturing, the plate was removed from the incubator, and the cells were pelleted by centrifugation at 200×g for 5 minutes. 20 µl of culture supernatant were transferred to a clean microplate provided from the manufacturer. Supernatant from the labeled cells incubated alone without NK cells was used to measure spontaneous release of fluorescence enhancing ligand 2,2': 6',2"-terpyridine-6,6"-dicarboxylic acid (TDA) (see Blomberg et al. *J. Immunol. Methods* (1996) 193 (2): 199-206). Supernatant from labeled cells incubated with 1% Triton-X was used to measure maximum lysis of the target cells. Supernatant from the labeled cells prior to the 2-3 hours of incubation was used to measure the background and for quality control purposes.

200 µl of room temperature europium solution (Perkin Elmer C135-100) was added to each well containing culture supernatant. The plate was protected from light and incubated on a plate shaker at 250 rpm for 15 minutes. Fluorescence was measured using a SpectraMax i3X instrument. The fluorescent levels represented lysis of the target cells. The values of % specific lysis were calculated as: % specific lysis=((Experimental release-Spontaneous release)/(Maximum release-Spontaneous release))×100%.

Figure 21:
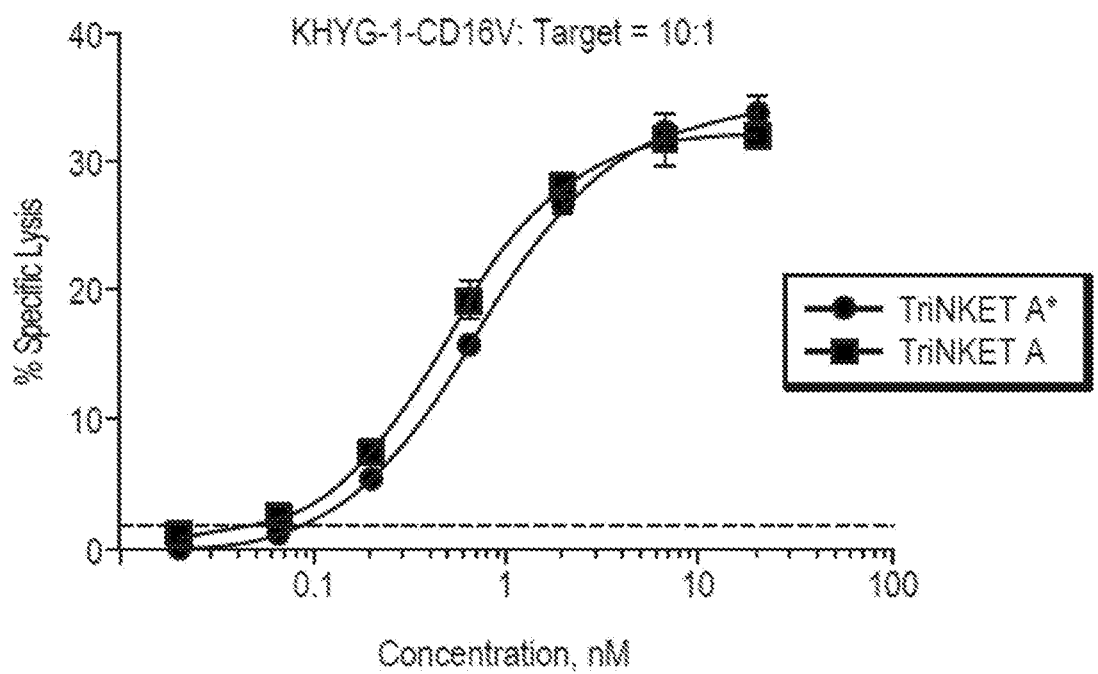
FIG. 21 is a line graph showing the potency of TriNKET A and TriNKET A* (in which M102 of A49-F3'-TriNKET-Trastuzumab is substituted with I) in mediating cytotoxicity of NK cells against SKBR-3 target cells.

The % specific lysis values were plotted in FIG. 21, and the $EC_{50}$ and maximum % specific lysis values are summarized in Table 13.

TABLE 13

| Protein | $EC_{50}$ (nM) | Max lysis (%) |
|---|---|---|
| TriNKET A | 0.39 | 35 |
| TriNKET A* | 0.65 | 36 |

The $EC_{50}$ was less than 2-fold increased and maximum % specific lysis values of TriNKET A* was identical to that of TriNKET A, suggesting that the M102 mutation did not have a substantial affect on the biological activity of TriNKET A.

NUMBERED EMBODIMENTS

Embodiments disclosed herein include embodiments P1 to P49, as provided in the numbered embodiments of the disclosure:

Embodiment P1

A protein comprising: (a) a first antigen-binding site comprising an Fab fragment that binds NKG2D; (b) a second antigen-binding site comprising a single-chain variable fragment (scFv) that binds HER2; and (c) an antibody Fc domain or a portion thereof sufficient to bind CD16, or a third antigen-binding site that binds CD16.

Embodiment P2

The protein of embodiment P1, wherein the scFv is linked to the antibody Fc domain or a portion thereof sufficient to bind CD16, or the third antigen-binding site that binds CD16, via a hinge comprising Ala-Ser, wherein the scFv comprises a heavy chain variable domain and a light chain variable domain.

Embodiment P3

The protein according to embodiment P2, wherein the scFv is linked to the antibody Fc domain.

Embodiment P4

The protein according to embodiment P2 or P3, wherein the heavy chain variable domain of the scFv forms a disulfide bridge with the light chain variable domain of the scFv.

Embodiment P5

The protein according to embodiment P4, wherein the disulfide bridge is formed between C44 from the heavy chain variable domain and C100 from the light chain variable domain.

Embodiment P6

The protein according to embodiment P5, wherein the scFv is linked to the antibody Fc domain, wherein the light chain variable domain of the scFv is positioned at the N-terminus of the heavy chain variable domain of the scFv, and is linked to the heavy chain variable domain of the scFv via a flexible linker (GlyGlyGlyGlySer) 4 (($G_4S$)$_4$) (SEQ ID NO:143), and the Fab is linked to the antibody Fc domain.

Embodiment P7

The protein according to any one of embodiments P2-P6, wherein the heavy chain variable domain of the scFv is linked to the light chain variable domain of the scFv via a flexible linker.

Embodiment P8

The protein according to embodiment P7, wherein the flexible linker comprises (GlyGlyGlyGlySer) 4 (($G_4S$)$_4$) (SEQ ID NO:143).

Embodiment P9

The protein according to any one of embodiments P2-P8, wherein the heavy chain variable domain of the scFv is positioned at the N-terminus or the C-terminus of the light chain variable domain of the scFv.

Embodiment P10

The protein according to embodiment P9, wherein the light chain variable domain of the scFv is positioned at the N-terminus of the heavy chain variable domain of the scFv.

Embodiment P11

The protein according to any one of embodiments P1 to P10, wherein the Fab fragment is linked to the antibody Fc domain or a portion thereof sufficient to bind CD16 or the third antigen-binding site that binds CD16.

Embodiment P12

The protein according to embodiment P11, wherein the heavy chain portion of the Fab fragment comprises a heavy chain variable domain and a CH1 domain, and wherein the heavy chain variable domain is linked to the CH1 domain.

Embodiment P13

The protein according to embodiment P11 or P12, wherein the Fab is linked to the antibody Fc domain.

Embodiment P14

A protein according to any of the preceding embodiments comprising a sequence of SEQ ID NO: 139.

Embodiment P15

A protein according to any one of embodiments P2-P14 comprising an scFv linked to an antibody Fc domain, wherein the scFv linked to the antibody Fc domain is represented by a sequence selected from SEQ ID NO:140 and SEQ ID NO: 146.

Embodiment P16

A protein according to any of the preceding embodiments comprising a sequence of SEQ ID NO: 141, SEQ ID NO: 145, SEQ ID NO: 147, or SEQ ID NO: 148.

Embodiment P17

A protein comprising a sequence at least 90% identical to an amino acid sequence of SEQ ID NO:139.

Embodiment P18

A protein comprising a sequence at least 95% identical to an amino acid sequence of SEQ ID NO:139.

Embodiment P19

A protein comprising a sequence at least 99% identical to an amino acid sequence of SEQ ID NO:139.

Embodiment P20

A protein comprising a sequence at least 90% identical to an amino acid sequence selected from SEQ ID NO: 140 and SEQ ID NO:146.

Embodiment P21

A protein comprising a sequence at least 95% identical to an amino acid sequence selected from SEQ ID NO:140 and SEQ ID NO:146.

Embodiment P22

A protein comprising a sequence at least 99% identical to an amino acid sequence selected from SEQ ID NO: 140 and SEQ ID NO:146.

Embodiment P23

The protein according any one of embodiments P1-P13, wherein the first antigen-binding site that binds NKG2D comprises a heavy chain variable domain at least 90% identical to an amino acid sequence selected from SEQ ID NO:86 and SEQ ID NO:94.

Embodiment P24

The protein according any one of embodiments P1-P13, wherein the first antigen-binding site that binds NKG2D comprises a heavy chain variable domain at least 90% identical to SEQ ID NO:86 and a light chain variable domain at least 90% identical to SEQ ID NO:90.

Embodiment P25

The protein according any one of embodiments P1-P13, wherein the first antigen-binding site that binds NKG2D comprises a heavy chain variable domain at least 95% identical to SEQ ID NO:86 and a light chain variable domain at least 95% identical to SEQ ID NO:90.

Embodiment P26

The protein according any one of embodiments P1-P13, wherein the first antigen-binding site that binds NKG2D comprises a heavy chain variable domain at least 90% identical to SEQ ID NO:94 and a light chain variable domain at least 90% identical to SEQ ID NO:98.

Embodiment P27

The protein according any one of embodiments P1-P13, wherein the first antigen-binding site that binds NKG2D comprises a heavy chain variable domain at least 95% identical to SEQ ID NO:94 and a light chain variable domain at least 95% identical to SEQ ID NO:98.

Embodiment P28

The protein according any one of embodiments P1-P13, wherein the first antigen-binding site that binds NKG2D comprises a heavy chain variable domain at least 90% identical to SEQ ID NO:144 and a light chain variable domain at least 90% identical to SEQ ID NO:98.

Embodiment P29

The protein according any one of embodiments P1-P13, wherein the first antigen-binding site that binds NKG2D comprises a heavy chain variable domain at least 95% identical to SEQ ID NO:144 and a light chain variable domain at least 95% identical to SEQ ID NO:98.

Embodiment P30

The protein according any one of embodiments P1-P13, wherein the first antigen-binding site that binds NKG2D comprises a heavy chain variable domain identical to SEQ ID NO:86 and a light chain variable domain identical to SEQ ID NO: 90.

Embodiment P31

The protein according any one of embodiments P1-P13, wherein the first antigen-binding site that binds NKG2D comprises a heavy chain variable domain identical to SEQ ID NO:94 and a light chain variable domain identical to SEQ ID NO: 98.

Embodiment P32

The protein according any one of embodiments P1-P13, wherein the first antigen-binding site that binds NKG2D comprises a heavy chain variable domain identical to SEQ ID NO:144 and a light chain variable domain identical to SEQ ID NO: 98.

Embodiment P33

The protein according any one of embodiments P1-P13 and P23-P32, wherein the antibody Fc domain comprises hinge and CH2 domains of a human IgG1 antibody.

Embodiment P34

The protein according to embodiment P33, wherein the Fc domain comprises an amino acid sequence at least 90% identical to amino acids 234-332 of a human IgG1 antibody.

Embodiment P35

The protein according to embodiment P33 or P34, wherein the Fc domain comprises amino acid sequence at least 90% identical to the Fc domain of human IgG1 and differs at one or more positions selected from the group consisting of Q347, Y349, T350, L351, S354, E356, E357, K360, Q362, S364, T366, L368, K370, N390, K392, T394, D399, S400, D401, F405, Y407, K409, T411, K439.

Embodiment P36

The protein according to any one of embodiments P1-P13 and P23-P34, wherein the Fc domain is an Fc domain of a human IgG1 comprising Q347R, D399V, and F405T substitutions.

Embodiment P37

The protein according to embodiment P36, wherein the Fc domain comprising the substitutions is linked to the scFv.

Embodiment P38

The protein according to any one of embodiments P1-P13 and P23-P34, wherein the Fc domain is an Fc domain of a human IgG1 comprising K360E and K409W substitutions.

Embodiment P39

The protein according to embodiment P38, wherein the Fc domain comprising the substitutions is linked to the Fab fragment.

Embodiment P40

The protein according to any one of embodiments P1-P13 and P23-P34, wherein the Fc domain is an Fc domain of a human IgG1 comprising a T366W substitution.

Embodiment P41

The protein according to embodiment P40, wherein the Fc domain comprising the substitution is linked to the Fab fragment.

Embodiment P42

The protein according to any one of embodiments P1-P13 and P23-P34, wherein the Fc domain is an Fc domain of a human IgG1 comprising T366S, L368A, and Y407V substitutions.

Embodiment P43

The protein according to embodiment P42, wherein the Fc domain comprising the substitutions is linked to the scFv.

Embodiment P44

A protein according to any one of embodiments P1-P43, wherein the protein binds to NKG2D with an affinity of KD of 10 nM or lower.

Embodiment P45

A formulation comprising a protein according to any one of the preceding embodiments and a pharmaceutically acceptable carrier.

Embodiment P46

A cell comprising one or more nucleic acids expressing a protein according to any one of embodiments P1-P44.

Embodiment P47

A method of directly and/or indirectly enhancing tumor cell death, the method comprising exposing a tumor and natural killer cells to a protein according to any one of embodiments P1-P44.

Embodiment P48

A method of treating cancer, wherein the method comprises administering a protein according to any one of embodiments P1-P44 or a formulation according to embodiment P45 to a patient.

Embodiment P49

The method of embodiment P48, wherein the cancer is selected from the group consisting of breast cancer, thyroid cancer, gastric cancer, renal cell carcinoma, adenocarcinoma of the lung, prostate cancer, cholangiocarcinoma, uterine cancer, pancreatic cancer, colorectal cancer, ovarian cancer, cervical cancer, head and neck cancer, lung squamous, mesothelioma, liver cancer, mesothelioma, sarcoma, and gall bladder cancer.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

---

What is claimed is:

1. A multi-specific binding protein comprising
   (a) a Fab that binds NKG2D;
   (b) a single-chain variable fragment (scFv) that binds HER2; and
   (c) an antibody Fc domain that binds CD16,
   wherein the multi-specific binding protein comprises:
      a first polypeptide comprising the amino acid sequence of SEQ ID NO: 141;
      a second polypeptide comprising the amino acid sequence of SEQ ID NO: 140; and
      a third polypeptide comprising the amino acid sequence of SEQ ID NO: 142.

2. A pharmaceutical composition comprising the multi-specific binding protein according to claim 1 and a pharmaceutically acceptable carrier.

3. A cell comprising one or more nucleic acids encoding the multi-specific binding protein according to claim 1.

4. A method of enhancing tumor cell death, the method comprising exposing a tumor cell and a natural killer cell to the multi-specific binding protein according to claim 1, and wherein the tumor cell expresses HER2.

5. A method of treating a HER2 expressing cancer, wherein the method comprises administering an effective amount of the multi-specific binding protein according to claim 1 to a patient in need thereof.

6. The method of claim 5, wherein the cancer is selected from the group consisting of breast cancer, thyroid cancer, gastric cancer, renal cell carcinoma, prostate cancer, cholangiocarcinoma, uterine cancer, pancreatic cancer, colorectal cancer, ovarian cancer, cervical cancer, head and neck cancer, lung cancer, mesothelioma, liver cancer, sarcoma, and gall bladder cancer.

* * * * *

SEQUENCE LISTING

```
<160> NUMBER OF SEQ ID NOS: 209

<210> SEQ ID NO 1
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 1

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
            115

<210> SEQ ID NO 2
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Ile
                85                  90                  95

Thr Phe Gly Gly Gly Thr Lys Val Glu Ile Lys
            100                 105

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Ser Phe Ser Gly Tyr Tyr Trp Ser
1               5

<210> SEQ ID NO 4
<211> LENGTH: 16
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 4

Glu Ile Asp His Ser Gly Ser Thr Asn Tyr Asn Pro Ser Leu Lys Ser
1               5                   10                  15

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Arg Ala Arg Gly Pro Trp Ser Phe Asp Pro
1               5                   10

<210> SEQ ID NO 6
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 7
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

```
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
             85                  90                  95

Ile Thr Phe Gly Gly Gly Thr Lys Val Glu Ile Lys
            100                 105

<210> SEQ ID NO 8
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
             20                  25                  30

Tyr Trp Ser Trp Ile Arg Gln Pro Pro Gly Lys Gly Leu Glu Trp Ile
         35                  40                  45

Gly Glu Ile Asp His Ser Gly Ser Thr Asn Tyr Asn Pro Ser Leu Lys
     50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
             85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 9
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Gly Ser Trp
             20                  25                  30

Leu Ala Trp Tyr Gln Gln Lys Pro Gly Lys Ala Pro Lys Leu Leu Ile
         35                  40                  45

Tyr Lys Ala Ser Ser Leu Glu Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr His Ser Phe Tyr Thr
             85                  90                  95

Phe Gly Gly Gly Thr Lys Val Glu Ile Lys
            100                 105

<210> SEQ ID NO 10
```

<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 11
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Ser Asn Ser Tyr Tyr Thr
                85                  90                  95

Phe Gly Gly Gly Thr Lys Val Glu Ile Lys
            100                 105

<210> SEQ ID NO 12
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Gln Gln Trp Gly Ala Gly Leu Leu Lys Pro Ser Glu
1               5                   10                  15

```
Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
50                      55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
            115

<210> SEQ ID NO 13
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Thr
                85                  90                  95

Phe Gly Gly Gly Thr Lys Val Glu Ile Lys
            100                 105

<210> SEQ ID NO 14
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80
```

```
Lys Leu Ser Ser Val Thr Ala Ala Asp Thr Ala Val Tyr Tyr Cys Ala
                85                  90                  95

Arg Ala Arg Gly Pro Trp Gly Phe Asp Pro Trp Gly Gln Gly Thr Leu
            100                 105                 110

Val Thr Val Ser Ser
            115

<210> SEQ ID NO 15
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Leu Gln Met Thr Gln Ser Pro Ser Ser Leu Ser Ala Ser Val Gly
1               5                   10                  15

Asp Arg Val Thr Ile Thr Cys Arg Thr Ser Gln Ser Ile Ser Ser Tyr
            20                  25                  30

Leu Asn Trp Tyr Gln Gln Lys Pro Gly Gln Pro Pro Lys Leu Leu Ile
        35                  40                  45

Tyr Trp Ala Ser Thr Arg Glu Ser Gly Val Pro Asp Arg Phe Ser Gly
50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Ser Tyr Asp Ile Pro Tyr
                85                  90                  95

Thr Phe Gly Gln Gly Thr Lys Leu Glu Ile Lys
            100                 105

<210> SEQ ID NO 16
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
            115

<210> SEQ ID NO 17
<211> LENGTH: 107
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gly Ser Phe Pro Ile
                85                  90                  95

Thr Phe Gly Gly Gly Thr Lys Val Glu Ile Lys
            100                 105

<210> SEQ ID NO 18
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 19
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Ile Gln Met Thr Gln Ser Pro Ser Thr Leu Ser Ala Ser Val Gly
1               5                   10                  15
```

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Ser Lys Glu Val Pro Trp
                85                  90                  95

Thr Phe Gly Gln Gly Thr Lys Val Glu Ile Lys
            100                 105

<210> SEQ ID NO 20
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 21
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

```
Asp Asp Phe Ala Thr Tyr Tyr Cys Gln Gln Tyr Asn Ser Phe Pro Thr
                85                  90                  95

Phe Gly Gly Gly Thr Lys Val Glu Ile Lys
            100                 105

<210> SEQ ID NO 22
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 23
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Ile Tyr Pro Thr
                85                  90                  95

Phe Gly Gly Gly Thr Lys Val Glu Ile Lys
            100                 105

<210> SEQ ID NO 24
<211> LENGTH: 117
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 24

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
            115

<210> SEQ ID NO 25
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Ser Tyr Pro Thr
                85                  90                  95

Phe Gly Gly Gly Thr Lys Val Glu Ile Lys
            100                 105

<210> SEQ ID NO 26
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30
```

```
Tyr Trp Ser Trp Ile Arg Gln Pro Pro Gly Lys Gly Leu Glu Trp Ile
            35                  40                  45

Gly Glu Ile Asp His Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
65                   70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
            115

<210> SEQ ID NO 27
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gly Ser Phe Pro Thr
                85                  90                  95

Phe Gly Gly Gly Thr Lys Val Glu Ile Lys
            100                 105

<210> SEQ ID NO 28
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
            35                  40                  45

Gly Glu Ile Asp His Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95
```

Arg Ala Arg Gly Pro Trp Ser Phe Asp Pro Trp Gly Gln Gly Thr Leu
            100                 105                 110

Val Thr Val Ser Ser
        115

<210> SEQ ID NO 29
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gln Ser Phe Pro Thr
                85                  90                  95

Phe Gly Gly Gly Thr Lys Val Glu Ile Lys
            100                 105

<210> SEQ ID NO 30
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 31
<211> LENGTH: 106
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 31

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Ser Phe Ser Thr
                85                  90                  95

Phe Gly Gly Gly Thr Lys Val Glu Ile Lys
            100                 105

<210> SEQ ID NO 32
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 33
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
          35                  40                  45

Tyr Lys Ala Ser Ser Leu Glu Ser Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Glu Ser Tyr Ser Thr
                 85                  90                  95

Phe Gly Gly Gly Thr Lys Val Glu Ile Lys
                100                 105

<210> SEQ ID NO 34
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
         35                  40                  45

Gly Glu Ile Asp His Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                 85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 35
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
         35                  40                  45

Tyr Lys Ala Ser Ser Leu Glu Ser Gly Val Pro Ser Arg Phe Ser Gly
         50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Ser Phe Ile Thr
                 85                  90                  95

```
Phe Gly Gly Gly Thr Lys Val Glu Ile Lys
            100                 105

<210> SEQ ID NO 36
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 37
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gln Ser Tyr Pro Thr
                85                  90                  95

Phe Gly Gly Gly Thr Lys Val Glu Ile Lys
            100                 105

<210> SEQ ID NO 38
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 38

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
                100                 105                 110

Val Thr Val Ser Ser
            115

<210> SEQ ID NO 39
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr His Ser Phe Pro Thr
                85                  90                  95

Phe Gly Gly Gly Thr Lys Val Glu Ile Lys
                100                 105

<210> SEQ ID NO 40
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45
```

Gly Glu Ile Asp His Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Ala Arg Gly Pro Trp Ser Phe Asp Pro Trp Gly Gln Gly Thr Leu
            100                 105                 110

Val Thr Val Ser Ser
            115

<210> SEQ ID NO 41
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Gly Ser Trp
                 20                  25                  30

Leu Ala Trp Tyr Gln Gln Lys Pro Gly Lys Ala Pro Lys Leu Leu Ile
             35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Glu Leu Tyr Ser Tyr
                 85                  90                  95

Thr Phe Gly Gly Gly Thr Lys Val Glu Ile Lys
            100                 105

<210> SEQ ID NO 42
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
                 20                  25                  30

Tyr Trp Ser Trp Ile Arg Gln Pro Pro Gly Lys Gly Leu Glu Trp Ile
             35                  40                  45

Gly Glu Ile Asp His Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Ala Arg Gly Pro Trp Ser Phe Asp Pro Trp Gly Gln Gly Thr Leu
            100                 105                 110

```
Val Thr Val Ser Ser
        115
```

<210> SEQ ID NO 43
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Thr Phe Ile Thr
                85                  90                  95

Phe Gly Gly Gly Thr Lys Val Glu Ile Lys
            100                 105
```

<210> SEQ ID NO 44
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

```
Gln Val Gln Leu Val Gln Ser Gly Ala Glu Val Lys Lys Pro Gly Ser
1               5                   10                  15

Ser Val Lys Val Ser Cys Lys Ala Ser Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Ser Ser Ile Arg His Ala Tyr Tyr Tyr Gly Met
            100                 105                 110

Asp Val Trp Gly Gln Gly Thr Thr Val Thr Val Ser Ser
        115                 120                 125
```

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 45

Gly Thr Phe Ser Ser Tyr Ala Ile Ser
1               5

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Ile Ile Pro Ile Phe Gly Thr Ala Asn Tyr Ala Gln Lys Phe Gln
1               5                   10                  15

Gly

<210> SEQ ID NO 47
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ala Arg Gly Asp Ser Ser Ile Arg His Ala Tyr Tyr Tyr Tyr Gly Met
1               5                   10                  15

Asp Val

<210> SEQ ID NO 48
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Ile Thr Phe Gly Gly Gly Thr Lys Val Glu Ile
            100                 105                 110

Lys

<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 49

Lys Ser Ser Gln Ser Val Leu Tyr Ser Ser Asn Asn Lys Asn Tyr Leu
1               5                   10                  15
Ala

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Trp Ala Ser Thr Arg Glu Ser
1               5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gln Gln Tyr Tyr Ser Thr Pro Ile Thr
1               5

<210> SEQ ID NO 52
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Ser Asp Arg Phe His Pro Tyr Phe Asp Tyr Trp Gly
            100                 105                 110

Gln Gly Thr Leu Val Thr Val Ser Ser
        115                 120

<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Ser Ile Ser Ser Ser Tyr Tyr Trp Gly
1               5                   10

<210> SEQ ID NO 54
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser Ile Tyr Tyr Ser Gly Ser Thr Tyr Tyr Asn Pro Ser Leu Lys Ser
1               5                   10                  15

<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ala Arg Gly Ser Asp Arg Phe His Pro Tyr Phe Asp Tyr
1               5                   10

<210> SEQ ID NO 56
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Asp Thr Trp Pro Pro
                85                  90                  95

Thr Phe Gly Gly Gly Thr Lys Val Glu Ile Lys
            100                 105

<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Arg Ala Ser Gln Ser Val Ser Arg Tyr Leu Ala
1               5                   10

```
<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Asp Ala Ser Asn Arg Ala Thr
1               5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gln Gln Phe Asp Thr Trp Pro Pro Thr
1               5

<210> SEQ ID NO 60
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 61
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Asp Ile Gln Met Thr Gln Ser Pro Ser Thr Leu Ser Ala Ser Val Gly
1               5                   10                  15
```

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Ser Tyr Pro Thr
                85                  90                  95

Phe Gly Gly Gly Thr Lys Val Glu Ile Lys
            100                 105

<210> SEQ ID NO 62
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Arg Lys Ala Ser Gly Ser Phe Tyr Tyr Tyr Tyr Gly
            100                 105                 110

Met Asp Val Trp Gly Gln Gly Thr Thr Val Thr Val Ser Ser
        115                 120                 125

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Thr Phe Ser Ser Tyr Ala Ile Ser
1               5

<210> SEQ ID NO 64
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 64

Gly Ile Ile Pro Ile Phe Gly Thr Ala Asn Tyr Ala Gln Lys Phe Gln
1               5                   10                  15

Gly

<210> SEQ ID NO 65
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ala Arg Arg Gly Arg Lys Ala Ser Gly Ser Phe Tyr Tyr Tyr Tyr Gly
1               5                   10                  15

Met Asp Val

<210> SEQ ID NO 66
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Leu Leu Asn Ser
                20                  25                  30

Gly Asn Gln Lys Asn Tyr Leu Thr Trp Tyr Gln Gln Lys Pro Gly Gln
            35                  40                  45

Pro Pro Lys Pro Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys

<210> SEQ ID NO 67
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Glu Ser Ser Gln Ser Leu Leu Asn Ser Gly Asn Gln Lys Asn Tyr Leu
1               5                   10                  15

Thr

<210> SEQ ID NO 68
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 68

Trp Ala Ser Thr Arg Glu Ser
1               5

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gln Asn Asp Tyr Ser Tyr Pro Tyr Thr
1               5

<210> SEQ ID NO 70
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ala Pro Asn Tyr Gly Asp Thr Thr His Asp Tyr Tyr Tyr
            100                 105                 110

Met Asp Val Trp Gly Lys Gly Thr Thr Val Thr Val Ser Ser
        115                 120                 125

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Tyr Thr Phe Thr Ser Tyr Tyr Met His
1               5

<210> SEQ ID NO 72
<211> LENGTH: 17
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 72

Ile Ile Asn Pro Ser Gly Gly Ser Thr Ser Tyr Ala Gln Lys Phe Gln
1               5                   10                  15

Gly

<210> SEQ ID NO 73
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ala Arg Gly Ala Pro Asn Tyr Gly Asp Thr Thr His Asp Tyr Tyr Tyr
1               5                   10                  15

Met Asp Val

<210> SEQ ID NO 74
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asp Asp Trp Pro Phe
                85                  90                  95

Thr Phe Gly Gly Gly Thr Lys Val Glu Ile Lys
            100                 105

<210> SEQ ID NO 75
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Arg Ala Ser Gln Ser Val Ser Ser Asn Leu Ala
1               5                   10

<210> SEQ ID NO 76
<211> LENGTH: 7
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 76

Gly Ala Ser Thr Arg Ala Thr
1               5

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gln Gln Tyr Asp Asp Trp Pro Phe Thr
1               5

<210> SEQ ID NO 78
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Thr Gly Glu Tyr Tyr Asp Thr Asp His Gly Met Asp
            100                 105                 110

Val Trp Gly Gln Gly Thr Thr Val Thr Val Ser Ser
        115                 120

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Tyr Thr Phe Thr Gly Tyr Tyr Met His
1               5

<210> SEQ ID NO 80
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Trp Ile Asn Pro Asn Ser Gly Gly Thr Asn Tyr Ala Gln Lys Phe Gln
1               5                   10                  15

Gly

<210> SEQ ID NO 81
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ala Arg Asp Thr Gly Glu Tyr Tyr Asp Thr Asp Asp His Gly Met Asp
1               5                   10                  15

Val

<210> SEQ ID NO 82
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Asp Asp Tyr Trp Pro Pro
                85                  90                  95

Thr Phe Gly Gly Gly Thr Lys Val Glu Ile Lys
            100                 105

<210> SEQ ID NO 83
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Gly Gly Ser Gly Gly Gly Gly Ser Gly Gly Gly Gly Ser Gly Gly Gly
1               5                   10                  15

Gly Ser Gly Gly Gly Gly Ser Gly Gly Gly Ser Gly Gly Gly Gly
            20                  25                  30

Ser Gly Gly Gly Gly Ser Gly Gly Gly Ser Gly Gly Gly Gly Ser
        35                  40                  45

Gly Gly
    50

<210> SEQ ID NO 84
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gln Gln Asp Asp Tyr Trp Pro Pro Thr
1               5

<210> SEQ ID NO 86
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Gly Tyr Tyr Asp Ser Gly Ala Gly Asp Tyr Trp Gly
            100                 105                 110

Gln Gly Thr Leu Val Thr Val Ser Ser
        115                 120

<210> SEQ ID NO 87
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 87

Phe Thr Phe Ser Ser Tyr Ala Met Ser
1               5

<210> SEQ ID NO 88
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ala Ile Ser Gly Ser Gly Gly Ser Thr Tyr Tyr Ala Asp Ser Val Lys
1               5                   10                  15

Gly

<210> SEQ ID NO 89
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ala Lys Asp Gly Gly Tyr Tyr Asp Ser Gly Ala Gly Asp Tyr
1               5                   10

<210> SEQ ID NO 90
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asp Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Val Ser Tyr Pro Arg
                85                  90                  95

Thr Phe Gly Gly Gly Thr Lys Val Glu Ile Lys
            100                 105

<210> SEQ ID NO 91
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 91

Arg Ala Ser Gln Gly Ile Asp Ser Trp Leu Ala
1               5                   10

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ala Ala Ser Ser Leu Gln Ser
1               5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gln Gln Gly Val Ser Tyr Pro Arg Thr
1               5

<210> SEQ ID NO 94
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Met Gly Ala Ala Ala Gly Trp Phe Asp Pro Trp
            100                 105                 110

Gly Gln Gly Thr Leu Val Thr Val Ser Ser
        115                 120

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Phe Thr Phe Ser Ser Tyr Ser Met Asn
1               5

<210> SEQ ID NO 96
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ser Ile Ser Ser Ser Ser Ser Tyr Ile Tyr Tyr Ala Asp Ser Val Lys
1               5                   10                  15

Gly

<210> SEQ ID NO 97
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ala Arg Gly Ala Pro Met Gly Ala Ala Ala Gly Trp Phe Asp Pro
1               5                   10                  15

<210> SEQ ID NO 98
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Val Ser Phe Pro Arg
                85                  90                  95

Thr Phe Gly Gly Gly Thr Lys Val Glu Ile Lys
            100                 105

<210> SEQ ID NO 99
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Arg Ala Ser Gln Gly Ile Ser Ser Trp Leu Ala
1               5                   10

<210> SEQ ID NO 100
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ala Ala Ser Ser Leu Gln Ser
1               5

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gln Gln Gly Val Ser Phe Pro Arg Thr
1               5

<210> SEQ ID NO 102
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Ala Gly Phe Ala Tyr Gly Met Asp Tyr Tyr Tyr Met
            100                 105                 110

Asp Val Trp Gly Lys Gly Thr Thr Val Thr Val Ser Ser
        115                 120                 125

<210> SEQ ID NO 103
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gly Gly Gly Ser Gly Gly Gly Ser Gly Gly Gly Ser
1               5                   10                  15

Gly Gly Gly Ser Gly Gly Gly Ser Gly Gly Gly Ser
            20                  25                  30

Gly Gly Gly Ser Gly Gly Gly Ser
        35                  40

<210> SEQ ID NO 104
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Gly Gly Ser Gly Gly Gly Ser Gly Gly Gly Ser Gly
1               5                   10                  15

Gly Gly Ser Gly Gly Gly Ser Gly Gly Gly Ser Gly
            20                  25                  30

Gly Gly Ser Gly Gly Gly Ser Gly
        35                  40

<210> SEQ ID NO 105
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ala Arg Glu Gly Ala Gly Phe Ala Tyr Gly Met Asp Tyr Tyr Tyr Met
1               5                   10                  15

Asp Val

<210> SEQ ID NO 106
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asp Asn Trp Pro Phe
                85                  90                  95

Thr Phe Gly Gly Gly Thr Lys Val Glu Ile Lys
            100                 105

<210> SEQ ID NO 107
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Arg Ala Ser Gln Ser Val Ser Ser Tyr Leu Ala
1               5                   10

<210> SEQ ID NO 108
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Asp Ala Ser Asn Arg Ala Thr
1               5

<210> SEQ ID NO 109
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gln Gln Ser Asp Asn Trp Pro Phe Thr
1               5

<210> SEQ ID NO 110
<211> LENGTH: 121
<212> TYPE: PRT
<213> ORGANISM: Homo sapiens

<400> SEQUENCE: 110

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Gly Leu Gly Asp Gly Thr Tyr Phe Asp Tyr Trp Gly
            100                 105                 110

Gln Gly Thr Thr Val Thr Val Ser Ser
        115                 120

<210> SEQ ID NO 111
<211> LENGTH: 110
<212> TYPE: PRT

<213> ORGANISM: Homo sapiens

<400> SEQUENCE: 111

Gln Ser Ala Leu Thr Gln Pro Ala Ser Val Ser Gly Ser Pro Gly Gln
1               5                   10                  15

Ser Ile Thr Ile Ser Cys Ser Gly Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Tyr Asp Asp Leu Leu Pro Ser Gly Val Ser Asp Arg Phe Ser
50                  55                  60

Gly Ser Lys Ser Gly Thr Ser Ala Phe Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110

<210> SEQ ID NO 112
<211> LENGTH: 115
<212> TYPE: PRT
<213> ORGANISM: Homo sapiens

<400> SEQUENCE: 112

Gln Val His Leu Gln Glu Ser Gly Pro Gly Leu Val Lys Pro Ser Glu
1               5                   10                  15

Thr Leu Ser Leu Thr Cys Thr Val Ser Asp Asp Ser Ile Ser Ser Tyr
            20                  25                  30

Tyr Trp Ser Trp Ile Arg Gln Pro Pro Gly Lys Gly Leu Glu Trp Ile
        35                  40                  45

Gly His Ile Ser Tyr Ser Gly Ser Ala Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Asn Trp Asp Asp Ala Phe Asn Ile Trp Gly Gln Gly Thr Met Val Thr
            100                 105                 110

Val Ser Ser
        115

<210> SEQ ID NO 113
<211> LENGTH: 108
<212> TYPE: PRT
<213> ORGANISM: Homo sapiens

<400> SEQUENCE: 113

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
            85                  90                  95

Trp Thr Phe Gly Gln Gly Thr Lys Val Glu Ile Lys
            100                 105

<210> SEQ ID NO 114
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
            115                 120

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gly Phe Asn Ile Lys Asp Thr
1               5

<210> SEQ ID NO 116
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Tyr Pro Thr Asn Gly Tyr
1               5

<210> SEQ ID NO 117
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 117

Trp Gly Gly Asp Gly Phe Tyr Ala Met Asp Tyr
1               5                   10

<210> SEQ ID NO 118
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 119
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Gln Asp Val Asn Thr Ala Val Ala
1               5

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Ser Ala Ser Phe Leu Tyr Ser
1               5

<210> SEQ ID NO 121
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Gln Gln His Tyr Thr Thr Pro Pro Thr
1               5
```

```
<210> SEQ ID NO 122
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala
        115                 120

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gly Phe Thr Phe Thr Asp Tyr
1               5

<210> SEQ ID NO 124
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Asn Pro Asn Ser Gly Gly
1               5

<210> SEQ ID NO 125
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Asn Leu Gly Pro Ser Phe Tyr Phe Asp Tyr
1               5                   10

<210> SEQ ID NO 126
```

<211> LENGTH: 108
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 126

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg
            100                 105

<210> SEQ ID NO 127
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 127

Gln Asp Val Ser Ile Gly Val Ala
1               5

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 128

Ser Ala Ser Tyr Arg Tyr Thr
1               5

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 129

Gln Gln Tyr Tyr Ile Tyr Pro Tyr Thr
1               5

<210> SEQ ID NO 130
<211> LENGTH: 120
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 130

Gln Val Gln Leu Gln Gln Ser Gly Pro Glu Leu Val Lys Pro Gly Ala
1               5                   10                  15

Ser Leu Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Tyr Pro Thr Asn Gly Tyr Thr Arg Tyr Asp Pro Lys Phe
    50                  55                  60

Gln Asp Lys Ala Thr Ile Thr Ala Asp Thr Ser Ser Asn Thr Ala Tyr
65                  70                  75                  80

Leu Gln Val Ser Arg Leu Thr Ser Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Ala Ser Val Thr Val Ser Ser
        115                 120

<210> SEQ ID NO 131
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Gly Phe Asn Ile Lys Asp Thr
1               5

<210> SEQ ID NO 132
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Tyr Pro Thr Asn Gly Tyr
1               5

<210> SEQ ID NO 133
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Trp Gly Gly Asp Gly Phe Tyr Ala Met Asp Tyr
1               5                   10

<210> SEQ ID NO 134
<211> LENGTH: 107
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 134

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Val Ala Trp Tyr Gln Gln Lys Pro Gly His Ser Pro Lys Leu Leu Ile
        35                  40                  45

Tyr Ser Ala Ser Phe Arg Tyr Thr Gly Val Pro Asp Arg Phe Thr Gly
50                  55                  60

Ser Arg Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Thr Thr Pro Pro
                85                  90                  95

Thr Phe Gly Gly Gly Thr Lys Val Glu Ile Lys
            100                 105

<210> SEQ ID NO 135
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gln Asp Val Asn Thr Ala Val Ala
1               5

<210> SEQ ID NO 136
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Ser Ala Ser Phe Arg Tyr Thr
1               5

<210> SEQ ID NO 137
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Gln Gln His Tyr Thr Thr Pro Pro Thr
1               5

<210> SEQ ID NO 138
<211> LENGTH: 1255
<212> TYPE: PRT
<213> ORGANISM: Homo sapiens

<400> SEQUENCE: 138

Met Glu Leu Ala Ala Leu Cys Arg Trp Gly Leu Leu Leu Ala Leu Leu
1               5                   10                  15

-continued

```
Pro Pro Gly Ala Ala Ser Thr Gln Val Cys Thr Gly Thr Asp Met Lys
         20                  25                  30

Leu Arg Leu Pro Ala Ser Pro Glu Thr His Leu Asp Met Leu Arg His
         35                  40                  45

Leu Tyr Gln Gly Cys Gln Val Val Gln Gly Asn Leu Glu Leu Thr Tyr
 50                  55                  60

Leu Pro Thr Asn Ala Ser Leu Ser Phe Leu Gln Asp Ile Gln Glu Val
 65                  70                  75                  80

Gln Gly Tyr Val Leu Ile Ala His Asn Gln Val Arg Gln Val Pro Leu
                 85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
            115                 120                 125

Val Thr Gly Ala Ser Pro Gly Gly Leu Arg Glu Leu Gln Leu Arg Ser
        130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430
```

```
Gly Arg Ile Leu His Asn Gly Ala Tyr Ser Leu Thr Leu Gln Gly Leu
            435                 440                 445

Gly Ile Ser Trp Leu Gly Leu Arg Ser Leu Arg Glu Leu Gly Ser Gly
450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845
```

```
Arg Asn Val Leu Val Lys Ser Pro Asn His Val Lys Ile Thr Asp Phe
    850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Arg Leu Pro Gln Pro
    930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
        995                 1000                1005

Leu Glu Asp Asp Asp Met Gly Asp Leu Val Asp Ala Glu Glu Tyr
    1010                1015                1020

Leu Val Pro Gln Gln Gly Phe Phe Cys Pro Asp Pro Ala Pro Gly
    1025                1030                1035

Ala Gly Gly Met Val His His Arg His Arg Ser Ser Ser Thr Arg
    1040                1045                1050

Ser Gly Gly Gly Asp Leu Thr Leu Gly Leu Glu Pro Ser Glu Glu
    1055                1060                1065

Glu Ala Pro Arg Ser Pro Leu Ala Pro Ser Glu Gly Ala Gly Ser
    1070                1075                1080

Asp Val Phe Asp Gly Asp Leu Gly Met Gly Ala Ala Lys Gly Leu
    1085                1090                1095

Gln Ser Leu Pro Thr His Asp Pro Ser Pro Leu Gln Arg Tyr Ser
    1100                1105                1110

Glu Asp Pro Thr Val Pro Leu Pro Ser Glu Thr Asp Gly Tyr Val
    1115                1120                1125

Ala Pro Leu Thr Cys Ser Pro Gln Pro Glu Tyr Val Asn Gln Pro
    1130                1135                1140

Asp Val Arg Pro Gln Pro Pro Ser Pro Arg Glu Gly Pro Leu Pro
    1145                1150                1155

Ala Ala Arg Pro Ala Gly Ala Thr Leu Glu Arg Pro Lys Thr Leu
    1160                1165                1170

Ser Pro Gly Lys Asn Gly Val Val Lys Asp Val Phe Ala Phe Gly
    1175                1180                1185

Gly Ala Val Glu Asn Pro Glu Tyr Leu Thr Pro Gln Gly Gly Ala
    1190                1195                1200

Ala Pro Gln Pro His Pro Pro Ala Phe Ser Pro Ala Phe Asp
    1205                1210                1215

Asn Leu Tyr Tyr Trp Asp Gln Asp Pro Pro Glu Arg Gly Ala Pro
    1220                1225                1230
```

Pro Ser Thr Phe Lys Gly Thr Pro Thr Ala Glu Asn Pro Glu Tyr
    1235                1240                1245

Leu Gly Leu Asp Val Pro Val
    1250            1255

<210> SEQ ID NO 139
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Cys Gly Thr Lys Val Glu Ile Lys Gly Gly Gly Gly Ser
            100                 105                 110

Gly Gly Gly Gly Ser Gly Gly Gly Ser Gly Gly Gly Gly Ser Glu
        115                 120                 125

Val Gln Leu Val Glu Ser Gly Gly Gly Leu Val Gln Pro Gly Gly Ser
    130                 135                 140

Leu Arg Leu Ser Cys Ala Ala Ser Gly Phe Asn Ile Lys Asp Thr Tyr
145                 150                 155                 160

Ile His Trp Val Arg Gln Ala Pro Gly Lys Cys Leu Glu Trp Val Ala
                165                 170                 175

Arg Ile Tyr Pro Thr Asn Gly Tyr Thr Arg Tyr Ala Asp Ser Val Lys
            180                 185                 190

Gly Arg Phe Thr Ile Ser Ala Asp Thr Ser Lys Asn Thr Ala Tyr Leu
        195                 200                 205

Gln Met Asn Ser Leu Arg Ala Glu Asp Thr Ala Val Tyr Tyr Cys Ser
    210                 215                 220

Arg Trp Gly Gly Asp Gly Phe Tyr Ala Met Asp Tyr Trp Gly Gln Gly
225                 230                 235                 240

Thr Leu Val Thr Val Ser Ser
                245

<210> SEQ ID NO 140
<211> LENGTH: 475
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gln Asp Val Asn Thr Ala
             20                  25                  30

Val Ala Trp Tyr Gln Gln Lys Pro Gly Lys Ala Pro Lys Leu Leu Ile
         35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Cys Gly Thr Lys Val Glu Ile Lys Gly Gly Gly Gly Ser
                100                 105                 110

Gly Gly Gly Gly Ser Gly Gly Gly Ser Gly Gly Gly Gly Ser Glu
            115                 120                 125

Val Gln Leu Val Glu Ser Gly Gly Leu Val Gln Pro Gly Gly Ser
130                 135                 140

Leu Arg Leu Ser Cys Ala Ala Ser Gly Phe Asn Ile Lys Asp Thr Tyr
145                 150                 155                 160

Ile His Trp Val Arg Gln Ala Pro Gly Lys Cys Leu Glu Trp Val Ala
                165                 170                 175

Arg Ile Tyr Pro Thr Asn Gly Tyr Thr Arg Tyr Ala Asp Ser Val Lys
                180                 185                 190

Gly Arg Phe Thr Ile Ser Ala Asp Thr Ser Lys Asn Thr Ala Tyr Leu
            195                 200                 205

Gln Met Asn Ser Leu Arg Ala Glu Asp Thr Ala Val Tyr Tyr Cys Ser
        210                 215                 220

Arg Trp Gly Gly Asp Gly Phe Tyr Ala Met Asp Tyr Trp Gly Gln Gly
225                 230                 235                 240

Thr Leu Val Thr Val Ser Ser Ala Ser Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
    290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Arg Val Tyr Thr Leu Pro Pro Cys Arg
    370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Val Ser Asp Gly Ser
            420                 425                 430
```

```
Phe Thr Leu Tyr Ser Lys Leu Thr Val Asp Lys Ser Arg Trp Gln Gln
                435                 440                 445

Gly Asn Val Phe Ser Cys Ser Val Met His Glu Ala Leu His Asn His
    450                 455                 460

Tyr Thr Gln Lys Ser Leu Ser Leu Ser Pro Gly
465                 470                 475

<210> SEQ ID NO 141
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Met Gly Ala Ala Gly Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320
```

```
Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
        340                 345                 350

Val Cys Thr Leu Pro Pro Ser Arg Asp Glu Leu Thr Glu Asn Gln Val
            355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Trp Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly
    450

<210> SEQ ID NO 142
<211> LENGTH: 210
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Val Ser Phe Pro Arg
                85                  90                  95

Thr Phe Gly Gly Gly Thr Lys Val Glu Ile Lys Arg Thr Val Ala Ala
            100                 105                 110

Pro Ser Pro Pro Ser Asp Glu Gln Leu Lys Ser Gly Thr Ala Ser Val
        115                 120                 125

Val Cys Leu Leu Asn Asn Phe Tyr Pro Arg Glu Ala Lys Val Gln Trp
    130                 135                 140

Lys Val Asp Asn Ala Leu Gln Ser Gly Asn Ser Gln Glu Ser Val Thr
145                 150                 155                 160

Glu Gln Asp Ser Lys Asp Ser Thr Tyr Ser Leu Ser Ser Thr Leu Thr
                165                 170                 175

Leu Ser Lys Ala Asp Tyr Glu Lys His Lys Val Tyr Ala Cys Glu Val
            180                 185                 190
```

```
Thr His Gln Gly Leu Ser Ser Pro Val Thr Lys Ser Phe Asn Arg Gly
        195                 200                 205

Glu Cys
    210

<210> SEQ ID NO 143
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gly Gly Gly Gly Ser Gly Gly Gly Ser Gly Gly Gly Gly Ser Gly
1               5                   10                  15

Gly Gly Gly Ser
            20

<210> SEQ ID NO 144
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Ile Gly Ala Ala Ala Gly Trp Phe Asp Pro Trp
            100                 105                 110

Gly Gln Gly Thr Leu Val Thr Val Ser Ser
        115                 120

<210> SEQ ID NO 145
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45
```

-continued

```
Ser Ser Ile Ser Ser Ser Ser Tyr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Ile Gly Ala Ala Ala Gly Trp Phe Asp Pro Trp
                100                 105                 110

Gly Gln Gly Thr Leu Val Thr Val Ser Ser Ala Ser Thr Lys Gly Pro
                115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Lys Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
                275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Cys Thr Leu Pro Pro Ser Arg Asp Glu Leu Thr Glu Asn Gln Val
                355                 360                 365

Ser Leu Thr Cys Leu Val Lys Gly Phe Tyr Pro Ser Asp Ile Ala Val
                370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Trp Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro Gly
450
```

<210> SEQ ID NO 146
<211> LENGTH: 475
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 146

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Cys Gly Thr Lys Val Glu Ile Lys Gly Gly Gly Gly Ser
            100                 105                 110

Gly Gly Gly Gly Ser Gly Gly Gly Ser Gly Gly Gly Gly Ser Glu
        115                 120                 125

Val Gln Leu Val Glu Ser Gly Gly Gly Leu Val Gln Pro Gly Gly Ser
130                 135                 140

Leu Arg Leu Ser Cys Ala Ala Ser Gly Phe Asn Ile Lys Asp Thr Tyr
145                 150                 155                 160

Ile His Trp Val Arg Gln Ala Pro Gly Lys Cys Leu Glu Trp Val Ala
                165                 170                 175

Arg Ile Tyr Pro Thr Asn Gly Tyr Thr Arg Tyr Ala Asp Ser Val Lys
            180                 185                 190

Gly Arg Phe Thr Ile Ser Ala Asp Thr Ser Lys Asn Thr Ala Tyr Leu
        195                 200                 205

Gln Met Asn Ser Leu Arg Ala Glu Asp Thr Ala Val Tyr Tyr Cys Ser
210                 215                 220

Arg Trp Gly Gly Asp Gly Phe Tyr Ala Met Asp Tyr Trp Gly Gln Gly
225                 230                 235                 240

Thr Leu Val Thr Val Ser Ser Ala Ser Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365
```

```
Lys Gly Gln Pro Arg Glu Pro Gln Val Cys Thr Leu Pro Pro Ser Arg
    370             375                 380

Asp Glu Leu Thr Lys Asn Gln Val Ser Leu Ser Cys Ala Val Lys Gly
385             390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
                420                 425                 430

Phe Phe Leu Val Ser Lys Leu Thr Val Asp Lys Ser Arg Trp Gln Gln
            435                 440                 445

Gly Asn Val Phe Ser Cys Ser Val Met His Glu Ala Leu His Asn His
    450                 455                 460

Tyr Thr Gln Lys Ser Leu Ser Leu Ser Pro Gly
465             470                 475

<210> SEQ ID NO 147
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65              70                  75                  80

Leu Gln Met Asn Ser Leu Arg Ala Glu Asp Thr Ala Val Tyr Tyr Cys
            85                  90                  95

Ala Arg Gly Ala Pro Met Gly Ala Ala Ala Gly Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145             150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255
```

```
Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Cys Arg Asp Glu Leu Thr Lys Asn Gln Val
        355                 360                 365

Ser Leu Trp Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 148
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Gly Tyr Tyr Asp Ser Gly Ala Gly Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140
```

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Thr Val
        180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
        340                 345                 350

Tyr Thr Leu Pro Pro Cys Arg Asp Glu Leu Thr Lys Asn Gln Val Ser
        355                 360                 365

Leu Trp Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
        435                 440                 445

Pro Gly
    450

<210> SEQ ID NO 149
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asp Ser Trp
            20                  25                  30
```

```
Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Val Ser Tyr Pro Arg
                 85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 150
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Gly Gly Gly Gly Ser Gly Gly Gly Gly Ser Gly Gly Gly Gly Ser
1               5                   10                  15

<210> SEQ ID NO 151
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Gln Val Gln Leu Gln Gln Ser Gly Pro Glu Leu Val Lys Pro Gly Ala
1               5                   10                  15

Ser Leu Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
            35                  40                  45

Gly Arg Ile Tyr Pro Thr Asn Gly Tyr Thr Arg Tyr Asp Pro Lys Phe
 50                  55                  60

Gln Asp Lys Ala Thr Ile Thr Ala Asp Thr Ser Ser Asn Thr Ala Tyr
65                  70                  75                  80

Leu Gln Val Ser Arg Leu Thr Ser Glu Asp Thr Ala Val Tyr Tyr Cys
                 85                  90                  95
```

Ser Arg Trp Gly Gly Asp Gly Phe Tyr Ala Met Asp Tyr Trp Gly Gln
        100                 105                 110

Gly Ala Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Val Gly Gly
225                 230                 235                 240

Pro Ser Val Phe Leu Leu Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Leu Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Leu Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 152
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
            20                  25                  30

Gly Gly Ser Gly Gly Gly Ser Gly Gly Gly Ser Gly Gly Gly
        35                  40                  45

Gly Ser Gly Gly Gly Ser Gly Gly Gly Ser Gly Gly Gly Gly
    50                  55                  60

Ser Gly Gly Gly Ser Gly Gly Gly Ser Gly Gly Gly Gly Ser
65                  70                  75                  80

Gly Gly Gly Ser Gly Gly Gly Ser Gly Gly Gly Ser Gly
                85                  90                  95

Gly Gly Gly Ser
            100

<210> SEQ ID NO 153
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Val Ala Trp Tyr Gln Gln Lys Pro Gly His Ser Pro Lys Leu Leu Ile
        35                  40                  45

Tyr Ser Ala Ser Phe Arg Tyr Thr Gly Val Pro Asp Arg Phe Thr Gly
    50                  55                  60

Ser Arg Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Thr Thr Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 154
<211> LENGTH: 100

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Gly Gly Ser Gly Gly Gly Ser Gly Gly Gly Ser Gly Gly Gly
1               5                   10                  15

Gly Ser Gly Gly Gly Ser Gly Gly Gly Ser Gly Gly Gly Gly
            20                  25                  30

Ser Gly Gly Gly Ser Gly Gly Gly Ser Gly Gly Gly Ser
        35                  40                  45

Gly Gly Gly Gly Ser Gly Gly Gly Ser Gly Gly Gly Ser Gly
50                  55                  60

Gly Gly Gly Ser Gly Gly Gly Ser Gly Gly Gly Ser Gly Gly
65                  70                  75                  80

Gly Gly Ser Gly Gly Gly Ser Gly Gly Gly Ser Gly Gly Gly
            85                  90                  95

Gly Ser Gly Gly
            100

<210> SEQ ID NO 155
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Gly Tyr Tyr Asp Ser Gly Ala Gly Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205
```

```
Lys Pro Ser Asn Thr Lys Val Asp Lys Lys Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
                260                 265                 270
Glu Asp Pro Glu Val Lys Phe Asn Trp Tyr Val Asp Gly Val Glu Val
            275                 280                 285
His Asn Ala Lys Thr Lys Pro Arg Glu Glu Gln Tyr Asn Ser Thr Tyr
        290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
                340                 345                 350
Cys Thr Leu Pro Pro Ser Arg Asp Glu Leu Thr Glu Asn Gln Val Ser
            355                 360                 365
Leu Thr Cys Leu Val Lys Gly Phe Tyr Pro Ser Asp Ile Ala Val Glu
        370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Trp Leu Thr Val
                405                 410                 415
Asp Lys Ser Arg Trp Gln Gln Gly Asn Val Phe Ser Cys Ser Val Met
                420                 425                 430
His Glu Ala Leu His Asn His Tyr Thr Gln Lys Ser Leu Ser Leu Ser
            435                 440                 445
Pro Gly
    450

<210> SEQ ID NO 156
<211> LENGTH: 475
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Asn Thr Ala
            20                  25                  30
Val Ala Trp Tyr Gln Gln Lys Pro Gly Lys Ala Pro Lys Leu Leu Ile
        35                  40                  45
Tyr Ser Ala Ser Phe Leu Tyr Ser Gly Val Pro Ser Arg Phe Ser Gly
    50                  55                  60
Ser Arg Ser Gly Thr Asp Phe Thr Leu Thr Ile Ser Ser Leu Gln Pro
65                  70                  75                  80
Glu Asp Phe Ala Thr Tyr Tyr Cys Gln Gln His Tyr Thr Thr Pro Pro
                85                  90                  95
Thr Phe Gly Cys Gly Thr Lys Val Glu Ile Lys Gly Gly Gly Gly Ser
                100                 105                 110
```

Gly Gly Gly Gly Ser Gly Gly Gly Ser Gly Gly Gly Ser Glu
            115                 120                 125

Val Gln Leu Val Glu Ser Gly Gly Leu Val Gln Pro Gly Gly Ser
        130                 135                 140

Leu Arg Leu Ser Cys Ala Ala Ser Gly Phe Asn Ile Lys Asp Thr Tyr
145                 150                 155                 160

Ile His Trp Val Arg Gln Ala Pro Gly Lys Cys Leu Glu Trp Val Ala
                165                 170                 175

Arg Ile Tyr Pro Thr Asn Gly Tyr Thr Arg Tyr Ala Asp Ser Val Lys
            180                 185                 190

Gly Arg Phe Thr Ile Ser Ala Asp Thr Ser Lys Asn Thr Ala Tyr Leu
            195                 200                 205

Gln Met Asn Ser Leu Arg Ala Glu Asp Thr Ala Val Tyr Tyr Cys Ser
        210                 215                 220

Arg Trp Gly Gly Asp Gly Phe Tyr Ala Met Asp Tyr Trp Gly Gln Gly
225                 230                 235                 240

Thr Leu Val Thr Val Ser Ser Ala Ser Asp Lys Thr His Thr Cys Pro
                245                 250                 255

Pro Cys Pro Ala Pro Glu Ala Ala Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
        290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Gly Ala Pro Ile Glu Lys Thr Ile Ser Lys Ala
        355                 360                 365

Lys Gly Gln Pro Arg Glu Pro Arg Val Tyr Thr Leu Pro Pro Cys Arg
        370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Val Ser Asp Gly Ser
            420                 425                 430

Phe Thr Leu Tyr Ser Lys Leu Thr Val Asp Lys Ser Arg Trp Gln Gln
        435                 440                 445

Gly Asn Val Phe Ser Cys Ser Val Met His Glu Ala Leu His Asn His
        450                 455                 460

Tyr Thr Gln Lys Ser Leu Ser Leu Ser Pro Gly
465                 470                 475

<210> SEQ ID NO 157
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Met Gly Ala Ala Gly Trp Phe Asp Pro Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Gly Ala Pro
                325                 330                 335

Ile Glu Lys Thr Ile Ser Lys Ala Lys Gly Gln Pro Arg Glu Pro Gln
            340                 345                 350

Val Cys Thr Leu Pro Pro Ser Arg Asp Glu Leu Thr Glu Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Trp Leu Thr
                405                 410                 415
```

```
Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly
    450

<210> SEQ ID NO 158
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Ser Tyr Ala Ile Ser
1               5

<210> SEQ ID NO 159
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Gly Asp Ser Ser Ile Arg His Ala Tyr Tyr Tyr Tyr Gly Met Asp Val
1               5                   10                  15

<210> SEQ ID NO 160
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Ser Ser Ser Tyr Tyr Trp Gly
1               5

<210> SEQ ID NO 161
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Gly Ser Asp Arg Phe His Pro Tyr Phe Asp Tyr
1               5                   10

<210> SEQ ID NO 162
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Ser Tyr Tyr Met His
1               5
```

```
<210> SEQ ID NO 163
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Gly Ala Pro Asn Tyr Gly Asp Thr Thr His Asp Tyr Tyr Tyr Met Asp
1               5                   10                  15

Val

<210> SEQ ID NO 164
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Gly Tyr Tyr Met His
1               5

<210> SEQ ID NO 165
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Asp Thr Gly Glu Tyr Tyr Asp Thr Asp Asp His Gly Met Asp Val
1               5                   10                  15

<210> SEQ ID NO 166
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Ser Tyr Ala Met Ser
1               5

<210> SEQ ID NO 167
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Asp Gly Gly Tyr Tyr Asp Ser Gly Ala Gly Asp Tyr
1               5                   10

<210> SEQ ID NO 168
<211> LENGTH: 5
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 168

Ser Tyr Ser Met Asn
1               5

<210> SEQ ID NO 169
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Gly Ala Pro Met Gly Ala Ala Ala Gly Trp Phe Asp Pro
1               5                   10

<210> SEQ ID NO 170
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Glu Gly Ala Gly Phe Ala Tyr Gly Met Asp Tyr Tyr Met Asp Val
1               5                   10                  15

<210> SEQ ID NO 171
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Val Ala Trp Tyr Gln Gln Lys Pro Gly His Ser Pro Lys Leu Leu Ile
        35                  40                  45

Tyr Ser Ala Ser Phe Arg Tyr Thr Gly Val Pro Asp Arg Phe Thr Gly
    50                  55                  60

Ser Arg Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Thr Thr Pro Pro
                85                  90                  95

Thr Phe Gly Cys Gly Thr Lys Val Glu Ile Lys Arg Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Gln Gln Ser Gly Pro Glu Leu Val Lys Pro Gly Ala
    130                 135                 140

Ser Leu Lys Leu Ser Cys Thr Ala Ser Gly Phe Asn Ile Lys Asp Thr
145                 150                 155                 160

Tyr Ile His Trp Val Lys Gln Arg Pro Glu Gln Cys Leu Glu Trp Ile
                165                 170                 175

```
Gly Arg Ile Tyr Pro Thr Asn Gly Tyr Thr Arg Tyr Asp Pro Lys Phe
            180                 185                 190

Gln Asp Lys Ala Thr Ile Thr Ala Asp Thr Ser Ser Asn Thr Ala Tyr
        195                 200                 205

Leu Gln Val Ser Arg Leu Thr Ser Glu Asp Thr Ala Val Tyr Tyr Cys
    210                 215                 220

Ser Arg Trp Gly Gly Asp Gly Phe Tyr Ala Met Asp Tyr Trp Gly Gln
225                 230                 235                 240

Gly Ala Ser Val Thr Val Ser Ser Ala
                245

<210> SEQ ID NO 172
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Ala Arg Gly Ala Pro Ile Gly Ala Ala Ala Gly Trp Phe Asp Pro
1               5                   10                  15

<210> SEQ ID NO 173
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Gly Ala Pro Ile Gly Ala Ala Ala Gly Trp Phe Asp Pro
1               5                   10

<210> SEQ ID NO 174
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Glu Val Gln Leu Val Glu Ser Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Gln Gly Ala Ala Ala Gly Trp Phe Asp Pro Trp
            100                 105                 110

Gly Gln Gly Thr Leu Val Thr Val Ser Ser
            115                 120
```

<210> SEQ ID NO 175
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Ala Arg Gly Ala Pro Gln Gly Ala Ala Ala Gly Trp Phe Asp Pro
1               5                   10                  15

<210> SEQ ID NO 176
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Gly Ala Pro Gln Gly Ala Ala Ala Gly Trp Phe Asp Pro
1               5                   10

<210> SEQ ID NO 177
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Leu Gly Ala Ala Ala Gly Trp Phe Asp Pro Trp
            100                 105                 110

Gly Gln Gly Thr Leu Val Thr Val Ser Ser
        115                 120

<210> SEQ ID NO 178
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Ala Arg Gly Ala Pro Leu Gly Ala Ala Ala Gly Trp Phe Asp Pro
1               5                   10                  15

<210> SEQ ID NO 179

```
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Gly Ala Pro Leu Gly Ala Ala Ala Gly Trp Phe Asp Pro
1               5                   10

<210> SEQ ID NO 180
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Glu Val Gln Leu Val Glu Ser Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
            35                  40                  45

Ser Ser Ile Ser Ser Ser Ser Tyr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Phe Gly Ala Ala Ala Gly Trp Phe Asp Pro Trp
            100                 105                 110

Gly Gln Gly Thr Leu Val Thr Val Ser Ser
        115                 120

<210> SEQ ID NO 181
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Ala Arg Gly Ala Pro Phe Gly Ala Ala Ala Gly Trp Phe Asp Pro
1               5                   10                  15

<210> SEQ ID NO 182
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Gly Ala Pro Phe Gly Ala Ala Ala Gly Trp Phe Asp Pro
1               5                   10

<210> SEQ ID NO 183
<211> LENGTH: 122
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 183

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Val Gly Ala Ala Gly Trp Phe Asp Pro Trp
            100                 105                 110

Gly Gln Gly Thr Leu Val Thr Val Ser Ser
        115                 120
```

<210> SEQ ID NO 184
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

```
Ala Arg Gly Ala Pro Val Gly Ala Ala Gly Trp Phe Asp Pro
1               5                   10                  15
```

<210> SEQ ID NO 185
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

```
Gly Ala Pro Val Gly Ala Ala Ala Gly Trp Phe Asp Pro
1               5                   10
```

<210> SEQ ID NO 186
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (102)..(102)
<223> OTHER INFORMATION: M, L, I, V, Q, or F

<400> SEQUENCE: 186

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30
```

```
Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Xaa Gly Ala Ala Ala Gly Trp Phe Asp Pro Trp
                100                 105                 110

Gly Gln Gly Thr Leu Val Thr Val Ser Ser
        115                 120

<210> SEQ ID NO 187
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: M, L, I, V, Q, or F

<400> SEQUENCE: 187

Ala Arg Gly Ala Pro Xaa Gly Ala Ala Ala Gly Trp Phe Asp Pro
1               5                   10                  15

<210> SEQ ID NO 188
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: M, L, I, V, Q, or F

<400> SEQUENCE: 188

Gly Ala Pro Xaa Gly Ala Ala Ala Gly Trp Phe Asp Pro
1               5                   10

<210> SEQ ID NO 189
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
                20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ile Tyr Pro Tyr
                 85                  90                  95

Thr Phe Gly Cys Gly Thr Lys Val Glu Ile Lys Arg Gly Gly Gly Gly
            100                 105                 110

Ser Gly Gly Gly Gly Ser Gly Gly Gly Ser Gly Gly Gly Gly Ser
            115                 120                 125

Glu Val Gln Leu Val Glu Ser Gly Gly Leu Val Gln Pro Gly Gly
            130                 135                 140

Ser Leu Arg Leu Ser Cys Ala Ala Ser Gly Phe Thr Phe Thr Asp Tyr
145                 150                 155                 160

Thr Met Asp Trp Val Arg Gln Ala Pro Gly Lys Cys Leu Glu Trp Val
                165                 170                 175

Ala Asp Val Asn Pro Asn Ser Gly Gly Ser Ile Tyr Asn Gln Arg Phe
                180                 185                 190

Lys Gly Arg Phe Thr Leu Ser Val Asp Arg Ser Lys Asn Thr Leu Tyr
                195                 200                 205

Leu Gln Met Asn Ser Leu Arg Ala Glu Asp Thr Ala Val Tyr Tyr Cys
210                 215                 220

Ala Arg Asn Leu Gly Pro Ser Phe Tyr Phe Asp Tyr Trp Gly Gln Gly
225                 230                 235                 240

Thr Leu Val Thr Val Ser Ser Ala
                245

<210> SEQ ID NO 190
<211> LENGTH: 476
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Val Ser Ile Gly
                 20                  25                  30

Val Ala Trp Tyr Gln Gln Lys Pro Gly Lys Ala Pro Lys Leu Leu Ile
             35                  40                  45

Tyr Ser Ala Ser Tyr Arg Tyr Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ile Tyr Pro Tyr
                 85                  90                  95

Thr Phe Gly Cys Gly Thr Lys Val Glu Ile Lys Arg Gly Gly Gly Gly
            100                 105                 110

Ser Gly Gly Gly Gly Ser Gly Gly Gly Ser Gly Gly Gly Gly Ser
            115                 120                 125

Glu Val Gln Leu Val Glu Ser Gly Gly Leu Val Gln Pro Gly Gly
            130                 135                 140

Ser Leu Arg Leu Ser Cys Ala Ala Ser Gly Phe Thr Phe Thr Asp Tyr
145                 150                 155                 160
```

Thr Met Asp Trp Val Arg Gln Ala Pro Gly Lys Cys Leu Glu Trp Val
                165                 170                 175

Ala Asp Val Asn Pro Asn Ser Gly Gly Ser Ile Tyr Asn Gln Arg Phe
            180                 185                 190

Lys Gly Arg Phe Thr Leu Ser Val Asp Arg Ser Lys Asn Thr Leu Tyr
        195                 200                 205

Leu Gln Met Asn Ser Leu Arg Ala Glu Asp Thr Ala Val Tyr Tyr Cys
    210                 215                 220

Ala Arg Asn Leu Gly Pro Ser Phe Tyr Phe Asp Tyr Trp Gly Gln Gly
225                 230                 235                 240

Thr Leu Val Thr Val Ser Ser Ala Ser Asp Lys Thr His Thr Cys
                245                 250                 255

Pro Pro Cys Pro Ala Pro Glu Leu Leu Gly Gly Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser His Glu Asp Pro Glu Val Lys
    290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Glu Tyr Lys Cys Lys
            340                 345                 350

Val Ser Asn Lys Ala Leu Pro Ala Pro Ile Glu Lys Thr Ile Ser Lys
        355                 360                 365

Ala Lys Gly Gln Pro Arg Glu Pro Arg Val Tyr Thr Leu Pro Pro Cys
    370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Val Ser Asp Gly
            420                 425                 430

Ser Phe Thr Leu Tyr Ser Lys Leu Thr Val Asp Lys Ser Arg Trp Gln
        435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly
465                 470                 475

<210> SEQ ID NO 191
<211> LENGTH: 476
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

```
Val Ala Trp Tyr Gln Gln Lys Pro Gly Lys Ala Pro Lys Leu Leu Ile
        35                  40                  45
Tyr Ser Ala Ser Tyr Arg Tyr Thr Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Tyr Ile Tyr Pro Tyr
                85                  90                  95
Thr Phe Gly Cys Gly Thr Lys Val Glu Ile Lys Arg Gly Gly Gly Gly
                100                 105                 110
Ser Gly Gly Gly Gly Ser Gly Gly Gly Ser Gly Gly Gly Gly Ser
        115                 120                 125
Glu Val Gln Leu Val Glu Ser Gly Gly Gly Leu Val Gln Pro Gly Gly
        130                 135                 140
Ser Leu Arg Leu Ser Cys Ala Ala Ser Gly Phe Thr Phe Thr Asp Tyr
145                 150                 155                 160
Thr Met Asp Trp Val Arg Gln Ala Pro Gly Lys Cys Leu Glu Trp Val
                165                 170                 175
Ala Asp Val Asn Pro Asn Ser Gly Gly Ser Ile Tyr Asn Gln Arg Phe
                180                 185                 190
Lys Gly Arg Phe Thr Leu Ser Val Asp Arg Ser Lys Asn Thr Leu Tyr
            195                 200                 205
Leu Gln Met Asn Ser Leu Arg Ala Glu Asp Thr Ala Val Tyr Tyr Cys
        210                 215                 220
Ala Arg Asn Leu Gly Pro Ser Phe Tyr Phe Asp Tyr Trp Gly Gln Gly
225                 230                 235                 240
Thr Leu Val Thr Val Ser Ser Ala Ala Ser Asp Lys Thr His Thr Cys
                245                 250                 255
Pro Pro Cys Pro Ala Pro Glu Leu Leu Gly Gly Pro Ser Val Phe Leu
            260                 265                 270
Phe Pro Pro Lys Pro Lys Asp Thr Leu Met Ile Ser Arg Thr Pro Glu
        275                 280                 285
Val Thr Cys Val Val Val Asp Val Ser His Glu Asp Pro Glu Val Lys
    290                 295                 300
Phe Asn Trp Tyr Val Asp Gly Val Glu Val His Asn Ala Lys Thr Lys
305                 310                 315                 320
Pro Arg Glu Glu Gln Tyr Asn Ser Thr Tyr Arg Val Val Ser Val Leu
                325                 330                 335
Thr Val Leu His Gln Asp Trp Leu Asn Gly Lys Glu Tyr Lys Cys Lys
            340                 345                 350
Val Ser Asn Lys Ala Leu Pro Ala Pro Ile Glu Lys Thr Ile Ser Lys
        355                 360                 365
Ala Lys Gly Gln Pro Arg Glu Pro Gln Val Cys Thr Leu Pro Pro Ser
370                 375                 380
Arg Asp Glu Leu Thr Lys Asn Gln Val Ser Leu Ser Cys Ala Val Lys
385                 390                 395                 400
Gly Phe Tyr Pro Ser Asp Ile Ala Val Glu Trp Glu Ser Asn Gly Gln
                405                 410                 415
Pro Glu Asn Asn Tyr Lys Thr Thr Pro Pro Val Leu Asp Ser Asp Gly
            420                 425                 430
Ser Phe Phe Leu Val Ser Lys Leu Thr Val Asp Lys Ser Arg Trp Gln
        435                 440                 445
```

-continued

```
Gln Gly Asn Val Phe Ser Cys Ser Val Met His Glu Ala Leu His Asn
    450                 455                 460

His Tyr Thr Gln Lys Ser Leu Ser Leu Ser Pro Gly
465                 470                 475

<210> SEQ ID NO 192
<211> LENGTH: 477
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
                20                  25                  30

Val Ala Trp Tyr Gln Gln Lys Pro Gly His Ser Pro Lys Leu Leu Ile
            35                  40                  45

Tyr Ser Ala Ser Phe Arg Tyr Thr Gly Val Pro Asp Arg Phe Thr Gly
        50                  55                  60

Ser Arg Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Thr Thr Pro Pro
                85                  90                  95

Thr Phe Gly Cys Gly Thr Lys Val Glu Ile Lys Arg Gly Gly Gly Gly
            100                 105                 110

Ser Gly Gly Gly Gly Ser Gly Gly Gly Ser Gly Gly Gly Gly Ser
        115                 120                 125

Gln Val Gln Leu Gln Gln Ser Gly Pro Glu Leu Val Lys Pro Gly Ala
    130                 135                 140

Ser Leu Lys Leu Ser Cys Thr Ala Ser Gly Phe Asn Ile Lys Asp Thr
145                 150                 155                 160

Tyr Ile His Trp Val Lys Gln Arg Pro Glu Gln Cys Leu Glu Trp Ile
                165                 170                 175

Gly Arg Ile Tyr Pro Thr Asn Gly Tyr Thr Arg Tyr Asp Pro Lys Phe
            180                 185                 190

Gln Asp Lys Ala Thr Ile Thr Ala Asp Thr Ser Ser Asn Thr Ala Tyr
        195                 200                 205

Leu Gln Val Ser Arg Leu Thr Ser Glu Asp Thr Ala Val Tyr Tyr Cys
    210                 215                 220

Ser Arg Trp Gly Gly Asp Gly Phe Tyr Ala Met Asp Tyr Trp Gly Gln
225                 230                 235                 240

Gly Ala Ser Val Thr Val Ser Ser Ala Ala Ser Asp Lys Thr His Thr
                245                 250                 255

Cys Pro Pro Cys Pro Ala Pro Glu Leu Leu Gly Gly Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Asp Val Ser His Glu Asp Pro Glu Val
    290                 295                 300

Lys Phe Asn Trp Tyr Val Asp Gly Val Glu Val His Asn Ala Lys Thr
305                 310                 315                 320

Lys Pro Arg Glu Glu Gln Tyr Asn Ser Thr Tyr Arg Val Val Ser Val
                325                 330                 335
```

Leu Thr Val Leu His Gln Asp Trp Leu Asn Gly Lys Glu Tyr Lys Cys
                340                 345                 350

Lys Val Ser Asn Lys Ala Leu Pro Ala Pro Ile Glu Lys Thr Ile Ser
            355                 360                 365

Lys Ala Lys Gly Gln Pro Arg Glu Pro Arg Val Tyr Thr Leu Pro Pro
370                 375                 380

Cys Arg Asp Glu Leu Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Val Ser Asp
            420                 425                 430

Gly Ser Phe Thr Leu Tyr Ser Lys Leu Thr Val Asp Lys Ser Arg Trp
        435                 440                 445

Gln Gln Gly Asn Val Phe Ser Cys Ser Val Met His Glu Ala Leu His
    450                 455                 460

Asn His Tyr Thr Gln Lys Ser Leu Ser Leu Ser Pro Gly
465                 470                 475

<210> SEQ ID NO 193
<211> LENGTH: 477
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Val Ala Trp Tyr Gln Gln Lys Pro Gly His Ser Pro Lys Leu Leu Ile
        35                  40                  45

Tyr Ser Ala Ser Phe Arg Tyr Thr Gly Val Pro Asp Arg Phe Thr Gly
    50                  55                  60

Ser Arg Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Thr Thr Pro Pro
                85                  90                  95

Thr Phe Gly Cys Gly Thr Lys Val Glu Ile Lys Arg Gly Gly Gly Gly
            100                 105                 110

Ser Gly Gly Gly Gly Ser Gly Gly Gly Ser Gly Gly Gly Gly Ser
        115                 120                 125

Gln Val Gln Leu Gln Gln Ser Gly Pro Glu Leu Val Lys Pro Gly Ala
    130                 135                 140

Ser Leu Lys Leu Ser Cys Thr Ala Ser Gly Phe Asn Ile Lys Asp Thr
145                 150                 155                 160

Tyr Ile His Trp Val Lys Gln Arg Pro Glu Gln Cys Leu Glu Trp Ile
                165                 170                 175

Gly Arg Ile Tyr Pro Thr Asn Gly Tyr Thr Arg Tyr Asp Pro Lys Phe
            180                 185                 190

Gln Asp Lys Ala Thr Ile Thr Ala Asp Thr Ser Ser Asn Thr Ala Tyr
        195                 200                 205

```
Leu Gln Val Ser Arg Leu Thr Ser Glu Asp Thr Ala Val Tyr Tyr Cys
            210                 215                 220

Ser Arg Trp Gly Gly Asp Gly Phe Tyr Ala Met Asp Tyr Trp Gly Gln
225                 230                 235                 240

Gly Ala Ser Val Thr Val Ser Ser Ala Ala Ser Asp Lys Thr His Thr
                245                 250                 255

Cys Pro Pro Cys Pro Ala Pro Glu Leu Leu Gly Gly Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Asp Val Ser His Glu Asp Pro Glu Val
290                 295                 300

Lys Phe Asn Trp Tyr Val Asp Gly Val Glu Val His Asn Ala Lys Thr
305                 310                 315                 320

Lys Pro Arg Glu Glu Gln Tyr Asn Ser Thr Tyr Arg Val Val Ser Val
                325                 330                 335

Leu Thr Val Leu His Gln Asp Trp Leu Asn Gly Lys Glu Tyr Lys Cys
            340                 345                 350

Lys Val Ser Asn Lys Ala Leu Pro Ala Pro Ile Glu Lys Thr Ile Ser
        355                 360                 365

Lys Ala Lys Gly Gln Pro Arg Glu Pro Gln Val Cys Thr Leu Pro Pro
        370                 375                 380

Ser Arg Asp Glu Leu Thr Lys Asn Gln Val Ser Leu Ser Cys Ala Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Asp Ser Asp
            420                 425                 430

Gly Ser Phe Phe Leu Val Ser Lys Leu Thr Val Asp Lys Ser Arg Trp
        435                 440                 445

Gln Gln Gly Asn Val Phe Ser Cys Ser Val Met His Glu Ala Leu His
    450                 455                 460

Asn His Tyr Thr Gln Lys Ser Leu Ser Leu Ser Pro Gly
465                 470                 475

<210> SEQ ID NO 194
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80
```

```
Leu Gln Met Asn Ser Leu Arg Ala Glu Asp Thr Ala Val Tyr Tyr Cys
                85                  90                  95

Ala Arg Gly Ala Pro Ile Gly Ala Ala Gly Trp Phe Asp Pro Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
        210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Cys Arg Asp Glu Leu Thr Lys Asn Gln Val
            355                 360                 365

Ser Leu Trp Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly
    450

<210> SEQ ID NO 195
<211> LENGTH: 120
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 195

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Cys Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 196
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 196

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Cys Gly Thr Lys Val Glu Ile Lys
            100                 105

<210> SEQ ID NO 197
<211> LENGTH: 120
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 197

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

```
Thr Met Asp Trp Val Arg Gln Ala Pro Gly Lys Cys Leu Glu Trp Val
        35                  40                  45

Ala Asp Val Asn Pro Asn Ser Gly Gly Ser Ile Tyr Asn Gln Arg Phe
 50                  55                  60

Lys Gly Arg Phe Thr Leu Ser Val Asp Arg Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asn Leu Gly Pro Ser Phe Tyr Phe Asp Tyr Trp Gly Gln Gly
                100                 105                 110

Thr Leu Val Thr Val Ser Ser Ala
            115                 120
```

<210> SEQ ID NO 198
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

```
Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Val Ser Ile Gly
             20                  25                  30

Val Ala Trp Tyr Gln Gln Lys Pro Gly Lys Ala Pro Lys Leu Leu Ile
         35                  40                  45

Tyr Ser Ala Ser Tyr Arg Tyr Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ile Tyr Pro Tyr
                 85                  90                  95

Thr Phe Gly Cys Gly Thr Lys Val Glu Ile Lys Arg
                100                 105
```

<210> SEQ ID NO 199
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

```
Gln Val Gln Leu Gln Ser Gly Pro Glu Leu Val Lys Pro Gly Ala
 1               5                  10                  15

Ser Leu Lys Leu Ser Cys Thr Ala Ser Gly Phe Asn Ile Lys Asp Thr
             20                  25                  30

Tyr Ile His Trp Val Lys Gln Arg Pro Glu Gln Cys Leu Glu Trp Ile
         35                  40                  45

Gly Arg Ile Tyr Pro Thr Asn Gly Tyr Thr Arg Tyr Asp Pro Lys Phe
 50                  55                  60

Gln Asp Lys Ala Thr Ile Thr Ala Asp Thr Ser Ser Asn Thr Ala Tyr
 65                  70                  75                  80

Leu Gln Val Ser Arg Leu Thr Ser Glu Asp Thr Ala Val Tyr Tyr Cys
                 85                  90                  95
```

```
Ser Arg Trp Gly Gly Asp Gly Phe Tyr Ala Met Asp Tyr Trp Gly Gln
            100                 105                 110

Gly Ala Ser Val Thr Val Ser Ser Ala
        115                 120

<210> SEQ ID NO 200
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Val Ala Trp Tyr Gln Gln Lys Pro Gly His Ser Pro Lys Leu Leu Ile
        35                  40                  45

Tyr Ser Ala Ser Phe Arg Tyr Thr Gly Val Pro Asp Arg Phe Thr Gly
50                  55                  60

Ser Arg Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Thr Thr Pro Pro
                85                  90                  95

Thr Phe Gly Cys Gly Thr Lys Val Glu Ile Lys Arg
            100                 105

<210> SEQ ID NO 201
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Gly Ser Gly Ser Gly Ser Gly Ser Gly Ser Gly Ser Gly Ser Gly Ser
1               5                   10                  15

Gly Ser Gly Ser
            20

<210> SEQ ID NO 202
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Gly Gly Ser Gly Gly Ser Gly Gly Ser Gly Ser Gly Gly Ser Gly
1               5                   10                  15

Gly Ser Gly Gly Ser Gly Gly Ser Gly Gly Ser
            20                  25                  30

<210> SEQ ID NO 203

<400> SEQUENCE: 203

000
```

<210> SEQ ID NO 204
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(40)
<223> OTHER INFORMATION: This sequence may encompass 1-20 "Gly Ser"
      repeating units

<400> SEQUENCE: 204

Gly Ser Gly Ser Gly Ser Gly Ser Gly Ser Gly Ser Gly Ser Gly Ser
1               5                   10                  15

Gly Ser Gly Ser Gly Ser Gly Ser Gly Ser Gly Ser Gly Ser Gly Ser
            20                  25                  30

Gly Ser Gly Ser Gly Ser Gly Ser
        35                  40

<210> SEQ ID NO 205
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(60)
<223> OTHER INFORMATION: This sequence may encompass 1-20 "Gly Gly Ser"
      repeating units

<400> SEQUENCE: 205

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser Gly Gly
            20                  25                  30

Ser Gly Gly Ser Gly Gly Ser Gly Gly Ser Gly Gly Ser Gly Gly Ser
        35                  40                  45

Gly Gly Ser Gly Gly Ser Gly Gly Ser Gly Gly Ser
    50                  55                  60

<210> SEQ ID NO 206
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(80)
<223> OTHER INFORMATION: This sequence may encompass 1-20 "Gly Gly Gly
      Ser" repeating units

<400> SEQUENCE: 206

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser Gly Gly Gly Ser Gly Gly Gly Ser
        35                  40                  45

Gly Gly Gly Ser Gly Gly Gly Ser Gly Gly Gly Ser
        50                  55                  60

Gly Gly Gly Ser Gly Gly Gly Ser Gly Gly Gly Ser
65                  70                  75                  80

<210> SEQ ID NO 207
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(80)
<223> OTHER INFORMATION: This sequence may encompass 1-20 "Gly Gly Ser
      Gly" repeating units

<400> SEQUENCE: 207

Gly Gly Ser Gly Gly Gly Ser Gly Gly Gly Ser Gly Gly Gly Ser Gly
1               5                   10                  15

Gly Gly Ser Gly Gly Gly Ser Gly Gly Gly Ser Gly Gly Gly Ser Gly
            20                  25                  30

Gly Gly Ser Gly Gly Gly Ser Gly Gly Gly Ser Gly Gly Gly Ser Gly
        35                  40                  45

Gly Gly Ser Gly Gly Gly Ser Gly Gly Gly Ser Gly Gly Gly Ser Gly
    50                  55                  60

Gly Gly Ser Gly Gly Gly Ser Gly Gly Gly Ser Gly Gly Gly Ser Gly
65                  70                  75                  80

<210> SEQ ID NO 208
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(100)
<223> OTHER INFORMATION: This sequence may encompass 1-20 "Gly Gly Ser
      Gly Gly" repeating units

<400> SEQUENCE: 208

Gly Gly Ser Gly Gly Gly Gly Ser Gly Gly Gly Gly Ser Gly Gly Gly
1               5                   10                  15

Gly Ser Gly Gly Gly Gly Ser Gly Gly Gly Gly Ser Gly Gly Gly Gly
            20                  25                  30

Ser Gly Gly Gly Gly Ser Gly Gly Gly Gly Ser Gly Gly Gly Gly Ser
        35                  40                  45

Gly Gly Gly Gly Ser Gly Gly Gly Gly Ser Gly Gly Gly Gly Ser Gly
    50                  55                  60

Gly Gly Gly Ser Gly Gly Gly Gly Ser Gly Gly Gly Gly Ser Gly Gly
65                  70                  75                  80

Gly Gly Ser Gly Gly Gly Gly Ser Gly Gly Gly Gly Ser Gly Gly Gly
                85                  90                  95

Gly Ser Gly Gly
            100

<210> SEQ ID NO 209
<211> LENGTH: 100
<212> TYPE: PRT
<213> ORGANISM: Artificial Sequence

```
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(100)
<223> OTHER INFORMATION: This sequence may encompass 1-20 "Gly Gly Gly
      Gly Ser" repeating units

<400> SEQUENCE: 209

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser Gly Gly Gly Gly Ser Gly
                85                  90                  95

Gly Gly Gly Ser
            100
```